(12) United States Patent
Khvorova et al.

(10) Patent No.: US 12,173,286 B2
(45) Date of Patent: Dec. 24, 2024

(54) FULLY STABILIZED ASYMMETRIC siRNA

(71) Applicant: UNIVERSITY OF MASSACHUSETTS, Boston, MA (US)

(72) Inventors: Anastasia Khvorova, Westborough, MA (US); Neil Aronin, Newtonville, MA (US); Julia Alterman, Worcester, MA (US); Matthew Hassler, Worcester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 257 days.

(21) Appl. No.: 16/927,543

(22) Filed: Jul. 13, 2020

(65) Prior Publication Data

US 2021/0024926 A1    Jan. 28, 2021

Related U.S. Application Data

(63) Continuation of application No. 15/089,423, filed on Apr. 1, 2016, now abandoned.

(Continued)

(51) Int. Cl.
*C12N 15/113*    (2010.01)
*C12N 15/11*    (2006.01)

(52) U.S. Cl.
CPC .......... *C12N 15/113* (2013.01); *C12N 15/111* (2013.01); *C12N 15/1138* (2013.01); *C12Y 207/10001* (2013.01); C12N 2310/14 (2013.01); C12N 2310/315 (2013.01); C12N 2310/321 (2013.01); C12N 2310/343 (2013.01); *C12N 2310/344* (2013.01); *C12N 2310/346* (2013.01); *C12N 2310/3515* (2013.01); *C12N 2320/51* (2013.01); *C12N 2320/53* (2013.01)

(58) Field of Classification Search
CPC ............ C12N 2310/321; C12N 15/111; C12N 15/113; C12N 15/1138; C12N 2320/51
See application file for complete search history.

(56) References Cited

U.S. PATENT DOCUMENTS 4,522,811 A    6/1985    Eppstein et al.
5,194,596 A    3/1993    Tischer et al.
(Continued)

FOREIGN PATENT DOCUMENTS

CN    101199858 A    6/2008
CN    101365801 A    2/2009
(Continued)

OTHER PUBLICATIONS

Ly et al. (Nucleic Acids Res. Jan. 9, 2017; 45(1): 15-25, plus Supplementary Data).*
(Continued)

*Primary Examiner* — Terra C Gibbs
(74) *Attorney, Agent, or Firm* — LATHROP GPM LLP; James H. Velema, Esq.; Michael J. Spellberg, Esq.

(57) ABSTRACT

Provided herein are self-delivering oligonucleotides that are characterized by efficient RISC entry, minimum immune response and off-target effects, efficient cellular uptake without formulation, and efficient and specific tissue distribution.

39 Claims, 64 Drawing Sheets
(16 of 64 Drawing Sheet(s) Filed in Color)
Specification includes a Sequence Listing.

Related U.S. Application Data

(60) Provisional application No. 62/287,255, filed on Jan. 26, 2016, provisional application No. 62/205,218, filed on Aug. 14, 2015, provisional application No. 62/142,786, filed on Apr. 3, 2015.

(56) References Cited

U.S. PATENT DOCUMENTS

| | | | |
|---|---|---|---|
| 5,219,739 A | 6/1993 | Tischer et al. |
| 5,240,848 A | 8/1993 | Keck et al. |
| 5,328,470 A | 7/1994 | Nabel et al. |
| 5,332,671 A | 7/1994 | Ferrara et al. |
| 5,684,143 A | 11/1997 | Gryaznov et al. |
| 5,814,014 A | 9/1998 | Elsberry et al. |
| 5,858,988 A | 1/1999 | Wang |
| 5,939,402 A | 8/1999 | Weis et al. |
| 6,025,335 A | 2/2000 | Weis et al. |
| 6,093,180 A | 7/2000 | Elsberry |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,312,900 B1 | 11/2001 | Dean et al. |
| 6,383,814 B1 | 5/2002 | Lee et al. |
| 6,447,768 B1 | 9/2002 | van Zonneveld et al. |
| 6,471,996 B1 | 10/2002 | Sokoll et al. |
| 6,472,375 B1 | 10/2002 | Hoon et al. |
| 6,489,464 B1 | 12/2002 | Agrawal et al. |
| 7,250,496 B2 | 7/2007 | Bentwich |
| 7,459,547 B2 | 12/2008 | Zamore et al. |
| 7,691,997 B2 | 4/2010 | Khvorova et al. |
| 7,723,512 B2 | 5/2010 | Manoharan et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 7,790,867 B2 | 9/2010 | Bentwich |
| 7,834,171 B2 | 11/2010 | Leake et al. |
| 8,013,136 B2 | 9/2011 | Manoharan et al. |
| 8,097,752 B2 | 1/2012 | Calogeropolou et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,501,706 B2 | 8/2013 | Yamada et al. |
| 8,507,661 B2 | 8/2013 | Manoharan et al. |
| 8,664,189 B2 | 3/2014 | Khvorova et al. |
| 8,703,731 B2 | 4/2014 | Jimenez et al. |
| 8,796,443 B2 | 8/2014 | Khvorova et al. |
| 8,815,818 B2 | 8/2014 | Samarsky et al. |
| 8,871,774 B2 | 10/2014 | Charifson et al. |
| 8,877,439 B2 | 11/2014 | Butora et al. |
| 8,906,874 B2 | 12/2014 | Rao et al. |
| 8,993,738 B2 | 3/2015 | Prakash et al. |
| 9,029,389 B2 | 5/2015 | No et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,198,981 B2 | 12/2015 | Ambati et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,745,574 B2 * | 8/2017 | Woolf .................. C12N 15/111 |
| 9,796,756 B2 | 10/2017 | Hadwiger et al. |
| 9,809,817 B2 | 11/2017 | Khvorova et al. |
| 9,862,350 B2 | 1/2018 | Guerrero et al. |
| 9,862,952 B2 | 1/2018 | Khvorova et al. |
| 9,867,882 B2 | 1/2018 | Manoharan et al. |
| 10,087,210 B2 | 10/2018 | Prakash et al. |
| 10,435,688 B2 | 10/2019 | Khvorova et al. |
| 10,478,503 B2 | 11/2019 | Khvorova et al. |
| 10,479,992 B2 | 11/2019 | Woolf et al. |
| 10,519,451 B2 | 12/2019 | Khvorova et al. |
| 10,633,653 B2 | 4/2020 | Khvorova et al. |
| 10,774,327 B2 | 9/2020 | Khvorova et al. |
| 10,799,591 B2 | 10/2020 | Khvorova et al. |
| 10,844,377 B2 | 11/2020 | Khvorova et al. |
| 11,230,713 B2 | 1/2022 | Khvorova et al. |
| 11,279,930 B2 | 3/2022 | Khvorova et al. |
| 11,345,917 B2 | 5/2022 | Khvorova et al. |
| 11,492,619 B2 | 11/2022 | Khvorova et al. |
| 11,667,915 B2 * | 6/2023 | Woolf .................. C12N 15/111 |
| | | 435/375 |
| 11,702,659 B2 | 7/2023 | Khvorova et al. |
| 11,753,638 B2 | 9/2023 | Khvorova et al. |
| 11,827,882 B2 | 11/2023 | Khvorova et al. |
| 11,896,669 B2 | 2/2024 | Khvorova et al. |
| 2001/0027251 A1 | 10/2001 | Cook et al. |
| 2003/0045705 A1 | 3/2003 | Cook |
| 2003/0143732 A1 | 7/2003 | Fosnaugh et al. |
| 2004/0121426 A1 | 6/2004 | Hsieh |
| 2004/0198640 A1 | 10/2004 | Leake et al. |
| 2004/0205839 A1 | 10/2004 | Doutriaux et al. |
| 2005/0220766 A1 | 10/2005 | Amalfitano et al. |
| 2005/0255487 A1 | 11/2005 | Khvorova et al. |
| 2006/0003322 A1 | 1/2006 | Bentwich et al. |
| 2006/0009409 A1 | 1/2006 | Woolf |
| 2006/0024715 A1 | 2/2006 | Liu et al. |
| 2006/0078542 A1 | 4/2006 | Mah et al. |
| 2006/0094032 A1 | 5/2006 | Fougerolles et al. |
| 2006/0105998 A1 | 5/2006 | Calogeropoulou et al. |
| 2007/0004664 A1 | 1/2007 | McSwiggen et al. |
| 2007/0004665 A1 | 1/2007 | McSwiggen et al. |
| 2007/0135372 A1 | 6/2007 | MacLachlan et al. |
| 2007/0160534 A1 | 7/2007 | Dennis et al. |
| 2007/0191273 A1 | 8/2007 | Ambati et al. |
| 2007/0259827 A1 | 11/2007 | Aronin et al. |
| 2008/0039415 A1 | 2/2008 | Stewart et al. |
| 2008/0108583 A1 | 5/2008 | Feinstein |
| 2008/0113369 A1 | 5/2008 | Khvorova et al. |
| 2008/0119427 A1 | 5/2008 | Bhat et al. |
| 2008/0269149 A1 | 10/2008 | Bowles et al. |
| 2009/0143322 A1 | 6/2009 | Burkoth et al. |
| 2009/0234109 A1 | 9/2009 | Han et al. |
| 2009/0269332 A1 | 10/2009 | Gimeno et al. |
| 2009/0281299 A1 | 11/2009 | Manorahan et al. |
| 2009/0318676 A1 | 12/2009 | Manoharan et al. |
| 2010/0093085 A1 | 4/2010 | Yamada et al. |
| 2010/0186103 A1 | 7/2010 | Gao et al. |
| 2010/0240730 A1 | 9/2010 | Beigelman et al. |
| 2011/0039914 A1 | 2/2011 | Pavco et al. |
| 2011/0086905 A1 | 4/2011 | Glazer |
| 2011/0097716 A1 | 4/2011 | Natt et al. |
| 2011/0201006 A1 | 8/2011 | Roehl et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0052487 A9 * | 3/2012 | Khvorova .............. G16B 20/00 |
| | | 536/23.1 |
| 2012/0059046 A1 | 3/2012 | Woolf et al. |
| 2012/0065243 A1 | 3/2012 | Woolf et al. |
| 2012/0136039 A1 | 5/2012 | Aronin et al. |
| 2013/0131141 A1 | 5/2013 | Khvorova et al. |
| 2013/0131142 A1 | 5/2013 | Libertine et al. |
| 2013/0178513 A1 | 7/2013 | Dobie et al. |
| 2013/0196434 A1 | 8/2013 | Maier et al. |
| 2013/0197055 A1 | 8/2013 | Kamens et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0113950 A1 | 4/2014 | Khvorova et al. |
| 2014/0155387 A1 | 6/2014 | No et al. |
| 2014/0288148 A1 | 9/2014 | Biegelman et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2015/0025122 A1 | 1/2015 | Smith |
| 2015/0209441 A1 | 7/2015 | Carell et al. |
| 2015/0232840 A1 | 8/2015 | Aronin et al. |

(56) References Cited

U.S. PATENT DOCUMENTS

| | | |
|---|---|---|
| 2015/0247142 A1 | 9/2015 | Esau et al. |
| 2015/0267200 A1 | 9/2015 | McSwiggen et al. |
| 2015/0315584 A1 | 11/2015 | MacDonald et al. |
| 2016/0017323 A1 | 1/2016 | Prakash et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0130583 A1 | 5/2016 | Yokota et al. |
| 2016/0244765 A1 | 8/2016 | Khvorova et al. |
| 2016/0281148 A1 | 9/2016 | Greenlee et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2016/0376598 A1 | 12/2016 | Lee et al. |
| 2017/0009239 A1 | 1/2017 | Khvorova et al. |
| 2017/0009304 A1 | 1/2017 | Zhou |
| 2017/0037456 A1 | 2/2017 | Kokoris et al. |
| 2017/0043024 A1 | 2/2017 | Khvorova et al. |
| 2017/0043204 A1 | 2/2017 | James |
| 2017/0051283 A1 | 2/2017 | Khvorova |
| 2017/0051286 A1 | 2/2017 | Smith |
| 2017/0067056 A1 | 3/2017 | Khvorova et al. |
| 2017/0183655 A1 | 6/2017 | Grabcysk et al. |
| 2017/0189541 A1 | 7/2017 | Foster |
| 2017/0281795 A1 | 10/2017 | Geall |
| 2017/0312367 A1 | 11/2017 | Alterman et al. |
| 2017/0327524 A1 | 11/2017 | Nanna et al. |
| 2017/0349903 A1 | 12/2017 | Wanqing et al. |
| 2017/0369882 A1 | 12/2017 | Khvorova et al. |
| 2018/0023082 A1 | 1/2018 | Stanek et al. |
| 2018/0087052 A1 | 3/2018 | Hung et al. |
| 2018/0094263 A1 | 4/2018 | Alterman et al. |
| 2018/0179546 A1 | 6/2018 | Khvorova et al. |
| 2018/0251764 A1 | 9/2018 | Albaek et al. |
| 2019/0002880 A1 | 1/2019 | Woolf et al. |
| 2019/0024082 A1 | 1/2019 | Khvorova et al. |
| 2019/0144860 A1 | 5/2019 | Konstantinova et al. |
| 2019/0185855 A1 | 6/2019 | Khvorova et al. |
| 2019/0211341 A1 | 7/2019 | Butler et al. |
| 2019/0225965 A1 | 7/2019 | Khvorova et al. |
| 2019/0247507 A1 | 8/2019 | Khvorova et al. |
| 2020/0087663 A1 | 3/2020 | Aronin |
| 2020/0095580 A1 | 3/2020 | Hauptmann et al. |
| 2020/0123543 A1 | 4/2020 | Khvorova et al. |
| 2020/0165618 A1 | 5/2020 | Khvorova et al. |
| 2020/0270605 A1 | 8/2020 | Khvorova et al. |
| 2020/0308578 A1 | 10/2020 | Woolf et al. |
| 2020/0308584 A1 | 10/2020 | Khvorova et al. |
| 2020/0339983 A1 | 10/2020 | Khvorova et al. |
| 2020/0362341 A1 | 11/2020 | Khvorova |
| 2020/0385737 A1 | 12/2020 | Khvorova |
| 2020/0385740 A1 | 12/2020 | Khvorova et al. |
| 2021/0024926 A1 | 1/2021 | Khvorova et al. |
| 2021/0071117 A9 | 3/2021 | Khvorova et al. |
| 2021/0071177 A1 | 3/2021 | Khvorova |
| 2021/0085793 A1 | 3/2021 | Khvorova et al. |
| 2021/0115442 A1 | 4/2021 | Khvorova et al. |
| 2021/0139901 A1 | 5/2021 | Khvorova et al. |
| 2021/0340535 A1 | 11/2021 | Khvorova |
| 2021/0355491 A1 | 11/2021 | Khvorova et al. |
| 2021/0363523 A1 | 11/2021 | Khvorova et al. |
| 2022/0010309 A1 | 1/2022 | Khvorova et al. |
| 2022/0090069 A1 | 3/2022 | Khvorova et al. |
| 2022/0228141 A1 | 7/2022 | Khvorova et al. |
| 2022/0251554 A1 | 8/2022 | Khvorova et al. |
| 2022/0251555 A1 | 8/2022 | Khvorova et al. |
| 2022/0364100 A1 | 11/2022 | Khvorova et al. |
| 2023/0021431 A1 | 1/2023 | Khvorova |
| 2023/0061751 A1 | 3/2023 | Khvorova et al. |
| 2023/0078622 A1 | 3/2023 | Khvorova et al. |
| 2023/0193281 A1 | 6/2023 | Khvorova et al. |
| 2023/0313198 A1 | 10/2023 | Khvorova et al. |
| 2023/0340475 A1 | 10/2023 | Khvorova et al. |
| 2023/0348907 A1 | 11/2023 | Khvorova et al. |
| 2023/0416735 A1 | 12/2023 | Khvorova et al. |

FOREIGN PATENT DOCUMENTS

| | | |
|---|---|---|
| CN | 104884618 A | 11/2015 |
| CN | 105194689 A | 12/2015 |
| EP | 1752536 A1 | 2/2007 |
| EP | 2407539 A1 | 1/2012 |
| EP | 2601204 A2 | 6/2013 |
| EP | 2853597 A1 | 4/2015 |
| EP | 3277811 A1 | 2/2018 |
| EP | 3277814 A1 | 2/2018 |
| EP | 3277815 A1 | 2/2018 |
| EP | 3408391 A1 | 12/2018 |
| EP | 3550021 A1 | 10/2019 |
| EP | 3642341 A1 | 4/2020 |
| EP | 3929293 A2 | 12/2021 |
| EP | 3946369 A2 | 2/2022 |
| EP | 4126040 A2 | 2/2023 |
| JP | H06-41183 A | 2/1994 |
| JP | H6-504680 A | 6/1994 |
| JP | 2001-501614 A | 2/2001 |
| JP | 2009-504782 A | 2/2009 |
| JP | 2010-506598 A | 3/2010 |
| JP | 2018-516091 A | 4/2010 |
| JP | 2012-502657 A | 2/2012 |
| JP | 2013-049714 A | 3/2013 |
| JP | 2015-061534 A | 4/2015 |
| JP | 2016-171815 A | 9/2016 |
| JP | 2016-526529 A | 9/2016 |
| WO | WO 1992/013869 A1 | 8/1992 |
| WO | WO 1993/009239 A1 | 5/1993 |
| WO | WO 1993/024641 A2 | 12/1993 |
| WO | WO 1994/022890 A1 | 10/1994 |
| WO | WO 1996/003500 A1 | 2/1996 |
| WO | WO 1998/013526 A1 | 4/1998 |
| WO | 2003/029459 A2 | 4/2003 |
| WO | 2004/008946 A2 | 1/2004 |
| WO | WO 2004/013280 A2 | 2/2004 |
| WO | 2004/044136 A2 | 5/2004 |
| WO | WO 2004/061081 A2 | 7/2004 |
| WO | WO 2004/108956 A1 | 12/2004 |
| WO | WO 2005/078095 A2 | 8/2005 |
| WO | 2006/019430 A2 | 2/2006 |
| WO | WO 2007/022470 A2 | 2/2007 |
| WO | WO 2007/022506 A2 | 2/2007 |
| WO | 2007/051045 A2 | 5/2007 |
| WO | 2007/094218 A1 | 8/2007 |
| WO | WO 2007/091269 A2 | 8/2007 |
| WO | 2007/112414 A1 | 10/2007 |
| WO | WO 2008/005562 A2 | 1/2008 |
| WO | 2008/154482 A2 | 12/2008 |
| WO | 2009/002944 A1 | 12/2008 |
| WO | 2009/054551 A2 | 4/2009 |
| WO | 2009/099991 A2 | 8/2009 |
| WO | 2009/102427 A2 | 8/2009 |
| WO | 2010/008582 A2 | 1/2010 |
| WO | 2010/011346 A1 | 1/2010 |
| WO | 2010/033246 A1 | 3/2010 |
| WO | 2010/033247 A2 | 3/2010 |
| WO | 2010/033248 A2 | 3/2010 |
| WO | 2010/048585 A2 | 4/2010 |
| WO | 2010/059226 A2 | 5/2010 |
| WO | 2010/078536 A1 | 7/2010 |
| WO | 2010/090762 A1 | 8/2010 |
| WO | WO 2010/048352 A2 | 9/2010 |
| WO | WO 2010/111503 A2 | 9/2010 |
| WO | WO 2010/118263 A1 | 10/2010 |
| WO | WO 2011/097643 A1 | 8/2011 |
| WO | 2011/109698 A1 | 9/2011 |
| WO | 2011/119852 A1 | 9/2011 |
| WO | 2011/119871 A1 | 9/2011 |
| WO | 2011/119887 A1 | 9/2011 |
| WO | WO 2011/125943 A1 | 10/2011 |
| WO | WO 2011/139702 A2 | 11/2011 |
| WO | WO 2011/158924 A1 | 12/2011 |
| WO | 2012/005898 A2 | 1/2012 |
| WO | WO 2012/058210 A1 | 5/2012 |
| WO | 2012/118911 A1 | 9/2012 |
| WO | WO 2012/131365 A1 | 10/2012 |
| WO | WO 2012/177906 A1 | 12/2012 |

(56) References Cited

FOREIGN PATENT DOCUMENTS

| | | |
|---|---|---|
| WO | WO 2013/089283 A1 | 6/2013 |
| WO | 2013/165816 A2 | 11/2013 |
| WO | WO 2014/009429 A1 | 1/2014 |
| WO | WO 2014/043544 A1 | 3/2014 |
| WO | 2014/076195 A1 | 5/2014 |
| WO | WO 2014/089313 A1 | 6/2014 |
| WO | WO 2014/201306 A1 | 12/2014 |
| WO | WO 2014/203518 A1 | 12/2014 |
| WO | WO 2015/025122 A1 | 2/2015 |
| WO | WO 2015/200078 A1 | 2/2015 |
| WO | WO 2015/113004 A2 | 7/2015 |
| WO | 2015/161184 A1 | 10/2015 |
| WO | WO 2016/028649 A1 | 2/2016 |
| WO | WO 2016/077321 A1 | 5/2016 |
| WO | WO 2016/077349 A1 | 5/2016 |
| WO | WO 2016/149331 A2 | 9/2016 |
| WO | 2016/161374 A1 | 10/2016 |
| WO | WO 2016/161378 A1 | 10/2016 |
| WO | WO 2016/161388 A1 | 10/2016 |
| WO | WO 2016/164866 A1 | 10/2016 |
| WO | WO 2016/205410 A2 | 12/2016 |
| WO | WO 2017/015555 A1 | 1/2017 |
| WO | WO 2017/024239 A1 | 2/2017 |
| WO | WO 2017/030973 A1 | 2/2017 |
| WO | WO 2017/062862 A2 | 4/2017 |
| WO | WO 2017/132669 A1 | 8/2017 |
| WO | WO 2018/031933 A2 | 2/2018 |
| WO | WO 2018/041973 A1 | 3/2018 |
| WO | WO 2018/185241 A1 | 10/2018 |
| WO | WO 2018/223056 A1 | 12/2018 |
| WO | WO 2018/237245 A1 | 12/2018 |
| WO | WO 2019/075418 A1 | 4/2019 |
| WO | WO 2019/075419 A1 | 4/2019 |
| WO | WO 2019/217459 A1 | 11/2019 |
| WO | WO 2019/232255 A1 | 12/2019 |
| WO | WO 2020/033899 A1 | 2/2020 |
| WO | WO 2020/041769 A1 | 2/2020 |
| WO | WO 2020/150636 A1 | 7/2020 |
| WO | WO 2020/198509 A2 | 10/2020 |
| WO | WO 2021/216556 A2 | 10/2021 |
| WO | WO 2021/195533 A2 | 11/2021 |
| WO | WO 2021/242883 A1 | 12/2021 |

OTHER PUBLICATIONS

Young et al. (2010) "Pathogenesis of preeclampsia," Annual Review of Pathology. 5:173-192.

Younis et al. (2013) "Overview of the Nonclinical Development Strategies and Class-Effects of Oligonucleotide-Based Therapeutics," Ch. 26 In; A Comprehensive Guide to Toxicology in Preclinical Drug Development. Ed.: Faqi. Academic Press. pp. 647-664.

Yu et al. (2002) "RNA interference by expression of short-interfering RNAs and hairpin RNAs in mammalian cells," Proc Natl Acad Sci USA. 99:6047-6052.

Yu et al. (Aug. 31, 2012) "Single-stranded RNAs use RNAi to potently and allele-selectively inhibit mutant huntingtin expression," Cell. 150(5):895-908.

Zeng et al. (2002) "Both natural and designed micro RNAs can inhibit the expression of cognate mRNAs when expressed in human cells," Mol. Cell. 9(6):1327-1333.

Zeng et al. (2003) "Sequence requirements for micro RNA processing and function in human cells," RNA. 9 (1):112-123.

International Search Report with Written Opinion corresponding to International Patent Application No. PCT/US2016/025722, mailed Aug. 12, 2016.

International Search Report with Written Opinion corresponding to International Patent Application No. PCT/US2016/025731, mailed Sep. 9, 2016.

International Search Report with Written Opinion corresponding to International Patent Application No. PCT/US2016/025753, mailed Sep. 14, 2016.

International Search Report with Written Opinion corresponding to International Patent Application No. PCT/US2016/046810, mailed Nov. 29, 2016.

International Search Report with Written Opinion corresponding to International Patent Application No. PCT/US2017/015633, mailed May 11, 2017.

Morrissey et al., "Activity of stabilized short interfering RNA in a mouse model of hepatitis B virus replication", Hepatology, 2005, vol. 41, pp. 1349-1356.

Raouane et al, "Lipid Conjugated Oligonucleotides: A Useful Strategy for Delivery", Bioconjugate Chemistry, 2012, 23: 1091-1104.

Extended European Search Report for European Patent Application No. 16837593.9, dated Mar. 20, 2019.

Partial European Search Report for European Patent Application No. 20216265.7, dated Nov. 10, 2021.

Extended European Search Report for European Patent Application No. 20216265.7, dated Feb. 10, 2022.

Lagos-Quintana et al. (2001) "Identification of novel genes coding for small expressed RNAs," Science. 294 (5543):853-858.

Lai et al. (2003) "Computational identification of *Drosophila* microRNA genes," Genome Biol. 4(7):R42. pp. 1-20.

Lau et al. (2001) "An abundant class of tiny RNAs with probable regulatory roles in Caenorhabditis elegans," Science. 294(5543):858-862.

Lau et al. (2006) "Characterization of the piRNA complex from rat testes," Science. 313(5785):363-367.

Lee et al. (2001) "An extensive class of small RNAs in Caenorhabditis elegans," Science. 294(5543):862-864.

Lee et al. (2002) "Expression of small interfering RNAs targeted against HIV-1 rev transcripts in human cells," Nat. Biotechnol. 20:500-505.

Lim et al. (2003) "The microRNAs of Caenorhabditis elegans," Genes Dev. 17(8):991-1008.

Lim et al. (2003) "Vertebrate microRNA genes," Science. 299(5612):1540.

Lima et al. (Aug. 31, 2012) "Single-stranded siRNAs activate RNAi in animals," Cell. 150:883-894.

Lorenz et al. (2004) "Steroid and lipid conjugates of siRNAs to enhance cellular uptake and gene silencing in liver cells," Bioorg. Med. Chem. Lett. 14:4975-4977.

Luo et al. (Jun. 18, 2013) "Photoreceptor avascular privilege is shielded by soluble VEGF receptor-1," eLife. 6:e19456. pp. 1-22.

McCaffrey et al. (2002) "RNA interference in adult mice," Nature. 418(6893):38-39.

McManus et al. (2002) "Gene silencing using micro-RNA designed hairpins," RNA. 8:842-850.

Miyagishi et al. (2002) "U6 promoter-driven siRNAs with four uridine 3' overhangs efficiently suppress targeted gene expression in mammalian cells," Nat. Biotechnol. 20:497-500.

Molitoris et al. (2009) "siRNA Targeted to p53 Attenuates Ischemic and Cisplatin-Induced Acute Kidney Injury," Journal of the American Society of Nephrology. 20:1754-1764.

Myers et al. (1988) "Optimal alignments in linear space," Comput. Appl. Biosci. 4(1):11-17.

Nair et al. (Dec. 10, 2014) "Multivalent N-Acetylgalactosamine-Conjugated siRNA Localizes in Hepatocytes and Elicits Robust RNAi-Mediated Gene Silencing," J. Am. Chem. Soc. 136(49):16958-16961.

Nielsen et al. (2001) "Sequence-selective recognition of DNA by strand displacement with a thymine-substituted polyamide," Science. 254:1497-1500.

Nikan et al. (Aug. 9, 2016) "Docosahexaenoic Acid Conjugation Enhances Distribution and Safety of siRNA upon Local Administration in Mouse Brain," Mol. Ther. Nucleic Acids. 5(8):e344. pp. 1-11.

Owen et al. (Mar. 15, 2012) "Morpholino-mediated increase in soluble Flt-1 expression results in decreased ocular and tumor neovascularization," PloS One. 7(3):e33576. pp. 1-9.

Paddison et al. (2002) "Short hairpin RNAs (shRNAs) induce sequence-specific silencing in mammalian cells," Gene Dev. 16:948-958.

(56) References Cited

OTHER PUBLICATIONS

Pasquinelli et al. (2000) "Conservation of the sequence and temporal expression of let-7 heterochronic regulatory RNA," Nature. 408(6808):86-89.
Paul et al. (2002) "Effective expression of small interfering RNA in human cells," Nature Biotechnol. 20:505-508.
Peel et al. (Feb. 12, 2015) "Conjugation and Evaluation of Small Hydrophobic Molecules to Triazole-Linked siRNAs," ACS Med. Chem. Lett. 6(2):117-122.
Petersen et al. (2003) "LNA: a versatile tool for therapeutics and genomics," Trends Biotechnol 21:74-81.
Pubchem Database [Online] (2003) "AMINO-TEG-DIOL," PubChem Accession No. 22136768. National Institute for Biotechnology Information. Accessible on the Internet at URL: https://pubchem.ncbi.nlm.nih.gov/compound/2213676. [Last Accessed Aug. 31, 2017], 13 pgs.
Pubchem Database [Online] (2005) "SCHEMBL867745," PubChem Accession No. 12454428. National Institute for Biotechnology Information. Accessible on the Internet at URL: https://pubchem.ncbi.nlm.nih.gov/compound/12454428. [Last Accessed Aug. 31, 2017], 12 pgs.
Putnam (1996) "Antisense strategies and therapeutic applications," Am. J. Health Syst. Pharm. 53(2):151-160.
Reinhart et al. (2002) "Small RNAs correspond to centromere heterochromatic repeats," Science. 297(5588):1831.
Rigo et al. (Apr. 20, 2014) "Pharmacology of a central nervous system delivered 2'-O-methoxyethyl-modified splicing oligonucleotide in mice and nonhuman primates," The Journal of Pharmacology and Experimental Therapeutics. 350:46-55.
Rodriguez-Lebron et al. (2005) "Intrastriatal rAAV-mediated delivery of anti-huntingtin shRNAs induces partial reversal of disease progression in R6/1 Huntington's disease transgenic mice," Mol. Ther. 12(4):618-633.
Ruscowski et al. (2000) "Biodistribution and metabolism of a mixed backbone oligonucleotide (GEM 231) following single and multiple dose administration in mice," Antisense Nucleic Acid Drug Dev. 10(5):333-345.
Schirle et al. (Oct. 31, 2014) "Gene Regulation. Structural basis for microRNA targeting," Science. 346:608-613.
Schwab et al. (1994) "An approach for new anticancer drugs: oncogene-targeted antisense DNA," Ann. Oncol. 5 (Suppl 4):55-58.
Schwarz et al. (2003) Asymmetry in the Assembly of the RNAi Enzyme Complex. Cell 115:199-208.
Song et al. (2003) "Sustained Small Interfering RNA-Mediated Human Immunodeficiency Virus Type 1 Inhibition in Primary Macrophages," Journal of Virology. 77:7174-7181.
Soutschek et al. (2004) "Therapeutic silencing of an endogenous gene by systemic administration of modified siRNAs," Nature. 432:173-178.
Stalder et al. (Mar. 19, 2013) "The rough endoplasmatic reticulum is a central nucleation site of siRNA-mediated RNA silencing," EMBO J. 32:1115-1127.
Stein (2001) "Inhibition of Vesivirus infections in mammalian tissue culture with antisense morpholino oligomers," Antisense Nucleic Acid Drug Dev. 11(5):317-25.
Stokman et al. (2010) "Application of siRNA in targeting protein expression in kidney disease," Advanced Drug Delivery Reviews. 62:1378-1389.
Sui et al. (2002) "A Dna vector-based RNAi technology to suppress gene expression in mammalian cells," Proc Natl Acad Sci USA. 99:5515-5520.
Tabernero et al. (Apr. 2013) "First-in-humans trial of an RNA interference therapeutic targeting VEGF and KSP in cancer patients with liver involvement," Cancer Discovery. 3:406-417.
Thomas et al. (2009) "A recently evolved novel trophoblast-enriched secreted form of fms-like tyrosine kinase-1 variant is up-regulated in hypoxia and preeclampsia," J. Clin. Endocrinol. Metabol. 94:2524-2530.

Tuschl (2002) "Expanding small RNA interference," Nat. Biotechnol. 20(5):446-448.
Tuschl et al. (May 6, 2004) "The siRNA User Guide," Accessible on the Internet at URL: http://diyhpl.US/~bryan/irc/ protocol-online/protocol-cache/sirna.html. [Last Accessed Aug. 11, 2016].
Vaught et al. (2004) "T7 Rna Polymerase Transcription with 5-Position Modified UTP Derivatives," J. Am. Chem. Soc. 126:11231-11237.
Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.
Watanabe et al. (2008) "Endogenous siRNAs from naturally formed dsRNAs regulate transcripts in mouse oocytes," Nature. 453(7194):539-543.
Wooddell et al. (Feb. 26, 2013) "Hepatocyte-targeted RNAi Therapeutics for the Treatment of Chronic Hepatitis B Virus Infection," Molecular Therapy. 21:973-985.
Xia et al. (2002) "siRNA-mediated gene silencing in vitro and in vivo," Nature Biotechnol. 20(10):1006-1010.
Alexopoulou et al. (2001) "Recognition of double-stranded RNA and activation of NF-κB by Toll-like receptor 3," Nature. 413:732-738.
Allerson et al. (2005) "Fully 2'-Modified Oligonucleotide Duplexes with Improved in Vitro Potency and Stability Compared to Unmodified Small Interfering Rna," J. Med. Chem. 48(4):901-904.
Alterman et al. (Dec. 12, 2015) "Hydrophobically Modified siRNAs Silence Huntingtin mRNA in Primary Neurons and Mouse Brain," Mol. Ther.: Nucleic Acids. 4(12):e266. pp. 1-12.
Altschul et al. (1997) "Gapped BLAST and PSI-BLAST: a new generation of protein database search programs," Nucleic Acids Res. 25(17):3389-3402.
Ameres et al. (2007) "Molecular basis for target RNA recognition and cleavage by human RISC," Cell. 130:101-112.
Anderson et al. (2008) "Experimental validation of the importance of seed complement frequency to siRNA specificity," RNA. 14:853-861.
Anderson et al. (2008) "Identifying siRNA-induced off-targets by microarray analysis," Ch.4 In; Methods in Molecular Biology. 442:45-63.
Bagella et al. (1998) "Cloning of murine CDK9/PITALRE and its tissue-specific expression in development," J. Cell. Physiol. 177:206-213.
Bartlett (2006) "Insights into the kinetics of siRNA-mediated gene silencing from live-cell and live-animal bioluminescent imaging," Nucleic Acids Research. 34:322-333.
Behlke et al. (2008) "Chemical modification of siRNAs for in vivo use," Oligonucleotides. 18:305-320.
Billy et al. (2001) "Specific interference with gene expression induced by long, double-stranded RNA in mouse embryonal teratocarcinoma cell lines," Proc Natl Acad Sci USA. 98(25):14428-14433.
Birmingham et al. (2006) "3' UTR seed matches, but not overall identity, are associated with RNAi off-targets," Nat. Methods. 3:199-204.
Birmingham et al. (2007) "A protocol for designing siRNAs with high functionality and specificity," Nature Protocols. 2:2068-2078.
Braasch et al. (2003) "RNA Interference in Mammalian Cells by Chemically-Modified RNA," Biochemistry 42:7967-7975.
Brennecke et al. (2003) "Towards a complete description of the microRNA complement of animal genomes," Genome Biol. 4(9):228.
Brummelkamp et al. (2002) "A system for stable expression of short interfering RNAs in mammalian cells," Science. 296:550-553.
Burchard et al. (2009) "MicroRNA-like off-target transcript regulation by siRNAs is species specific," RNA. 15:308-315.
Byrne et al. (Nov. 1, 2013) "Novel hydrophobically modified asymmetric RNAi compounds (sd-rxRNA) demonstrate robust efficacy in the eye," Journal of Ocular Pharmacology and Therapeutics. 29:855-864.
Calegari et al. (2002) "Tissue-specific RNA interference in postimplantation mouse embryos with endoribonuclease-prepared short interfering RNA," Proc. Natl. Acad. Sci. USA. 99(22):14236-14240.

(56) References Cited

OTHER PUBLICATIONS

Charrier et al. (May 3, 2012) "Inhibition of SRGAP2 function by its human-specific paralogs induces neoteny during spine maturation," Cell. 149(4):923-935.

Cho et al. (Feb. 13, 2012) "Vascular endothelial growth factor receptor 1 morpholino decreases angiogenesis in a murine corneal suture model," Invest. Opthamol. Visual Sci. 53(2):685-692.

Choe et al. (2005) "Crystal structure of human toll-like receptor 3 (TLR3) ectodomain," Science. 309:581-585.

Coelho et al. (Aug. 29, 2013) "Safety and efficacy of RNAi therapy for transthyretin amyloidosis," The New England Journal of Medicine. 369:819-829.

Deleavey et al. (Jan. 5, 2013) "The 5' binding MID domain of human Argonaute2 tolerates chemically modified nucleotide analogues" Nucleic Acid Therapeutics. 23:81-87.

Difiglia et al. (2007) "Therapeutic silencing of mutant huntingtin with siRNA attenuates striatal and cortical neuropathology and behavioral deficits," Proc. Natl. Acad. Sci. USA. 104(43):17204-17209.

Doench et al. (2003) "siRNAs can function as miRNAs," Genes Dev. 17(4):438-442.

Eckstein (2000) "Phosphorothioate Oligodeoxynucleotides: What Is Their Origin and What Is Unique About Them?" Antisense Nucleic Acid Drug Dev. 10(2):117-121.

Elmen et al. (2005) "Locked nucleic acid (LNA) mediated improvements in siRNA stability and functionality," Nucleic Acids Res. 33(1):439-447.

Fan et al. (Oct. 20, 2014) "Endometrial VEGF induces placental sFLT1 and leads to pregnancy complications," J. Clin. Inves. 124(11):4941-4952.

Federov et al. (2006) "Off-target effects by siRNA can induce toxic phenotype," RNA. 12:1188-1196.

Felber et al. (Sep. 2012) "The interactions of amphiphilic antisense oligonucleotides with serum proteins and their effects on in vitro silencing activity," Biomaterials. 33(25):5955-5965.

Frazier (Nov. 9, 2015) "Antisense Oligonucleotide Therapies: The Promise and the Challenges from a Toxicologic Pathologist's Perspective," Toxicologic Pathology. 43:78-89.

Gaglione et al. (2010) "Recent progress in chemically modified siRNAs," Mini Rev. Med. Chem. 10(7):578-595.

Godard et al. (1995) "Antisense Effects of Cholesterol-Oligodeoxynucleotide Conjugates Associated with Poly (alkylcyanoacrylate) Nanoparticles," Eur. J. Biochem. 232(2):404-410.

Grad et al. (2003) "Computational and experimental identification of C. elegans microRNAs," Mol. Cell. 11 (5):1253-1263.

Griffiths-Jones (2004) "The microRNA Registry," Nuc. Acids Res. 32(Database Issue):D109-D111.

Grimm et al. (2006) "Fatality in mice due to oversaturation of cellular microRNA/short hairpin RNA pathways," Nature. 441:537-541.

Herdewijn (2000) "Heterocyclic modifications of oligonucleotides and antisense technology," Antisense Nucleic Acid Drug Dev. 10(4):297-310.

Heydarian et al. (2009) "Novel splice variants of sFlt1 are upregulated in preeclampsia," Placenta. 30:250-255.

Heyer et al. (Dec. 12, 2014) "An optimized kit-free method for making strand-specific deep sequencing libraries from RNA fragments," Nucleic Acids Res. 43(1):e2. pp. 1-14.

Hutvagner et al. (2002) "A microRNA in a multiple-turnover RNAi enzyme complex," Science. 297 (5589):2056-2060.

Jackson et al. (2006) "Position-specific chemical modification of siRNAs reduces 'off-target' transcript silencing," RNA. 12:1197-1205.

Jackson et al. (2010) "Recognizing and avoiding siRNA off-target effects for target identification and therapeutic application," Nature Reviews in Drug Discovery. 9:57-67.

Jacque et al. (2002) "Modulation of HIV-1 replication by RNA interference," Nature. 418:435-438.

Judge et al. (2006) "Design of Noninflammatory Synthetic siRNA Mediating Potent Gene Silencing in Vivo," Molecular Therapy. 13:494-505.

Karlin et al. (1990) "Methods for assessing the statistical significance of molecular sequence features by using general scoring schemes," Proc. Natl. Acad. Sci. USA. 87:2264-2268.

Karlin et al. (1993) "Applications and statistics for multiple high-scoring segments in molecular sequences," Proc. Natl. Acad. Sci. USA 90:5873-5877.

Kenski et al. (2012) "siRNA-optimized Modifications for Enhanced In Vivo Activity," Mol. Ther. Nucleic Acids. 1:e5. pp. 1-8.

Khvorova et al. (2003) "Functional siRNAs and miRNAs Exhibit Strand Bias," Cell. 115:209-216.

Khvorova et al. (Mar. 15, 2016) "Abstract IA27: Advances in oligonucleotide chemistry for the treatment of neurodegenerative disorders and brain tumors," Cancer Res. 76(6) Abstract No. IA27.

Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.

Alvarez-Erviti, et al., "Delivery of siRNA To The Mouse Brain By Systemic Injection Of Targeted Exosomes", Nature Biotechnology, vol. 29, No. 4, pp. 341-345, Apr. 2011.

Alves, et al., Selectivity, Cooperativity, and Reciprocity in the Interactions between the δ-Opioid Receptor, Its Ligands, and G-proteins, Journal of Biological Chemistry, vol. 279 No. 43, pp. 4673-44682, Aug. 17, 2004.

Amarzguioui, et al., "Tolerance for Mutations And Chemical Modifications in a SIRNA", Nucleic Acids Research, Jan. 15, 2003, 31(2): 589-595.

Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).

Ambros, et al., MicroRNAs and Other Tiny Endogenous RNAs in C. elegans, Current Biology, vol. 13, Issue 10, pp. 807-818, May 13, 2003.

Atwell, et al., Stable Heterodimers From Remodeling The Domain Interface Of A Homodimer Using A Phage Display Library, Journal Of Molecular Biology, vol. 270, Issue 1, pp. 26-35, Jul. 4, 1997.

Aubuchon, et al., "Preeclampsia: Animal Models for a Human Cure", Proceedings of the National Academy of Sciences, vol. 108, No. 4, pp. 1197-1198, Jan. 25, 2011.

Aureli, et al., GM1 Ganglioside: Past Studies and Future Potential, Molecular Neurobiology, vol. 53, Issue 3, pp. 1824-1842, Apr. 2016.

Avino, et al., Branched Rna: A New Architecture for RNA Interference, Journal of Nucleic Acids, Article IC586935, 7 pages, Mar. 6, 2011.

Bartlett, et al., Can Metastatic Colorectal Cancer Be Cured?, Journal Oncology, Cancer Network, vol. 26, No. 3, pp. 266-275, Mar. 15, 2012.

Bell, et al., Liposomal Transfection Efficiency And Toxicity On Glioma Cell Lines: In Vitro And In Vitro Studies, Neuroreport, vol. 9, Issue 5, pp. 793-798, Mar. 30, 1998.

Boutla et al., "Short 5'-phosphorylated double-stranded RNAs induce RNA interference in *Drosophila*", Biology, 2001, 11: 1776-1780.

Burke, et al., "Spiral Arterial Remodeling Is Not Essential for Normal Blood Pressure Regulation in Pregnant Mice", Hypertension, vol. 55, No. 3, pp. 729-737, Jan. 25, 2010.

Carter, "Handbook of Parvoviruses", ed., P. Tijsser, CRC Press, pp. 155-168, 1990.

Chang, et al., Enhanced intracellular delivery and multi-target gene silencing triggered by tripodal RNA Structure, The journal of gene Medicine, vol. 14, No. 2, pp. 138-146, Feb. 2012.

Chang, et al., Transgenic Animal Models For Study of The Pathogenesis Of Huntington's Disease And Therapy, Drug design, development and therapy, vol. 9, pp. 2179-2188, Apr. 2015.

Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993.

Chen et al., "Thermoresponsive polypeptides from pegylated poly-L-glutamates", Biomacromolecules 2011, 12: 2859-2863.

(56) References Cited

OTHER PUBLICATIONS

Chen, et al., "Gene Therapy For Brain Tumors: Regression Of Experimental Gliomas By Adenovirus-Mediated Gene Transfer In Vivo", Proceedings of the National Academy of Sciences, vol. 91, No. 8, pp. 3054-3057, 1994.
Chen, et al., For Brain Tumors: Regression Of Experimental Gliomas By Adenovirus-Mediated Gene Transfer In Vivo, Proceedings of the National Academy of Sciences, vol. 91, No. 8, pp. 3054-3057, Apr. 12, 1994.
Cheng, et al., Enhanced Hepatic Uptake and Bioactivity of Type α1(I) Collagen Gene Promoter-Specific Triplex-Forming Oligonucleotides after Conjugation with Cholesterol, Journal of Pharmacology and Experimental Therapeutics, vol. 370, Issue 2, pp. 797-805, Aug. 1, 2019.
Cheung, et al., Effects of All-Trans-Retinoic Acid on Human SH-SYSY Neuroblastoma as in Vitro Model in Neurotoxicity Research, Neurotoxicology, vol. 30, No. 1, pp. 127-135, Jan. 1, 2009.
Chung et al., "Reducible siRNA Dimeric Conjugates for Efficient Cellular Uptake and Gene Silencing", Bioconjugate Chem., 2011, 22(2): 299-306.
Coles, et al., A High-Throughput Method for Direct Detection of Therapeutic Oligonucleotide-Induced Gene Silencing In Vivo, Nucleic Acid Therapeutics, vol. 26, Issue 2, pp. 86-92, Apr. 11, 2016.
Cui, et al., "Role of Corin in Trophoblast Invasion and Uterine Spiral Artery Remodelling in Pregnancy", Nature, vol. 484, No. 7393, pp. 246-250, Mar. 21, 2012.
Damha et al. (1990) "An improved procedure for derivatization of controlled-pore glass beads for solid-phase oligonucleotide synthesis," Nucleic Acids Research, 18(13):3813-3821.
Dass, Crispin R., Cytotoxicity Issues Pertinent To Lipoplex-Mediated Gene Therapy In-Vivo, Journal of Pharmacy and Pharmacology, vol. 54, Issue 5, pp. 593-601, Feb. 18, 2010.
Davidson, et al., A Model System For In Vivo Gene Transfer Into The Central Nervous System Using An Adenoviral Vector, Nature Genetics, vol. 3, No. 3, pp. 219-223, Mar. 1, 1993.
Davidson, et al., Recombinant Adeno-Associated Virus Type 2, 4, and 5 Vectors: Transduction of Variant Cell Types And Regions In The Mammalian Central Nervous System, Proceedings of the National Academy of Sciences, vol. 97, No. 7, pp. 3428-3432, Mar. 28, 2000.
De Fougerolles, et al., "Interfering With Disease: a Progress Report on siRNA-based Therapeutics", Nature Reviews Drug Discovery, vol. 6, pp. 443-453, Jun. 2007.
De Marre et al., "Synthesis, characterization, and in vitro biodegradation of poly(ethylene glycol) modified poly[5N-(2-hydroxyethyl-L-glutamine]", J Bioact Compat Polym, 1996, 11: 85-99.
Dinusha, Differnce Between Sterol and Steroid, Home / Health / Medicine / Nutrients & Drugs, Aug. 4, 2011.
Dohmen et al., "Defined Folate-PEG-siRNA Conjugates for Receptor-specific Gene Slicing", Molecular Therapy-Nucleic Acids, 2012, 1(1): e7.
Dufour, et al., Intrajugular Vein Delivery of AAV9-RNAi Prevents Neuropathological Changes and Weight Loss in Huntington's Disease Mice, Molecular Therapy, vol. 22, No. 4, pp. 797-810, Jan. 6, 2014.
Dyall, et al., Long-chain omega-3 fatty acids and the brain: a review of the independent and shared effects of EPA, DPA and DHA, Frontiers in Aging Neuroscience, vol. 7, p. 52, Apr. 21, 2015.
Egusquiaguirre, et al., "Nanoparticle Delivery Systems For Cancer Therapy: Advances In Clinical And Preclinical Research", Clinical and Translational Oncology, vol. 14, pp. 83-93, 2012.
El Andaloussi, et al., "Exosome-Mediated Delivery of siRNA In Vitro And In Vivo", Nature Protocols, vol. 7, No. 12, pp. 2112-2126, Nov. 15, 2012.
El Andaloussi, et al., "Exosomes For Targeted siRNA Delivery Across Biological Barriers", Advanced Drug Delivery Reviews, vol. 65, pp. 391-397, 2013.
El Andaloussi, et al., "Extracellular Vesicles: Biology And Emerging Therapeutic Opportunities", Nature Reviews Drug Discovery, vol. 12, pp. 347-357, May 2013.
EMBL Database, WO 2005116204-A/113070: Double Strand Polynucleotides Generating RNA Interference, EBI Accession No. EM PAT:FW706544, XP055753619, , Apr. 18, 2011.
Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.
Eremina, et al., "VEGF Inhibition and Renal Thrombotic Microangiopathy", New England Journal of Medicine, vol. 358, No. 11, pp. 1129-1136, Mar. 13, 2008.
Evers, et al., Antisense Oligonucleotides In Therapy For Neurodegenerative Disorders, Advanced Drug Delivery Reviews, vol. 87, pp. 90-103, Jun. 29, 2015.
Extended European Search Report for European Patent Application No. 17745083.0 , dated on Jul. 31, 2019.
Extended European Search Report for European Patent Application No. 17840367.1, dated Oct. 14, 2020.
Extended European Search Report for European Patent Application No. 20164108.1, dated on Dec. 3, 2020.
Extended European Search Report Received for EP Patent Application No. 18819571.3, dated May 14, 2021.
Fattal, et al., Biodegradable Polyalkylcyanoacrylate Nanoparticles For The Delivery Of Oligonucleotides, Journal of Controlled Release, vol. 53, pp. 137-143, May 1998.
Figueroa, et al., Neurorestorative Targets of Dietary Long-Chain Omega-3 Fatty Acids in Neurological Injury, Molecular Neurobiology, vol. 50, Issue 1, pp. 197-213, Aug. 2014.
Fisher, et al., Transduction With Recombinant Adeno-Associated Virus For Gene Therapy Is Limited By Leading-Strand Synthesis, Journal of virology, vol. 70, No. 1, pp. 520-532, Jan. 1996.
Franich, et al., AAV Vector-Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.
Frigg et al., Relationships between vitamin A and vitamin E in the chick, Int J Vitam Nutr Res., 1984, 54(2-3): 125-133—Abstract only in U.S. Appl. No. 16/322,212; full document has been ordered from external library.
Frigg et al., Relationships between vitamin A and vitamin E in the chick, Int J Vitam Nutr Res., 1984, 54(2-3): 125-133.
Furuhashi et al., Expression of Low Density Lipoprotein Receptor Gene in Hjuman Placenta during Pregnancy, Molecular Endocrinology, 1989, 3: 1252-1256.
Gavrilov et al. (Jun. 2012) "Therapeutic siRNA: principles, challenges, and strategies", Yale Journal of Biology and Medicine, 85:187-200.
Geary, et al., Pharmacokinetics, Biodistribution And Cell Uptake of Antisense Oligonucleotides, Advanced Drug Delivery Reviews, vol. 87, pp. 46-51, Jun. 29, 2015.
GenBank, Mus Musculus Non-Coding RNA, Oocyte_Clustered_Small_RNA6599, Complete Sequence, GenBank Accession No. AB341398.1, May 24, 2008, 1 page.
GenBank, Rattus Norvegicus piRNA piR-182271, Complete Sequence, GenBank Accession No. DQ766949.1, Jul. 12, 2006, 1 Page.
GenBank, Signal Recognition Particle 54 kDa protein 2 [Perkinsus marinus ATCC 50983], NCBI Reference Sequence: XP_002784438.1, Apr. 30, 2010.
Gilany, et al., The Proteome of The Human Neuroblastoma Cell Line SH-SY5Y: An Enlarged Proteome, Biochimica et Biophysica Acta (BBA)—Proteins and Proteomics, vol. 1784, Issues 7-8, pp. 983-985, Jul.-Aug. 2008.
Gilbert, et al., "Hypertension Produced by Reduced Uterine Perfusion in Pregnant Rats Is Associated With Increased Soluble fms-like Tyrosine Kinase-1 Expression", Hypertension, vol. 50, No. 6, pp. 1142-1147, Oct. 8, 2007.
Gille, et al., "Analysis of Biological Effects and Signaling Properties of Flt-1 (VEGFR-1) and KDR (VEGFR-2)", Mechanisms of Signal Transduction, vol. 276, Issue 5, pp. 3222-3230, Feb. 2001.

(56) References Cited

OTHER PUBLICATIONS

Gray, et al., Human Mutant Huntingtin with a Stable Polyglutamine Repeat Can Elicit Progressive and Selective Neuropathogenesis in BACHD Mice, Journal of Neuroscience, vol. 28, Issue 24, pp. 6182-6195, Jun. 11, 2008.

Grimm, et al., Fatality In Mice Due To Oversaturation Of Cellular MicroRNA/short Hairpin RNA Pathways, Nature, vol. 441, No. 7092, pp. 537-541, May 25, 2006.

Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.

Haraszti, et al., "5'-Vinylphosphonate improves tissue accumulation and efficacy of conjugated siRNAs in vivo", Nucleic Acids Research, Jul. 27, 2017, 45(13): 7581-7592.

Hirashima, et al., "Trophoblast Expression of Fms-like Tyrosine Kinase 1 Is Not Required for the Establishment of the Maternal-fetal Interface in the Mouse Placenta", Proceedings of the National Academy of Sciences of the United States of America, vol. 100, No. 26, pp. 15637-15642, Dec. 23, 2003.

Hodgson, et al., A YAC Mouse Model for Huntington's Disease with Full-Length Mutant Huntingtin, Cytoplasmic Toxicity, and Selective Striatal Neurodegeneration, Neuron, vol. 23, Issue 1, pp. 181-192, May 1999.

Hult, et al., Mutant Huntingtin Causes Metabolic Imbalance by Disruption of Hypothalamic Neurocircuits, Cell Metabolism, vol. 13, Issue 4, pp. 428-439, Apr. 6, 2011.

Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.

International Search Report & Written Opinion Received for PCT Application No. PCT/US2019/046013, mailed on Jan. 9, 2020, 18 Pages.

International Search Report and Written Opinion received for PCT Patent Application No. PCT/US2018/038952, mailed on Sep. 24, 2018.

International Search Report and Written Opinion received for PCT Patent Application No. PCT/US2020/045487, mailed on Dec. 31, 2020, 26 Pages.

Iriyama et al., Hypoxia-independent up-regulation of placental HIF-1α gene expression contributes to the pathogenesis of preeclampsia, Hypertension, Jun. 2015, 65(6): 1307-1315, Supplemental Data.

Iriyama et al., Hypoxia-independent up-regulation of placental HIF-1α gene expression contributes to the pathogenesis of preeclampsia, Hypertension, Jun. 2015, 65(6): 1307-1315.

Janssen, et al., Long-Chain Polyunsaturated Fatty Acids (LCPUFA) From Genesis To Senescence: The Influence of LCPUFA On Neural Development, Aging, And Neurodegeneration, Progress in Lipid Research, vol. 53, pp. 1-17, Jan. 2014.

Jebbink et al., "Expression of Placental FLT1 Transcript Variants Relates to Both Gestational Hypertensive Disease and Fetal Growth", Hypertension, Apr. 25, 2011, 58(1): 70-76.

Jin, et al., DARPP-32 to Quantify Intracerebral Hemorrhage-induced Neuronal Death in Basal Ganglia, Translational Stroke Research, vol. 4, No. 1, pp. 130-134, Feb. 1, 2013.

Jo, et al., Selection and Optimization of Asymmetric siRNA Targeting the Human c-MET Gene, Molecules and cells, vol. 32, No. 6, pp. 543-548, Dec. 31, 2011.

Kamba, et al., "VEGF-dependent Plasticity of Fenestrated Capillaries in the Normal Adult Microvasculature", American Journal of Physiology—Heart and Circulatory Physiology, vol. 29, pp. H560-H576, Feb. 1, 2006.

Karra, et al., Transfection Techniques for Neuronal Cells, Journal of Neuroscience, vol. 30, No. 18, pp. 6171-6177, May 5, 2010.

Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.

Kordasiewicz, et al., Sustained Therapeutic Reversal of Huntington's Disease by Transient Repression of Huntingtin Synthesis, Neuron, vol. 74, Issue 6, pp. 1031-1044, Jun. 21, 2012.

Kubo et al., "Lipid-Conjugated 27-Nucleotide Double-Stranded RNAs with Dicer-Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).

Kubo et al., "Palmitic Acid-Conjugated 21-Nucleotide siRNA Enhances Gene-Silencing Activity", Molecular Pharmaceutics, vol. 8, No. 6, pp. 2193-2203, DOI: 10.1021/mp200250f. (Oct. 10, 2011).

Kumar, et al., "Shielding of Lipid Nanoparticles for siRNA Delivery: Impact on Physicochemical Properties", Cytokine Induction, and Efficacy, Molecular Therapy-Nucleic Acids, vol. 3, e210, pp. 1-7, Nov. 18, 2014.

Lagos-Quintana, et al., Identification of Tissue-Specific MicroRNAs from Mouse, Current Biology, vol. 12, Issue 9, pp. 735-739, Apr. 30, 2002.

Lagos-Quintana, et al., New microRNAs From Mouse And Human, RNA, vol. 9, No. 2, pp. 175-179, 2003.

Lam, et al., "A New Type of Synthetic Peptide Library For Identifying Ligand-Binding Activity", Nature, vol. 354, pp. 82-84, Nov. 7, 1991.

Lambert, et al., "Nanoparticulate Systems For The Delivery Of Antisense Oligonucleotides", Advanced Drug Delivery Reviews, vol. 47, pp. 99-112, 2001.

Lan, et al., Neuroactive Steroid Actions at the GABAA Receptor, Hormones and Behavior, vol. 28, Issue 4, pp. 537-544, Dec. 1994.

Landis, et al., "A Call for Transparent Reporting to Optimize the Predictive Value of Preclinical Research", Nature, vol. 490, pp. 187-191, Oct. 10, 2012.

Lau, et al., Characterization of the piRNA Complex from Rat Testes, Science, vol. 313, Issue 5785, pp. 363-367, Jul. 21, 2006.

Laufer, et al., "Selected Strategies for the Delivery of siRNA In Vitro and In Vivo", RNA Technologies and Their Applications, 2010, pp. 29-58.

Lee, et al., "Recent Developments In Nanoparticle-Based siRNA Delivery For Cancer Therapy", BioMed Research International, vol. 2013, Article ID 782041, 10 Pages, Jun. 2013.

Lee, et al., RNA Interference-Mediated Simultaneous Silencing of Four Genes Using Cross-Shaped RNA, Molecules and Cells, vol. 35, No. 4, pp. 320-326, Apr. 4, 2013.

Lee, et al., Small-interfering RNA (siRNA)-based functional micro- and nanostructures for efficient and selective gene silencing, Accounts of Chemical Research, vol. 45, No. 7, pp. 1014-1025, Jul. 17, 2012.

Levine, et al., "Circulating Angiogenic Factors and the Risk of Preeclampsia", The New England Journal of Medicine, vol. 350, pp. 672-683, 2004.

Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.

Li, et al., Distribution of 5-Hydroxymethylcytosine in Different Human Tissues, "SAGE—Hindawi Access to Research, Journal of Nucleic Acids, vol. 2011", pp. 1-7, 2011.

Li, et al., Huntington's Disease Gene (IT15) Is Widely Expressed In Human And Rat Tissues, Neuron, vol. 11, No. 5, pp. 985-993, Nov. 1993.

Lopes, et al., Comparison Between Proliferative And Neuron-Like SH-SY5Y Cells As An In Vitro Model For Parkinson Disease Studies, Brain Research, vol. 1337, pp. 85-94, Jun. 14, 2010.

Lundh, et al., Hypothalamic Expression Of Mutant Huntingtin Contributes To The Development Of Depressive-Like Behavior In The Bac Transgenic Mouse Model Of Huntington's Disease, Human Molecular Genetics, vol. 22, Issue 17, pp. 3485-3497, Sep. 1, 2013.

Makris, et al., "Uteroplacental Ischemia Results in Proteinuric Hypertension and Elevated sFLT-1", Kidney International, vol. 71, Issue 1, pp. 977-984, May 2, 2007.

Maltepe, et al., "The Placenta: Transcriptional, Epigenetic, and Physiological Integration During Development", The Journal of Clinical Investigation, vol. 120, No. 4, pp. 1016-1025, Apr. 1, 2010.

(56) References Cited

OTHER PUBLICATIONS

Mangiarini, et al., Exon 1 of the HD Gene with an Expanded CAG Repeat Is Sufficient to Cause a Progressive Neurological Phenotype in Transgenic Mice, Cell, vol. 87, Issue 3, pp. 493-506, Nov. 1, 1996.

Mantha, et al., Rnai-Based Therapies For Huntington's Disease: Delivery Challenges And Opportunities, Therapeutic Delivery, vol. 3, No. 9, pp. 1061-1076, Aug. 29, 2012.

Marcus, et al., FedExosomes: Engineering Therapeutic Biological Nanoparticles that Truly Deliver, Pharmaceuticals, vol. 6, No. 5, pp. 659-680, Apr. 29, 2013.

Marques, et al., A Structural Basis For Discriminating Between Self And Nonself Double-Stranded Rnas In Mammalian Cells, Nature biotechnology, vol. 23, No. 11, pp. 1399-1405, 2005.

Masotti, et al., Comparison of Different Commercially Available Cationic Liposome-DNA Lipoplexes: Parameters Influencing Toxicity And Transfection Efficiency, Colloids and Surfaces B: Biointerfaces, vol. 68, Issue 2, pp. 136-144, Feb. 1, 2009.

Maynard, et al., "Excess Placental Soluble fms-like Tyrosine Kinase 1 (sFlt1) may Contribute to Endothelial Dysfunction", Hypertension, and Proteinuria in Preeclampsia, The Journal of Clinical Investigation, vol. 111, pp. 649-658, 2003.

Mok, et al., Multimeric small interfering ribonucleic acid for highly efficient sequence-specific gene silencing~, Nature Materials, vol. 9, pp. 272-278, Jan. 24, 2010.

Mourelatos, et al., miRNPs: A Novel Class Of Ribonucleoproteins Containing Numerous microRNAs, Genes & Development, vol. 16, No. 6, pp. 720-728, 2002.

Mullen, et al., NeuN, A Neuronal Specific Nuclear Protein In Vertebrates, Development, vol. 116, No. 1, pp. 201-211, 1992.

Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-484, Nov. 1, 2004.

Nelson et al. (1992) "Oligonucleotide labeling methods 3. Direct labeling of oligonucleotides employing a novel, non-nucleosidic, 2-aminobutyl-1 ,3-propanediol backbone," 20(23):6253-6259.

Neufeld, et al., "Similarities and Differences Between the Vascular Endothelial Growth Factor (VEGF) Splice Variants", Cancer and Metastasis Reviews, vol. 15, pp. 153-158, Jun. 1996.

Nishina et al., "Efficient In Vivo Delivery of siRNA to the Liver by Conjugation of α-Tocopherol", Mol Ther., Apr. 2008, 16(4): 734-740.

Ohnishi, et al., "Enhancement of Allele Discrimination by Introduction of Nucleotide Mismatches into siRNA in Allele-Specific Gene Silencing by RNAi", Plos One, vol. 3, Issue 5, e2248, 9 Pages, May 2008.

Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.

Ouimet, et al., DARPP-32, A Dopamine- And Adenosine 3':5'-Monophosphate-Regulated Phosphoprotein Enriched In Dopamine-Innervated Brain Regions. III. Immunocytochemical Localization, Journal of Neuroscience, vol. 4, No. 1, pp. 111-124, Jan. 1, 1984.

Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.

Partial European Search Report for European Patent Application No. 21197881.2, mailed Mar. 14, 2022.

Pei, et al., Quantitative Evaluation of siRNA Delivery in Vivo, RNA, vol. 16, No. 12, pp. 2553-2563, Oct. 12, 2010.

Pfister, et al., "Five siRNAs Targeting Three SNPs in Huntingtin May Provide Therapy for Three-Quarters of Huntington's Disease Patients", Current Biology, vol. 19, No. 9, pp. 774-778., May 12, 2009.

Podbevsek et al., "Solution-state structure of a fully alternately 2'-F/2'-OMe modified 42-nt dimeric siRNA construct", Nucleic Acids Research, vol. 38, No. 20, pp. 7298-7307, DOI: 10.1093/nar/gkq621. (Jul. 12, 2010).

Powe, et al., "Preeclampsia, a Disease of the Maternal Endothelium: the Role of Antiangiogenic Factors and Implications for Later Cardiovascular Disease", Circulation, vol. 123, No. 24, pp. 2856-2869, Jun. 11, 2011.

Rupprecht, et al., Neuroactive Steroids: Mechanisms Of Action And Neuropsychopharmacological Properties, Psychoneuroendocrinology, vol. 28, Issue 2, pp. 139-168, Feb. 2003.

Samuelson, Kristin W., Post-Traumatic Stress Disorder And Declarative Memory Functioning: A Review, Dialogues In Clinical Neuroscience, vol. 13, No. 3, pp. 346-351, Sep. 2011.

Seq Id No. 1112 from U.S. Pat. No. 7790867. [Accessed Nov. 28, 2018, http://seqdata.uspto.gov/.psipsv?pageRequest=viewSequence&DocID=7790867&seqID=1112.].

Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.

Tang, et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.

Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.

Thomas et al. (2007) "Intronic polyadenylation signal sequences and alternate splicing generate human soluble Flt1 variants and regulate the abundance of soluble Flt1 in the placenta," The FASEB Journal, 21(14):3885-3895.

Tischer, et al., "The Human Gene for Vascular Endothelial Growth Factor. Multiple Protein Forms are Encoded Through Alternative Exon Splicing", The Journal of Biological Chemistry, vol. 266, pp. 11947-11954, Jun. 25, 1991.

Turanov et al., "RNAi Modulation of Placental sFLT1 for the Treatment of Preeclampsia", Nature Biotechnology, Nov. 19, 2018, 36: 1164-1173.

Uchida, et al., "An Integrated Approach for the Systematic Identification and Characterization of Heart-enriched Genes With Unknown Functions", BMC Genomics, vol. 10, No. 100, pp. 1-12, Mar. 2009.

Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).

Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.

Vorlová, et al., "Induction of Antagonistic Soluble Decoy Receptor Tyrosine Kinases by Intronic polyA Activation", Molecular Cell, vol. 43, Issue 6, pp. 927-939, Sep. 16, 2011.

Wada et al., "Evaluation of the effects of chemically different linkers on hepatic accumulations, cell tropism and gene silencing ability of cholesterol-conjugated antisense oligonucleotides", Journal Of Controlled Release, Elsevier, vol. 226, pp. 57-65, DOI: 10.1016/J.JCONREL.2016.02.007. (Feb. 5, 2016).

Wang, et al., Nanoparticle-Based Delivery System for Application of siRNA In Vivo, Current Drug Metabolism, vol. 11, No. 2, pp. 182-196, 2010.

Weyer, et al., Developmental And Cell Type-Specific Expression Of The Neuronal Marker NeuN In The Murine Cerebellum, Journal of Neuroscience Research, vol. 73, Issue 3, pp. 400-409, May 23, 2003.

Whitehead, et al., "Knocking Down Barriers: Advances in siRNA Delivery", Nature Reviews Drug Discovery, vol. 8, No. 2, pp. 129-138, Feb. 2009.

Wolfrum et al., "Mechanisms and optimization of in vivo delivery of lipophilic siRNAs", Nature Biotechnology, Oct. 2007, 25(10): 1149-1157.

Wong, et al., Co-Injection of a Targeted, Reversibly Masked Endosomolytic Polymer Dramatically Improves the Efficacy of

(56) References Cited

OTHER PUBLICATIONS

Cholesterol-Conjugated Small Interfering RNAs In Vivo, Nucleic Acid Therapeutics, vol. 22, No. 6, pp. 380-390, Nov. 26, 2012.
Wright, et al., Identification Of Factors That Contribute To Recombinant AAV2 Particle Aggregation And Methods To Prevent Its Occurrence During Vector Purification And Formulation, Molecular Therapy, vol. 12, Issue 1,, pp. 171-178, Jul. 2005.
Yuan, et al., Recent Advances of siRNA Delivery By Nanoparticles, Expert Opinion on Drug Delivery vol. 8, Issue 4, pp. 521-536, 2011.
Zhang, et al., "Birth-weight-for-gestational-age Patterns by Race, Sex, and Parity in the United States Population", Obstetrics & Gynecology, vol. 86, No. 2, pp. 200-208, 1995.
Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zhang, et al., Cyclohexane 1,3-Diones And Their Inhibition Of Mutant SOD1-Dependent Protein Aggregation And Toxicity In PC12 Cells, Bioorganic & Medicinal Chemistry, vol. 20, Issue 2, pp. 1029-1045, Jan. 15, 2012.
Zou, et al., Liposome-Mediated NGF Gene Transfection Following Neuronal Injury: Potential Therapeutic Applications, Gene Therapy, vol. 6, No. 6, pp. 994-1005, Jun. 25, 1999.
Zuccato, et al., Molecular Mechanisms and Potential Therapeutical Targets in Huntington's Disease, Physiological Reviews, vol. 90, No. 3, pp. 905-981, Jul. 1, 2010.
Akinc et al., A Combinatorial Library of Lipid-like Materials for Delivery of RNAi Therapeutics, Nature Biotechnology, vol. 26, No. 5, 20 Pages, May 2008.
Alagia, et al., Exploring PAZ/3'-overhang Interaction to Improve siRNA Specificity. A Combined Experimental and Modeling Study, Chemical Science, vol. 9, No. 8, pp. 2074-2086, 2018.
Alterman et al., "A divalent siRNA chemical scaffold for potent and sustained modulation of gene expression throughout the central nervous system", Nat Biotechnol., Aug. 2019, 37(8): 884-894.
Ämmälä, et al., Targeted Delivery of Antisense Oligonucleotides to Pancreatic β-cells, Science Advances, vol. 4, No. 10, eaat3386, pp. 1-11, Oct. 17, 2018.
Betkekar, et al., A Tandem Enyne/Ring Closing Metathesis Approach to 4-Methylene-2-cyclohexenols: An Efficient Entry to Otteliones and Loloanolides, Organic Letters, Dec. 6, 2011, vol. 14, No. 1, pp. 198-201.
Biscans et al., "Docosanoic acid conjugation to siRNA enables functional and safe delivery to skeletal and cardiac muscles", Molecular Therapy, Apr. 2021, vol. 29, No. 4, pp. 1382-1394.
Biscans et al., "Hydrophobicity of Lipid-Conjugated siRNAs Predicts Productive Loading to Small Extracellular Vesicles", Molecular Therapy, Jun. 2018, vol. 26, No. 6, pp. 1520-1528.
Biscans et al., "The Chemical Structure and Phosphorothioate content of hydrophobically modified siRNAs impact extrahepatic distribution and efficacy", Nucleic Acids Research, 2020, vol. 48, No. 14, pp. 7665-7680.
Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.
Biscans, et al., The Valency of Fatty Acid Conjugates Impacts siRNA Pharmacokinetics, Distribution, and Efficacy in Vivo, Journal of Controlled Release, vol. 302, pp. 116-125, Mar. 2019.
Brown, et al., Effect of Phosphorothioate Modification of Oligodeoxynucleotides on Specific Protein Binding, Journal of Biological Chemistry, vol. 269, No. 43, pp. 26801-26805, 1994.
Chang, et al., Asymmetric Shorter-duplex siRNA Structures Trigger Efficient Gene Silencing With Reduced Nonspecific Effects, Molecular Therapy, vol. 17, Issue 4, pp. 725-732, Apr. 2009.
Chappell, et al., Mechanisms of Palmitic Acid-conjugated Antisense Oligonucleotide Distribution in Mice, Nucleic Acids Research, vol. 48, Issue 8, ,, pp. 4382-4395, May 7, 2020.
Chen et al., "Lipophilic siRNAs mediate efficient gene silencing in oligodendrocytes with direct CNC delivery", Journal Of Controlled Release, Elsevier, vol. 144, pp. 227-232. (Feb. 17, 2010).
Chen et al., Influence of Particle Size on the in Vivo Potency of Lipid Nanoparticle Formulations of siRNA, Journal of Controlled Release, vol. 235, pp. 236-244, Aug. 10, 2016.
Choi et al., Suppression of diacylglycerol acyltransferase-2 (DGAT2), but not DGAT1, with antisense oligonucleotides reverses diet-induced hepatic steatosis and insulin resistance, J Biol Chem., Aug. 3, 2007, 282(31): 22678-22688.
Chu, et al., Potent RNAi by Short RNA Triggers, RNA, vol. 14, pp. 1714-1719, 2008.
Collis, "The synthesis of vinylphosphonate-linked RNA", Ph.D. Thesis, University of Nottingham, Feb. 2008.
Crooke, et al., Cellular Uptake and Trafficking of Antisense Oligonucleotides, Nature Biotechnology, vol. 35, No. 3, pp. 230-237, Mar. 2017.
Crooke, et al., Phosphorothioate Modified Oligonucleotide-Protein Interactions, Nucleic Acids Research, May 1, 2020, 48(10): 5235-5253.
Czauderna, et al., Structural Variations and Stabilising Modifications of Synthetic SiRNAs in Mammalian Cells, Nucleic Acids Research, vol. 31, Issue 11, pp. 2705-2716, Jun. 2003.
Dahlman et al., In Vivo Endothelial siRNA Delivery using Polymeric Nanoparticles with Low Molecular Weight, Nature Nanotechnology, vol. 9, No. 8, 17 Pages, Aug. 2014.
De Paula et al., "Hydrophobization and bioconjugation for enhanced siRNA delivery and targeting", RNA, Feb. 28, 2007, vol. 13, No. 4, pp. 431-456.
Doddridge et al., Effects of Vinylphosphonate Internucleotide Linkages on the Cleavage Specificity of Exonuclease III and on the Activity of DNA Polymerase I, Biochemistry, Mar. 25, 2003, 42(11): 3239-3246.
Dowdy, Overcoming Cellular Barriers for RNA Therapeutics, Nature Biotechnology, vol. 35, pp. 222-229, Feb. 27, 2017.
Dua et al., "Modified siRNA Structure With a Single Nucleotide Bulge Overcomes Conventional siRNA-mediated Off-target Silencing", Molecular Therapy, Jun. 2011, 16(9): 1676-1687.
Ducruix, et al., Crystallization of Nucleic Acids and Proteins: A Practical Approach, Second Edition, 1999, pp. 201-216.
Echevarría, et al., Evaluating the Impact of Variable Phosphorothioate Content in Tricyclo-DNA Antisense Oligonucleotides in a Duchenne Muscular Dystrophy Mouse Model, Nucleic Acid Therapeutics, vol. 29, No. 3, pp. 148-160, May 30, 2019.
Eckstein, Developments in RNA Chemistry, A Personal View, Biochimie, vol. 84, No. 9, pp. 841-848, Sep. 2002.
Egli, et al., Re-engineering RNA Molecules Into Therapeutic Agents, Accounts of Chemical Research, vol. 52, pp. 1036-1047, 2019.
Elbashir, et al., RNA Interference Is Mediated By 21- and 22-Nucleotide RNAs, Genes & Development, vol. 15, No. 2, pp. 188-200, 2001.
Etzold et al., "The extension of the sugar chain of thymidine: a new route to 5'-deoxyhexose nucleosides", Chemical Communications (London), 1968, Issue 7.
Extended European Search Report for European Patent Application No. 19847586.5, dated Jun. 21, 2023.
Extended European Search Report for European Patent Application No. 19852320.1, dated May 2, 2022.
Extended European Search Report for European Patent Application No. 20741865.8, dated Apr. 26, 2023.
Extended European Search Report for European Patent Application No. 21197881.2, dated Oct. 31, 2022.
Fitzgerald, et al., A Highly Durable RNAi Therapeutic Inhibitor of PCSK9, New England Journal of Medicine, vol. 376, No. 1, pp. 41-51, Jan. 5, 2017.
Foster et al., "Advanced siRNA Designs Further Improve In Vivo Performance of GalNAc-siRNA Conjugates", Molecular Therapy, vol. 26, No. 3, pp. 709-717, Mar. 2018.
Frank et al., Structural Basis for 5'-Nucleotide Base-specific Recognition of Guide RNA by Human AGO2, Nature, vol. 465, pp. 818-822, Jun. 2010.
Gaus, et al., Characterization of the Interactions of Chemically-modified Therapeutic Nucleic Acids With Plasma Proteins Using a Fluorescence Polarization Assay, Nucleic Acids Research, vol. 47, No. 3, pp. 1110-1122, 2019.

(56) References Cited

OTHER PUBLICATIONS

Geary, Antisense Oligonucleotide Pharmacokinetics and Metabolism, Expert Opinion on Drug Metabolism & Toxicology, vol. 5, pp. 381-391, Apr. 1, 2009.

Ghidini et al., "An RNA modification with remarkable resistance to RNase A", Chemical Communicaitons, Aug. 8, 2013, 49(79): 9036-9038.

Godinho et al., Pharmacokinetic Profiling of Conjugated Therapeutic Oligonucleotides: A High-Throughput Method based upon Serial Blood Microsampling Coupled to Peptide Nucleic Acid Hybridization Assay, Nucleic Acid Therapeutics, vol. 27, pp. 323-334, Dec. 1, 2017.

Goodson et al., Dental Applications, Medical Applications of Controlled Release, vol. 2, pp. 115-138, 1984.

Grimm, D, Asymmetry in siRNA Design, Gene Therapy, vol. 16, No. 7, pp. 827-829, Apr. 30, 2009.

Gvozdeva et al., "Noncanonical Synthetic RNAi Inducers InL RNA Interference", InTech, Apr. 6, 2016.

Haly et al., "An extended phosphate linkage: Synthesis, hybridization and modeling studies of modified oligonucleotides", Nucleosides and Nucleotides, 1996, 15(7-8): 1383-1395.

Hammerling et al., Monoclonal Antibodies and T-Cell Hybridomas, Research Monographs in Immunology, vol. 3, pp. 563-681, 1981.

Hanu et al., "-CH2-lengthening of the internucleotide linkage in the ApA dimer can improve its conformational compatibility with its natural polynucleotide counterpart", Nucleic Acids Research, Dec. 15, 2001, 29(24): 5182-5194.

Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.

Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.

Hillier et al., yw97a12.r1 Soares_placenta_8to9weeks_2NbHP8to9W Homo sapiens cDNA clone Image:260158 5' similar to gb:X51602_cds1 Vascular Endothelial Growth Factor Receptor 1 (Human);contains element OFR repetitive element, mRNA sequence, NIH, Genbank Accession No. N47911.1, Feb. 14, 1996.

Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.

Huang, Preclinical and Clinical Advances of GalNAc-Decorated Nucleic Acid Therapeutics, Molecular Therapy—Nucleic Acids, vol. 6,, pp. 116-132, Mar. 17, 2017.

International Preliminary Report on Patentability for PCT International Patent Application No. PCT/US2019/046013, mailed Apr. 28, 2020.

International Preliminary Report on Patentability for PCT Patent Application No. PCT/US2020/025017, mailed Sep. 28, 2021.

International Preliminary Report on Patentability for PCT Patent Application No. PCT/US2021/034290, mailed Nov. 17, 2022.

International Search Report & Written Opinion Received for PCT Application No. PCT/US2020/014181, mailed on Jun. 2, 2020.

International Search Report and Written Opinion for PCT International Patent Application No. PCT/US2019/048027 mailed Nov. 15, 2019.

International Search Report and Written Opinion for PCT International Patent Application No. PCT/US2020/025017, mailed Sep. 18, 2020.

International Search Report and Written Opinion for PCT International Patent Application No. PCT/US2020/047492, mailed Feb. 17, 2022.

International Search Report and Written Opinion in related PCT Application No. PCT/US2020/014146, mailed May 22, 2020.

International Search Report and Written Opinion in related PCT Application No. PCT/US2021/024425, mailed Oct. 15, 2021.

International Search Report and Written Opinion received for PCT Patent Application No. PCT/US2021/013620, mailed on Apr. 26, 2021.

International Search Report and Written Opinion received for PCT Patent Application No. PCT/US2021/034290, mailed on Nov. 4, 2021.

International Search Report and Written Opinion received for PCT Patent Application No. PCT/US2021/041946, mailed on Oct. 29, 2021.

International Search Report and Written Opinion received for PCT Patent Application No. PCT/US2021/060356, mailed on Apr. 13, 2022.

Iversen et al., "Optimized siRNA-PEG Conjugates for Extended Blood Circulation and Reduced Urine Excretion in Mice", Feb. 25, 2013, Theranostics 2013, vol. 3, Issue 3, pp. 201-209.

Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.

Kachare et al., "Phospho-carboxylic anhydride of a homologated nucleoside leads to primer degradation in the presence of a polymerase", Bioorg Med Chem Letters, Jun. 15, 2014, 24(12): 2720-2723.

Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.

Kaura, et al., Synthesis, Hybridization Characteristics, and Fluorescence Properties of Oligonucleotides Modified with Nucleobase-Functionalized Locked Nucleic Acid Adenosine and Cytidine Monomers, The Journal of Organic Chemistry, Jun. 16, 2014, 79: 6256-6268.

Khan et al., Silencing Myostatin using Cholesterol-Conjugated siRNAs Induces Muscle Growth, Molecular Therapy, Nucleic Acids, vol. 5, 9 Pages, Jan. 1, 2016.

Khvorova, Oligonucleotide Therapeutics—A New Class of Cholesterol-Lowering Drugs, The New England Journal of Medicine, vol. 376, No. 1, pp. 4-7, Jan. 5, 2017.

Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.

Kim et al., "PEG conjugated VEGF siRNA for anti-angiogenic gene therapy", Journal of Controlled Release, Jun. 3, 2006, vol. 116, No. 2, pp. 123-129.

Kofoed et al., "Oligodeoxynucleotides with Extended 3'- and 5'-Homologous Internucleotide Linkages", Acta Chemica Scandanavia, 1997, 51: 318-324.

Kubo, et al., Modified 27-nt dsRNAs With Dramatically Enhanced Stability in Serum and Long-term RNAi Activity, Oligonucleotides, vol. 17, No. 4, pp. 445-464, 2007.

Lebedeva et al., "Phosphorothioate oligodeoxynucleotides as inhibitors of gene expression: antisense and non-antisense effects", Applications of Antisense therapies to restenosis, 1999, p. 101.

Lee et al., "Current preclinical small interfering RNA (siRNA)-based conjugate systems for RNA therapeutics", Advanced Drug Delivery Reviews, Oct. 27, 2015, vol. 104, pp. 78-92.

Liang, et al., Identification and Characterization of Intracellular Proteins That Bind Oligonucleotides With Phosphorothioate Linkages, Nucleic Acids Research, vol. 43, Issue 5, pp. 2927-2945, Mar. 11, 2015.

Liu et al., Snapshot PK: A Rapid Rodent in Vivo Preclinical Screening Approach, Drug Discovery Today, vol. 13, No. 7-8, pp. 360-367, Apr. 1, 2008.

Loy et al., "Allele-Specific Gene Silencing in Two Mouse Models of Autosomal Dominant Skeletal Myopathy", PLoS One, Nov. 2012, 7(11): e49757, 11 pages.

Ly et al., Visualization of Self-Delivering Hydrophobically Modified siRNA Cellular Internalization, Nucleic Acids Research, vol. 45, pp. 15-25, Nov. 29, 2016.

Ma et al., Structural Basis For 5'-End-Specific Recognition Of Guide RNA By The A. Fulgidus Piwi Protein, Nature, vol. 434, No. 7033, pp. 666-670, Mar. 31, 2005.

Ma, et al., Structural Basis For Overhang-Specific Small Interfering RNA Recognition By The PAZ Domain, Nature, vol. 429, No. 6989, pp. 318-322, May 20, 2004.

(56) References Cited

OTHER PUBLICATIONS

Magner et al., "Influence of mismatched and bulged nucleotides on SNP-preferential RNase H cleavage of RNA-antisense gapmer heteroduplexes", Scientific Reports, Oct. 2017, 7(12532), 16 pages.

Matsuda et al., siRNA Conjugates Carrying Sequentially Assembled Trivalent N-Acetylgalactosamine Linked Through Nucleosides Elicit Robust Gene Silencing In Vivo in Hepatocytes, ACS Chemical Biology, vol. 10, No. 5, pp. 1181-1187, Mar. 2, 2015.

Mazur et al., "Isosteres of natural phosphates. 11. Synthesis of a phosphonic acid analogue of an oligonucleotide", Tetrahedron, 1984, 40(20): 3949-3956.

Mikhailov et al., "Use of 5-deoxy-ribo-hexofuranose derivatives for the preparation of 5'-nucleotide phosphonates and homoribonucleosides", Collect Czech Chem Commun., 1989, 54(4): 1055-1066.

Miller, et al., Receptor-mediated Uptake of Phosphorothioate Antisense Oligonucleotides in Different Cell Types of the Liver, Nucleic Acid Therapeutics, vol. 28, No. 3, pp. 119-127, 2018.

Monteys et al., "Artificial miRNAs Targeting Mutant Huntingtin Show Preferential Silencing In Vitro and In Vivo", Molecular Therapy, Nucleic Acids, 2015, 4: E234, 11 pages.

Nair, et al., Impact of Enhanced Metabolic Stability on Pharmacokinetics and Pharmacodynamics of GalNAc-siRNA Conjugates, Nucleic Acids Research, vol. 45, Issue 19, pp. 10969-10977, Nov. 2, 2017.

Nallagatla et al., Nucleoside Modifications Modulate Activation of the Protein Kinase PKR in an RNA Structure-Specific Manner, RNA, vol. 14, pp. 1201-1213, Jun. 1, 2008.

Namjou et al., "GWAS and enrichment analyses of non-alcoholic fatty liver disease identify new trait-associated genes and pathways across eMERGE Network", BMC Medicine, Jul. 2019, 17: 135, 19 pages.

Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.

Noguchi et al., "Allele-specific Gene Silencing of Mutant mRNA Restores Cellular Function in Ullrich Congenital Muscular Dystrophy Fibroblasts", Molecular Therapy-Nucleic Acids, Jun. 2014, 3: e171.

Oberbauer et al., Renal Uptake of an 18-mer Phosphorothioate Oligonucleotide, Kidney International, vol. 48, pp. 1226-1232, 1995.

Ohtsuka et al., "Joining of synthetic ribotrinucleotides with defined catalyzed by T4 RNA ligase", European Journal of Biochemistry, 1977, 81(2): 285-291.

Osborn et al., Hydrophobicity Drives the Systemic Distribution of Lipid-Conjugated SiRNAs Via Lipid Transport Pathways, Nucleic Acids Research, vol. 47, No. 3, pp. 1070-1081, Dec. 8, 2018.

Osborn, et al., "Improving siRNA Delivery In Vivo Through Lipid Conjugation", Nucleic Acid Therapeutics, vol. 28, No. 3, pp. 128-136, May 10, 2018.

Padiukova et al., "Synthesis of 5'-derivatives of thymidine", Bioorg Khim., 1990, 16(5): 668-673 [Article in Russian—no abstract available].

Parmar, et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.

Partial Supplementary European Search Report for European Patent Application No. 20741865.8, mailed Dec. 20, 2022.

Partial Supplementary European Search Report for European Patent Application No. 20777915.8, mailed Apr. 5, 2023.

Pokholenko et al., Lipid Oligonucleotide Conjugates as Responsive Nanomaterials for Drug Delivery, Journal of Materials Chemistry B, vol. 1, 6 Pages, 2013.

Posocco, et al., "Impact of siRNA Overhangs for Dendrimer-mediated siRNA Delivery and Gene Silencing", Molecular Pharmaceutics, Aug. 5, 2013, 10(8): 3262-3273.

Prakash et al., Targeted Delivery Of Antisense Oligonucleotides To Hepatocytes Using Triantennary N-Acetyl Galactosamine Improves Potency 10-Fold In Mice, Nucleic Acids Research, vol. 42, Issue 13, pp. 8796-8807, Jul. 29, 2014.

Prakash, et al., Identification of Metabolically Stable 5'-Phosphate Analogs That Support Single-Stranded siRNA Activity, Nucleic Acids Research, Mar. 9, 2015, 43(6): 2993-3011.

PubChem Detabase, CID-16131506, Compund Summary: dGTGGGTGGGT, Jul. 3, 2007, Retrieved from url: https://pubchem.ncbi.nlm.nih.gov/compound/16131506.

Raal, et al., Inclisiran for the Treatment of Heterozygous Familial Hypercholesterolemia, New England Journal of Medicine, vol. 382, No. 16, pp. 1520-1530, Apr. 16, 2020.

Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.

Reed et al., Forty Mouse Strain Survey of Body Composition, Physiology & Behavior, vol. 91, No. 5, 15 Pages, Aug. 15, 2007.

Reynolds, A, et al., Rational siRNA Design for RNA Interference, Nature Biotechnology, vol. 22, No. 3, pp. 326-330, Apr. 2004.

Roy et al., "Synthesis of DNA/RNA and Their Analogs via Phosphoramidite and H-Phosphonate Chemistries", Molecules, 2013, 18(11): 14268-14284.

Rozners et al., "Synthesis and Properties of RNA Analogues Having Amides as Interuridine Linkages at Selected Positions", JACS Articles, Sep. 6, 2003, 125: 12125-12136.

Sah, et al., Oligonucleotide Therapeutic Approaches for Huntington disease, The Journal of Clinical Investigation, vol. 121, No. 2, pp. 500-507, Feb. 1, 2011.

Sarett et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.

Scherman et al., Genetic Pharmacology: Progresses in siRNA Delivery and Therapeutic Applications, Gene Therapy, vol. 24, pp. 151-156, Mar. 2017.

Schlegal et al., "Chirality Dependent Potency Enhancement and Structural Impact of Glycol Nucleic Acid Modification on siRNA", JACS, Jun. 1, 2017, pp. 1-28.

Schoch, et al., Antisense Oligonucleotides: Translation From Mouse Models to Human Neurodegenerative Diseases, Neuron, vol. 94, Issue 6, pp. 1056-1070, Jun. 21, 2017.

Schwarz et al., "Designing siRNA that distinguish between genes that differ by a single nucleotide", PLOS Genetics, Sep. 2006, 2(9): e140.

Setten, et al., The Current State and Future Directions of RNAi-based Therapeutics, Nature Reviews Drug Discovery, vol. 18, pp. 421-446, Mar. 7, 2019.

Shen, et al., 2'-fluoro-modified Phosphorothioate Oligonucleotide Can Cause Rapid Degradation of P54nrb and PSF, Nucleic Acids Research, vol. 43, Issue 9, pp. 4569-4578, May 19, 2015.

Shen, et al., Acute Hepatotoxicity of 2' Fluoro-modified 5-10-5 Gapmer Phosphorothioate Oligonucleotides in Mice Correlates With Intracellular Protein Binding and the Loss of DBHS Proteins, Nucleic Acids Research, vol. 46, Issue 5, pp. 2204-2217, Mar. 16, 2018.

Shen, et al., Chemical Modification of PS-ASO Therapeutics Reduces Cellular Protein-binding and Improves the Therapeutic Index, Nature Biotechnology, vol. 37, pp. 640-650, Apr. 29, 2019.

Shukla et al., "Exploring Chemical Modifications for siRNA Therapeutics: A Structural and Functional Outlook", ChemMedChem, Feb. 19, 2010, 5(3): 328-349.

Sibley et al., "Identification of Allele-Specific RNAi Effectors Targeting Genetic Forms of Parkinson's Disease", PLOS One, Oct. 2011, 6(10): e26194.

Sipova et al., "5'-O-Methylphosphonate nucleic acids—new modified DNAs that increase the *Escherichia coli* RNase H cleavage rate of hybrid duplexes", Nucleic Acids Research, 2014, 42(8): 5378-5389.

Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.

Solano et al., Toxicological and Pharmacokinetic Properties of QPI-1007, a Chemically Modified Synthetic siRNA Targeting Caspase

(56) References Cited

OTHER PUBLICATIONS 2 mRNA, Following Intravitreal Injection, Nucleic Acid Therapeutics, vol. 24, pp. 258-266, Aug. 1, 2014.
Stein, et al., Physicochemical Properties Of Phosphorothioate Oligodeoxynucleotides, Nucleic Acids Research, vol. 16, No. 8, pp. 3209-3221, Apr. 25, 1988.
Sugo et al., "Development of antibody-siRNA conjugate targeted to cardiac and skeletal muscles", Journal of Controlled Release, Jun. 29, 2016, vol. 237, pp. 1-13.
Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.
Sun, et al., Asymmetric RNA Duplexes Mediate RNA Interference in Mammalian Cells, Nature Biotechnology, vol. 26, pp. 1379-1382, Dec. 2008.
Tan et al., "Allele-Specific Targeting of microRNAs to HLA-G and Risk of Asthma", American Journal of Human Genetics, Oct. 2007, 81(4): 829-834.
Taniguchi et al., Plasmodium Berghei ANKA Causes Intestinal Malaria Associated with Dysbiosis, Scientific Reports, vol. 5, pp. 1-12, Oct. 27, 2015.
Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.
Teng et al., "A GDF15 3' UTR variant, rs1054564, results in allele-specific translational repression of GDF15 by hsa-miR-1233-3p", PLoS One, Aug. 2017, 12(8): e0183187, 15 pages.
Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.
Vickers, et al., Development of a Quantitative BRET Affinity Assay for Nucleic Acid-protein Interactions, PloS One, vol. 11, No. 8, p. e0161930, pp. 1-17, Aug. 29, 2016.
Wanke et al., Overgrowth of Skin in Growth Hormone Transgenic Mice Depends on the Presence of Male Gonads, Journal of Investigative Dermatology, vol. 113, pp. 967-971, Dec. 1, 1999.
Whitehead et al., Degradable Lipid Nanoparticles with Predictable in Vivo siRNA Delivery Activity, Nature Communications, vol. 5, pp. 1-10, Jun. 27, 2014.
Wickstrom, Oligodeoxynucleotide Stability in Subcellular Extracts and Culture Media, Journal of Biochemical and Biophysical Methods, vol. 13, Issue 2, pp. 97-102, Sep. 1986.
Yamana, et al., 2'-Pyrene Modified Oligonucleotide Provides a Highly Sensitive Fluorescent Probe of RNA, Nucleic Acids Research, 1999, 27(11): 2387-2392.
Yekta, et al., MicroRNA-Directed Cleavage of HOXB8 mRNA, Science, Apr. 23, 2004, 304(5670): 594-596.
You et al., "Design of LNA probes that improve mismatch discrimination", Nucleic Acids Research, May 2006, 34(8): e60, 11 pages.
Zamore, et al., Ancient Pathways Programmed by Small RNAs, Science, May 17, 2002, 296(5571): 1265-1269.
Zhou et al., Nanoparticle-based Delivery of RNAi Therapeutics: Progress and Challenges, Pharmaceuticals, vol. 6, pp. 85-107, Jan. 2013.
Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.
Zlatev, et al., Reversal of siRNA-mediated Gene Silencing in Vivo, Nature Biotechnology, vol. 36, No. 6, pp. 509-511, 2018.
Bertram et al., "Vinylphosphonate Internucleotide Linkages Inhibit the Activity of PcrA DNA Helicase", Biochemistry, Jun. 18, 2002, 41(24): 7725-7731.
Extended European Search Report for European Patent Application No. 20856904.6, mailed Jan. 2, 2024.
Extended European Search Report for European Patent Application No. 21741867.2, mailed Mar. 12, 2024.

Extended Supplementary European Search Report for European Patent Application No. 20777915.8, mailed Sep. 15, 2023.
Flower et al., MSH3 Modifies Somatic instability and Disease Severity in Huntington's and Myotonic Dystrophy Type 1, Brain, A Journal of Neurology, Jul. 2019, 142(7): 1876-1886.
Ghosh et al., "Comparing 2-nt 3' overhangs against blunt-ended siRNAs: a systems biology based study", BMC Genomics, 2009, 10(Suppl. 1):S17.
Godinho et al., "PK-modifying anchors significantly alter clearance kinetics, tissue distribution, and efficacy of therapeutics siRNAs", Mol Ther Nucleic Acids, Jun. 13, 2022,29: 116-132, ePublished Sep. 13, 2022.
Harlow et al., "Antibodies: A Laboratory Manual", Cold Spring Harbor Laboratory Chapter 14, Second Edition, 2013.
International Search Report & Written Opinion Received for PCT Application No. PCT/US2021/028166, mailed on Nov. 26, 2021.
International Search Report & Written Opinion Received for PCT Application No. PCT/US2021/044158, dated Jan. 31, 2022.
International Search Report & Written Opinion Received for PCT Application No. PCT/US2022/039047, dated Mar. 3, 2023.
Jo et al., "Small Interfering RNA Nunchucks with a Hydrophobic Linker for Efficient Intracellular Delivery", Macromol Biosci., 2014, 14: 195-201.
Khorev et al., Trivalent, Gal//GalNAc-containing ligands designed for the asialoglycoprotein receptor, Bioorgan. & Medicin. Chem., 2008, 16: 5216-5231.
Lee et al., A Novel Approach to Investigate Tissue-specific Trinucleotide Repeat Instability, BMC Systems Biology, Mar. 19, 2010, 4(29): 1-16.
Lee et al., Adeno-associated virus (AAV) vectors: Rational design strategies for capsid engineering, Current Opinion in Biomed. Eng., 2018, 58-63.
Miller et al., Adaptable Synthesis of C-Glycosidic Multivalent Carbohydrates and Succinamide-Linked Derivization, Org. Letter., 2010, 12(22): 5262-5265.
Moss et al., Identification of Genetic Variants Associated with Huntington's Disease Progression: A Genome-wide Association Study, The Lancet, Neurology, Sep. 2017, 16(9): 701-711.
Oishi et al., "Lactosylated Poly(ethylene glycol)-siRNA Conjugate through Acid-Labile B-Thiopropionate Linkage to Construct pH-Sensitive Polyion Complex Micelles Achieving Enhanced Gene Silencing in Hepatoma Cells", J. Am. Chem. Soc., 2005, 127: 1624-1625.
Old et al., "Cloning in Yeast and Microbial Eukaryotes", Principles of Gene Manipulation: An Introduction to Genetic Engineering, Studies in Microbiology, 1989, 2(11): 199-221.
ØStergaard et al., "Conjugation of hydrophobic moieties enhances potency of antisense oligonucleotides in the muscle of rodents and non-human primates", Nucleic Acids Research, 2019, 47(12): 6045-6058.
Partial Supplementary European Search Report for European Patent Application No. 20852443.9, mailed Aug. 25, 2023.
Partial Supplementary European Search Report for European Patent Application No. 20856904.6, mailed Sep. 13, 2023.
Smith et al., "RNA Nanotherapeutics for the Amelioration of Astroglial Reactivity", Mol Ther Nucleic Acids, Mar. 2, 2018, 10: 103-121, ePublished Nov. 24, 2017.
Tai et al., "Current Aspects of siRNA Bioconjugate for In Vitro and In Vivo Delivery", Molecules, Jun. 2019, 24(12): 2211, ePublished Jun. 13, 2019.
Tome et al., MSH3 Polymorphisms and Protein Levels Affect CAG Repeat Instability in Huntington's Disease Mice, PLOS Genetics, Feb. 28, 2013, 9(2): e1003280, 1-16.
Zeng et al., "RNA Interference in human cells is restricted to the cytoplasm", RNA, Jul. 1, 2002, 8(7): 855-860.
Zhou et al., "Functional In Vivo Delivery of Multiplexed Anti-HIV-1 siRNAs via a Chemically Synthesized Aptamer With a Sticky Bridge", Mol Ther., Jan. 2013, 21(1): 192-200.

* cited by examiner

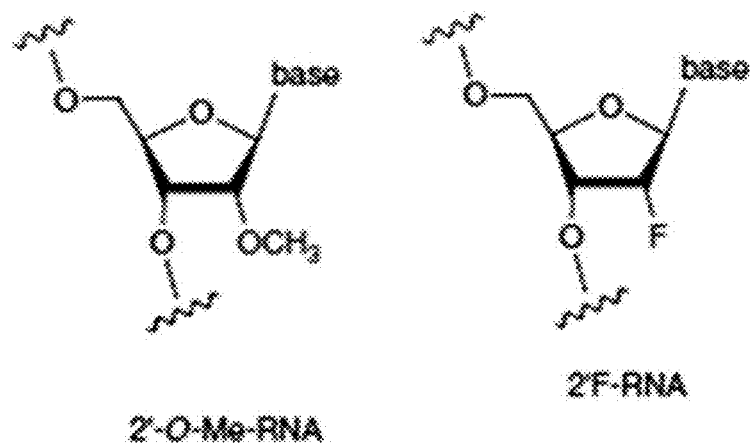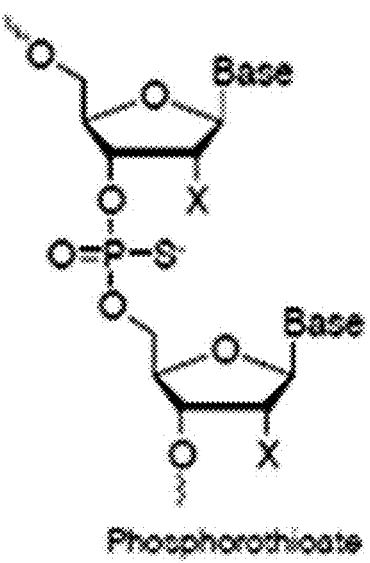
Fig. 2 sFlt1 i13

Exon 13 Intron 13      2283
GAAGAAGAATTACAATCTCA GTGAGCACTGCAACAAAAAGGCTGTTTTCTCTCGGATCTCCAAATTTAAAAGCA 2318
CAAGGAATGATTGTACCACACAAAGTAATGTAAAACATTAAAGGACTCATTAAAAAGTAACAGTTGTCTCATATCAT
CTTGATTTATTGTCACTGTTGCTAACTTTCAGGCTCGGAGGAGATGCTCCTCCCAAAATGAGTTCGGAGATGATAGC
AGTAATAATGAGACCCCCGGGCTCCAGCTCTGGGCCCCCATTCAGGCCGAGGGGGCTGCTCCGGGGGGCCGACTTG
GTGCACGTTTGGATTTGGAGGATCCCTGCACTGCCTTCTCTGTGTTTGTTGCTCTTGCTGTTTTCTCCTGCCTGATA
AACAACAACTTGGGATGATCCTTTCCATTTTGATGCCAACCTCTTTTTATTTTTAAGCGGCGCCCTATAGT sFlt1 i14

Exon 14 Exon e15
ACAACAAAGCCT AACTGTATACATCAACGTCACCATCGTCATCGTCATCATCACCATTGTCATCATCATCATCAT 2519
CGTCATCATCATCATCATCATAGCTATCATCATTATCATCATCATCATCATCATCATCATAGCTACCATTTATTGAA 2585
AACTATTATGTGTCAACTTCAAAGAACTTATCCTTTAGTTGGAGAGCCAAGACAATCATAACAATAACAAATGGCCG
GGCATGGTGGCTCACGCCTGTAATCCCAGCACTTTGGGAGGCCAAGGCAGGTGGATCATTTGAGGTCAGGAGTCCAA
GACCAGCCTGACCAAGATGGTGAAATGCTGTCTCTATTAAAAATACAAAATTAGCCAGGCATGGTGGCTCATGCCTG
TAATGCCAGCTACTCGGAGGCTGAGACAGGAG...

| | hsiRNA | Targeting region | IC50, nM (HeLa) | IC50, nM (CTB) |
|---|---|---|---|---|
| Lead | sFLT1_i13_2283 | CTCTCGGATCTCCAAATTTA | 35.5 | 40 |
| | sFLT1_i14_2519 | CATCATAGCTACCATTTATT | 81 | 58 |
| Backup | sFLT1_i13_2318 | ATTGTACCACACAAAGTAAT | 54 | 130 |
| | sFLT1_i14_2585 | GAGCCAAGACAATCATAACA | 49 | 172 |

*Fig. 3*

| | | Pos | Targeting region (20 mer) | Targeting Region (30 mer) |
|---|---|---|---|---|
| 2 | sFLT1-i13 | 2247 | AAUCAGAGGUGAGCACUGCA | AUUACAAUCAGAGGUGAGCACUGCAACAAA |
| 3 | sFLT1-i13 | 2252 | GAGGUGAGCACUGCAACAAA | AAUCAGAGGUGAGCACUGCAACAAAAGGC |
| 4 | sFLT1-i13 | 2253 | AGGUGAGCACUGCAACAAAA | AUCAGAGGUGAGCACUGCAACAAAAGGCU |
| 5 | sFLT1-i13 | 2256 | UGAGCACUGCAACAAAAAGG | AGAGGUGAGCACUGCAACAAAAGGCUGUU |
| 6 | sFLT1-i13 | 2279 | UUUUCUCUCGGAUCUCCAAA | GGCUGUUUCUCUCGGAUCUCCAAAUUUAA |
| 7 | sFLT1-i13 | 2280 | UUUCUCUCGGAUCUCCAAAU | GCUGUUUCUCUCGGAUCUCCAAAUUUAAA |
| 8 | sFLT1-i14 | 2283 | CUCUCGGAUCUCCAAAUUUA | GUUUCUCUCGGAUCUCCAAAUUUAAAAGC |
| 9 | sFLT1-i13 | 2284 | UCUCGGAUCUCCAAAUUUAA | UUUUCUCUCGGAUCUCCAAAUUUAAAAGCA |
| 10 | sFLT1-i13 | 2286 | UCGGAUCUCCAAAUUUAAAA | UUCUCUCGGAUCUCCAAAUUUAAAAGCACA |
| 11 | sFLT1-i13 | 2293 | UCCAAAUUUAAAAGCACAAG | GGAUCUCCAAAUUUAAAAGCACAAGGAAUG |
| 12 | sFLT1-i13 | 2294 | CCAAAUUUAAAAGCACAAGG | GAUCUCCAAAUUUAAAAGCACAAGGAAUGA |
| 13 | sFLT1-i13 | 2295 | CAAAUUUAAAAGCACAAGGA | AUCUCCAAAUUUAAAAGCACAAGGAAUGAU |
| 14 | sFLT1-i13 | 2304 | AAGCACAAGGAAUGAUUGUA | UUUAAAAGCACAAGGAAUGAUUGUACCACA |
| 15 | sFLT1-i13 | 2313 | GAAUGAUUGUACCACACAAA | ACAAGGAAUGAUUGUACCACACAAAGUAAU |
| 16 | sFLT1-i13 | 2318 | AUUGUACCACACAAAGUAAU | GAAUGAUUGUACCACACAAAGUAAUGUAAA |
| 17 | sFLT1-i13 | 2321 | GUACCACACAAAGUAAUGUA | UGAUUGUACCACACAAAGUAAUGUAAAACA |
| 18 | sFLT1-i13 | 2322 | UACCACACAAAGUAAUGUAA | GAUUGUACCACACAAAGUAAUGUAAAACAU |
| 19 | sFLT1-i13 | 2324 | CCACACAAAGUAAUGUAAAA | UUGUACCACACAAAGUAAUGUAAAACAUUA |
| 20 | sFLT1-i13 | 2326 | ACACAAAGUAAUGUAAAACA | GUACCACACAAAGUAAUGUAAAACAUUAAA |
| 21 | sFLT1-i13 | 2332 | AGUAAUGUAAAACAUUAAAG | CACAAAGUAAUGUAAAACAUUAAAGGACUC |
| 22 | sFLT1-i13 | 2333 | GUAAUGUAAAACAUUAAAGG | ACAAAGUAAUGUAAAACAUUAAAGGACUCA |
| 23 | sFLT1-i13 | 2339 | UAAAACAUUAAAGGACUCAU | UAAUGUAAAACAUUAAAGGACUCAUUAAAA |
| 24 | sFLT1-i13 | 2343 | ACAUUAAAGGACUCAUUAAA | GUAAAACAUUAAAGGACUCAUUAAAAGUA |
| 25 | sFLT1-i13 | 2351 | GGACUCAUUAAAAGUAACA | UUAAAGGACUCAUUAAAAGUAACAGUUGU |
| 26 | sFLT1-i13 | 2353 | ACUCAUUAAAAGUAACAGU | AAAGGACUCAUUAAAAGUAACAGUUGUCU |
| 27 | sFLT1-i13 | 2362 | AAAGUAACAGUUGUCUCAUA | AUUAAAAGUAACAGUUGUCUCAUAUCAUC |
| 28 | | | | |
| 29 | sFLT1-i15a | 2471 | CAUCAUCAUCAUAGCUA | GUCAUCAUCAUCAUCAUAGCUAUCAUC |
| 30 | sFLT1-i15a | 2474 | CAUCAUCAUCAUAGCUAUCA | AUCAUCAUCAUCAUAGCUAUCAUCAUU |
| 31 | sFLT1-i15a | 2477 | CAUCAUCAUCAUAGCUAUCA | AUCAUCAUCAUCAUAGCUAUCAUCAUUAUC |
| 32 | sFLT1-i15a | 2508 | AUCAUCAUCAUCAUCAUAGC | UCAUCAUCAUCAUCAUCAUAGCUACCA |
| 33 | sFLT1-i15a | 2510 | CAUCAUCAUCAUCAUAGCUA | AUCAUCAUCAUCAUCAUAGCUACCAUU |
| 34 | sFLT1-i15a | 2513 | CAUCAUCAUCAUAGCUACCA | AUCAUCAUCAUCAUCAUAGCUACCAUUUAU |
| 35 | sFLT1-i15a | 2516 | UCAUCAUAGCUACCAUUUAU | CAUCAUCAUCAUAGCUACCAUUUAUUGAAA |
| 36 | sFLT1-i15a | 2519 | CAUCAUAGCUACCAUUUAUU | AUCAUCAUCAUAGCUACCAUUUAUUGAAAA |
| 37 | sFLT1-i15a | 2525 | AGCUACCAUUUAUUGAAAC | AUCAUAGCUACCAUUUAUUGAAAACUAUUA |
| 38 | sFLT1-i15a | 2528 | UACCAUUUAUUGAAAACUAU | AUAGCUACCAUUUAUUGAAAACUAUUAUGU |
| 39 | sFLT1-i15a | 2556 | AACUUCAAAGAACUUAUCCU | GUGUCAACUUCAAAGAACUUAUCCUUUAGU |
| 40 | sFLT1-i15a | 2561 | CAAAGAACUUAUCCUUUAGU | AACUUCAAAGAACUUAUCCUUUAGUUGGAG |
| 41 | sFLT1-i15a | 2572 | UCCUUUAGUUGGAGAGCCAA | ACUUAUCCUUUAGUUGGAGAGCCAAGACAA |
| 42 | sFLT1-i15a | 2574 | CUUUAGUUGGAGAGCCAAGA | UUAUCCUUUAGUUGGAGAGCCAAGACAAUC |
| 43 | sFLT1-i15a | 2576 | UUAGUUGGAGAGCCAAGACA | AUCCUUUAGUUGGAGAGCCAAGACAAUCAU |
| 44 | sFLT1-i15a | 2577 | UAGUUGGAGAGCCAAGACAA | UCCUUUAGUUGGAGAGCCAAGACAAUCAUA |
| 45 | sFLT1-i15a | 2580 | UUGGAGAGCCAAGACAAUCA | UUUAGUUGGAGAGCCAAGACAAUCAUACA |
| 46 | sFLT1-i15a | 2582 | GGAGAGCCAAGACAAUCAUA | UAGUUGGAGAGCCAAGACAAUCAUACAAU |
| 47 | sFLT1-i15a | 2585 | GAGCCAAGACAAUCAUAACA | UUGGAGAGCCAAGACAAUCAUAACAAUUAC |
| 48 | sFLT1-i15a | 2588 | CCAAGACAAUCAUAACAAUA | GAGAGCCAAGACAAUCAUAACAAUAACAAA |
| 49 | sFLT1-i15a | 2590 | AAGACAAUCAUAACAAUAAC | GAGCCAAGACAAUCAUAACAAUAACAAAUG |
| 50 | | | | |
| 51 | FLT1 | 301 | AGCUGUCUGCUUCUCACAGG | UGCUCAGCUGUCUGCUUCUCACAGGAUCUA |
| 52 | FLT1 | 376 | GAUCCUGAACUGAGUUUAAA | UAAAAGAUCCUGAACUGAGUUUAAAAGGCA |
| 53 | FLT1 | 377 | AUCCUGAACUGAGUUUAAAA | AAAAGAUCCUGAACUGAGUUUAAAAGGCAC |
| 54 | FLT1 | 381 | UGAACUGAGUUUAAAAGGCA | GAUCCUGAACUGAGUUUAAAAGGCACCCAG |
| 55 | FLT1 | 383 | GUUUAAAAGGCACCCAGCAG | ACUGAGUUUAAAAGGCACCCAGCACAUCAU |
| 56 | FLT1 | 867 | AUCAAAUGCAACGUACAAAG | AUCAUAUCAAAUGCAACGUACAAAGAAAUA |
| 57 | FLT1 | 868 | UCAAAUGCAACGUACAAAGA | UCAUAUCAAAUGCAACGUACAAAGAAAUAG |
| 58 | FLT1 | 1364 | GUUGUGUAUGGUUAAAGAUG | CGGAAGUGUAUGGUUAAAGAUGGGGUUAC |
| 59 | FLT1 | 1526 | UUUUAAAAACCUCACUGCCAC | AUGUGUUUAAAAACCUCACUGCCACUCUAA |
| 60 | FLT1 | 1530 | UAAAAACCUCACUGCCACUC | GUGUUUAAAAACCUCACUGCCACUCUAAUU |
| 61 | FLT1 | 1532 | AAAACCUCACUGCCACUCUA | GUUUAAAAACCUCACUGCCACUCUAAUUGU |
| 62 | FLT1 | 1781 | GAAACAGAAUUGAGAGCAUC | CAUGGGAAACAGAAUUGAGAGCAUCACUCA |

*Fig. 23*

| # | Name | Pos | Targeting region (20 mer) | Sense Naked | Guide 20 mer |
|---|---|---|---|---|---|
| 2 | sFLT1-i13 | 2247 | AAUCAGAGGUGAGCACUGCA | AAUCAGAGGUGAGCACUGCA | UGCAGUGCUCACCUCUGAUU |
| 3 | sFLT1-i13 | 2252 | GAGGUGAGCACUGCAACAAA | GAGGUGAGCACUGCAACAAA | UUUGUUGCAGUGCUCACCUC |
| 4 | sFLT1-i13 | 2253 | AGGUGAGCACUGCAACAAAA | AGGUGAGCACUGCAACAAAA | UUUUGUUGCAGUGCUCACCU |
| 5 | sFLT1-i13 | 2256 | UGAGCACUGCAACAAAAAGG | UGAGCACUGCAACAAAAAGG | CCUUUUGUUGCAGUGCUCA |
| 6 | sFLT1-i13 | 2279 | UUUUCUCUCGGAUCUCCAAA | UUUUCUCUCGGAUCUCCAAA | UUUGGAGAUCCGAGAGAAAA |
| 7 | sFLT1-i13 | 2280 | UUUCUCUCGGAUCUCCAAAU | UUUCUCUCGGAUCUCCAAAU | AUUUGGAGAUCCGAGAGAAA |
| 8 | sFLT1-i14 | 2283 | CUCUCGGAUCUCCAAAUUUA | CUCUCGGAUCUCCAAAUUUA | UAAAUUUGGAGAUCCGAGAG |
| 9 | sFLT1-i13 | 2284 | UCUCGGAUCUCCAAAUUUAA | UCUCGGAUCUCCAAAUUUAA | UUAAAUUUGGAGAUCCGAGA |
| 10 | sFLT1-i13 | 2286 | UCGGAUCUCCAAAUUUAAAA | UCGGAUCUCCAAAUUUAAAA | UUUUAAAUUUGGAGAUCCGA |
| 11 | sFLT1-i13 | 2293 | UCCAAAUUUAAAAGCACAAG | UCCAAAUUUAAAAGCACAAG | CUUGUGCUUUUAAAUUUGGA |
| 12 | sFLT1-i13 | 2294 | CCAAAUUUAAAAGCACAAGG | CCAAAUUUAAAAGCACAAGG | CCUUGUGCUUUUAAAUUUGG |
| 13 | sFLT1-i13 | 2295 | CAAAUUUAAAAGCACAAGGA | CAAAUUUAAAAGCACAAGGA | UCCUUGUGCUUUUAAAUUUG |
| 14 | sFLT1-i13 | 2304 | AAGCACAAGGAAUGAUUGUA | AAGCACAAGGAAUGAUUGUA | UACAAUCAUUCCUUGUGCUU |
| 15 | sFLT1-i13 | 2313 | GAAUGAUUGUACCACACAAA | GAAUGAUUGUACCACACAAA | UUUGUGGUACAAUCAUUC |
| 16 | sFLT1-i13 | 2318 | AUUGUACCACACAAAGUAAU | AUUGUACCACACAAAGUAAU | AUUACUUUGUGGUACAAU |
| 17 | sFLT1-i13 | 2321 | GUACCACACAAAGUAAUGUA | GUACCACACAAAGUAAUGUA | UACAUUACUUUGUGUGGUAC |
| 18 | sFLT1-i13 | 2322 | UACCACACAAAGUAAUGUAA | UACCACACAAAGUAAUGUAA | UUACAUUACUUUGUGUGGUA |
| 19 | sFLT1-i13 | 2324 | CCACACAAAGUAAUGUAAAA | CCACACAAAGUAAUGUAAAA | UGUUACAUUACUUUGUGUGG |
| 20 | sFLT1-i13 | 2326 | ACACAAAGUAAUGUAAAACA | ACACAAAGUAAUGUAAAACA | UGUUUUACAUUACUUUGUGU |
| 21 | sFLT1-i13 | 2333 | AGUAAUGUAAAACAUUAAAG | AGUAAUGUAAAACAUUAAAG | CUUUAAUGUUUUACAUUACU |
| 22 | sFLT1-i13 | 2335 | GUAAUGUAAAACAUUAAAGG | GUAAUGUAAAACAUUAAAGG | CCUUUAAUGUUUUACAUUAC |
| 23 | sFLT1-i13 | 2339 | UAAAACAUUAAAGGACUCAU | UAAAACAUUAAAGGACUCAU | AUGAGUCCUUUAAUGUUUUA |
| 24 | sFLT1-i13 | 2343 | ACAUUAAAGGACUCAUUAAA | ACAUUAAAGGACUCAUUAAA | UUUAAUGAGUCCUUUAAUGU |
| 25 | sFLT1-i13 | 2351 | GGACUCAUUAAAAGUAACA | GGACUCAUUAAAAGUAACA | UGUUACUUUUAAUGAGUCC |
| 26 | sFLT1-i13 | 2353 | ACUCAUUAAAAGUAACAGU | ACUCAUUAAAAGUAACAGU | ACUGUUACUUUUAAUGAGU |
| 27 | sFLT1-i13 | 2362 | AAAGUAACAGUUGUCUCAUA | AAAGUAACAGUUGUCUCAUA | UAUGAGACAACUGUUACUUU |
| 29 | sFLT1-i15a | 2471 | CAUCAUCAUCAUCAUAGCUA | CAUCAUCAUCAUCAUAGCUA | UAGCUAUGAUGAUGAUGAU |
| 30 | sFLT1-i15a | 2474 | CAUCAUCAUCAUAGCUAUCA | CAUCAUCAUCAUAGCUAUCA | UGAUAGCUAUGAUGAUGAU |
| 31 | sFLT1-i15a | 2477 | CAUCAUCAUAGCUAUCAUCA | CAUCAUCAUAGCUAUCAUCA | UGAUGAUAGCUAUGAUGAUG |
| 32 | sFLT1-i15a | 2508 | AUCAUCAUCAUCAUCAUAGC | AUCAUCAUCAUCAUCAUAGC | GCUAUGAUGAUGAUGAUGAU |
| 33 | sFLT1-i15a | 2510 | CAUCAUCAUCAUCAUAGCUA | CAUCAUCAUCAUCAUAGCUA | UAGCUAUGAUGAUGAUGAUG |
| 34 | sFLT1-i15a | 2513 | CAUCAUCAUCAUAGCUACCA | CAUCAUCAUCAUAGCUACCA | UGGUAGCUAUGAUGAUGAUG |
| 35 | sFLT1-i15a | 2516 | UCAUCAUAGCUACCAUUUAU | UCAUCAUAGCUACCAUUUAU | AUAAAUGGUAGCUAUGAUGA |
| 36 | sFLT1-i15a | 2519 | CAUCAUAGCUACCAUUUAUU | CAUCAUAGCUACCAUUUAUU | AAUAAAUGGUAGCUAUGAUG |
| 37 | sFLT1-i15a | 2525 | AGCUACCAUUUAUUGAAAAC | AGCUACCAUUUAUUGAAAAC | GUUUUCAAUAAAUGGUAGCU |
| 38 | sFLT1-i15a | 2528 | UACCAUUUAUUGAAAACUAU | UACCAUUUAUUGAAAACUAU | AUAGUUUUCAAUAAAUGGUA |
| 39 | sFLT1-i15a | 2556 | AACUUCAAGAACUUAUCCU | AACUUCAAAGAACUUAUCCU | AGGAUAAGUUCUUUGAAGUU |
| 40 | sFLT1-i15a | 2561 | CAAAGAACUUAUCCUUUAGU | CAAAGAACUUAUCCUUUAGU | ACUAAAGGAUAAGUUCUUUG |
| 41 | sFLT1-i15a | 2572 | UCCUUUAGUUGGAGAGCCAA | UCCUUUAGUUGGAGAGCCAA | UUGGCUCUCCAACUAAAGGA |
| 42 | sFLT1-i15a | 2574 | CUUUAGUUGGAGAGCCAAGA | CUUUAGUUGGAGAGCCAAGA | UCUUGGCUCUCCAACUAAAG |
| 43 | sFLT1-i15a | 2576 | UUAGUUGGAGAGCCAAGACA | UUAGUUGGAGAGCCAAGACA | UGUCUUGGCUCUCCAACUAA |
| 44 | sFLT1-i15a | 2577 | UAGUUGGAGAGCCAAGACAA | UAGUUGGAGAGCCAAGACAA | UUGUCUUGGCUCUCCAACUA |
| 45 | sFLT1-i15a | 2580 | UUGGAGAGCCAAGACAAUCA | UUGGAGAGCCAAGACAAUCA | UGAUUGUCUUGGCUCUCCAA |
| 46 | sFLT1-i15a | 2582 | GGAGAGCCAAGACAAUCAUA | GGAGAGCCAAGACAAUCAUA | UAUGAUUGUCUUGGCUCUCC |
| 47 | sFLT1-i15a | 2585 | GAGCCAAGACAAUCAUAACA | GAGCCAAGACAAUCAUAACA | UGUUAUGAUUGUCUUGGCUC |
| 48 | sFLT1-i15a | 2588 | CCAAGACAAUCAUAACAAUA | CCAAGACAAUCAUAACAAUA | UAUUGUUAUGAUUGUCUUGG |
| 49 | sFLT1-i15a | 2590 | AAGACAAUCAUAACAAUAAC | AAGACAAUCAUAACAAUAAC | GUUAUUGUUAUGAUUGUCUU |
| 51 | FLT1 | 331 | AGCUGUCUGCUUCUCACAGG | AGCUGUCUGCUUCUCACAGG | CCUGUGAGAAGCAGACAGCU |
| 52 | FLT1 | 376 | GAUCCUGAACUGAGUUUAAA | GAUCCUGAACUGAGUUUAAA | UUUAAACUCAGUUCAGGAUC |
| 53 | FLT1 | 377 | AUCCUGAACUGAGUUUAAAA | AUCCUGAACUGAGUUUAAAA | UUUUAAACUCAGUUCAGGAU |
| 54 | FLT1 | 381 | UGAACUGAGUUUAAAAGGCA | UGAACUGAGUUUAAAAGGCA | UGCCUUUUAAACUCAGUUCA |
| 55 | FLT1 | 389 | GUUUAAAAGGCACCCAGCAC | GUUUAAAAGGCACCCAGCAC | GUGCUGGGUGCCUUUUAAAC |
| 56 | FLT1 | 867 | AUCAAAUGCAACGUACAAAG | AUCAAAUGCAACGUACAAAG | CUUUGUACGUUGCAUUUGAU |
| 57 | FLT1 | 868 | UCAAAUGCAACGUACAAAGA | UCAAAUGCAACGUACAAAGA | UCUUUGUACGUUGCAUUUGA |
| 58 | FLT1 | 1364 | GUUGUAUGGUUAAAAGAUGG | GUUGUAUGGUUAAAAGAUGG | CCAUCUUUUAACCAUACAAC |
| 59 | FLT1 | 1528 | UUUUAAAACCUCACUGCCAC | UUUUAAAACCUCACUGCCAC | GUGGCAGUGAGGUUUUAAAA |
| 60 | FLT1 | 1530 | UAAAACCUCACUGCCACUC | UAAAACCUCACUGCCACUC | GAGUGGCAGUGAGGUUUUA |
| 61 | FLT1 | 1532 | AAAACCUCACUGCCACUCUA | AAAACCUCACUGCCACUCUA | UAGAGUGGCAGUGAGGUUUU |
| 62 | FLT1 | 1781 | GAAACAGAAUUGAGAGCAUC | GAAACAGAAUUGAGAGCAUC | GAUGCUCUCAAUUCUGUUUC |

| # | Name | Pos | H. sapiens | M. musculus | Papio hamadryas (baboon) | Target mRNA Expression (% control) |
|---|---|---|---|---|---|---|
| 1 | | | | | | |
| 2 | sFLT1-i13 | 2247 | yes | | yes | 85.1 |
| 3 | sFLT1-i13 | 2252 | yes | | yes | 101.7 |
| 4 | sFLT1-i13 | 2253 | yes | | yes | 55.2 |
| 5 | sFLT1-i13 | 2256 | yes | | yes | 56.8 |
| 6 | sFLT1-i13 | 2273 | yes | | yes | 71.5 |
| 7 | sFLT1-i13 | 2280 | yes | | yes | 105.2 |
| 8 | sFLT1-i14 | 2283 | yes | yes | yes | 8.0 |
| 9 | sFLT1-i13 | 2284 | yes | | yes | 34.4 |
| 10 | sFLT1-i13 | 2286 | yes | | yes | 98.2 |
| 11 | sFLT1-i13 | 2293 | yes | | yes | 106.2 |
| 12 | sFLT1-i13 | 2294 | yes | | yes | 92.7 |
| 13 | sFLT1-i13 | 2295 | yes | | yes | 87.2 |
| 14 | sFLT1-i13 | 2304 | yes | | yes | 73.3 |
| 15 | sFLT1-i13 | 2313 | yes | | yes | 111.4 |
| 16 | sFLT1-i13 | 2318 | yes | | yes | 24.4 |
| 17 | sFLT1-i13 | 2321 | yes | | yes | 87.0 |
| 18 | sFLT1-i13 | 2322 | yes | | yes | 87.4 |
| 19 | sFLT1-i13 | 2324 | yes | | yes | 63.8 |
| 20 | sFLT1-i13 | 2326 | yes | | yes | 96.6 |
| 21 | sFLT1-i13 | 2332 | yes | | yes | 60.6 |
| 22 | sFLT1-i13 | 2333 | yes | | yes | 67.2 |
| 23 | sFLT1-i13 | 2339 | yes | | yes | 24.3 |
| 24 | sFLT1-i13 | 2343 | yes | | yes | 16.7 |
| 25 | sFLT1-i13 | 2351 | yes | | yes | 34.3 |
| 26 | sFLT1-i13 | 2353 | yes | | yes | 70.6 |
| 27 | sFLT1-i13 | 2362 | yes | | yes | 11.3 |
| 28 | | | | | | |
| 29 | sFLT1-i15a | 2471 | yes | No | yes | 92.4 |
| 30 | sFLT1-i15a | 2474 | yes | No | yes | 123.3 |
| 31 | sFLT1-i15a | 2477 | yes | No | yes | 108.5 |
| 32 | sFLT1-i15a | 2508 | yes | No | yes | 75.2 |
| 33 | sFLT1-i15a | 2510 | yes | No | yes | 61.3 |
| 34 | sFLT1-i15a | 2513 | yes | No | yes | 103.2 |
| 35 | sFLT1-i15a | 2518 | yes | No | yes | 34.0 |
| 36 | sFLT1-i15a | 2519 | yes | No | yes | 15.1 |
| 37 | sFLT1-i15a | 2525 | yes | No | yes | 69.5 |
| 38 | sFLT1-i15a | 2528 | yes | No | yes | 98.6 |
| 39 | sFLT1-i15a | 2556 | yes | No | yes | 29.0 |
| 40 | sFLT1-i15a | 2561 | yes | No | yes | 41.1 |
| 41 | sFLT1-i15a | 2572 | yes | No | yes | 41.9 |
| 42 | sFLT1-i15a | 2574 | yes | No | yes | 35.9 |
| 43 | sFLT1-i15a | 2576 | yes | No | yes | 58.8 |
| 44 | sFLT1-i15a | 2577 | yes | No | yes | 86.8 |
| 45 | sFLT1-i15a | 2580 | yes | No | yes | 64.7 |
| 46 | sFLT1-i15a | 2582 | yes | No | yes | 24.7 |
| 47 | sFLT1-i15a | 2585 | yes | No | yes | 21.9 |
| 48 | sFLT1-i15a | 2586 | yes | No | yes | 10.3 |
| 49 | sFLT1-i15a | 2590 | yes | No | yes | 47.3 |
| 50 | | | | | | |
| 51 | FLT1 | 321 | yes | yes | yes | 24.3 |
| 52 | FLT1 | 376 | yes | yes | yes | 32.2 |
| 53 | FLT1 | 377 | yes | yes | yes | 28.3 |
| 54 | FLT1 | 381 | yes | yes | yes | 10.7 |
| 55 | FLT1 | 383 | yes | yes | yes | 60.8 |
| 56 | FLT1 | 867 | yes | yes | yes | 27.3 |
| 57 | FLT1 | 868 | yes | yes | yes | 63.1 |
| 58 | FLT1 | 1364 | yes | yes | yes | 56.2 |
| 59 | FLT1 | 1528 | yes | yes | yes | 56.1 |
| 60 | FLT1 | 1530 | yes | yes | yes | 59.2 |
| 61 | FLT1 | 1532 | yes | yes | yes | 54.8 |
| 62 | FLT1 | 1781 | yes | yes | yes | 26.6 |

*Fig. 24*

| | Active hsiRNAs | |
|---|---|---|
| Gene | Position | Target Sequence |
| HTT | 1214 | GGUUAUGAACUGAC |
| HTT | 1218 | UAUGAACUGACGUUA |
| HTT | 1219 | AUGAACUGACGUUAC |
| HTT | 1357 | AAUGUUGUGACCGGA |
| HTT | 1894 | UAGACGGUACCGACA |
| HTT | 1907 | CAACCAGUAUUGGG |
| HTT | 2866 | UGCUCAAUAAUGUUG |
| HTT | 4041 | UCCUGCUUUAGUCGA |
| HTT | 4049 | UAGUCGAGAACCAAU |
| HTT | 5301 | AGUACUUCAACGCUA |
| HTT | 6016 | UUCAGUCUCGUUGUG |
| HTT | 6579 | CUAGCUCCAUGCUUA |
| HTT | 8603 | CUGCGUGAACAUUCA |
| HTT | 10125 | CUCAGGAUUUAAAAU (SEQ ID NO:3) |
| HTT | 10146 | AUAUCAGUAAAGAGA (SEQ ID NO:2) |
| HTT | 10150 | CAGUAAAGAGAUUAA (SEQ ID NO:1) |
| HTT | 424 | CAGCUACCAAGAAAG |
| HTT | 456 | CUGACAAUAUGUGAA |
| HTT | 522 | GGCAUCGCUAUGGAA |
| HTT | 527 | CGCUAUGGAACUUUU |
| HTT | 878 | UGACAAUGAAAUUAA |
| HTT | 879 | GACAAUGAAAUUAAG |
| HTT | 908 | CUUCAUAGCGAACCU |
| HTT | 1024 | AUGUGCUCUUAGGCU |
| HTT | 1165 | UGACAAGGAAAGAAA |
| HTT | 1207 | UUGUCCAGGUUUAUG |
| HTT | 1212 | CAGGUUUAUGAACUG |
| HTT | 1217 | UUAUGAACUGACGUU |
| HTT | 1220 | UGAACUGACGUUACA |
| HTT | 1223 | ACUGACGUUACAUCA |
| HTT | 1227 | ACGUUACAUCAUACA |
| HTT | 1229 | GUUACAUCAUACACA |
| HTT | 1260 | GUUGUGACCGGAGCC |
| HTT | 1403 | UAUUGUGGAACUUAU |
| HTT | 1470 | AAAGUGCUCUUAGGA |
| HTT | 1901 | UACCGACAACCAGUA |
| HTT | 1903 | CCGACAACCAGUAUU |
| HTT | 2411 | CUACAUCGAUCAUGG |
| HTT | 2412 | UACAUCGAUCAUGGA |
| HTT | 2865 | GUGCUCAAUAAUGUU |
| HTT | 3801 | GUUACAACAAGUAAA |
| HTT | 4040 | AUCCUGCUUUAGUCG |
| HTT | 4048 | UUAGUCGAGAACCAA |
| HTT | 4052 | UCGAGAACCAAUGAU |
| HTT | 4055 | AGAACCAAUGAUGGC |

*Fig. 24*
(Cont.)

| Active hsiRNAs | | Strand Modifications | |
|---|---|---|---|
| Gene | Position | Sense Strand | Antisense Strand |
| HTT | 1214 | mC.mC.mU.mU.mA.mU.G.A.A.mC.mU.G#mA#mAtegChol | PmU.fU.fC.A.G.fU.fU.fC.A.fU.A.A.mA.fC#fC#U#G#G#mA#C |
| HTT | 1218 | mU.mA.mU.G.A.A.mC.mU.G.A.mC.G.mU#mU#mAtegChol | PmU.A.A.fC.G.fU.fC.A.G.fU.fU.fC.A.fU#A#A#mA#fC#fC#U |
| HTT | 1219 | mA.mU.G.A.A.mC.mU.G.A.mC.G.mU.mU#mA#mAtegChol | PmU.fU.A.A.fC.G.fU.fC.A.G.fU.fU.fC.A#fU#A#A#mA#fC#C |
| HTT | 1287 | mA.mA.mU.G.mU.mU.G.mU.G.A.mC.mC.G#mU#mAtegChol | PmU.fC.fC.G.G.fU.C.A.fC.A.A.fC.A.fC#fU#fU#U#G#C#U |
| HTT | 1894 | mU.mA.G.A.mC.G.G.mU.A.mC.mC.G.A#mC#mAtegChol | PmU.G.fU.fC.G.G.fU.A.fC.fC.G.fU.fU#A#A#fC#A#A#C#A |
| HTT | 1907 | mC.mA.A.mC.mC.A.G.mU.A.mU.mU.G.mG#mU#mAtegChol | PmU.fC.fC.A.A.mA.fU.A.fC.G.G.fU.fU#G#fC#fU#C#G#U |
| HTT | 2866 | mU.mC.mC.mU.mC.A.A.mU.A.A.mU.G.mU#mU#mAtegChol | PmU.A.A.fC.A.fU.fU.A.fU.fU.G.A.mG.fC#U#fC#fC#C#U |
| HTT | 4041 | mU.mC.mC.mU.G.mC.mU.mU.mU.mU.A.G.mU#mC#mG#mAtegChol | PmU.fC.G.A.fC.fU.A.A.mA.G.fC.A.G.mG#A#fC#fU#fU#fC#A |
| HTT | 4049 | mU.mA.G.mU.mC.G.A.mG.A.A.mC.mC.A#mA#mAtegChol | PmU.fU.fU.G.G.fU.fU.fC.fU.fC.G.A.fC.fU#A#A#mA#fC#fC#A |
| HTT | 5301 | mA.mG.mU.A.mC.mU.mC.A.A.mC.G.mC#mU#mAtegChol | PmU.A.G.fC.G.fU.fU.G.A.mG.fU.A.fC#fU#G#fU#fC#C#C |
| HTT | 6016 | mU.mU.mC.A.G.mU.mC.mU.C.G.mU.mU.G#mU#mAtegChol | PmU.A.fC.A.A.fC.G.A.mG.A.fC.fU.G.A#A#fC#fC#C |
| HTT | 6879 | mC.mU.A.G.mC.mU.mC.A.A.mU.C.mC.mU#mU#mAtegChol | PmU.A.A.mG.fC.A.fU.G.G.mA.G.fC.fU.A#G#fC#A#G#mG#C |
| HTT | 8803 | mC.mU.G.mC.G.mU.G.A.A.mC.A.mU.mU#mC#mAtegChol | PmU.G.A.mA.fU.G.fU.fU.fC.A.fC.G.fC#A#G#fC#G#mG#C |
| HTT | 10128 | mC.mU.mC.A.G.G.A.mU.mU.mU.A.A.A#mA#mAtegChol | PmU.fU.fU.fU.A.A.A.mA.fU.fC.fC.fU.G.A#mG#A#A#mG#A#A |
| HTT | 10146 | mA.mU.A.mU.mC.A.C.mU.A.A.A.G.A#mC#mAtegChol | PmU.fC.fU.fC.fU.fU.fU.A.fU.G.A.fU.A#fC#A#fC#U#U#A |
| HTT | 10150 | mC.mA.G.mU.A.A.A.mG.A.G.A.mU.mU#mA#mAtegChol | PmU.fU.A.A.fU.fC.fU.fC.fU.fU.fU.A.fC#fU#G#A#fU#A#U#A |
| HTT | 424 | mC.mA.G.mC.mU.A.mC.mC.A.A.G.A#mA#mAtegChol | PmU.fU.fU.fC.fU.fU.G.G.fU.A.G.fC#U#G#A#mA#A#G#U |
| HTT | 466 | mC.mU.G.A.mC.A.A.mU.A.mU.G.mU.G#mA#mAtegChol | PmU.fC.fC.A.fC.A.fU.A.fU.fU.G.fU.C.A#G#mA#fC#A#A#A |
| HTT | 522 | mC.mG.mC.A.mU.mC.G.mC.mU.A.mU.G.G#mA#mAtegChol | PmU.fU.fC.A.fU.A.G.C.G.A.fU.G.C.G#A#fC#G#mA#A |
| HTT | 527 | mC.mC.mC.mU.A.mU.G.G.mA.A.mC.mU.mU#mU#mAtegChol | PmU.A.A.mA.G.fU.fU.fC.fC.A.fU.A.G.fC#A#A#G#fC#C |
| HTT | 878 | mU.mG.A.mC.A.A.mU.G.A.mA.A.mU#mU#mAtegChol | PmU.A.A.fU.fU.fU.C.A.fU.fU.G.fU.fC#A#fU#U#U#G#C |
| HTT | 879 | mG.mA.mC.A.A.mU.G.A.mA.A.mU.mU.A#mA#mAtegChol | PmU.fU.A.A.fU.fU.fU.C.A.fU.fU.G#fC#A#fU#U#fU#G |
| HTT | 968 | mC.mU.mU.mC.A.mU.A.G.mC.G.A.A#mC#mAtegChol | PmU.G.G.fU.fC.fC.fC.fU.A.fU.G.A.mA#G#G#fC#C#fU#U |
| HTT | 1024 | mA.mU.G.mU.G.mC.mU.mC.mU.A.G.G#mC#mAtegChol | PmU.G.fC.fC.fU.A.A.mG.A.G.fC.A.fC#A#fU#U#A#G#U |
| HTT | 1168 | mU.mG.A.mC.A.A.G.mG.A.A.mA.G.A#mA#mAtegChol | PmU.fU.fU.fU.fC.fU.fU.fC.fC.fU.G.fU.fC#A#fU#U#fC#C#G |
| HTT | 1207 | mU.mU.C.mU.mC.mC.A.G.G.mU.mU.A#mU#mAtegChol | PmU.A.fU.A.A.mA.fC.fC.fU.G.G.mA.fC.A#A#mC#fU#fU#G#C |
| HTT | 1212 | mC.mA.G.mU.mU.mU.A.mU.G.A.A.mC#mU#mAtegChol | PmU.A.G.fU.fU.fC.A.fU.A.A.mA.fC.fU#C#G#mA#fC#A#A |
| HTT | 1217 | mU.mU.A.mU.G.A.A.mC.mU.G.A.mC.G#mU#mAtegChol | PmU.A.fC.G.fU.fC.A.G.fU.fU.fC.A.fU#A#A#mA#fC#C#U#G |
| HTT | 1220 | mU.mG.A.A.mC.mU.G.A.mC.G.mU.mU.A#mC#mAtegChol | PmU.G.fU.A.A.fC.G.fU.fC.A.G.fU.fU.fC#A#fU#A#A#mA#C |
| HTT | 1223 | mA.mC.mU.G.A.mC.G.mU.mU.A.mC.mU#mC#mAtegChol | PmU.G.A.fU.G.fU.A.A.fC.G.fU.fC.A.G#fU#fU#C#A#fU#A |
| HTT | 1227 | mA.mC.G.mU.mU.A.mC.A.mU.mC.A.mU.A#mC#mAtegChol | PmU.G.fU.A.fU.G.A.fU.fU.A.A.fC.G#fU#C#A#G#fU#U |
| HTT | 1229 | mG.mU.mU.A.mC.A.mU.C.A.mU.A.mC.A#mC#mAtegChol | PmU.G.fU.G.fU.A.fU.G.A.fU.G.fU.A.A#C#G#fU#fU#C#A#G |
| HTT | 1260 | mC.mU.mU.G.mU.G.A.mC.mC.G.mG.A.G#mC#mAtegChol | PmU.G.fC.fC.fC.fC.G.G.fU.fC.A.fC.A.A#mG#A#fC#fU#G#U |
| HTT | 1403 | mU.mA.mU.mU.G.mU.C.G.A.A.mU.mU.A#mA#mAtegChol | PmU.fU.fU.A.A.fU.fU.fC.G.A.fC.A.A.fU.A#A#C#fU#fU#C#U |
| HTT | 1470 | mA.mA.A.mU.C.mC.mU.mC.mU.mU.A.G#mC#mAtegChol | PmU.fC.fC.fU.A.A.mG.A.G.A.fC.fU.fU#fU#fC#fC#fC#fU#U |
| HTT | 1901 | mU.mA.mC.mC.G.A.mC.A.A.mC.mC.A.G#mU#mAtegChol | PmU.A.fC.fU.G.G.fU.fU.G.fU.fC.G.G.fU.A#fC#fC#C#C |
| HTT | 1903 | mC.mC.G.A.mC.A.A.mC.mC.A.G.mU.A#mU#mAtegChol | PmU.A.fU.A.fC.fU.G.G.fU.fU.G.fU.fC.G#fU#A#fC#C#G |
| HTT | 2411 | mC.mU.A.mC.A.mU.mC.G.A.mU.mC.A.A#mG#mAtegChol | PmU.fC.A.fU.G.A.fU.fC.G.A.fU.G.fU.A#G#fC#U#C#A#A |
| HTT | 2412 | mU.mA.mC.A.mU.mC.G.A.mU.mC.A.A.G#mU#mAtegChol | PmU.fC.fC.A.fU.G.A.fU.fC.G.A.fU.G.fU#A#G#fC#U#C#A |
| HTT | 2865 | mC.mU.G.mC.mU.mC.A.A.mU.A.A.mU.G#mU#mAtegChol | PmU.A.fC.A.fU.fU.A.fU.fU.G.A.mG.fC.A#G#fC#fC#G#fU#U |
| HTT | 3801 | mG.mU.mU.A.mC.A.A.mC.A.A.G.mU.A#mA#mAtegChol | PmU.fU.fU.A.fC.fU.fU.G.fU.fU.G.fU.A.A#fC#A#G#mC#A#C |
| HTT | 4040 | mA.mU.mC.mU.G.mC.mU.mU.mU.A.G.mU#mC#mAtegChol | PmU.G.A.fC.fU.A.A.mA.G.fC.A.G.mG.A#fC#fU#fU#fC#A#G |
| HTT | 4048 | mU.mU.A.G.mU.mC.G.A.G.A.A.mC.mC#mA#mAtegChol | PmU.U.G.G.fU.fU.fC.fU.fC.G.A.fC.fU.A#A#mA#fC#C#A#G |
| HTT | 4052 | mU.mC.G.A.G.A.A.mC.mC.A.A.mU.G#mA#mAtegChol | PmU.fU.fC.A.fU.fU.G.G.fU.fU.fC.fU.fC#G#A#fC#fU#A#A#A |
| HTT | 4055 | mA.mG.A.A.mC.mC.A.A.mU.G.A.mU.G#mC#mAtegChol | PmU.fC.fC.A.fU.fC.A.fU.fU.G.G.fU.fU.fC#fU#fC#C#fU#C#U |

*Fig. 24*
(Cont.)

| Active hsiRNAs | | Homology | | | Primary Screen | IC50 (nM) | |
| --- | --- | --- | --- | --- | --- | --- | --- |
| Gene | Position | H. sapien | M. musculus | M. mulatta | Huntingtin mRNA Expression (% control) | Passive Uptake | Lipid-Mediated Uptake |
| HTT | 1214 | yes | yes | yes | 34.3 | 197.4 | N/A |
| HTT | 1218 | yes | | yes | 44.8 | 293.2 | N/A |
| HTT | 1219 | yes | | yes | 29.6 | 163.6 | 0.053 |
| HTT | 1257 | yes | | yes | 28.5 | 156.7 | N/A |
| HTT | 1894 | yes | | yes | 23.7 | 95.53 | 0.048 |
| HTT | 1907 | yes | | yes | 39.3 | 217.9 | N/A |
| HTT | 2866 | yes | | yes | 35.3 | 191.7 | 0.091 |
| HTT | 4041 | yes | yes | yes | 53.5 | 765.7 | N/A |
| HTT | 4049 | yes | yes | yes | 41.2 | 217.8 | N/A |
| HTT | 5301 | yes | | | 36.6 | 230.2 | 0.08 |
| HTT | 6016 | yes | | yes | 26.4 | 147.9 | N/A |
| HTT | 6579 | yes | | yes | 28.3 | 89.8 | 0.056 |
| HTT | 8603 | yes | yes | yes | 40 | 236.1 | N/A |
| HTT | 10125 | yes | | yes | 31.1 | 158.7 | 0.059 |
| HTT | 10146 | yes | yes | yes | 25.9 | 217.7 | 0.052 |
| HTT | 10150 | yes | yes | yes | 28.6 | 82.2 | 0.004 |
| HTT | 424 | yes | | yes | 67.4 | N/A | N/A |
| HTT | 456 | yes | | yes | 51.5 | N/A | N/A |
| HTT | 522 | yes | | yes | 68.2 | N/A | N/A |
| HTT | 527 | yes | | yes | 45.5 | N/A | N/A |
| HTT | 878 | yes | | yes | 64.8 | N/A | N/A |
| HTT | 879 | yes | | yes | 51.5 | N/A | N/A |
| HTT | 908 | yes | | yes | 99.6 | N/A | N/A |
| HTT | 1024 | yes | | yes | 52.9 | N/A | N/A |
| HTT | 1165 | yes | | | 77 | N/A | N/A |
| HTT | 1207 | yes | yes | yes | 109.5 | N/A | N/A |
| HTT | 1212 | yes | yes | yes | 74.9 | N/A | N/A |
| HTT | 1217 | yes | | yes | 104 | N/A | N/A |
| HTT | 1220 | yes | | yes | 83.9 | N/A | N/A |
| HTT | 1223 | yes | | yes | 92.2 | N/A | N/A |
| HTT | 1227 | yes | | yes | 81.4 | N/A | N/A |
| HTT | 1229 | yes | | yes | 82.2 | N/A | N/A |
| HTT | 1260 | yes | | yes | 108.4 | N/A | N/A |
| HTT | 1403 | yes | | yes | 138.6 | N/A | N/A |
| HTT | 1470 | yes | yes | yes | 85.6 | N/A | N/A |
| HTT | 1901 | yes | | yes | 81.4 | N/A | N/A |
| HTT | 1903 | yes | | yes | 72.7 | N/A | N/A |
| HTT | 2411 | yes | | yes | 53 | N/A | N/A |
| HTT | 2412 | yes | | yes | 57.1 | N/A | N/A |
| HTT | 2865 | yes | | yes | 83.1 | N/A | N/A |
| HTT | 3801 | yes | | yes | 48.9 | N/A | N/A |
| HTT | 4040 | yes | yes | yes | 56.2 | N/A | N/A |
| HTT | 4048 | yes | yes | yes | 72.2 | N/A | N/A |
| HTT | 4052 | yes | yes | yes | 90.8 | N/A | N/A |
| HTT | 4055 | yes | yes | yes | 37.2 | N/A | N/A |

*Fig. 24*
(Cont.)

Active hsiRNAs

| Gene | Position | Target Sequence |
|---|---|---|
| HTT | 4083 | CAACAAUGUUGAAG |
| HTT | 4275 | AACAUGGUGCAGGCG |
| HTT | 4372 | CAAAGAACCGUGCAG |
| HTT | 4374 | AAGAACCGUGCAGAU |
| HTT | 4376 | GAACCGUGCAGAUAA |
| HTT | 4425 | CCUCUUGUUAUAAAA |
| HTT | 4562 | UGGCUUUGUAUUGAA |
| HTT | 4692 | GGAAUUCCUAAAAUC |
| HTT | 4721 | UGGCAUCAUGGCCAG |
| HTT | 5200 | CCCAGUCAACUGAAG |
| HTT | 5443 | AGCAGCAACAUACUU |
| HTT | 5515 | GAAUGUUCCGGAGAA |
| HTT | 8609 | GAACAUCACAGCCA |
| HTT | 10130 | GAUUUAAAAUUUAAU |
| HTT | 10134 | UAAAAUUUAAUUAUA |
| HTT | 10142 | AAUUAUAUCAGUAAA |
| HTT | 10169 | AACGUAACUCUUUCU |
| HTT | 10182 | CUAUGCCCGUGUAAA |
| HTT | 10186 | GCCCGUGUAAAGUAU |
| HTT | 10809 | AGUCAGGAGAGUGCA |
| HTT | 11116 | UGGGUAUUGAAUGUG |
| HTT | 11129 | UGGUAAGUGGAGGAA |
| HTT | 11134 | AGUGGACGAAAUGUU |
| HTT | 11147 | UUGGAACUCUGUGCA |
| HTT | 11412 | UGAGGAGGCCCUUAA |
| HTT | 11426 | AGGGAAGCUACUGAA |
| HTT | 11443 | AUAACACGUAAGAAA |
| HTT | 11659 | UACAUUUGUAAGAAA |
| HTT | 11666 | GUAAGAAAUAACACU |
| HTT | 11677 | CACUGUGAAUGUAAA |
| HTT | 11863 | GAGCUCAUUAGUAAA |
| HTT | 11890 | CACGCAUAUACAUAA |

Fig. 24
(Cont.)

| Active hsiRNAs | | Strand Modifications | |
|---|---|---|---|
| Gene | Position | Sense Strand | Antisense Strand |
| HTT | 4083 | mCmAAmCAAmUmUGmUmCGA#mA#mAtegChol | PmUfCfUfCfCAAfCAAfUfUGfUfC#G#A#mA#C#A#C |
| HTT | 4275 | mAmAmCAmUGGmUGmCAGG#mC#mAtegChol | PmUfCfCfCfUGfCAfCfCAfUfG#fU#fC#fU#fC#A |
| HTT | 4372 | mCmAAAGAAmCmCGmUGmC#mA#mAtegChol | PmUfUGfCAfCGGfUfCfUfCfUfU#G#fU#G#A#fCA |
| HTT | 4374 | mAmAGAAmCmCGmUGmCAG#mA#mAtegChol | PmUfCfCfUGfCAfCGGfUfCfUfU#G#fU#G#fU#G#A |
| HTT | 4376 | mCmAAmCmCGmUGmCAGAmU#mA#mAtegChol | PmUfCfAfCfCGfCAfCGGfUfCfU#fU#fC#fU#G#fU |
| HTT | 4425 | mCmCmUmCmUmUGmUmUAmUAA#mA#mAtegChol | PmUfUfUfCfCAAAfCAAmCAG#mG#fU#fU#C#A#A |
| HTT | 4562 | mUmGGmCmUmUmUGmUAmUmUG#mA#mAtegChol | PmUfUfCAAfUAfCAAmAGfCfCAA#A#fU#A#A#A |
| HTT | 4692 | mGmGAAmUmUmCmCmUAAA#mU#mAtegChol | PmUAfUfUfCfUAGmGAAfUfUfC#C#A#A#fU#G#A |
| HTT | 4721 | mUmGGmCAmUmCAmUGGmCmC#mA#mAtegChol | PmUfUGGfCfCAfUGAfCfCGfC#A#fC#A#C#A |
| HTT | 5200 | mCmCmCAGmUmCAAmCmUGA#mA#mAtegChol | PmUfCfUfCAGfUfUGAfCfUGG#mG#A#A#mA#fU#C |
| HTT | 5443 | mAmGmCAGmCAAmCAmUAmCmU#mU#mAtegChol | PmUAGfUAfUGfUfUGfCfUGfC#fU#C#A#fC#fU#C |
| HTT | 5515 | mGmAAmUGmUmUmCmCGGG#mA#mAtegChol | PmUfCfCfUfCfCGGmAAfCAfU#fC#C#A#GmA#C |
| HTT | 8669 | mGmAAmCAmUmUmCAmCAGmC#mC#mAtegChol | PmUGGfCfUGfUGmAfCfUfUGfU#C#A#G#C |
| HTT | 10130 | mGmAmUmUmUAAAAmUmUmUA#mA#mAtegChol | PmUfUfUAAmAfCfUfUfUAAmA#fU#C#fU#G#A#G |
| HTT | 10134 | mUmAAAAmUmUmUAAmUmUAmU#mAtegChol | PmUAAAfUfCAAmAfUfUfUfUA#A#mA#fU#C#C |
| HTT | 10142 | mAmAmUmUAmUAmUmCAGmUA#mA#mAtegChol | PmUfUfCAfCfUGAfUAfUAA#fU#A#A#mA#fU#U |
| HTT | 10169 | mAmAmCGmUAAmCmUmCmUmUmC#mAtegChol | PmUGAmAGmAGfUfUAfCCGfU#A#A#mA#A#U |
| HTT | 10182 | mCmUAmUGmCmCmCGmUGmUA#mA#mAtegChol | PmUfUfCAfCACCGmGfCAfUAG#mA#A#mGA |
| HTT | 10186 | mGmCmCmCGmUGmUAAAGmU#mA#mAtegChol | PmUfUfCfUfUfUAfCAfCGmG#A#fU#A#GA |
| HTT | 10809 | mAmGmUmCAGGAGAGmUG#mC#mAtegChol | PmUGfCAfCfUfCfUfCfCGAfC#fU#A#A#mA#G |
| HTT | 11116 | mUmGGGmUAmUmUGAAmUG#mU#mAtegChol | PmUAfCAfUfUfCAAfUfCfC#A#A#mA#C#A |
| HTT | 11129 | mUmCGGmUAAGmUGGAGG#mA#mAtegChol | PmUfCfCfCfUfCfCAfCfUfCfC#A#fC#A#fU#C |
| HTT | 11134 | mAmGmUGGAGGAAAmUG#mU#mAtegChol | PmUAfCAfUfUfCfCfUfCfCAfC#A#fC#fU#C |
| HTT | 11147 | mUmUGGAAmCmUmCmUGmUG#mC#mAtegChol | PmUGfCAfCAmAGfCfUfCfCA#fC#fU#U |
| HTT | 11412 | mUmGAGGmAGGmCmCmCmUmUmA#mAtegChol | PmUfUAAmGGGfCfCfUfCfC#A#mA#C#U |
| HTT | 11426 | mAmGGAAGmCmUAmCmUG#mA#mAtegChol | PmUfUfCAGfUAGfCfUfCfCfUfU#A#A#mG#G |
| HTT | 11443 | mAmUAAmCAmCCGmUAAGA#mA#mAtegChol | PmUfCfUfCfUAfCfGGfUGfUA#A#A#fU#C |
| HTT | 11669 | mUmAmCAmUmUmCmUAAGA#mA#mAtegChol | PmUfUfCfUfUAfCAAmAfUG#A#A#mA#C#A#fU |
| HTT | 11686 | mGmUAAGmAAAmUAAmCmA#mC#mAtegChol | PmUGfCfUfUfUfCfUfUAfCAA#A#fU#G |
| HTT | 11677 | mCmAAmCmUGmUCAAmUGmA#mA#mAtegChol | PmUfUAfCAfUfUfCAfCAGfU#G#fU#A#fU |
| HTT | 11863 | mCmAmCmCmUmCAmUmUAGmUA#mA#mAtegChol | PmUfUfAfCfUAAfCAmGfCfU#C#A#fU#A#fU |
| HTT | 11890 | mCmAmCGmCAmUAmUAmCA#mA#mAtegChol | PmUfUAfCGfUAfUGfCGfU#G#C#mG#fU#GA |

*Fig. 24*
(Cont.)

| | Active hsiRNAs | | Homology | | | Primary Screen | IC50 (nM) | |
|---|---|---|---|---|---|---|---|---|
| | Gene | Position | H. sapien | M. musculus | M. mulatta | Huntingtin mRNA Expression (% control) | Passive Uptake | Lipid-Mediated Uptake |
| 49 | HTT | 4083 | yes | | yes | 91.7 | N/A | N/A |
| 50 | HTT | 4275 | yes | yes | yes | 77.2 | N/A | N/A |
| 51 | HTT | 4372 | yes | | yes | 44.5 | N/A | N/A |
| 52 | HTT | 4374 | yes | | yes | 97.5 | N/A | N/A |
| 53 | HTT | 4376 | yes | | yes | 64.1 | N/A | N/A |
| 54 | HTT | 4425 | yes | yes | yes | 44.6 | N/A | N/A |
| 55 | HTT | 4562 | yes | | yes | 102.1 | N/A | N/A |
| 56 | HTT | 4692 | yes | yes | yes | 53.8 | N/A | N/A |
| 57 | HTT | 4721 | yes | | yes | 124.2 | N/A | N/A |
| 58 | HTT | 5200 | yes | | yes | 43.8 | N/A | N/A |
| 59 | HTT | 5443 | yes | | yes | 48.9 | N/A | N/A |
| 60 | HTT | 5515 | yes | yes | yes | 62 | N/A | N/A |
| 61 | HTT | 8609 | yes | yes | yes | 47.4 | N/A | N/A |
| 62 | HTT | 10130 | yes | | yes | 49.6 | N/A | N/A |
| 63 | HTT | 10134 | yes | yes | yes | 113.7 | N/A | N/A |
| 64 | HTT | 10142 | yes | yes | yes | 78 | N/A | N/A |
| 65 | HTT | 10169 | yes | | yes | 69 | N/A | N/A |
| 66 | HTT | 10182 | yes | yes | yes | 100.1 | N/A | N/A |
| 67 | HTT | 10186 | yes | | yes | 83.5 | N/A | N/A |
| 68 | HTT | 10809 | yes | | | 101.7 | N/A | N/A |
| 69 | HTT | 11116 | yes | | | 90 | N/A | N/A |
| 70 | HTT | 11129 | yes | | | 105.9 | N/A | N/A |
| 71 | HTT | 11134 | yes | | | 85.1 | N/A | N/A |
| 72 | HTT | 11147 | yes | | | 109.9 | N/A | N/A |
| 73 | HTT | 11412 | yes | | | 122 | N/A | N/A |
| 74 | HTT | 11426 | yes | yes | | 106.3 | N/A | N/A |
| 75 | HTT | 11443 | yes | | | 91.7 | N/A | N/A |
| 76 | HTT | 11659 | yes | | | 80.7 | N/A | N/A |
| 77 | HTT | 11666 | yes | | | 98.5 | N/A | N/A |
| 78 | HTT | 11677 | yes | | | 87.8 | N/A | N/A |
| 79 | HTT | 11863 | yes | | | 77.4 | N/A | N/A |
| 80 | HTT | 11890 | yes | | | 114.3 | N/A | N/A |

*Fig. 24*
(Cont.)

| | Active hsiRNAs | | |
|---|---|---|---|
| | Gene | Position | Target Sequence |
| 81 | HTT | 11927 | GACACAUCUAUAAUU |
| 82 | HTT | 11947 | CACACACCUCUCAAG |
| 83 | HTT | 12163 | UAUCAUGUUCCUAAA |
| 84 | HTT | 12218 | GCAAAUGUGAUUAAU |
| 85 | HTT | 12223 | UGUGAUUAAUUUGGU |
| 86 | HTT | 12235 | GGUUGUCAAGUUUG |
| 87 | HTT | 12279 | UUUCCUGCUGGUAAU |
| 88 | HTT | 12282 | CCUGCUGGUAAUAUC |
| 89 | HTT | 12297 | GGGAAAGAUUUUAAU |
| 90 | HTT | 12309 | AAUGAAACCAGGGUA |
| 91 | HTT | 12313 | AAACCAGGGUAGAAU |
| 92 | HTT | 12331 | UUGGCAAUGCACUGA |
| 93 | HTT | 13136 | CAGUUGUUUCUAAGA |
| 94 | HTT | 13398 | GACCAGAGAUGUAUA |
| 95 | HTT | 13403 | GAGAUGUAUAUUUAA |
| 96 | HTT | 13423 | UAACUGCUGCAAACA |
| 97 | HTT | 13428 | GCUGCAAACAUUGUA |
| 98 | NTC | N/A | ACAAAUACGAUUA |

| | Active hsiRNAs | | Homology | | | Primary Screen | IC50 (nM) | |
|---|---|---|---|---|---|---|---|---|
| | Gene | Position | H. sapien | M. musculus | M. mulatta | Huntingtin mRNA Expression (% control) | Passive Uptake | Lipid-Mediated Uptake |
| 81 | HTT | 11927 | yes | | | 113.3 | N/A | N/A |
| 82 | HTT | 11947 | yes | | | 99.8 | N/A | N/A |
| 83 | HTT | 12163 | yes | | | 70.7 | N/A | N/A |
| 84 | HTT | 12218 | yes | | | 115.3 | N/A | N/A |
| 85 | HTT | 12223 | yes | | | 114.6 | N/A | N/A |
| 86 | HTT | 12235 | yes | | | 108.3 | N/A | N/A |
| 87 | HTT | 12279 | yes | | | 83.9 | N/A | N/A |
| 88 | HTT | 12282 | yes | | | 89.9 | N/A | N/A |
| 89 | HTT | 12297 | yes | | | 82.9 | N/A | N/A |
| 90 | HTT | 12309 | yes | | | 73.4 | N/A | N/A |
| 91 | HTT | 12313 | yes | | | 89.8 | N/A | N/A |
| 92 | HTT | 12331 | yes | | | 109.9 | N/A | N/A |
| 93 | HTT | 13136 | yes | | | 113.2 | N/A | N/A |
| 94 | HTT | 13398 | yes | | | 102.1 | N/A | N/A |
| 95 | HTT | 13403 | yes | | | 84.1 | N/A | N/A |
| 96 | HTT | 13423 | yes | | | 124.8 | N/A | N/A |
| 97 | HTT | 13428 | yes | | | 114.1 | N/A | N/A |
| 98 | NTC | N/A | yes | | | 102 | N/A | N/A |

*Fig. 24*
(Cont.)

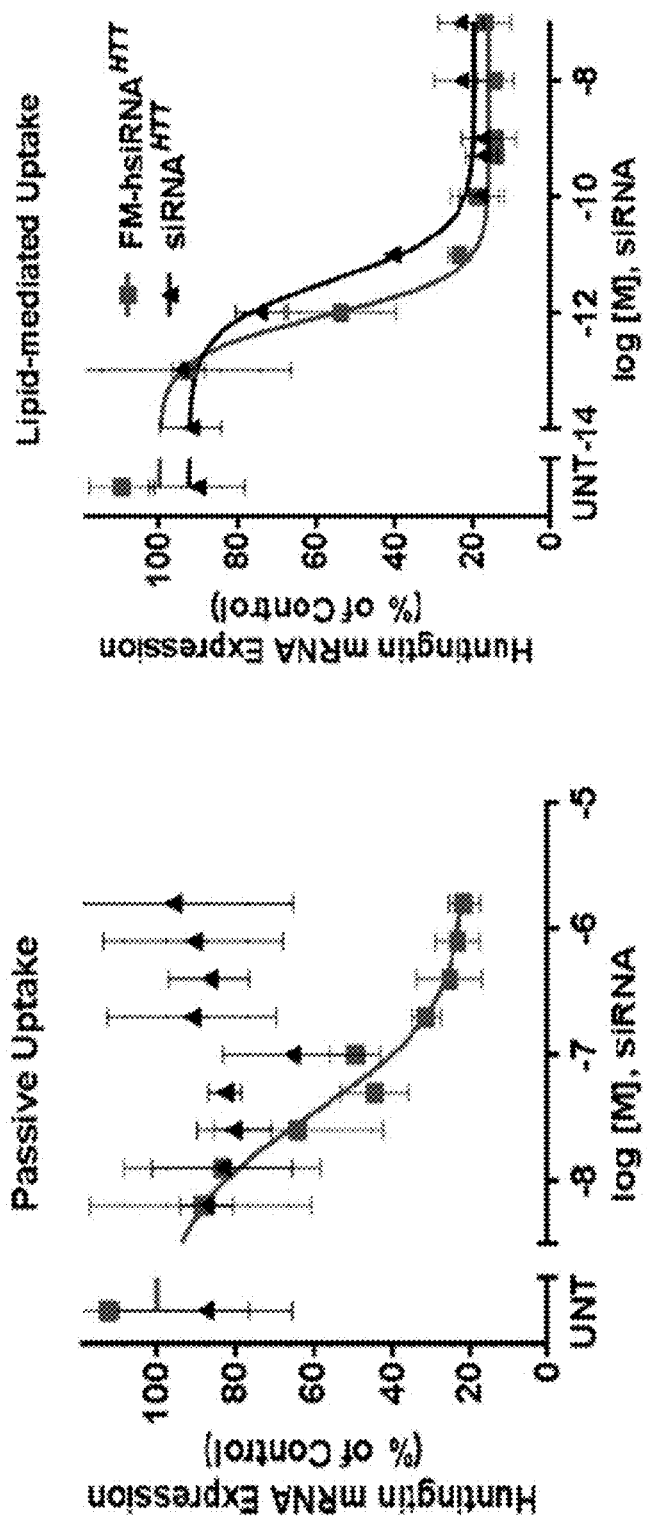

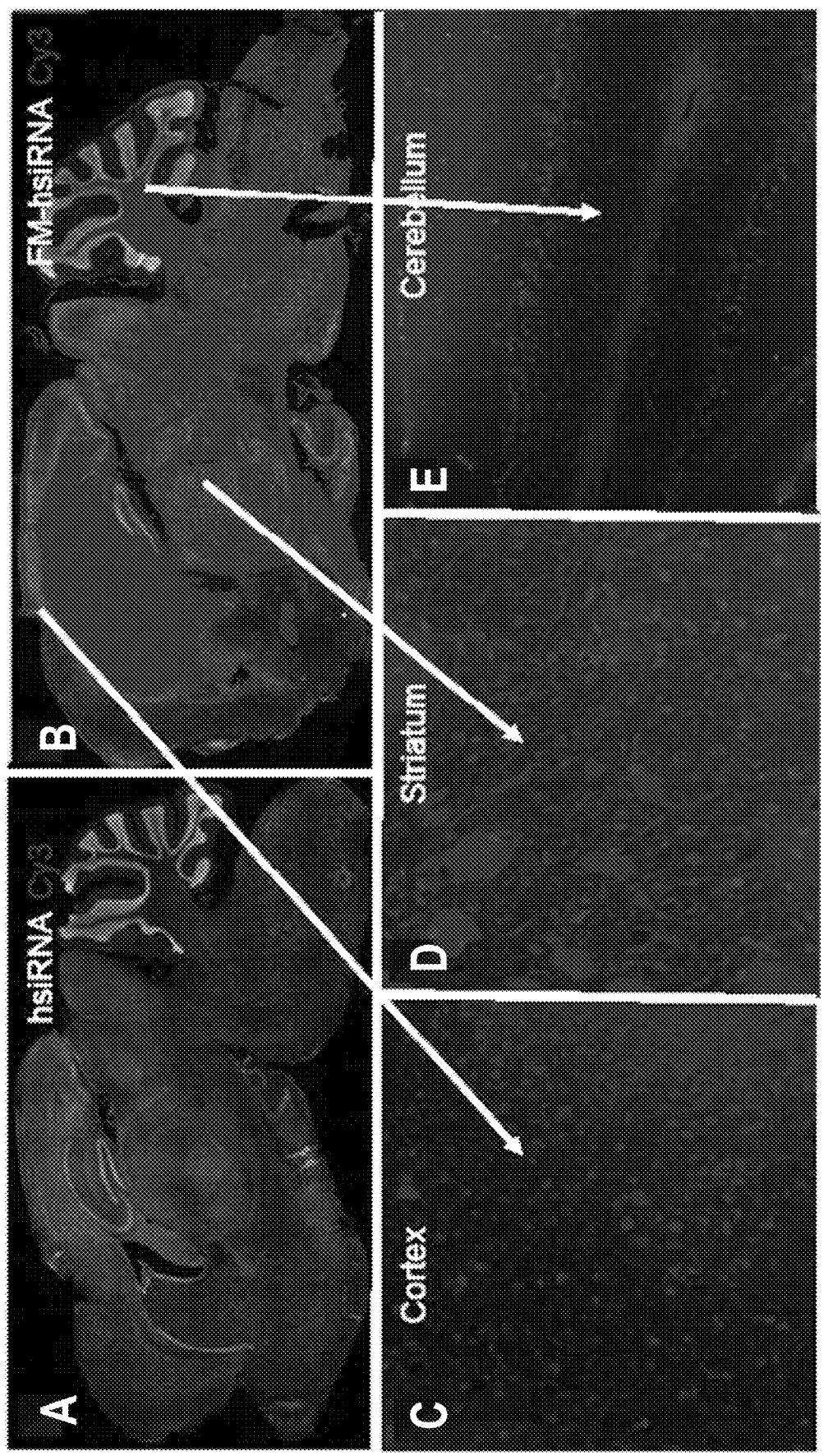
Fig. 31A-E

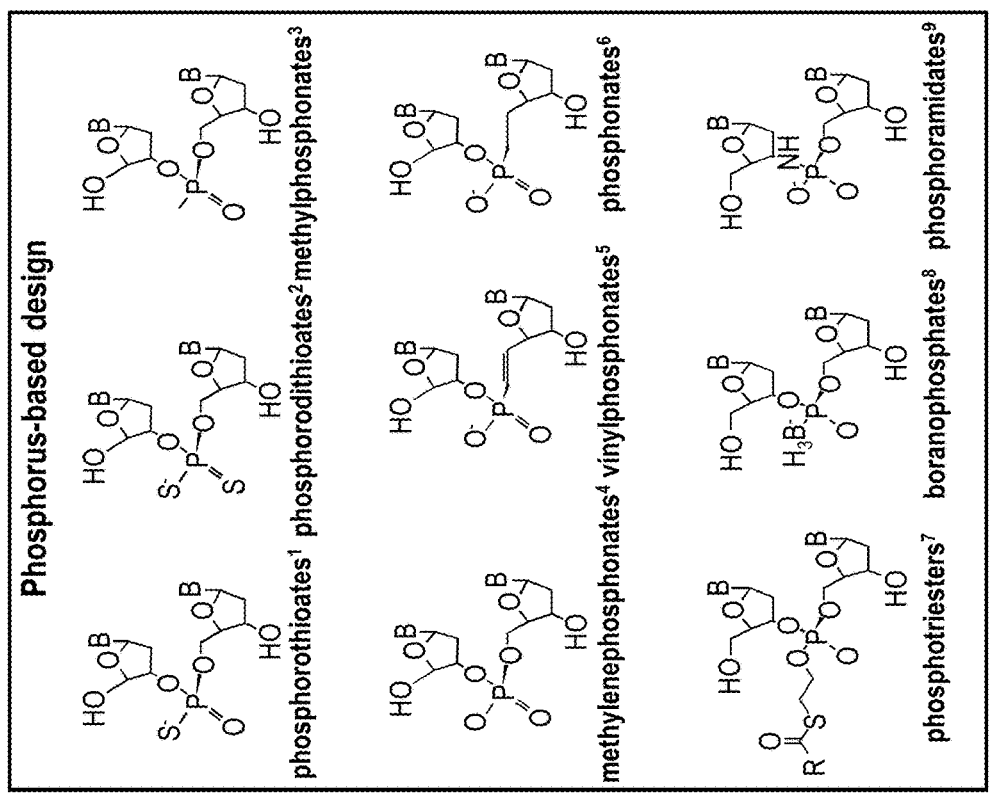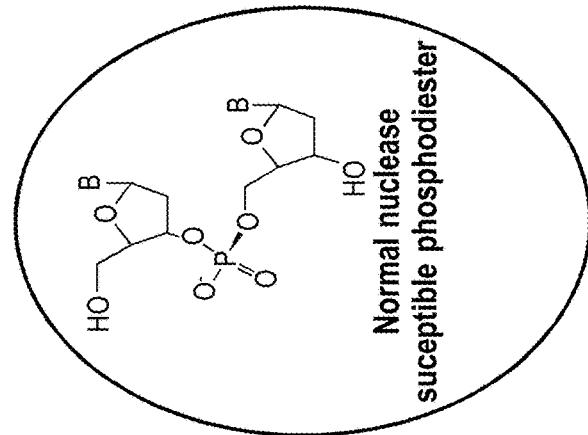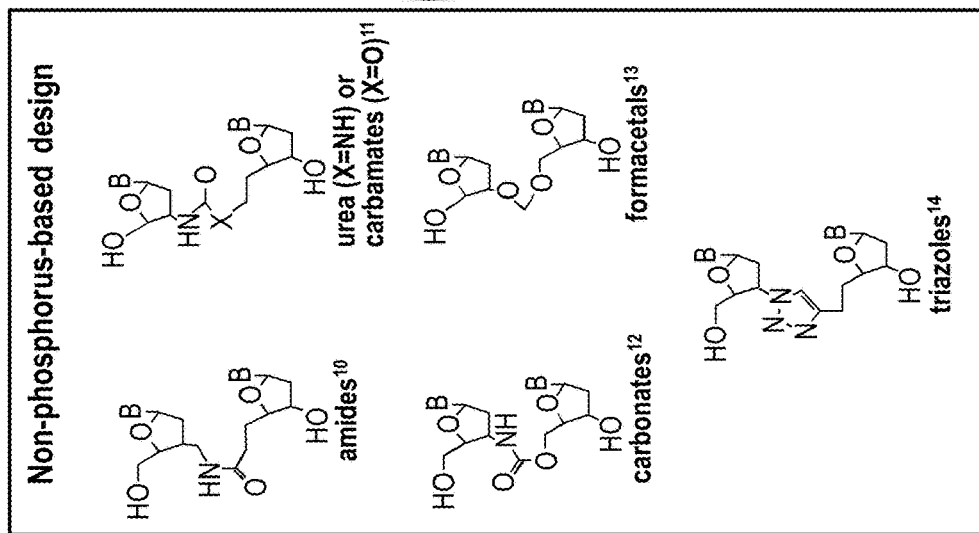
Fig. 36

SEQUENCE LISTING

```
<160> NUMBER OF SEQ ID NOS: 893

<210> SEQ ID NO 1
<211> LENGTH: 15
<212> TYPE: RNA
<213> ORGANISM: Homo sapiens

<400> SEQUENCE: 1
caguaaagag auuaa                                                          15

<210> SEQ ID NO 2
<211> LENGTH: 15
<212> TYPE: RNA
<213> ORGANISM: Homo sapiens

<400> SEQUENCE: 2
auaucaguaa agaga                                                          15

<210> SEQ ID NO 3
<211> LENGTH: 15
<212> TYPE: RNA
<213> ORGANISM: Homo sapiens

<400> SEQUENCE: 3
cucaggauuu aaaau                                                          15

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uaaauuugga gauccgagag                                                     20
```

```
<210> SEQ ID NO 5
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggaucuccaa auuua                                                          15

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uauaaauggu agcuaugaug                                                     20

<210> SEQ ID NO 7
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uagcuaccau uuaua                                                          15

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uuaaucucuu uacugauaua                                                     20

<210> SEQ ID NO 9
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
caguaaagag auuaa                                                          15

<210> SEQ ID NO 10
<211> LENGTH: 20
<212> TYPE: DNA
<213> ORGANISM: Homo sapiens

<400> SEQUENCE: 10
ctctcggatc tccaaattta                                                     20

<210> SEQ ID NO 11
<211> LENGTH: 20
<212> TYPE: DNA
<213> ORGANISM: Homo sapiens
```

<400> SEQUENCE: 11
catcatagct accatttatt                                                20

<210> SEQ ID NO 12
<211> LENGTH: 20
<212> TYPE: DNA
<213> ORGANISM: Homo sapiens

<400> SEQUENCE: 12
attgtaccac acaaagtaat                                                20

<210> SEQ ID NO 13
<211> LENGTH: 20
<212> TYPE: DNA
<213> ORGANISM: Homo sapiens

<400> SEQUENCE: 13
gagccaagac aatcataaca                                                20

<210> SEQ ID NO 14
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gaagaaagaa attacaatca gaggtgagca ctgcaacaaa aaggctgttt tctctcggat     60
ctccaaattt aaaagcacaa ggaatgattg taccacacaa agtaatgtaa aacattaaag    120
gactcattaa aaagtaacag ttgtctcata tcatcttgat ttattgtcac tgttgctaac    180
tttcaggctc ggaggagatg ctcctcccaa aatgagttcg gagatgatag cagtaataat    240
gagacccccg ggctccagct ctgggccccc cattcaggcc gaggggggctg ctccgggggg    300 ccgacttggt gcacgtttgg atttggagga tccctgcact gccttctctg tgtttgttgc    360
tcttgctgtt ttctcctgcc tgataaacaa caacttggga tgatcctttc cattttgatg    420
ccaacctctt tttattttta agcggcgccc tatagt                              456

<210> SEQ ID NO 15
<211> LENGTH: 418
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
acaacaagag cctgaactgt atacatcaac gtcaccatcg tcatcgtcat catcaccatt     60
gtcatcatca tcatcatcgt catcatcatc atcatcatag ctatcatcat tatcatcatc    120
atcatcatca tcatcatagc taccatttat tgaaaactat tatgtgtcaa cttcaaagaa    180
cttatccttt agttggagag ccaagacaat cataacaata acaaatggcc gggcatggtg    240
gctcacgcct gtaatcccag cactttggga ggccaaggca ggtggatcat ttgaggtcag    300
gagtccaaga ccagcctgac caagatggtg aaatgctgtc tctattaaaa atacaaaatt    360
agccaggcat ggtggctcat gcctgtaatg ccagctactc gggaggctga cacaggag      418

<210> SEQ ID NO 16

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
caguaaagag auuaa                                                          15

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uuaaucucuu uacugauaua                                                     20

<210> SEQ ID NO 18
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
caguaaagag auuaa                                                          15

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uuaaucucuu uacugauaua                                                     20

<210> SEQ ID NO 20
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
caguaaagag auuaa                                                          15

<210> SEQ ID NO 21
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uuaaucucuu uacugauaua                                                     20

<210> SEQ ID NO 22
<211> LENGTH: 20
```

```
<212> TYPE: RNA
<213> ORGANISM: Homo sapiens

<400> SEQUENCE: 22
aaucagaggu gagcacugca                                               20

<210> SEQ ID NO 23
<211> LENGTH: 20
<212> TYPE: RNA
<213> ORGANISM: Homo sapiens

<400> SEQUENCE: 23
gaggugagca cugcaacaaa                                               20

<210> SEQ ID NO 24
<211> LENGTH: 20
<212> TYPE: RNA
<213> ORGANISM: Homo sapiens

<400> SEQUENCE: 24
aggugagcac ugcaacaaaa                                               20

<210> SEQ ID NO 25
<211> LENGTH: 20
<212> TYPE: RNA
<213> ORGANISM: Homo sapiens

<400> SEQUENCE: 25
ugagcacugc aacaaaaagg                                               20

<210> SEQ ID NO 26
<211> LENGTH: 20
<212> TYPE: RNA
<213> ORGANISM: Homo sapiens

<400> SEQUENCE: 26
uuuucucucg gaucuccaaa                                               20

<210> SEQ ID NO 27
<211> LENGTH: 20
<212> TYPE: RNA
<213> ORGANISM: Homo sapiens

<400> SEQUENCE: 27
uuucucucgg aucuccaaau                                               20

<210> SEQ ID NO 28
<211> LENGTH: 20
<212> TYPE: RNA
<213> ORGANISM: Homo sapiens

<400> SEQUENCE: 28
cucucggauc uccaaauuua                                               20

<210> SEQ ID NO 29
<211> LENGTH: 20
<212> TYPE: RNA
<213> ORGANISM: Homo sapiens

<400> SEQUENCE: 29
ucucggaucu ccaaauuuaa                                               20

<210> SEQ ID NO 30
```

```
<211> LENGTH: 20
<212> TYPE: RNA
<213> ORGANISM: Homo sapiens

<400> SEQUENCE: 30
ucggaucucc aaauuuaaaa                                               20

<210> SEQ ID NO 31
<211> LENGTH: 20
<212> TYPE: RNA
<213> ORGANISM: Homo sapiens

<400> SEQUENCE: 31
uccaaauuua aaagcacaag                                               20

<210> SEQ ID NO 32
<211> LENGTH: 20
<212> TYPE: RNA
<213> ORGANISM: Homo sapiens

<400> SEQUENCE: 32
ccaaauuuaa aagcacaagg                                               20

<210> SEQ ID NO 33
<211> LENGTH: 20
<212> TYPE: RNA
<213> ORGANISM: Homo sapiens

<400> SEQUENCE: 33
caaauuuaaa agcacaagga                                               20

<210> SEQ ID NO 34
<211> LENGTH: 20
<212> TYPE: RNA
<213> ORGANISM: Homo sapiens

<400> SEQUENCE: 34
aagcacaagg aaugauugua                                               20

<210> SEQ ID NO 35
<211> LENGTH: 20
<212> TYPE: RNA
<213> ORGANISM: Homo sapiens

<400> SEQUENCE: 35
gaaugauugu accacacaaa                                               20

<210> SEQ ID NO 36
<211> LENGTH: 20
<212> TYPE: RNA
<213> ORGANISM: Homo sapiens

<400> SEQUENCE: 36
auuguaccac acaaaguaau                                               20

<210> SEQ ID NO 37
<211> LENGTH: 20
<212> TYPE: RNA
<213> ORGANISM: Homo sapiens

<400> SEQUENCE: 37
guaccacaca aaguaaugua                                               20
```

```
<210> SEQ ID NO 38
<211> LENGTH: 20
<212> TYPE: RNA
<213> ORGANISM: Homo sapiens

<400> SEQUENCE: 38
uaccacacaa aguaauguaa                                               20

<210> SEQ ID NO 39
<211> LENGTH: 20
<212> TYPE: RNA
<213> ORGANISM: Homo sapiens

<400> SEQUENCE: 39
ccacacaaag uaauguaaaa                                               20

<210> SEQ ID NO 40
<211> LENGTH: 20
<212> TYPE: RNA
<213> ORGANISM: Homo sapiens

<400> SEQUENCE: 40
acacaaagua auguaaaaca                                               20

<210> SEQ ID NO 41
<211> LENGTH: 20
<212> TYPE: RNA
<213> ORGANISM: Homo sapiens

<400> SEQUENCE: 41
aguaauguaa aacauuaaag                                               20

<210> SEQ ID NO 42
<211> LENGTH: 20
<212> TYPE: RNA
<213> ORGANISM: Homo sapiens

<400> SEQUENCE: 42
guaauguaaa acauuaaagg                                               20

<210> SEQ ID NO 43
<211> LENGTH: 20
<212> TYPE: RNA
<213> ORGANISM: Homo sapiens

<400> SEQUENCE: 43
uaaaacauua aaggacucau                                               20

<210> SEQ ID NO 44
<211> LENGTH: 20
<212> TYPE: RNA
<213> ORGANISM: Homo sapiens

<400> SEQUENCE: 44
acauuaaagg acucauuaaa                                               20

<210> SEQ ID NO 45
<211> LENGTH: 20
<212> TYPE: RNA
<213> ORGANISM: Homo sapiens

<400> SEQUENCE: 45
ggacucauua aaaaguaaca                                               20
```

```
<210> SEQ ID NO 46
<211> LENGTH: 20
<212> TYPE: RNA
<213> ORGANISM: Homo sapiens

<400> SEQUENCE: 46
acucauuaaa aaguaacagu                                               20

<210> SEQ ID NO 47
<211> LENGTH: 20
<212> TYPE: RNA
<213> ORGANISM: Homo sapiens

<400> SEQUENCE: 47
aaaguaacag uugucucaua                                               20

<210> SEQ ID NO 48
<211> LENGTH: 20
<212> TYPE: RNA
<213> ORGANISM: Homo sapiens

<400> SEQUENCE: 48
caucaucauc aucauagcua                                               20

<210> SEQ ID NO 49
<211> LENGTH: 20
<212> TYPE: RNA
<213> ORGANISM: Homo sapiens

<400> SEQUENCE: 49
caucaucauc auagcuauca                                               20

<210> SEQ ID NO 50
<211> LENGTH: 20
<212> TYPE: RNA
<213> ORGANISM: Homo sapiens

<400> SEQUENCE: 50
caucaucaua gcuaucauca                                               20

<210> SEQ ID NO 51
<211> LENGTH: 20
<212> TYPE: RNA
<213> ORGANISM: Homo sapiens

<400> SEQUENCE: 51
aucaucauca ucaucauagc                                               20

<210> SEQ ID NO 52
<211> LENGTH: 20
<212> TYPE: RNA
<213> ORGANISM: Homo sapiens

<400> SEQUENCE: 52
caucaucauc aucauagcua                                               20

<210> SEQ ID NO 53
<211> LENGTH: 20
<212> TYPE: RNA
<213> ORGANISM: Homo sapiens

<400> SEQUENCE: 53
caucaucauc auagcuacca                                               20
```

<210> SEQ ID NO 54
<211> LENGTH: 20
<212> TYPE: RNA
<213> ORGANISM: Homo sapiens

<400> SEQUENCE: 54
ucaucauagc uaccauuuau                                               20

<210> SEQ ID NO 55
<211> LENGTH: 20
<212> TYPE: RNA
<213> ORGANISM: Homo sapiens

<400> SEQUENCE: 55
caucauagcu accauuuauu                                               20

<210> SEQ ID NO 56
<211> LENGTH: 20
<212> TYPE: RNA
<213> ORGANISM: Homo sapiens

<400> SEQUENCE: 56
agcuaccauu uauugaaaac                                               20

<210> SEQ ID NO 57
<211> LENGTH: 20
<212> TYPE: RNA
<213> ORGANISM: Homo sapiens

<400> SEQUENCE: 57
uaccauuuau ugaaaacuau                                               20

<210> SEQ ID NO 58
<211> LENGTH: 20
<212> TYPE: RNA
<213> ORGANISM: Homo sapiens

<400> SEQUENCE: 58
aacuucaaag aacuuauccu                                               20

<210> SEQ ID NO 59
<211> LENGTH: 20
<212> TYPE: RNA
<213> ORGANISM: Homo sapiens

<400> SEQUENCE: 59
caaagaacuu auccuuuagu                                               20

<210> SEQ ID NO 60
<211> LENGTH: 20
<212> TYPE: RNA
<213> ORGANISM: Homo sapiens

<400> SEQUENCE: 60
uccuuuaguu ggagagccaa                                               20

<210> SEQ ID NO 61
<211> LENGTH: 20
<212> TYPE: RNA
<213> ORGANISM: Homo sapiens

<400> SEQUENCE: 61
cuuuaguugg agagccaaga          20

<210> SEQ ID NO 62
<211> LENGTH: 20
<212> TYPE: RNA
<213> ORGANISM: Homo sapiens

<400> SEQUENCE: 62
uuaguuggag agccaagaca          20

<210> SEQ ID NO 63
<211> LENGTH: 20
<212> TYPE: RNA
<213> ORGANISM: Homo sapiens

<400> SEQUENCE: 63
uaguuggaga gccaagacaa          20

<210> SEQ ID NO 64
<211> LENGTH: 20
<212> TYPE: RNA
<213> ORGANISM: Homo sapiens

<400> SEQUENCE: 64
uuggagagcc aagacaauca          20

<210> SEQ ID NO 65
<211> LENGTH: 20
<212> TYPE: RNA
<213> ORGANISM: Homo sapiens

<400> SEQUENCE: 65
ggagagccaa gacaaucaua          20

<210> SEQ ID NO 66
<211> LENGTH: 20
<212> TYPE: RNA
<213> ORGANISM: Homo sapiens

<400> SEQUENCE: 66
gagccaagac aaucauaaca          20

<210> SEQ ID NO 67
<211> LENGTH: 20
<212> TYPE: RNA
<213> ORGANISM: Homo sapiens

<400> SEQUENCE: 67
ccaagacaau cauaacaaua          20

<210> SEQ ID NO 68
<211> LENGTH: 20
<212> TYPE: RNA
<213> ORGANISM: Homo sapiens

<400> SEQUENCE: 68
aagacaauca uaacaauaac          20

<210> SEQ ID NO 69
<211> LENGTH: 20
<212> TYPE: RNA
<213> ORGANISM: Homo sapiens

<400> SEQUENCE: 69

| | |
|---|---|
| agcugucugc uucucacagg | 20 |

<210> SEQ ID NO 70
<211> LENGTH: 20
<212> TYPE: RNA
<213> ORGANISM: Homo sapiens

<400> SEQUENCE: 70

| | |
|---|---|
| gauccugaac ugaguuuaaa | 20 |

<210> SEQ ID NO 71
<211> LENGTH: 20
<212> TYPE: RNA
<213> ORGANISM: Homo sapiens

<400> SEQUENCE: 71

| | |
|---|---|
| auccugaacu gaguuuaaaa | 20 |

<210> SEQ ID NO 72
<211> LENGTH: 20
<212> TYPE: RNA
<213> ORGANISM: Homo sapiens

<400> SEQUENCE: 72

| | |
|---|---|
| ugaacugagu uuaaaaggca | 20 |

<210> SEQ ID NO 73
<211> LENGTH: 20
<212> TYPE: RNA
<213> ORGANISM: Homo sapiens

<400> SEQUENCE: 73

| | |
|---|---|
| guuuaaaagg cacccagcac | 20 |

<210> SEQ ID NO 74
<211> LENGTH: 20
<212> TYPE: RNA
<213> ORGANISM: Homo sapiens

<400> SEQUENCE: 74

| | |
|---|---|
| aucaaaugca acguacaaag | 20 |

<210> SEQ ID NO 75
<211> LENGTH: 20
<212> TYPE: RNA
<213> ORGANISM: Homo sapiens

<400> SEQUENCE: 75

| | |
|---|---|
| ucaaaugcaa cguacaaaga | 20 |

<210> SEQ ID NO 76
<211> LENGTH: 20
<212> TYPE: RNA
<213> ORGANISM: Homo sapiens

<400> SEQUENCE: 76

| | |
|---|---|
| guuguauggu uaaaagaugg | 20 |

<210> SEQ ID NO 77
<211> LENGTH: 20
<212> TYPE: RNA
<213> ORGANISM: Homo sapiens

```
<400> SEQUENCE: 77
uuuaaaaacc ucacugccac                                              20

<210> SEQ ID NO 78
<211> LENGTH: 20
<212> TYPE: RNA
<213> ORGANISM: Homo sapiens

<400> SEQUENCE: 78
uaaaaaccuc acugccacuc                                              20

<210> SEQ ID NO 79
<211> LENGTH: 20
<212> TYPE: RNA
<213> ORGANISM: Homo sapiens

<400> SEQUENCE: 79
aaaaccucac ugccacucua                                              20

<210> SEQ ID NO 80
<211> LENGTH: 20
<212> TYPE: RNA
<213> ORGANISM: Homo sapiens

<400> SEQUENCE: 80
gaaacagaau ugagagcauc                                              20

<210> SEQ ID NO 81
<211> LENGTH: 30
<212> TYPE: RNA
<213> ORGANISM: Homo sapiens

<400> SEQUENCE: 81
auuacaauca gaggugagca cugcaacaaa                                   30

<210> SEQ ID NO 82
<211> LENGTH: 30
<212> TYPE: RNA
<213> ORGANISM: Homo sapiens

<400> SEQUENCE: 82
aaucagaggu gagcacugca acaaaaaggc                                   30

<210> SEQ ID NO 83
<211> LENGTH: 30
<212> TYPE: RNA
<213> ORGANISM: Homo sapiens

<400> SEQUENCE: 83
aucagaggug agcacugcaa caaaaaggcu                                   30

<210> SEQ ID NO 84
<211> LENGTH: 30
<212> TYPE: RNA
<213> ORGANISM: Homo sapiens

<400> SEQUENCE: 84
agaggugagc acugcaacaa aaaggcuguu                                   30

<210> SEQ ID NO 85
<211> LENGTH: 30
<212> TYPE: RNA
<213> ORGANISM: Homo sapiens
```

```
<400> SEQUENCE: 85
ggcuguuuuc ucucggaucu ccaaauuuaa                              30

<210> SEQ ID NO 86
<211> LENGTH: 30
<212> TYPE: RNA
<213> ORGANISM: Homo sapiens

<400> SEQUENCE: 86
gcuguuuucu cucggaucuc caaauuuaaa                              30

<210> SEQ ID NO 87
<211> LENGTH: 30
<212> TYPE: RNA
<213> ORGANISM: Homo sapiens

<400> SEQUENCE: 87
guuuucucuc ggaucuccaa auuuaaaagc                              30

<210> SEQ ID NO 88
<211> LENGTH: 30
<212> TYPE: RNA
<213> ORGANISM: Homo sapiens

<400> SEQUENCE: 88
uuuucucucg gaucuccaaa uuuaaaagca                              30

<210> SEQ ID NO 89
<211> LENGTH: 30
<212> TYPE: RNA
<213> ORGANISM: Homo sapiens

<400> SEQUENCE: 89
uucucucgga ucuccaaauu uaaaagcaca                              30

<210> SEQ ID NO 90
<211> LENGTH: 30
<212> TYPE: RNA
<213> ORGANISM: Homo sapiens

<400> SEQUENCE: 90
ggaucuccaa auuuaaaagc acaaggaaug                              30

<210> SEQ ID NO 91
<211> LENGTH: 30
<212> TYPE: RNA
<213> ORGANISM: Homo sapiens

<400> SEQUENCE: 91
gaucuccaaa uuuaaaagca caaggaauga                              30

<210> SEQ ID NO 92
<211> LENGTH: 30
<212> TYPE: RNA
<213> ORGANISM: Homo sapiens

<400> SEQUENCE: 92
aucuccaaau uuaaaagcac aaggaaugau                              30

<210> SEQ ID NO 93
<211> LENGTH: 30
<212> TYPE: RNA
```

```
<213> ORGANISM: Homo sapiens

<400> SEQUENCE: 93
uuuaaaagca caaggaauga uuguaccaca                                    30

<210> SEQ ID NO 94
<211> LENGTH: 30
<212> TYPE: RNA
<213> ORGANISM: Homo sapiens

<400> SEQUENCE: 94
acaaggaaug auuguaccac acaaaguaau                                    30

<210> SEQ ID NO 95
<211> LENGTH: 30
<212> TYPE: RNA
<213> ORGANISM: Homo sapiens

<400> SEQUENCE: 95
gaaugauugu accacacaaa guaauguaaa                                    30

<210> SEQ ID NO 96
<211> LENGTH: 30
<212> TYPE: RNA
<213> ORGANISM: Homo sapiens

<400> SEQUENCE: 96
ugauuguacc acacaaagua auguaaaaca                                    30

<210> SEQ ID NO 97
<211> LENGTH: 30
<212> TYPE: RNA
<213> ORGANISM: Homo sapiens

<400> SEQUENCE: 97
gauuguacca cacaaaguaa uguaaaacau                                    30

<210> SEQ ID NO 98
<211> LENGTH: 30
<212> TYPE: RNA
<213> ORGANISM: Homo sapiens

<400> SEQUENCE: 98
uuguaccaca caaaguaaug uaaaacauua                                    30

<210> SEQ ID NO 99
<211> LENGTH: 30
<212> TYPE: RNA
<213> ORGANISM: Homo sapiens

<400> SEQUENCE: 99
guaccacaca aaguaaugua aaacauuaaa                                    30

<210> SEQ ID NO 100
<211> LENGTH: 30
<212> TYPE: RNA
<213> ORGANISM: Homo sapiens

<400> SEQUENCE: 100
cacaaaguaa uguaaaacau uaaaggacuc                                    30

<210> SEQ ID NO 101
<211> LENGTH: 30
```

```
<212> TYPE: RNA
<213> ORGANISM: Homo sapiens

<400> SEQUENCE: 101
acaaaguaau guaaaacauu aaaggacuca                                30

<210> SEQ ID NO 102
<211> LENGTH: 30
<212> TYPE: RNA
<213> ORGANISM: Homo sapiens

<400> SEQUENCE: 102
uaauguaaaa cauuaaagga cucauuaaaa                                30

<210> SEQ ID NO 103
<211> LENGTH: 30
<212> TYPE: RNA
<213> ORGANISM: Homo sapiens

<400> SEQUENCE: 103
guaaaacauu aaaggacuca uuaaaaagua                                30

<210> SEQ ID NO 104
<211> LENGTH: 30
<212> TYPE: RNA
<213> ORGANISM: Homo sapiens

<400> SEQUENCE: 104
uuaaaggacu cauuaaaaag uaacaguugu                                30

<210> SEQ ID NO 105
<211> LENGTH: 30
<212> TYPE: RNA
<213> ORGANISM: Homo sapiens

<400> SEQUENCE: 105
aaaggacuca uuaaaaagua acaguugucu                                30

<210> SEQ ID NO 106
<211> LENGTH: 30
<212> TYPE: RNA
<213> ORGANISM: Homo sapiens

<400> SEQUENCE: 106
auuaaaaagu aacaguuguc ucauaucauc                                30

<210> SEQ ID NO 107
<211> LENGTH: 30
<212> TYPE: RNA
<213> ORGANISM: Homo sapiens

<400> SEQUENCE: 107
gucaucauca ucaucaucau agcuaucauc                                30

<210> SEQ ID NO 108
<211> LENGTH: 30
<212> TYPE: RNA
<213> ORGANISM: Homo sapiens

<400> SEQUENCE: 108
aucaucauca ucaucauagc uaucaucauu                                30

<210> SEQ ID NO 109
```

```
<211> LENGTH: 30
<212> TYPE: RNA
<213> ORGANISM: Homo sapiens

<400> SEQUENCE: 109
aucaucauca ucauagcuau caucauuauc                                          30

<210> SEQ ID NO 110
<211> LENGTH: 30
<212> TYPE: RNA
<213> ORGANISM: Homo sapiens

<400> SEQUENCE: 110
ucaucaucau caucaucauc auagcuacca                                          30

<210> SEQ ID NO 111
<211> LENGTH: 30
<212> TYPE: RNA
<213> ORGANISM: Homo sapiens

<400> SEQUENCE: 111
aucaucauca ucaucaucau agcuaccauu                                          30

<210> SEQ ID NO 112
<211> LENGTH: 30
<212> TYPE: RNA
<213> ORGANISM: Homo sapiens

<400> SEQUENCE: 112
aucaucauca ucaucauagc uaccauuuau                                          30

<210> SEQ ID NO 113
<211> LENGTH: 30
<212> TYPE: RNA
<213> ORGANISM: Homo sapiens

<400> SEQUENCE: 113
caucaucauc auagcuacca uuuauugaaa                                          30

<210> SEQ ID NO 114
<211> LENGTH: 30
<212> TYPE: RNA
<213> ORGANISM: Homo sapiens

<400> SEQUENCE: 114
aucaucauca uagcuaccau uuauugaaaa                                          30

<210> SEQ ID NO 115
<211> LENGTH: 30
<212> TYPE: RNA
<213> ORGANISM: Homo sapiens

<400> SEQUENCE: 115
aucauagcua ccauuuauug aaaacuauua                                          30

<210> SEQ ID NO 116
<211> LENGTH: 30
<212> TYPE: RNA
<213> ORGANISM: Homo sapiens

<400> SEQUENCE: 116
auagcuacca uuuauugaaa acuauuaugu                                          30
```

```
<210> SEQ ID NO 117
<211> LENGTH: 30
<212> TYPE: RNA
<213> ORGANISM: Homo sapiens

<400> SEQUENCE: 117
gugucaacuu caaagaacuu auccuuuagu                                        30

<210> SEQ ID NO 118
<211> LENGTH: 30
<212> TYPE: RNA
<213> ORGANISM: Homo sapiens

<400> SEQUENCE: 118
aacuucaaag aacuuauccu uuaguuggag                                        30

<210> SEQ ID NO 119
<211> LENGTH: 30
<212> TYPE: RNA
<213> ORGANISM: Homo sapiens

<400> SEQUENCE: 119
acuuauccuu uaguuggaga gccaagacaa                                        30

<210> SEQ ID NO 120
<211> LENGTH: 30
<212> TYPE: RNA
<213> ORGANISM: Homo sapiens

<400> SEQUENCE: 120
uuauccuuua guuggagagc caagacaauc                                        30

<210> SEQ ID NO 121
<211> LENGTH: 30
<212> TYPE: RNA
<213> ORGANISM: Homo sapiens

<400> SEQUENCE: 121
auccuuuagu uggagagcca agacaaucau                                        30

<210> SEQ ID NO 122
<211> LENGTH: 30
<212> TYPE: RNA
<213> ORGANISM: Homo sapiens

<400> SEQUENCE: 122
uccuuuaguu ggagagccaa gacaaucaua                                        30

<210> SEQ ID NO 123
<211> LENGTH: 30
<212> TYPE: RNA
<213> ORGANISM: Homo sapiens

<400> SEQUENCE: 123
uuuaguugga gagccaagac aaucauaaca                                        30

<210> SEQ ID NO 124
<211> LENGTH: 30
<212> TYPE: RNA
<213> ORGANISM: Homo sapiens

<400> SEQUENCE: 124
uaguuggaga gccaagacaa ucauaacaau                                        30
```

```
<210> SEQ ID NO 125
<211> LENGTH: 30
<212> TYPE: RNA
<213> ORGANISM: Homo sapiens

<400> SEQUENCE: 125
uuggagagcc aagacaauca uaacaauaac                                          30

<210> SEQ ID NO 126
<211> LENGTH: 30
<212> TYPE: RNA
<213> ORGANISM: Homo sapiens

<400> SEQUENCE: 126
gagagccaag acaaucauaa caauaacaaa                                          30

<210> SEQ ID NO 127
<211> LENGTH: 30
<212> TYPE: RNA
<213> ORGANISM: Homo sapiens

<400> SEQUENCE: 127
gagccaagac aaucauaaca auaacaaaug                                          30

<210> SEQ ID NO 128
<211> LENGTH: 30
<212> TYPE: RNA
<213> ORGANISM: Homo sapiens

<400> SEQUENCE: 128
ugcucagcug ucugcuucuc acaggaucua                                          30

<210> SEQ ID NO 129
<211> LENGTH: 30
<212> TYPE: RNA
<213> ORGANISM: Homo sapiens

<400> SEQUENCE: 129
uaaaagaucc ugaacugagu uuaaaaggca                                          30

<210> SEQ ID NO 130
<211> LENGTH: 30
<212> TYPE: RNA
<213> ORGANISM: Homo sapiens

<400> SEQUENCE: 130
aaaagauccu gaacugaguu uaaaaggcac                                          30

<210> SEQ ID NO 131
<211> LENGTH: 30
<212> TYPE: RNA
<213> ORGANISM: Homo sapiens

<400> SEQUENCE: 131
gauccugaac ugaguuuaaa aggcacccag                                          30

<210> SEQ ID NO 132
<211> LENGTH: 30
<212> TYPE: RNA
<213> ORGANISM: Homo sapiens

<400> SEQUENCE: 132
acugaguuua aaaggcaccc agcacaucau                                          30
```

<210> SEQ ID NO 133
<211> LENGTH: 30
<212> TYPE: RNA
<213> ORGANISM: Homo sapiens

<400> SEQUENCE: 133
aucauaucaa augcaacgua caaagaaaua                                      30

<210> SEQ ID NO 134
<211> LENGTH: 30
<212> TYPE: RNA
<213> ORGANISM: Homo sapiens

<400> SEQUENCE: 134
ucauaucaaa ugcaacguac aaagaaauag                                      30

<210> SEQ ID NO 135
<211> LENGTH: 30
<212> TYPE: RNA
<213> ORGANISM: Homo sapiens

<400> SEQUENCE: 135
cggaaguugu augguaaaaa gauggguuac                                      30

<210> SEQ ID NO 136
<211> LENGTH: 30
<212> TYPE: RNA
<213> ORGANISM: Homo sapiens

<400> SEQUENCE: 136
auguguuuaa aaaccucacu gccacucuaa                                      30

<210> SEQ ID NO 137
<211> LENGTH: 30
<212> TYPE: RNA
<213> ORGANISM: Homo sapiens

<400> SEQUENCE: 137
guguuuaaaa accucacugc cacucuaauu                                      30

<210> SEQ ID NO 138
<211> LENGTH: 30
<212> TYPE: RNA
<213> ORGANISM: Homo sapiens

<400> SEQUENCE: 138
guuuaaaaac cucacugcca cucuaauugu                                      30

<210> SEQ ID NO 139
<211> LENGTH: 30
<212> TYPE: RNA
<213> ORGANISM: Homo sapiens

<400> SEQUENCE: 139
caugggaaac agaauugaga gcaucacuca                                      30

<210> SEQ ID NO 140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aaucagaggu gagcacugca                                              20

<210> SEQ ID NO 141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gaggugagca cugcaacaaa                                              20

<210> SEQ ID NO 142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
aggugagcac ugcaacaaaa                                              20

<210> SEQ ID NO 143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ugagcacugc aacaaaaagg                                              20

<210> SEQ ID NO 144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
uuuucucucg gaucuccaaa                                              20

<210> SEQ ID NO 145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uuucucucgg aucuccaaau                                              20

<210> SEQ ID NO 146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 146
cucucggauc uccaaauuua                                               20

<210> SEQ ID NO 147
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ucucggaucu ccaaauuuaa                                               20

<210> SEQ ID NO 148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ucggaucucc aaauuuaaaa                                               20

<210> SEQ ID NO 149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
uccaaauuua aaagcacaag                                               20

<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ccaaauuuaa aagcacaagg                                               20

<210> SEQ ID NO 151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
caaauuuaaa agcacaagga                                               20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
```
aagcacaagg aaugauugua                                              20

<210> SEQ ID NO 153
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gaaugauugu accacacaaa                                              20

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
auuguaccac acaaaguaau                                              20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
guaccacaca aaguaaugua                                              20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uaccacacaa aguaauguaa                                              20

<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ccacacaaag uaauguaaaa                                              20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
acacaaagua auguaaaaca                                               20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
aguaauguaa aacauuaaag                                               20

<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
guaauguaaa acauuaaagg                                               20

<210> SEQ ID NO 161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uaaaacauua aaggacucau                                               20

<210> SEQ ID NO 162
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
acauuaaagg acucauuaaa                                               20

<210> SEQ ID NO 163
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ggacucauua aaaguaaca                                                20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
acucauuaaa aaguaacagu                                               20

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aaaguaacag uugucucaua                                                    20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
caucaucauc aucauagcua                                                    20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
caucaucauc auagcuauca                                                    20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
caucaucaua gcuaucauca                                                    20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aucaucauca ucaucauagc                                                    20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
caucaucauc aucauagcua                                                    20

```
<210> SEQ ID NO 171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
caucaucauc auagcuacca                                                     20

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
ucaucauagc uaccauuuau                                                     20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
caucauagcu accauuuauu                                                     20

<210> SEQ ID NO 174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
agcuaccauu uauugaaaac                                                     20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uaccauuuau ugaaaacuau                                                     20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
aacuucaaag aacuuauccu                                                     20
```

```
<210> SEQ ID NO 177
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
caaagaacuu auccuuuagu                                                      20

<210> SEQ ID NO 178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
uccuuuaguu ggagagccaa                                                      20

<210> SEQ ID NO 179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
cuuuaguugg agagccaaga                                                      20

<210> SEQ ID NO 180
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uuaguuggag agccaagaca                                                      20

<210> SEQ ID NO 181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uaguuggaga gccaagacaa                                                      20

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uuggagagcc aagacaauca                                                      20

<210> SEQ ID NO 183
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
ggagagccaa gacaaucaua                                               20

<210> SEQ ID NO 184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gagccaagac aaucauaaca                                               20

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
ccaagacaau cauaacaaua                                               20

<210> SEQ ID NO 186
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
aagacaauca uaacaauaac                                               20

<210> SEQ ID NO 187
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
agcugucugc uucucacagg                                               20

<210> SEQ ID NO 188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gauccugaac ugaguuuaaa                                               20

<210> SEQ ID NO 189
<211> LENGTH: 20
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189 auccgaacu gaguuuaaaa                                                  20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
ugaacugagu uuaaaaggca                                                 20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
guuuaaaagg cacccagcac                                                 20

<210> SEQ ID NO 192
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
aucaaaugca acguacaaag                                                 20

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
ucaaaugcaa cguacaaaga                                                 20

<210> SEQ ID NO 194
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
guuguauggu uaaaagaugg                                                 20

<210> SEQ ID NO 195
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 195
uuuaaaaacc ucacugccac                                                      20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uaaaaaccuc acugccacuc                                                      20

<210> SEQ ID NO 197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
aaaaccucac ugccacucua                                                      20

<210> SEQ ID NO 198
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gaaacagaau ugagagcauc                                                      20

<210> SEQ ID NO 199
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
ugcagugcuc accucugauu                                                      20

<210> SEQ ID NO 200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uuuguugcag ugcucaccuc                                                      20

<210> SEQ ID NO 201
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 201
uuuuguugca gugcucaccu                                                   20

<210> SEQ ID NO 202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ccuuuuuguu gcagugcuca                                                   20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uuuggagauc cgagagaaaa                                                   20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
auuuggagau ccgagagaaa                                                   20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uaaauuugga gauccgagag                                                   20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uuaaauuugg agauccgaga                                                   20

<210> SEQ ID NO 207
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 207
uuuuaaauuu ggagauccga                                           20

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
cuugugcuuu uaaauuugga                                           20

<210> SEQ ID NO 209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
ccuugugcuu uuaaauuugg                                           20

<210> SEQ ID NO 210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
uccuugugcu uuuaaauuug                                           20

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
uacaaucauu ccuugugcuu                                           20

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
uuuguguggu acaaucauuc                                           20

<210> SEQ ID NO 213
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 213
auuacuuugu gugguacaau                                             20

<210> SEQ ID NO 214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
uacauuacuu uguguggua c                                            20

<210> SEQ ID NO 215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uuacauuacu uuguguggua                                             20

<210> SEQ ID NO 216
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
uuuuacauua cuuugugugg                                             20

<210> SEQ ID NO 217
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uguuuuacau uacuuugugu                                             20

<210> SEQ ID NO 218
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
cuuuaauguu uuacauuacu                                             20

<210> SEQ ID NO 219
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
ccuuuaaugu uuuacauuac                                           20

<210> SEQ ID NO 220
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
augaguccuu uaauguuuua                                           20

<210> SEQ ID NO 221
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
uuuaaugagu ccuuuaaugu                                           20

<210> SEQ ID NO 222
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
uguuacuuuu uaaugagucc                                           20

<210> SEQ ID NO 223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
acuguuacuu uuuaaugagu                                           20

<210> SEQ ID NO 224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uaugagacaa cuguuacuuu                                           20

<210> SEQ ID NO 225
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 225
uagcuaugau gaugaugaug                                              20

<210> SEQ ID NO 226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ugauagcuau gaugaugaug                                              20

<210> SEQ ID NO 227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
ugaugauagc uaugaugaug                                              20

<210> SEQ ID NO 228
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
gcuaugauga ugaugaugau                                              20

<210> SEQ ID NO 229
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uagcuaugau gaugaugaug                                              20

<210> SEQ ID NO 230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
ugguagcuau gaugaugaug                                              20

<210> SEQ ID NO 231
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
```
auaaauggua gcuaugauga                                            20

<210> SEQ ID NO 232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
aauaaauggu agcuaugaug                                            20

<210> SEQ ID NO 233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233 guuucaaua aaugguagcu                                             20

<210> SEQ ID NO 234
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
auaguuuuca auaaauggua                                            20

<210> SEQ ID NO 235
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
aggauaaguu cuuugaaguu                                            20

<210> SEQ ID NO 236
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
acuaaaggau aaguucuuug                                            20

<210> SEQ ID NO 237
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
uuggcucucc aacuaaagga                                             20

<210> SEQ ID NO 238
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
ucuuggcucu ccaacuaaag                                             20

<210> SEQ ID NO 239
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
ugucuuggcu cuccaacuaa                                             20

<210> SEQ ID NO 240
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uugucuuggc ucccaacua                                              20

<210> SEQ ID NO 241
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ugauugucuu ggcucuccaa                                             20

<210> SEQ ID NO 242
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
uaugauuguc uuggcucucc                                             20

<210> SEQ ID NO 243
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
uguuaugauu gucuuggcuc                                             20

```
<210> SEQ ID NO 244
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uauuguuaug auugucuugg                                               20

<210> SEQ ID NO 245
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
guuauuguua ugauugucuu                                               20

<210> SEQ ID NO 246
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
ccugugagaa gcagacagcu                                               20

<210> SEQ ID NO 247
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
uuuaaacuca guucaggauc                                               20

<210> SEQ ID NO 248
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uuuuaaacuc aguucaggau                                               20

<210> SEQ ID NO 249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ugccuuuuaa acucaguuca                                               20
```

<210> SEQ ID NO 250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gugcugggug ccuuuuaaac                                               20

<210> SEQ ID NO 251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
cuuuguacgu ugcauuugau                                               20

<210> SEQ ID NO 252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ucuuuguacg uugcauuuga                                               20

<210> SEQ ID NO 253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ccaucuuuua accauacaac                                               20

<210> SEQ ID NO 254
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
guggcaguga gguuuuuaaa                                               20

<210> SEQ ID NO 255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gaguggcagu gagguuuuua                                               20

```
<210> SEQ ID NO 256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
uagaguggca gugagguuuu                                                   20

<210> SEQ ID NO 257
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gaugcucuca auucuguuuc                                                   20

<210> SEQ ID NO 258
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
aaucagaggu gagca                                                        15

<210> SEQ ID NO 259
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gaggugagca cugca                                                        15

<210> SEQ ID NO 260
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
aggugagcac ugcaa                                                        15

<210> SEQ ID NO 261
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
ugagcacugc aacaa                                                        15

<210> SEQ ID NO 262
```

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
uuuucucucg gaucu                                                          15

<210> SEQ ID NO 263
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
uuucucucgg aucuc                                                          15

<210> SEQ ID NO 264
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
cucucggauc uccaa                                                          15

<210> SEQ ID NO 265
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ucucggaucu ccaaa                                                          15

<210> SEQ ID NO 266
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ucggaucucc aaauu                                                          15

<210> SEQ ID NO 267
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
uccaaauuua aaagc                                                          15

<210> SEQ ID NO 268
<211> LENGTH: 15
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
ccaaauuuaa aagca                                                    15

<210> SEQ ID NO 269
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
caaauuuaaa agcac                                                    15

<210> SEQ ID NO 270
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
aagcacaagg aauga                                                    15

<210> SEQ ID NO 271
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
gaaugauugu accac                                                    15

<210> SEQ ID NO 272
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
auuguaccac acaaa                                                    15

<210> SEQ ID NO 273
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
guaccacaca aagua                                                    15

<210> SEQ ID NO 274
<211> LENGTH: 15
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 274
uaccacacaa aguaa                                                    15

<210> SEQ ID NO 275
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ccacacaaag uaaug                                                    15

<210> SEQ ID NO 276
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
acacaaagua augua                                                    15

<210> SEQ ID NO 277
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
aguaauguaa aacau                                                    15

<210> SEQ ID NO 278
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
guaauguaaa acauu                                                    15

<210> SEQ ID NO 279
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
uaaaacauua aagga                                                    15

<210> SEQ ID NO 280
<211> LENGTH: 15
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 280
acauuaaagg acuca                                                          15

<210> SEQ ID NO 281
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ggacucauua aaaag                                                          15

<210> SEQ ID NO 282
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
acucauuaaa aagua                                                          15

<210> SEQ ID NO 283
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
aaaguaacag uuguc                                                          15

<210> SEQ ID NO 284
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
caucaucauc aucau                                                          15

<210> SEQ ID NO 285
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
caucaucauc auagc                                                          15

<210> SEQ ID NO 286
<211> LENGTH: 15
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 286
caucaucaua gcuau                                                    15

<210> SEQ ID NO 287
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
aucaucauca ucauc                                                    15

<210> SEQ ID NO 288
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
caucaucauc aucau                                                    15

<210> SEQ ID NO 289
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
caucaucauc auagc                                                    15

<210> SEQ ID NO 290
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
ucaucauagc uacca                                                    15

<210> SEQ ID NO 291
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
caucauagcu accau                                                    15

<210> SEQ ID NO 292
<211> LENGTH: 15
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 292
agcuaccauu uauug                                                          15

<210> SEQ ID NO 293
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uaccauuuau ugaaa                                                          15

<210> SEQ ID NO 294
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
aacuucaaag aacuu                                                          15

<210> SEQ ID NO 295
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
caaagaacuu auccu                                                          15

<210> SEQ ID NO 296
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
uccuuuaguu ggaga                                                          15

<210> SEQ ID NO 297
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
cuuuaguugg agagc                                                          15

<210> SEQ ID NO 298
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uuaguuggag agcca                                                    15

<210> SEQ ID NO 299
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
uaguuggaga gccaa                                                    15

<210> SEQ ID NO 300
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
uuggagagcc aagac                                                    15

<210> SEQ ID NO 301
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ggagagccaa gacaa                                                    15

<210> SEQ ID NO 302
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
gagccaagac aauca                                                    15

<210> SEQ ID NO 303
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ccaagacaau cauaa                                                    15

<210> SEQ ID NO 304
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
aagacaauca uaaca                                                      15

<210> SEQ ID NO 305
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
agcugucugc uucuc                                                      15

<210> SEQ ID NO 306
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gauccugaac ugagu                                                      15

<210> SEQ ID NO 307
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
auccugaacu gaguu                                                      15

<210> SEQ ID NO 308
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
ugaacugagu uuaaa                                                      15

<210> SEQ ID NO 309
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
guuuaaaagg caccc                                                      15

<210> SEQ ID NO 310
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310

```
aucaaaugca acgua                                             15

<210> SEQ ID NO 311
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
ucaaaugcaa cguac                                             15

<210> SEQ ID NO 312
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
guuguauggu uaaaa                                             15

<210> SEQ ID NO 313
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
uuuaaaaacc ucacu                                             15

<210> SEQ ID NO 314
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uaaaaaccuc acugc                                             15

<210> SEQ ID NO 315
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aaaaccucac ugcca                                             15

<210> SEQ ID NO 316
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
```
gaaacagaau ugaga					15

<210> SEQ ID NO 317
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
ucagugcuca ccucugauu					19

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uuguugcagu gcucaccuc					19

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uuuguugcag ugcucaccu					19

<210> SEQ ID NO 320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
uuuuuuguug cagugcuca					19

<210> SEQ ID NO 321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
uuggagaucc gagagaaaa					19

<210> SEQ ID NO 322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uuuggagauc cgagagaaa					19

```
<210> SEQ ID NO 323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
uaauuuggag auccgagag                                                    19

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uaaauuugga gauccgaga                                                    19

<210> SEQ ID NO 325
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
uuuaaauuug gagauccga                                                    19

<210> SEQ ID NO 326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
uugugcuuuu aaauuugga                                                    19

<210> SEQ ID NO 327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
uuugugcuuu uaaauuugg                                                    19

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
ucuugugcuu uuaaauuug                                                    19
```

<210> SEQ ID NO 329
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
ucaaucauuc cuugugcuu                                                   19

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uuguguggua caaucauuc                                                   19

<210> SEQ ID NO 331
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
uuacuuugug ugguacaau                                                   19

<210> SEQ ID NO 332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
ucauuacuuu gugggguac                                                   19

<210> SEQ ID NO 333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
uacauuacuu uguguggua                                                   19

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
uuuacauuac uuugugugg                                                   19

```
<210> SEQ ID NO 335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
uuuuuacauu acuugugu                                                 19

<210> SEQ ID NO 336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
uuuaauguuu uacauuacu                                                19

<210> SEQ ID NO 337
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
uuuuaauguu uuacauuac                                                19

<210> SEQ ID NO 338
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338 ugagccuuu aauguuuua                                                 19

<210> SEQ ID NO 339
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339 uuaauguaguc cuuuaaugu                                               19

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
uuuacuuuuu aaugagucc                                                19

<210> SEQ ID NO 341
```

-continued

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
uuguuacuuu uuaaugagu                                                      19

<210> SEQ ID NO 342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
uugagacaac uguuacuuu                                                      19

<210> SEQ ID NO 343
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
ugcuaugaug augaugaug                                                      19

<210> SEQ ID NO 344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
uauagcuaug augaugaug                                                      19

<210> SEQ ID NO 345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
uaugauagcu augaugaug                                                      19

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
uuaugaugau gaugaugau                                                      19

<210> SEQ ID NO 347
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
ugcuaugaug augaugaug                                                  19

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
uguagcuaug augaugaug                                                  19

<210> SEQ ID NO 349
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
uaaaugguag cuaugauga                                                  19

<210> SEQ ID NO 350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
uuaaauggua gcuaugaug                                                  19

<210> SEQ ID NO 351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uuuucaauaa augguagcu                                                  19

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
uaguuuucaa uaaauggua                                                  19

<210> SEQ ID NO 353
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 353
ugauaaguuc uuugaaguu                                               19

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
uuaaaggaua aguucuuug                                               19

<210> SEQ ID NO 355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
uggcucucca acuaaagga                                               19

<210> SEQ ID NO 356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
uuuggcucuc caacuaaag                                               19

<210> SEQ ID NO 357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
uucuuggcuc uccaacuaa                                               19

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ugucuuggcu cuccaacua                                               19

<210> SEQ ID NO 359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
uauugucuug gcucuccaa                                               19

<210> SEQ ID NO 360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
uugauugucu uggcucucc                                               19

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
uuuaugauug ucuuggcuc                                               19

<210> SEQ ID NO 362
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
uuuguuauga uugucuugg                                               19

<210> SEQ ID NO 363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
uuauuguuau gauugucuu                                               19

<210> SEQ ID NO 364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
uugugagaag cagacagcu                                               19

<210> SEQ ID NO 365
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 365
uuaaacucag uucaggauc                                                19

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
uuuaaacuca guucaggau                                                19

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
uccuuuuaaa cucaguuca                                                19

<210> SEQ ID NO 368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
ugcugggugc cuuuuaaac                                                19

<210> SEQ ID NO 369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
uuuguacguu gcauuugau                                                19

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
uuuuguacgu ugcauuuga                                                19

<210> SEQ ID NO 371
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 371
uaucuuuuaa ccauacaac                                        19

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
uggcagugag guuuuaaa                                         19

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
uguggcagug agguuuuua                                        19

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ugaguggcag ugagguuuu                                        19

<210> SEQ ID NO 375
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
uugcucucaa uucuguuuc                                        19

<210> SEQ ID NO 376
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aaucagaggu gagca                                            15

<210> SEQ ID NO 377
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 377
gaggugagca cugca                                              15

<210> SEQ ID NO 378
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
aggugagcac ugcaa                                              15

<210> SEQ ID NO 379
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ugagcacugc aacaa                                              15

<210> SEQ ID NO 380
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
uuuucucucg gauca                                              15

<210> SEQ ID NO 381
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
uuucucucgg aucua                                              15

<210> SEQ ID NO 382
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cucucggauc uccaa                                              15

<210> SEQ ID NO 383
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 383
ucucggaucu ccaaa                                                    15

<210> SEQ ID NO 384
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
ucggaucucc aaaua                                                    15

<210> SEQ ID NO 385
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
uccaaauuua aaaga                                                    15

<210> SEQ ID NO 386
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
ccaaauuuaa aagca                                                    15

<210> SEQ ID NO 387
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
caaauuuaaa agcaa                                                    15

<210> SEQ ID NO 388
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
aagcacaagg aauga                                                    15

<210> SEQ ID NO 389
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
```
gaaugauugu accaa                                              15

<210> SEQ ID NO 390
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
auuguaccac acaaa                                              15

<210> SEQ ID NO 391
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
guaccacaca aagua                                              15

<210> SEQ ID NO 392
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
uaccacacaa aguaa                                              15

<210> SEQ ID NO 393
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
ccacacaaag uaaua                                              15

<210> SEQ ID NO 394
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
acacaaagua augua                                              15

<210> SEQ ID NO 395
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
aguaauguaa aacaa                                                      15

<210> SEQ ID NO 396
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
guaauguaaa acaua                                                      15

<210> SEQ ID NO 397
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uaaaacauua aagga                                                      15

<210> SEQ ID NO 398
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
acauuaaagg acuca                                                      15

<210> SEQ ID NO 399
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
ggacucauua aaaaa                                                      15

<210> SEQ ID NO 400
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
acucauuaaa aagua                                                      15

<210> SEQ ID NO 401
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
aaaguaacag uugua                                                      15

<210> SEQ ID NO 402
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
caucaucauc aucaa                                                    15

<210> SEQ ID NO 403
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
caucaucauc auaga                                                    15

<210> SEQ ID NO 404
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
caucaucaua gcuaa                                                    15

<210> SEQ ID NO 405
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
aucaucauca ucaua                                                    15

<210> SEQ ID NO 406
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
caucaucauc aucaa                                                    15

<210> SEQ ID NO 407
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
caucaucauc auaga                                                    15

```
<210> SEQ ID NO 408
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
ucaucauagc uacca                                                         15

<210> SEQ ID NO 409
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
caucauagcu accaa                                                         15

<210> SEQ ID NO 410
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
agcuaccauu uauua                                                         15

<210> SEQ ID NO 411
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
uaccauuuau ugaaa                                                         15

<210> SEQ ID NO 412
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
aacuucaaag aacua                                                         15

<210> SEQ ID NO 413
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
caaagaacuu aucca                                                         15
```

```
<210> SEQ ID NO 414
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uccuuuaguu ggaga                                                          15

<210> SEQ ID NO 415
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
cuuuaguugg agaga                                                          15

<210> SEQ ID NO 416
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
uuaguuggag agcca                                                          15

<210> SEQ ID NO 417
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
uaguuggaga gccaa                                                          15

<210> SEQ ID NO 418
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
uuggagagcc aagaa                                                          15

<210> SEQ ID NO 419
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
ggagagccaa gacaa                                                          15

<210> SEQ ID NO 420
```

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
gagccaagac aauca                                                     15

<210> SEQ ID NO 421
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
ccaagacaau cauaa                                                     15

<210> SEQ ID NO 422
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
aagacaauca uaaca                                                     15

<210> SEQ ID NO 423
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
agcugucugc uucua                                                     15

<210> SEQ ID NO 424
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
gauccugaac ugaga                                                     15

<210> SEQ ID NO 425
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
auccugaacu gagua                                                     15

<210> SEQ ID NO 426
<211> LENGTH: 15
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
ugaacugagu uuaaa                                                       15

<210> SEQ ID NO 427
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
guuuaaaagg cacca                                                       15

<210> SEQ ID NO 428
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
aucaaaugca acgua                                                       15

<210> SEQ ID NO 429
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
ucaaaugcaa cguaa                                                       15

<210> SEQ ID NO 430
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
guuguauggu uaaaa                                                       15

<210> SEQ ID NO 431
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
uuuaaaaacc ucaca                                                       15

<210> SEQ ID NO 432
<211> LENGTH: 15
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 432
uaaaaaccuc acuga                                                        15

<210> SEQ ID NO 433
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
aaaaccucac ugcca                                                        15

<210> SEQ ID NO 434
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
gaaacagaau ugaga                                                        15

<210> SEQ ID NO 435
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
ugcagugcuc accucugauu                                                   20

<210> SEQ ID NO 436
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
uuuguugcag ugcucaccuc                                                   20

<210> SEQ ID NO 437
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
uuuuguugca gugcucaccu                                                   20

<210> SEQ ID NO 438
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 438
ucuuuuuguu gcagugcuca                                               20

<210> SEQ ID NO 439
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
uuuggagauc cgagagaaaa                                               20

<210> SEQ ID NO 440
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
uuuuggagau ccgagagaaa                                               20

<210> SEQ ID NO 441
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
uaaauuugga gauccgagag                                               20

<210> SEQ ID NO 442
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
uuaaauuugg agauccgaga                                               20

<210> SEQ ID NO 443
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
uuuuaaauuu ggagauccga                                               20

<210> SEQ ID NO 444
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 444
uuugugcuuu uaaauuugga                                                    20

<210> SEQ ID NO 445
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ucuugugcuu uuaaauuugg                                                    20

<210> SEQ ID NO 446
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
uccuugugcu uuuaaauuug                                                    20

<210> SEQ ID NO 447
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
uacaaucauu ccuugugcuu                                                    20

<210> SEQ ID NO 448
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uuuguguggu acaaucauuc                                                    20

<210> SEQ ID NO 449
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
uuuacuuugu gugguacaau                                                    20

<210> SEQ ID NO 450
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 450
uacauuacuu ugugugguac                                           20

<210> SEQ ID NO 451
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
uuacauuacu uuguguggua                                           20

<210> SEQ ID NO 452
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
uuuuacauua cuugugugg                                            20

<210> SEQ ID NO 453
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
uguuuuacau uacuuugugu                                           20

<210> SEQ ID NO 454
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uuuuaauguu uuacauuacu                                           20

<210> SEQ ID NO 455
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
ucuuuaaugu uuuacauuac                                           20

<210> SEQ ID NO 456
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 456
uugaguccuu uaauguuuua                                                20

<210> SEQ ID NO 457
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
uuuaaugagu ccuuuaaugu                                                20

<210> SEQ ID NO 458
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uguuacuuuu uaaugagucc                                                20

<210> SEQ ID NO 459
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
ucuguuacuu uuuaaugagu                                                20

<210> SEQ ID NO 460
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
uaugagacaa cuguuacuuu                                                20

<210> SEQ ID NO 461
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
uagcuaugau gaugaugaug                                                20

<210> SEQ ID NO 462
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
ugauagcuau gaugaugaug 20

<210> SEQ ID NO 463
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ugaugauagc uaugaugaug 20

<210> SEQ ID NO 464
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
ucuaugauga ugaugaugau 20

<210> SEQ ID NO 465
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
uagcuaugau gaugaugaug 20

<210> SEQ ID NO 466
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
ugguagcuau gaugaugaug 20

<210> SEQ ID NO 467
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
uuaaauggua gcuaugauga 20

<210> SEQ ID NO 468
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468

-continued uauaaauggu agcuaugaug                                          20

<210> SEQ ID NO 469
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
uuuuucaaua aaugguagcu                                          20

<210> SEQ ID NO 470
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
uuaguuuuca auaaauggua                                          20

<210> SEQ ID NO 471
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
uggauaaguu cuuugaaguu                                          20

<210> SEQ ID NO 472
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ucuaaaggau aaguucuuug                                          20

<210> SEQ ID NO 473
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
uuggcucucc aacuaaagga                                          20

<210> SEQ ID NO 474
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
ucuuggcucu ccaacuaaag          20

<210> SEQ ID NO 475
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
ugucuuggcu cuccaacuaa          20

<210> SEQ ID NO 476
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
uugucuuggc ucuccaacua          20

<210> SEQ ID NO 477
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
ugauugucuu ggcucuccaa          20

<210> SEQ ID NO 478
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
uaugauuguc uuggcucucc          20

<210> SEQ ID NO 479
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
uguuaugauu gucuuggcuc          20

<210> SEQ ID NO 480
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
uauuguuaug auugucuugg          20

<210> SEQ ID NO 481
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
uuuauuguua ugauugucuu                                              20

<210> SEQ ID NO 482
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
ucugugagaa gcagacagcu                                              20

<210> SEQ ID NO 483
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
uuuaaacuca guucaggauc                                              20

<210> SEQ ID NO 484
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
uuuuaaacuc aguucaggau                                              20

<210> SEQ ID NO 485
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
ugccuuuuaa acucaguuca                                              20

<210> SEQ ID NO 486
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
uugcugggug ccuuuuaaac                                              20

<210> SEQ ID NO 487
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
uuuuguacgu ugcauuugau                                              20

<210> SEQ ID NO 488
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
ucuuuguacg uugcauuuga                                              20

<210> SEQ ID NO 489
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
ucaucuuuua accauacaac                                              20

<210> SEQ ID NO 490
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
uuggcaguga gguuuuuaaa                                              20

<210> SEQ ID NO 491
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
uaguggcagu gagguuuuua                                              20

<210> SEQ ID NO 492
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
uagaguggca gugagguuuu                                              20

```
<210> SEQ ID NO 493
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
uaugcucuca auucuguuuc                                                    20

<210> SEQ ID NO 494
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
aaucagaggu gagca                                                         15

<210> SEQ ID NO 495
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
gaggugagca cugca                                                         15

<210> SEQ ID NO 496
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
aggugagcac ugcaa                                                         15

<210> SEQ ID NO 497
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
ugagcacugc aacaa                                                         15

<210> SEQ ID NO 498
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
uuuucucucg gauca                                                         15

<210> SEQ ID NO 499
```

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
uuucucucgg aucua                                                          15

<210> SEQ ID NO 500
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
cucucggauc uccaa                                                          15

<210> SEQ ID NO 501
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
ucucggaucu ccaaa                                                          15

<210> SEQ ID NO 502
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
ucggaucucc aaaua                                                          15

<210> SEQ ID NO 503
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
uccaaauuua aaaga                                                          15

<210> SEQ ID NO 504
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
ccaaauuuaa aagca                                                          15

<210> SEQ ID NO 505
<211> LENGTH: 15
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
caaauuuaaa agcaa                                                      15

<210> SEQ ID NO 506
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
aagcacaagg aauga                                                      15

<210> SEQ ID NO 507
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
gaaugauugu accaa                                                      15

<210> SEQ ID NO 508
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
auuguaccac acaaa                                                      15

<210> SEQ ID NO 509
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
guaccacaca aagua                                                      15

<210> SEQ ID NO 510
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
uaccacacaa aguaa                                                      15

<210> SEQ ID NO 511
<211> LENGTH: 15
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 511
ccacacaaag uaaua                                                        15

<210> SEQ ID NO 512
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
acacaaagua augua                                                        15

<210> SEQ ID NO 513
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
aguaauguaa aacaa                                                        15

<210> SEQ ID NO 514
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
guaauguaaa acaua                                                        15

<210> SEQ ID NO 515
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
uaaaacauua aagga                                                        15

<210> SEQ ID NO 516
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
acauuaaagg acuca                                                        15

<210> SEQ ID NO 517
<211> LENGTH: 15
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 517
ggacucauua aaaaa                                                          15

<210> SEQ ID NO 518
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
acucauuaaa aagua                                                          15

<210> SEQ ID NO 519
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
aaaguaacag uugua                                                          15

<210> SEQ ID NO 520
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
caucaucauc aucaa                                                          15

<210> SEQ ID NO 521
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
caucaucauc auaga                                                          15

<210> SEQ ID NO 522
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
caucaucaua gcuaa                                                          15

<210> SEQ ID NO 523
<211> LENGTH: 15
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 523
aucaucauca ucaua                                                    15

<210> SEQ ID NO 524
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
caucaucauc aucaa                                                    15

<210> SEQ ID NO 525
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
caucaucauc auaga                                                    15

<210> SEQ ID NO 526
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
ucaucauagc uacca                                                    15

<210> SEQ ID NO 527
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
caucauagcu accaa                                                    15

<210> SEQ ID NO 528
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
agcuaccauu uauua                                                    15

<210> SEQ ID NO 529
<211> LENGTH: 15
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 529
uaccauuuau ugaaa                                                  15

<210> SEQ ID NO 530
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
aacuucaaag aacua                                                  15

<210> SEQ ID NO 531
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
caaagaacuu aucca                                                  15

<210> SEQ ID NO 532
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
uccuuuaguu ggaga                                                  15

<210> SEQ ID NO 533
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
cuuuaguugg agaga                                                  15

<210> SEQ ID NO 534
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
uuaguuggag agcca                                                  15

<210> SEQ ID NO 535
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 535
uaguuggaga gccaa                                                    15

<210> SEQ ID NO 536
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
uuggagagcc aagaa                                                    15

<210> SEQ ID NO 537
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
ggagagccaa gacaa                                                    15

<210> SEQ ID NO 538
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
gagccaagac aauca                                                    15

<210> SEQ ID NO 539
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
ccaagacaau cauaa                                                    15

<210> SEQ ID NO 540
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
aagacaauca uaaca                                                    15

<210> SEQ ID NO 541
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 541
agcugucugc uucua                                              15

<210> SEQ ID NO 542
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
gauccugaac ugaga                                              15

<210> SEQ ID NO 543
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
auccugaacu gagua                                              15

<210> SEQ ID NO 544
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
ugaacugagu uuaaa                                              15

<210> SEQ ID NO 545
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
guuuaaaagg cacca                                              15

<210> SEQ ID NO 546
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
aucaaaugca acgua                                              15

<210> SEQ ID NO 547
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
```
ucaaaugcaa cguaa                                                          15

<210> SEQ ID NO 548
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
guuguauggu uaaaa                                                          15

<210> SEQ ID NO 549
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
uuuaaaaacc ucaca                                                          15

<210> SEQ ID NO 550
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
uaaaaaccuc acuga                                                          15

<210> SEQ ID NO 551
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
aaaaccucac ugcca                                                          15

<210> SEQ ID NO 552
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
gaaacagaau ugaga                                                          15

<210> SEQ ID NO 553
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
ugcagugcuc accucugauu                                                    20

<210> SEQ ID NO 554
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
uuuguugcag ugcucaccuc                                                    20

<210> SEQ ID NO 555
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
uuuuguugca gugcucaccu                                                    20

<210> SEQ ID NO 556
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556 ucuuuuguu gcagugcuca                                                     20

<210> SEQ ID NO 557
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
uuuggagauc cgagagaaaa                                                    20

<210> SEQ ID NO 558
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
uuuuggagau ccgagagaaa                                                    20

<210> SEQ ID NO 559
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
uaaauuugga gauccgagag                                                    20

<210> SEQ ID NO 560
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
uuaaauuugg agauccgaga                                               20

<210> SEQ ID NO 561
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
uuuuaaauuu ggagauccga                                               20

<210> SEQ ID NO 562
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
uuugugcuuu uaaauuugga                                               20

<210> SEQ ID NO 563
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
ucuugugcuu uuaaauuugg                                               20

<210> SEQ ID NO 564
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
uccuugugcu uuuaaauuug                                               20

<210> SEQ ID NO 565
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
uacaaucauu ccuugugcuu                                               20

<210> SEQ ID NO 566
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
uuuguguggu acaaucauuc                                              20

<210> SEQ ID NO 567
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
uuuacuuugu gugguacaau                                              20

<210> SEQ ID NO 568
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
uacauuacuu ugugugguac                                              20

<210> SEQ ID NO 569
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
uuacauuacu uugugugggua                                             20

<210> SEQ ID NO 570
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
uuuuacauua cuuugugugg                                              20

<210> SEQ ID NO 571
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
uguuuuacau uacuuugugu                                              20

```
<210> SEQ ID NO 572
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
uuuuaauguu uuacauuacu                                               20

<210> SEQ ID NO 573
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
ucuuuaaugu uuuacauuac                                               20

<210> SEQ ID NO 574
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
uugaguccuu uaauguuuua                                               20

<210> SEQ ID NO 575
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
uuuaaugagu ccuuuaaugu                                               20

<210> SEQ ID NO 576
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
uguuacuuuu uaaugagucc                                               20

<210> SEQ ID NO 577
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
ucuguuacuu uuuaaugagu                                               20

<210> SEQ ID NO 578
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
uaugagacaa cguuacuuu                                                    20

<210> SEQ ID NO 579
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
uagcuaugau gaugaugaug                                                   20

<210> SEQ ID NO 580
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
ugauagcuau gaugaugaug                                                   20

<210> SEQ ID NO 581
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
ugaugauagc uaugaugaug                                                   20

<210> SEQ ID NO 582
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
ucuaugauga ugaugaugau                                                   20

<210> SEQ ID NO 583
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
uagcuaugau gaugaugaug                                                   20

<210> SEQ ID NO 584
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
ugguagcuau gaugaugaug                                               20

<210> SEQ ID NO 585
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
uuaaauggua gcuaugauga                                               20

<210> SEQ ID NO 586
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
uauaaauggu agcuaugaug                                               20

<210> SEQ ID NO 587
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
uuuuucaaua aaugguagcu                                               20

<210> SEQ ID NO 588
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
uuaguuuuca auaaauggua                                               20

<210> SEQ ID NO 589
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
uggauaaguu cuuugaaguu                                               20

<210> SEQ ID NO 590
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 590
ucuaaaggau aaguucuuug                                             20

<210> SEQ ID NO 591
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
uuggcucucc aacuaaagga                                             20

<210> SEQ ID NO 592
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
ucuuggcucu ccaacuaaag                                             20

<210> SEQ ID NO 593
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
ugucuuggcu cuccaacuaa                                             20

<210> SEQ ID NO 594
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
uugucuuggc ucuccaacua                                             20

<210> SEQ ID NO 595
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
ugauugucuu ggcucuccaa                                             20

<210> SEQ ID NO 596
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 596
uaugauuguc uuggcucucc                                                20

<210> SEQ ID NO 597
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597 uguaugauu gucuuggcuc                                                 20

<210> SEQ ID NO 598
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
uauuguuaug auugucuugg                                                20

<210> SEQ ID NO 599
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
uuuauuguua ugauugucuu                                                20

<210> SEQ ID NO 600
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
ucugugagaa gcagacagcu                                                20

<210> SEQ ID NO 601
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
uuuaaacuca guucaggauc                                                20

<210> SEQ ID NO 602
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 602
uuuuaaacuc aguucaggau                                              20

<210> SEQ ID NO 603
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
ugccuuuuaa acucaguuca                                              20

<210> SEQ ID NO 604
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
uugcugggug ccuuuuaaac                                              20

<210> SEQ ID NO 605
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
uuuuguacgu ugcauuugau                                              20

<210> SEQ ID NO 606
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
ucuuuguacg uugcauuuga                                              20

<210> SEQ ID NO 607
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
ucaucuuuua accauacaac                                              20

<210> SEQ ID NO 608
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 608
uuggcaguga gguuuuaaa                                          20

<210> SEQ ID NO 609
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
uaguggcagu gagguuuua                                          20

<210> SEQ ID NO 610
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
uagaguggca gugagguuuu                                         20

<210> SEQ ID NO 611
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
uaugcucuca auucuguuuc                                         20

<210> SEQ ID NO 612
<211> LENGTH: 15
<212> TYPE: RNA
<213> ORGANISM: Homo sapiens

<400> SEQUENCE: 612
gguuuaugaa cugac                                              15

<210> SEQ ID NO 613
<211> LENGTH: 15
<212> TYPE: RNA
<213> ORGANISM: Homo sapiens

<400> SEQUENCE: 613
uaugaacuga cguua                                              15

<210> SEQ ID NO 614
<211> LENGTH: 15
<212> TYPE: RNA
<213> ORGANISM: Homo sapiens

<400> SEQUENCE: 614
augaacugac guuac                                              15

<210> SEQ ID NO 615
<211> LENGTH: 15
<212> TYPE: RNA

<213> ORGANISM: Homo sapiens

<400> SEQUENCE: 615
aauguuguga ccgga                                                         15

<210> SEQ ID NO 616
<211> LENGTH: 15
<212> TYPE: RNA
<213> ORGANISM: Homo sapiens

<400> SEQUENCE: 616
uagacgguac cgaca                                                         15

<210> SEQ ID NO 617
<211> LENGTH: 15
<212> TYPE: RNA
<213> ORGANISM: Homo sapiens

<400> SEQUENCE: 617
caaccaguau uuggg                                                         15

<210> SEQ ID NO 618
<211> LENGTH: 15
<212> TYPE: RNA
<213> ORGANISM: Homo sapiens

<400> SEQUENCE: 618
ugcucaauaa uguug                                                         15

<210> SEQ ID NO 619
<211> LENGTH: 15
<212> TYPE: RNA
<213> ORGANISM: Homo sapiens

<400> SEQUENCE: 619
uccugcuuua gucga                                                         15

<210> SEQ ID NO 620
<211> LENGTH: 15
<212> TYPE: RNA
<213> ORGANISM: Homo sapiens

<400> SEQUENCE: 620
uagucgagaa ccaau                                                         15

<210> SEQ ID NO 621
<211> LENGTH: 15
<212> TYPE: RNA
<213> ORGANISM: Homo sapiens

<400> SEQUENCE: 621
aguacuucaa cgcua                                                         15

<210> SEQ ID NO 622
<211> LENGTH: 15
<212> TYPE: RNA
<213> ORGANISM: Homo sapiens

<400> SEQUENCE: 622
uucagucucg uugug                                                         15

<210> SEQ ID NO 623
<211> LENGTH: 15

```
<212> TYPE: RNA
<213> ORGANISM: Homo sapiens

<400> SEQUENCE: 623
cuagcuccau gcuua                                                    15

<210> SEQ ID NO 624
<211> LENGTH: 15
<212> TYPE: RNA
<213> ORGANISM: Homo sapiens

<400> SEQUENCE: 624
cugcgugaac auuca                                                    15

<210> SEQ ID NO 625
<211> LENGTH: 15
<212> TYPE: RNA
<213> ORGANISM: Homo sapiens

<400> SEQUENCE: 625
cagcuaccaa gaaag                                                    15

<210> SEQ ID NO 626
<211> LENGTH: 15
<212> TYPE: RNA
<213> ORGANISM: Homo sapiens

<400> SEQUENCE: 626
cugacaauau gugaa                                                    15

<210> SEQ ID NO 627
<211> LENGTH: 15
<212> TYPE: RNA
<213> ORGANISM: Homo sapiens

<400> SEQUENCE: 627
ggcaucgcua uggaa                                                    15

<210> SEQ ID NO 628
<211> LENGTH: 15
<212> TYPE: RNA
<213> ORGANISM: Homo sapiens

<400> SEQUENCE: 628
cgcuauggaa cuuuu                                                    15

<210> SEQ ID NO 629
<211> LENGTH: 15
<212> TYPE: RNA
<213> ORGANISM: Homo sapiens

<400> SEQUENCE: 629
ugacaaugaa auuaa                                                    15

<210> SEQ ID NO 630
<211> LENGTH: 15
<212> TYPE: RNA
<213> ORGANISM: Homo sapiens

<400> SEQUENCE: 630
gacaaugaaa uuaag                                                    15

<210> SEQ ID NO 631
```

```
<211> LENGTH: 15
<212> TYPE: RNA
<213> ORGANISM: Homo sapiens

<400> SEQUENCE: 631
cuucauagcg aaccu                                                    15

<210> SEQ ID NO 632
<211> LENGTH: 15
<212> TYPE: RNA
<213> ORGANISM: Homo sapiens

<400> SEQUENCE: 632
augugcucuu aggcu                                                    15

<210> SEQ ID NO 633
<211> LENGTH: 15
<212> TYPE: RNA
<213> ORGANISM: Homo sapiens

<400> SEQUENCE: 633
ugacaaggaa agaaa                                                    15

<210> SEQ ID NO 634
<211> LENGTH: 15
<212> TYPE: RNA
<213> ORGANISM: Homo sapiens

<400> SEQUENCE: 634
uuguccaggu uuaug                                                    15

<210> SEQ ID NO 635
<211> LENGTH: 15
<212> TYPE: RNA
<213> ORGANISM: Homo sapiens

<400> SEQUENCE: 635
cagguuuaug aacug                                                    15

<210> SEQ ID NO 636
<211> LENGTH: 15
<212> TYPE: RNA
<213> ORGANISM: Homo sapiens

<400> SEQUENCE: 636
uuaugaacug acguu                                                    15

<210> SEQ ID NO 637
<211> LENGTH: 15
<212> TYPE: RNA
<213> ORGANISM: Homo sapiens

<400> SEQUENCE: 637
ugaacugacg uuaca                                                    15

<210> SEQ ID NO 638
<211> LENGTH: 15
<212> TYPE: RNA
<213> ORGANISM: Homo sapiens

<400> SEQUENCE: 638
acugacguua cauca                                                    15
```

-continued

```
<210> SEQ ID NO 639
<211> LENGTH: 15
<212> TYPE: RNA
<213> ORGANISM: Homo sapiens

<400> SEQUENCE: 639
acguuacauc auaca                                                    15

<210> SEQ ID NO 640
<211> LENGTH: 15
<212> TYPE: RNA
<213> ORGANISM: Homo sapiens

<400> SEQUENCE: 640
guuacaucau acaca                                                    15

<210> SEQ ID NO 641
<211> LENGTH: 15
<212> TYPE: RNA
<213> ORGANISM: Homo sapiens

<400> SEQUENCE: 641
guugugaccg gagcc                                                    15

<210> SEQ ID NO 642
<211> LENGTH: 15
<212> TYPE: RNA
<213> ORGANISM: Homo sapiens

<400> SEQUENCE: 642
uauuguggaa cuuau                                                    15

<210> SEQ ID NO 643
<211> LENGTH: 15
<212> TYPE: RNA
<213> ORGANISM: Homo sapiens

<400> SEQUENCE: 643
aaagugcucu uagga                                                    15

<210> SEQ ID NO 644
<211> LENGTH: 15
<212> TYPE: RNA
<213> ORGANISM: Homo sapiens

<400> SEQUENCE: 644
uaccgacaac cagua                                                    15

<210> SEQ ID NO 645
<211> LENGTH: 15
<212> TYPE: RNA
<213> ORGANISM: Homo sapiens

<400> SEQUENCE: 645
ccgacaacca guauu                                                    15

<210> SEQ ID NO 646
<211> LENGTH: 15
<212> TYPE: RNA
<213> ORGANISM: Homo sapiens

<400> SEQUENCE: 646
cuacaucgau caugg                                                    15
```

```
<210> SEQ ID NO 647
<211> LENGTH: 15
<212> TYPE: RNA
<213> ORGANISM: Homo sapiens

<400> SEQUENCE: 647
uacaucgauc augga                                                        15

<210> SEQ ID NO 648
<211> LENGTH: 15
<212> TYPE: RNA
<213> ORGANISM: Homo sapiens

<400> SEQUENCE: 648
gugcucaaua auguu                                                        15

<210> SEQ ID NO 649
<211> LENGTH: 15
<212> TYPE: RNA
<213> ORGANISM: Homo sapiens

<400> SEQUENCE: 649
guuacaacaa guaaa                                                        15

<210> SEQ ID NO 650
<211> LENGTH: 15
<212> TYPE: RNA
<213> ORGANISM: Homo sapiens

<400> SEQUENCE: 650
auccugcuuu agucg                                                        15

<210> SEQ ID NO 651
<211> LENGTH: 15
<212> TYPE: RNA
<213> ORGANISM: Homo sapiens

<400> SEQUENCE: 651
uuagucgaga accaa                                                        15

<210> SEQ ID NO 652
<211> LENGTH: 15
<212> TYPE: RNA
<213> ORGANISM: Homo sapiens

<400> SEQUENCE: 652
ucgagaacca augau                                                        15

<210> SEQ ID NO 653
<211> LENGTH: 15
<212> TYPE: RNA
<213> ORGANISM: Homo sapiens

<400> SEQUENCE: 653
agaaccaaug auggc                                                        15

<210> SEQ ID NO 654
<211> LENGTH: 15
<212> TYPE: RNA
<213> ORGANISM: Homo sapiens

<400> SEQUENCE: 654
caacaauugu ugaag                                                        15
```

<210> SEQ ID NO 655
<211> LENGTH: 15
<212> TYPE: RNA
<213> ORGANISM: Homo sapiens

<400> SEQUENCE: 655
aacauggugc aggcg                                                    15

<210> SEQ ID NO 656
<211> LENGTH: 15
<212> TYPE: RNA
<213> ORGANISM: Homo sapiens

<400> SEQUENCE: 656
caaagaaccg ugcag                                                    15

<210> SEQ ID NO 657
<211> LENGTH: 15
<212> TYPE: RNA
<213> ORGANISM: Homo sapiens

<400> SEQUENCE: 657
aagaaccgug cagau                                                    15

<210> SEQ ID NO 658
<211> LENGTH: 15
<212> TYPE: RNA
<213> ORGANISM: Homo sapiens

<400> SEQUENCE: 658
gaaccgugca gauaa                                                    15

<210> SEQ ID NO 659
<211> LENGTH: 15
<212> TYPE: RNA
<213> ORGANISM: Homo sapiens

<400> SEQUENCE: 659
ccucuuguua uaaaa                                                    15

<210> SEQ ID NO 660
<211> LENGTH: 15
<212> TYPE: RNA
<213> ORGANISM: Homo sapiens

<400> SEQUENCE: 660
uggcuuugua uugaa                                                    15

<210> SEQ ID NO 661
<211> LENGTH: 15
<212> TYPE: RNA
<213> ORGANISM: Homo sapiens

<400> SEQUENCE: 661
ggaauuccua aaauc                                                    15

<210> SEQ ID NO 662
<211> LENGTH: 15
<212> TYPE: RNA
<213> ORGANISM: Homo sapiens

<400> SEQUENCE: 662
uggcaucaug gccag    15

<210> SEQ ID NO 663
<211> LENGTH: 15
<212> TYPE: RNA
<213> ORGANISM: Homo sapiens

<400> SEQUENCE: 663
cccagucaac ugaag    15

<210> SEQ ID NO 664
<211> LENGTH: 15
<212> TYPE: RNA
<213> ORGANISM: Homo sapiens

<400> SEQUENCE: 664
agcagcaaca uacuu    15

<210> SEQ ID NO 665
<211> LENGTH: 15
<212> TYPE: RNA
<213> ORGANISM: Homo sapiens

<400> SEQUENCE: 665
gaauguuccg gagaa    15

<210> SEQ ID NO 666
<211> LENGTH: 15
<212> TYPE: RNA
<213> ORGANISM: Homo sapiens

<400> SEQUENCE: 666
gaacauucac agcca    15

<210> SEQ ID NO 667
<211> LENGTH: 15
<212> TYPE: RNA
<213> ORGANISM: Homo sapiens

<400> SEQUENCE: 667
gauuuaaaau uuaau    15

<210> SEQ ID NO 668
<211> LENGTH: 15
<212> TYPE: RNA
<213> ORGANISM: Homo sapiens

<400> SEQUENCE: 668
uaaaauuuaa uuaua    15

<210> SEQ ID NO 669
<211> LENGTH: 15
<212> TYPE: RNA
<213> ORGANISM: Homo sapiens

<400> SEQUENCE: 669
aauuauauca guaaa    15

<210> SEQ ID NO 670
<211> LENGTH: 15
<212> TYPE: RNA
<213> ORGANISM: Homo sapiens

<400> SEQUENCE: 670

```
aacguaacuc uuucu                                             15

<210> SEQ ID NO 671
<211> LENGTH: 15
<212> TYPE: RNA
<213> ORGANISM: Homo sapiens

<400> SEQUENCE: 671
cuaugcccgu guaaa                                             15

<210> SEQ ID NO 672
<211> LENGTH: 15
<212> TYPE: RNA
<213> ORGANISM: Homo sapiens

<400> SEQUENCE: 672
gcccguguaa aguau                                             15

<210> SEQ ID NO 673
<211> LENGTH: 15
<212> TYPE: RNA
<213> ORGANISM: Homo sapiens

<400> SEQUENCE: 673
agucaggaga gugca                                             15

<210> SEQ ID NO 674
<211> LENGTH: 15
<212> TYPE: RNA
<213> ORGANISM: Homo sapiens

<400> SEQUENCE: 674
uggguauuga augug                                             15

<210> SEQ ID NO 675
<211> LENGTH: 15
<212> TYPE: RNA
<213> ORGANISM: Homo sapiens

<400> SEQUENCE: 675
ugguaagugg aggaa                                             15

<210> SEQ ID NO 676
<211> LENGTH: 15
<212> TYPE: RNA
<213> ORGANISM: Homo sapiens

<400> SEQUENCE: 676
aguggaggaa auguu                                             15

<210> SEQ ID NO 677
<211> LENGTH: 15
<212> TYPE: RNA
<213> ORGANISM: Homo sapiens

<400> SEQUENCE: 677
uuggaacucu gugca                                             15

<210> SEQ ID NO 678
<211> LENGTH: 15
<212> TYPE: RNA
<213> ORGANISM: Homo sapiens
```

-continued

```
<400> SEQUENCE: 678
ugaggaggcc cuuaa                                                    15

<210> SEQ ID NO 679
<211> LENGTH: 15
<212> TYPE: RNA
<213> ORGANISM: Homo sapiens

<400> SEQUENCE: 679
agggaagcua cugaa                                                    15

<210> SEQ ID NO 680
<211> LENGTH: 15
<212> TYPE: RNA
<213> ORGANISM: Homo sapiens

<400> SEQUENCE: 680
auaacacgua agaaa                                                    15

<210> SEQ ID NO 681
<211> LENGTH: 15
<212> TYPE: RNA
<213> ORGANISM: Homo sapiens

<400> SEQUENCE: 681
uacauuugua agaaa                                                    15

<210> SEQ ID NO 682
<211> LENGTH: 15
<212> TYPE: RNA
<213> ORGANISM: Homo sapiens

<400> SEQUENCE: 682
guaagaaaua acacu                                                    15

<210> SEQ ID NO 683
<211> LENGTH: 15
<212> TYPE: RNA
<213> ORGANISM: Homo sapiens

<400> SEQUENCE: 683
cacugugaau guaaa                                                    15

<210> SEQ ID NO 684
<211> LENGTH: 15
<212> TYPE: RNA
<213> ORGANISM: Homo sapiens

<400> SEQUENCE: 684
gagcucauua guaaa                                                    15

<210> SEQ ID NO 685
<211> LENGTH: 15
<212> TYPE: RNA
<213> ORGANISM: Homo sapiens

<400> SEQUENCE: 685
cacgcauaua cauaa                                                    15

<210> SEQ ID NO 686
<211> LENGTH: 15
<212> TYPE: RNA
<213> ORGANISM: Homo sapiens
```

```
<400> SEQUENCE: 686
gacacaucua uaauu                                                    15

<210> SEQ ID NO 687
<211> LENGTH: 15
<212> TYPE: RNA
<213> ORGANISM: Homo sapiens

<400> SEQUENCE: 687
cacacaccuc ucaag                                                    15

<210> SEQ ID NO 688
<211> LENGTH: 15
<212> TYPE: RNA
<213> ORGANISM: Homo sapiens

<400> SEQUENCE: 688
uaucauguuc cuaaa                                                    15

<210> SEQ ID NO 689
<211> LENGTH: 15
<212> TYPE: RNA
<213> ORGANISM: Homo sapiens

<400> SEQUENCE: 689 gcaauguga uuaau                                                     15

<210> SEQ ID NO 690
<211> LENGTH: 15
<212> TYPE: RNA
<213> ORGANISM: Homo sapiens

<400> SEQUENCE: 690
ugugauuaau uuggu                                                    15

<210> SEQ ID NO 691
<211> LENGTH: 15
<212> TYPE: RNA
<213> ORGANISM: Homo sapiens

<400> SEQUENCE: 691
gguugucaag uuuug                                                    15

<210> SEQ ID NO 692
<211> LENGTH: 15
<212> TYPE: RNA
<213> ORGANISM: Homo sapiens

<400> SEQUENCE: 692
uuuccugcug guaau                                                    15

<210> SEQ ID NO 693
<211> LENGTH: 15
<212> TYPE: RNA
<213> ORGANISM: Homo sapiens

<400> SEQUENCE: 693
ccugcuggua auauc                                                    15

<210> SEQ ID NO 694
<211> LENGTH: 15
<212> TYPE: RNA
```

```
<213> ORGANISM: Homo sapiens

<400> SEQUENCE: 694
gggaaagauu uuaau                                                    15

<210> SEQ ID NO 695
<211> LENGTH: 15
<212> TYPE: RNA
<213> ORGANISM: Homo sapiens

<400> SEQUENCE: 695
aaugaaacca gggua                                                    15

<210> SEQ ID NO 696
<211> LENGTH: 15
<212> TYPE: RNA
<213> ORGANISM: Homo sapiens

<400> SEQUENCE: 696
aaaccagggu agaau                                                    15

<210> SEQ ID NO 697
<211> LENGTH: 15
<212> TYPE: RNA
<213> ORGANISM: Homo sapiens

<400> SEQUENCE: 697
uuggcaaugc acuga                                                    15

<210> SEQ ID NO 698
<211> LENGTH: 15
<212> TYPE: RNA
<213> ORGANISM: Homo sapiens

<400> SEQUENCE: 698
caguuguuuc uaaga                                                    15

<210> SEQ ID NO 699
<211> LENGTH: 15
<212> TYPE: RNA
<213> ORGANISM: Homo sapiens

<400> SEQUENCE: 699
gacgagagau guaua                                                    15

<210> SEQ ID NO 700
<211> LENGTH: 15
<212> TYPE: RNA
<213> ORGANISM: Homo sapiens

<400> SEQUENCE: 700
gagauguaua uuuaa                                                    15

<210> SEQ ID NO 701
<211> LENGTH: 15
<212> TYPE: RNA
<213> ORGANISM: Homo sapiens

<400> SEQUENCE: 701
uaacugcugc aaaca                                                    15

<210> SEQ ID NO 702
<211> LENGTH: 15
```

```
<212> TYPE: RNA
<213> ORGANISM: Homo sapiens

<400> SEQUENCE: 702
gcugcaaaca uugua                                                        15

<210> SEQ ID NO 703
<211> LENGTH: 13
<212> TYPE: RNA
<213> ORGANISM: Homo sapiens

<400> SEQUENCE: 703
acaaauacga uua                                                          13

<210> SEQ ID NO 704
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
gguuuaugaa cugaa                                                        15

<210> SEQ ID NO 705
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
uaugaacuga cguua                                                        15

<210> SEQ ID NO 706
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
augaacugac guuaa                                                        15

<210> SEQ ID NO 707
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
aauguuguga ccgga                                                        15

<210> SEQ ID NO 708
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
```
uagacgguac cgaca                                                        15

<210> SEQ ID NO 709
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
caaccaguau uugga                                                        15

<210> SEQ ID NO 710
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
ugcucaauaa uguua                                                        15

<210> SEQ ID NO 711
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
uccugcuuua gucga                                                        15

<210> SEQ ID NO 712
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
uagucgagaa ccaaa                                                        15

<210> SEQ ID NO 713
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
aguacuucaa cgcua                                                        15

<210> SEQ ID NO 714
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
uucagucucg uugua                    15

<210> SEQ ID NO 715
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
cuagcuccau gcuua                    15

<210> SEQ ID NO 716
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
cugcgugaac auuca                    15

<210> SEQ ID NO 717
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
cucaggauuu aaaaa                    15

<210> SEQ ID NO 718
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
auaucaguaa agaga                    15

<210> SEQ ID NO 719
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
caguaaagag auuaa                    15

<210> SEQ ID NO 720
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
cagcuaccaa gaaaa                    15

<210> SEQ ID NO 721
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 721
cugacaauau gugaa                                              15

<210> SEQ ID NO 722
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
ggcaucgcua uggaa                                              15

<210> SEQ ID NO 723
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
cgcuauggaa cuuua                                              15

<210> SEQ ID NO 724
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
ugacaaugaa auuaa                                              15

<210> SEQ ID NO 725
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
gacaaugaaa uuaaa                                              15

<210> SEQ ID NO 726
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
cuucauagcg aacca                                              15

```
<210> SEQ ID NO 727
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 727
augugcucuu aggca                                                          15

<210> SEQ ID NO 728
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
ugacaaggaa agaaa                                                          15

<210> SEQ ID NO 729
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
uuguccaggu uuaua                                                          15

<210> SEQ ID NO 730
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
cagguuuaug aacua                                                          15

<210> SEQ ID NO 731
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 731
uuaugaacug acgua                                                          15

<210> SEQ ID NO 732
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 732
ugaacugacg uuaca                                                          15
```

<210> SEQ ID NO 733
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 733
acugacguua cauca                                                        15

<210> SEQ ID NO 734
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 734
acguuacauc auaca                                                        15

<210> SEQ ID NO 735
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 735
guuacaucau acaca                                                        15

<210> SEQ ID NO 736
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 736
guugugaccg gagca                                                        15

<210> SEQ ID NO 737
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 737
uauuguggaa cuuaa                                                        15

<210> SEQ ID NO 738
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 738
aaagugcucu uagga                                                        15

<210> SEQ ID NO 739

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 739
uaccgacaac cagua                                                    15

<210> SEQ ID NO 740
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
ccgacaacca guaua                                                    15

<210> SEQ ID NO 741
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
cuacaucgau cauga                                                    15

<210> SEQ ID NO 742
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
uacaucgauc augga                                                    15

<210> SEQ ID NO 743
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
gugcucaaua augua                                                    15

<210> SEQ ID NO 744
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
guuacaacaa guaaa                                                    15

<210> SEQ ID NO 745
<211> LENGTH: 15
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
auccugcuuu aguca                                                          15

<210> SEQ ID NO 746
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
uuagucgaga accaa                                                          15

<210> SEQ ID NO 747
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
ucgagaacca augaa                                                          15

<210> SEQ ID NO 748
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
agaaccaaug augga                                                          15

<210> SEQ ID NO 749
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
caacaauugu ugaaa                                                          15

<210> SEQ ID NO 750
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 750
aacauggugc aggca                                                          15

<210> SEQ ID NO 751
<211> LENGTH: 15
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 751
caaagaaccg ugcaa                                                       15

<210> SEQ ID NO 752
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
aagaaccgug cagaa                                                       15

<210> SEQ ID NO 753
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753
gaaccgugca gauaa                                                       15

<210> SEQ ID NO 754
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
ccucuuguua uaaaa                                                       15

<210> SEQ ID NO 755
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 755
uggcuuugua uugaa                                                       15

<210> SEQ ID NO 756
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 756
ggaauuccua aaaua                                                       15

<210> SEQ ID NO 757
<211> LENGTH: 15
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 757
uggcaucaug gccaa                                                          15

<210> SEQ ID NO 758
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 758
cccagucaac ugaaa                                                          15

<210> SEQ ID NO 759
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 759
agcagcaaca uacua                                                          15

<210> SEQ ID NO 760
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 760
gaauguuccg gagaa                                                          15

<210> SEQ ID NO 761
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 761
gaacauucac agcca                                                          15

<210> SEQ ID NO 762
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 762
gauuuaaaau uuaaa                                                          15

<210> SEQ ID NO 763
<211> LENGTH: 15
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 763
uaaaauuuaa uuaua                                                    15

<210> SEQ ID NO 764
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 764
aauuauauca guaaa                                                    15

<210> SEQ ID NO 765
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765
aacguaacuc uuuca                                                    15

<210> SEQ ID NO 766
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 766
cuaugcccgu guaaa                                                    15

<210> SEQ ID NO 767
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767
gcccguguaa aguaa                                                    15

<210> SEQ ID NO 768
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768
agucaggaga gugca                                                    15

<210> SEQ ID NO 769
<211> LENGTH: 15
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 769
uggguauuga augua                                                    15

<210> SEQ ID NO 770
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
ugguaagugg aggaa                                                    15

<210> SEQ ID NO 771
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
aguggaggaa augua                                                    15

<210> SEQ ID NO 772
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
uuggaacucu gugca                                                    15

<210> SEQ ID NO 773
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 773
ugaggaggcc cuuaa                                                    15

<210> SEQ ID NO 774
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 774
agggaagcua cugaa                                                    15

<210> SEQ ID NO 775
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 775
auaacacgua agaaa                                                    15

<210> SEQ ID NO 776
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 776
uacauuugua agaaa                                                    15

<210> SEQ ID NO 777
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 777
guaagaaaua acaca                                                    15

<210> SEQ ID NO 778
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 778
cacugugaau guaaa                                                    15

<210> SEQ ID NO 779
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
gagcucauua guaaa                                                    15

<210> SEQ ID NO 780
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
cacgcauaua cauaa                                                    15

<210> SEQ ID NO 781
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 781
gacacaucua uaaua                                                    15

<210> SEQ ID NO 782
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
cacacaccuc ucaaa                                                    15

<210> SEQ ID NO 783
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
uaucauguuc cuaaa                                                    15

<210> SEQ ID NO 784
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
gcaaauguga uuaaa                                                    15

<210> SEQ ID NO 785
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785
ugugauuaau uugga                                                    15

<210> SEQ ID NO 786
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786
gguugucaag uuuua                                                    15

<210> SEQ ID NO 787
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787
```

-continued uuuccugcug guaaa                                                    15

<210> SEQ ID NO 788
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788
ccugcuggua auaua                                                    15

<210> SEQ ID NO 789
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789
gggaaagauu uuaaa                                                    15

<210> SEQ ID NO 790
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
aaugaaacca gggua                                                    15

<210> SEQ ID NO 791
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
aaaccagggu agaaa                                                    15

<210> SEQ ID NO 792
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
uuggcaaugc acuga                                                    15

<210> SEQ ID NO 793
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793

```
caguuguuuc uaaga                                                 15

<210> SEQ ID NO 794
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
gacgagagau guaua                                                 15

<210> SEQ ID NO 795
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
gagauguaua uuuaa                                                 15

<210> SEQ ID NO 796
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
uaacugcugc aaaca                                                 15

<210> SEQ ID NO 797
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
gcugcaaaca uugua                                                 15

<210> SEQ ID NO 798
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
acaaauacga uua                                                   13

<210> SEQ ID NO 799
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
uucaguucau aaaccuggac                                            20
```

```
<210> SEQ ID NO 800
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
uaacgucagu ucauaaaccu                                                    20

<210> SEQ ID NO 801
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 801
uuaacgucag uucauaaacc                                                    20

<210> SEQ ID NO 802
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
uccggucaca acauuguggu                                                    20

<210> SEQ ID NO 803
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
ugucgguacc gucuaacaca                                                    20

<210> SEQ ID NO 804
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
uccaaauacu gguugucggu                                                    20

<210> SEQ ID NO 805
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
uaacauuauu gagcacucgu                                                    20
```

<210> SEQ ID NO 806
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 806
ucgacuaaag caggauuuca                                           20

<210> SEQ ID NO 807
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 807
uuugguucuc gacuaaagca                                           20

<210> SEQ ID NO 808
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 808
uagcguugaa guacuguccc                                           20

<210> SEQ ID NO 809
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 809
uacaacgaga cugaauugcc                                           20

<210> SEQ ID NO 810
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 810
uaagcaugga gcuagcaggc                                           20

<210> SEQ ID NO 811
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 811
ugaauguuca cgcagugggc                                           20

```
<210> SEQ ID NO 812
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 812
uuuuuaaauc cugagaagaa                                                     20

<210> SEQ ID NO 813
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 813
ucucuuuacu gauauaauua                                                     20

<210> SEQ ID NO 814
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 814
uuaaucucuu uacugauaua                                                     20

<210> SEQ ID NO 815
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 815
uuuucuuggu agcugaaagu                                                     20

<210> SEQ ID NO 816
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 816
uucacauauu gucagacaau                                                     20

<210> SEQ ID NO 817
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 817
uuccauagcg augcccagaa                                                     20

<210> SEQ ID NO 818
```

<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 818
uaaaguucca uagcgaugcc                                              20

<210> SEQ ID NO 819
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 819
uuaauuucau ugucauuugc                                              20

<210> SEQ ID NO 820
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 820
uuuaauuuca uugucauuug                                              20

<210> SEQ ID NO 821
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
ugguucgcua ugaaggccuu                                              20

<210> SEQ ID NO 822
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
ugccuaagag cacauuuagu                                              20

<210> SEQ ID NO 823
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 823
uuucuuuccu ugucacuccg                                              20

<210> SEQ ID NO 824
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 824
uauaaaccug gacaagcugc                                                    20

<210> SEQ ID NO 825
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 825
uaguucauaa accuggacaa                                                    20

<210> SEQ ID NO 826
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 826
uacgucaguu cauaaaccug                                                    20

<210> SEQ ID NO 827
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
uguaacguca guucauaaac                                                    20

<210> SEQ ID NO 828
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 828
ugauguaacg ucaguucaua                                                    20

<210> SEQ ID NO 829
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
uguaugaugu aacgucaguu                                                    20

<210> SEQ ID NO 830
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 830
uguguaugau guaacgucag                                                   20

<210> SEQ ID NO 831
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
ugcuccgguc acaacauugu                                                   20

<210> SEQ ID NO 832
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
uuaaguucca caauacuccc                                                   20

<210> SEQ ID NO 833
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 833
uccuaagagc acuuugccuu                                                   20

<210> SEQ ID NO 834
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
uacugguugu cgguaccguc                                                   20

<210> SEQ ID NO 835
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 835
uauacugguu gucgguaccg                                                   20

<210> SEQ ID NO 836
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 836
ucaugaucga uguaguucaa                                                   20

<210> SEQ ID NO 837
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 837
uccaugaucg auguaguuca                                                   20

<210> SEQ ID NO 838
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
uacauuauug agcacucguu                                                   20

<210> SEQ ID NO 839
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 839
uuuacuuguu guaacaggac                                                   20

<210> SEQ ID NO 840
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 840
ugacuaaagc aggauuucag                                                   20

<210> SEQ ID NO 841
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 841
uugguucucg acuaaagcag                                                   20

<210> SEQ ID NO 842
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 842
uucauugguu cucgacuaaa                                                    20

<210> SEQ ID NO 843
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 843
uccaucauug guucucgacu                                                    20

<210> SEQ ID NO 844
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 844
uuucaacaau uguugaacac                                                    20

<210> SEQ ID NO 845
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 845
ugccugcacc auguccuca                                                     20

<210> SEQ ID NO 846
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 846
uugcacgguu cuuugugaca                                                    20

<210> SEQ ID NO 847
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 847
uucugcacgg uucuuuguga                                                    20

<210> SEQ ID NO 848
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 848
uuaucugcac gguucuuugu                                               20

<210> SEQ ID NO 849
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
uuuuauaaca agagguucaa                                               20

<210> SEQ ID NO 850
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
uucaauacaa agccauaaa                                                20

<210> SEQ ID NO 851
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
uauuuuagga auuccaauga                                               20

<210> SEQ ID NO 852
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
uuggccauga ugccaucaca                                               20

<210> SEQ ID NO 853
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 853
uuucaguuga cugggaaauc                                               20

<210> SEQ ID NO 854
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 854
uaguauguug cugcucacuc                                              20

<210> SEQ ID NO 855
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
uucuccggaa cauuccagac                                              20

<210> SEQ ID NO 856
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 856
uggcugugaa uguucacgca                                              20

<210> SEQ ID NO 857
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 857
uuuaaauuuu aaauccugag                                              20

<210> SEQ ID NO 858
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 858
uauaauuaaa uuuuaaaucc                                              20

<210> SEQ ID NO 859
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
uuuacugaua uaauuaaauu                                              20

<210> SEQ ID NO 860
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 860
ugaaagaguu acguuaaaau                                               20

<210> SEQ ID NO 861
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 861
uuuacacggg cauagaaaga                                               20

<210> SEQ ID NO 862
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 862
uuacuuuaca cgggcauaga                                               20

<210> SEQ ID NO 863
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 863
ugcacucucc ugacuaaaag                                               20

<210> SEQ ID NO 864
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 864
uacauucaau acccaaaaca                                               20

<210> SEQ ID NO 865
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 865
uuccuccacu uaccacauuc                                               20

<210> SEQ ID NO 866
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 866
```
uacauuuccu ccacuuacca                                              20

<210> SEQ ID NO 867
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 867
ugcacagagu uccaacauuu                                              20

<210> SEQ ID NO 868
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 868
uuaagggccu ccucaaacau                                              20

<210> SEQ ID NO 869
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 869
uucaguagcu ucccuuaagg                                              20

<210> SEQ ID NO 870
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 870
uuucuuacgu guuauaauuc                                              20

<210> SEQ ID NO 871
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
uuucuuacaa auguaaacau                                              20

<210> SEQ ID NO 872
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 872
uguguuauuu cuuacaaaug    20

<210> SEQ ID NO 873
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 873
uuuacauuca caguguuauu    20

<210> SEQ ID NO 874
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 874
uuuacuaaug agcucauauu    20

<210> SEQ ID NO 875
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 875
uuauguauau gcguggguga    20

<210> SEQ ID NO 876
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 876
uauuauagau gugucuauau    20

<210> SEQ ID NO 877
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877
uuugagaggu guguguguaa    20

<210> SEQ ID NO 878
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 878
uuuaggaaca ugauaaaguc    20

<210> SEQ ID NO 879
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 879
uuuaaucaca uuugcaacaa                                                   20

<210> SEQ ID NO 880
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 880
uccaaauuaa ucacauuugc                                                   20

<210> SEQ ID NO 881
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 881
uaaaacuuga caaccaaauu                                                   20

<210> SEQ ID NO 882
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 882
uuuaccagca ggaaaacaaa                                                   20

<210> SEQ ID NO 883
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 883
uauauuacca gcaggaaaac                                                   20

<210> SEQ ID NO 884
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 884
uuuaaaaucu uucccgauau                                                   20

<210> SEQ ID NO 885
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 885
uacccugguu ucauuaaaau                                               20

<210> SEQ ID NO 886
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 886
uuucuacccu gguuucauua                                               20

<210> SEQ ID NO 887
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 887
ucagugcauu gccaaacaau                                               20

<210> SEQ ID NO 888
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 888
ucuuagaaac aacugagggg                                               20

<210> SEQ ID NO 889
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 889
uauacaucuc ucgucagucc                                               20

<210> SEQ ID NO 890
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 890
uuaaauauac aucucucguc                                               20

```
<210> SEQ ID NO 891
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 891
uguuugcagc aguuaaaaaa                                               20

<210> SEQ ID NO 892
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 892
uacaauguuu gcagcaguua                                               20

<210> SEQ ID NO 893
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 893
uaaucguauu ugucaauca                                                19
```

FULLY STABILIZED ASYMMETRIC siRNA

RELATED APPLICATIONS

This application is a continuation of U.S. patent application Ser. No. 15/089,423, filed Apr. 1, 2016, which claims priority to U.S. Provisional Patent Application No. 62/142,786, filed Apr. 3, 2015, U.S. Provisional Patent Application No. 62/205,218, filed Aug. 14, 2015, and U.S. Provisional Patent Application No. 62/287,255, filed Jan. 26, 2016. The entire contents of these applications are incorporated herein by reference.

STATEMENT REGARDING FEDERALLY FUNDED RESEARCH

This invention was made with government support under grant numbers NS038194, GM108803 and TR000888 awarded by the National Institutes of Health, and grant number OPP1086170 awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 13, 2020, is named 708016_UM9-209CON2_ST25.txt and is 192,854 bytes in size.

TECHNICAL FIELD

This disclosure relates to novel oligonucleotides useful for RNA interference (RNAi), consisting of fully chemically-modified ribonucleotides. The chemically-modified nucleotides and linkers are patterned to achieve unexpectedly high efficacy, uptake and tissue distribution.

BACKGROUND

Oligonucleotides comprising chemically-modified ribonucleotides (e.g., 2'-fluoro and 2'-methoxy modifications) and/or chemically-modified linkers (e.g., a phosphorothioate modification) are known to exhibit increased nuclease resistance relative to the corresponding unmodified oligonucleotides, while maintaining the ability to promote RNAi. See, e.g., Fosnaugh, et al. (U.S. Publication No. 2003/0143732). Oligonucleotides comprising alternating chemically-modified nucleotides are known. See, e.g., Bhat et al. (U.S. Publication No. 2008/0119427). Hydrophobic modification of therapeutic RNA (e.g., siRNA) is known. See, e.g., Khvorova, et al. (PCT/US2009/005247).

There remains a need for self-delivering siRNA that is characterized by efficient RISC entry, minimum immune response and off-target effects, efficient cellular uptake without formulation and efficient and specific tissue distribution.

SUMMARY

Accordingly, provided herein in certain embodiments are siRNA compounds having the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications); (5) single-stranded, fully phosphorothioated tails of 5-8 bases. The number of phosphorothioate modifications is varied from 6 to 17 total in different embodiments.

In certain embodiments, the siRNA compounds described herein can be conjugated to a variety of targeting agents, including, but not limited to, cholesterol, DHA, phenyltropanes, cortisol, Vitamin A, Vitamin D, GalNac, and Gangliosides. The cholesterol-modified version showed 5-10 fold improvement in efficacy in vitro versus previously used chemical stabilization patterns (e.g., wherein all purine but not pyrimidines are modified) in wide range of cell types (e.g., HeLa, Neurons, Hepatocytes, Trophoblasts).

Certain compounds of the invention having the structural properties described above and herein may be referred to as "hsiRNA-ASP" (hydrophobically-modified, small interfering RNA, featuring an advanced stabilization pattern), and may also be referred to as "FM-hsiRNA" (Fully Modified hydrophobically-modified, small interfering RNA). In addition, this hsiRNA-ASP pattern showed a dramatically improved distribution through the brain, spinal cord, delivery to liver, placenta, kidney, spleen and several other tissues, making them accessible for therapeutic intervention.

In liver, hsiRNA-ASP is delivered specifically to endothelial and kupffer cells, but not hepatocytes, making this chemical modification pattern a complimentary, rather than competitive, technology to GalNac conjugates.

The compounds of the invention can be described in the following aspects and embodiments.

In a first aspect, provided herein is compound (I): an oligonucleotide of at least 16 contiguous nucleotides, said oligonucleotide having a 5' end, a 3' end and complementarity to a target, wherein:

(1) the oligonucleotide comprises alternating 2'-methoxy-ribonucleotides and 2'-fluoro-ribonucleotides;

(2) the nucleotides at positions 2 and 14 from the 5' end are not 2'-methoxy-ribonucleotides;

(3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a second aspect, provided herein is a double-stranded, chemically-modified nucleic acid, comprising a first oligonucleotide compound (I) and a second oligonucleotide compound (II), wherein:

(1) a portion of the first oligonucleotide is complementary to a portion of the second oligonucleotide;

(2) the second oligonucleotide comprises alternating 2'-methoxy-ribonucleotides and 2'-fluoro-ribonucleotides;

(3) the nucleotides at positions 2 and 14 from the 3' end of the second oligonucleotide are 2'-methoxy-ribonucleotides; and (4) the nucleotides of the second oligonucleotide are connected via phosphodiester or phosphorothioate linkages.

In a third aspect, provided herein is an oligonucleotide having the structure of compound (Ia):

(Ia)

wherein:
X is selected from the group consisting of:

(X1) 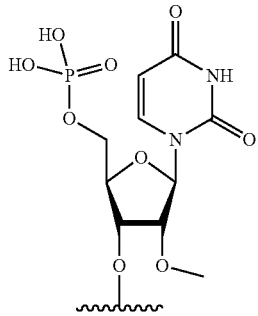

(X2) 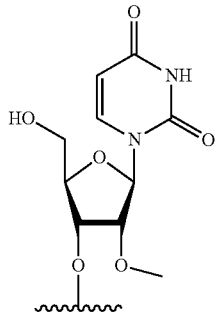

(X3) 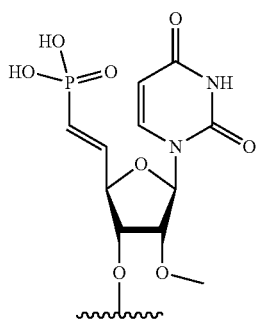

(X4) 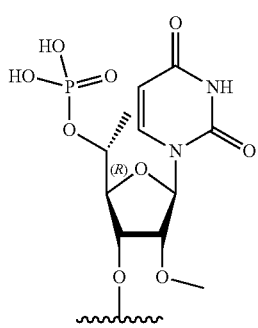

-continued (X5) 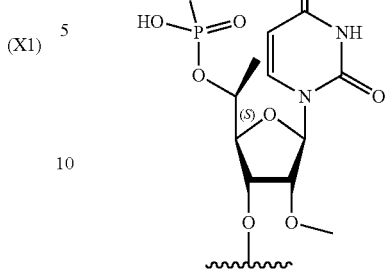

(X6) 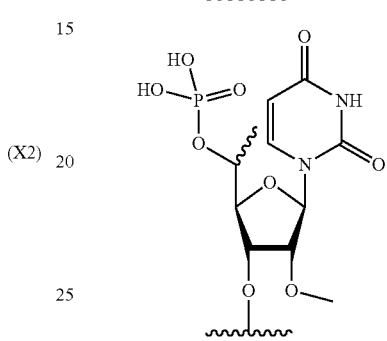

(X7) 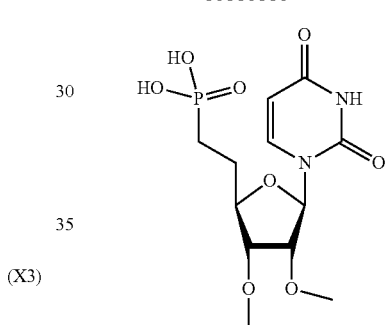

(X8) 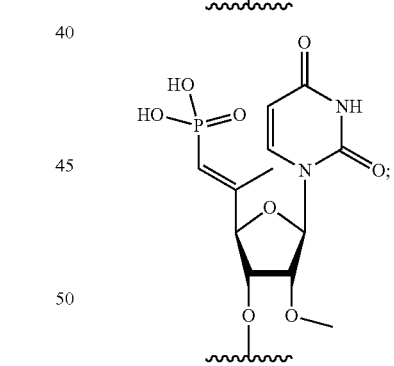

A, for each occurrence, independently is a 2'-methoxy-ribonucleotide; B, for each occurrence, independently is a 2'-fluoro-ribonucleotide; K, for each occurrence independently is a phosphodiester or phosphorothioate linker; S is a phosphorothioate linker; R, for each occurrence, independently is selected from hydrogen and a capping group (e.g., an acyl group such as acetyl); j is 4, 5, 6 or 7; r is 2 or 3; and t is 0 or 1.

In a fourth aspect, provided herein is a double-stranded, chemically-modified nucleic acid comprising a first oligonucleotide and a second oligonucleotide, wherein:
 (1) the first oligonucleotide is an oligonucleotide as described herein (e.g., compound (I), (Ia) or (Ib));

(2) a portion of the first oligonucleotide is complementary to a portion of the second oligonucleotide; and
(3) the second oligonucleotide has the structure of compound (IIa):

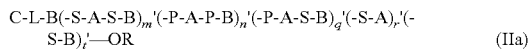

(IIa)

wherein: C is a hydrophobic molecule; A, for each occurrence, independently is a 2'-methoxy-ribonucleotide; B, for each occurrence, independently is a 2'-fluoro-ribonucleotide; L is a linker comprising one or more moiety selected from the group consisting of: 0-20 repeat units of ethyleneglycol, a phosphodiester, and a phosphorothioate; S is a phosphorothioate linker; P is a phosphodiester linker; R is selected from hydrogen and a capping group (e.g., an acyl group such as acetyl); m' is 0 or 1; n' is 4, 5 or 6; q' is 0 or 1; r' is 0 or 1; and t' is 0 or 1.

BRIEF DESCRIPTION OF THE DRAWINGS

Color Drawings

The patent or application file contains at least one drawing executed in color. Copies of this patent or patent application publication with color drawing(s) will be provided by the Office upon request and payment of the necessary fee.

FIG. 2 depicts particular nucleotide and linker chemical modifications.

FIG. 3 depicts the identification and validation of compounds of the invention targeting i13 and i14 isoforms of sFLT1. FIG. 3 discloses SEQ ID NOS 14-15 and 10-13, respectively, in order of appearance.

FIG. 14 discloses SEQ ID NOS 16-21, respectively, in order of appearance.

FIG. 23 depicts a list of siRNA having efficacy, representing different chemical scaffolds and unique sequences of I13 short, I13 long and I15a isoforms of sFlt1. In the table, "Guide" refers to the antisense strand; "C" represents cytidine; "U" represents uridine; "A" represents adenosine; "G" represents guanosine; "m" indicates a 2'-methoxy chemical modification; "f" indicates a 2'-fluoro chemical modification; "#" represents a phosphorothioate linker; "P" represents a 5' phosphate; "teg" represents triethylene glycol; and "Chol" represents cholesterol. FIG. 23 discloses "Targeting region (20 mer)" sequences as SEQ ID NOS 22-80, "Targeting region (30 mer)" sequences as SEQ ID NOS 81-139, "Sense Naked" sequences as SEQ ID NOS 140-198, "Guide 20 mer" sequences as SEQ ID NOS 199-257, "Sense P0" sequences as SEQ ID NOS 258-316, "Guide P0" sequences as SEQ ID NOS 317-375, "Sense P1" sequences as SEQ ID NOS 376-434, "Guide P1" sequences as SEQ ID NOS 435-493, "Sense P2" sequences as SEQ ID NOS 494-552, "Guide P2" sequences as SEQ ID NOS 553-611, all respectively, in order of columns.

FIG. 24 depicts target sequences, modified oligonucleotides and their efficacy according to certain embodiments. In the table, "C" represents cytidine; "U" represents uridine; "A" represents adenosine; "G" represents guanosine; "m" indicates a 2'-methoxy chemical modification; "f" indicates a 2'-fluoro chemical modification; "#" represents a phosphorothioate linker; "P" represents a 5' phosphate; "." represents a phosphodiester linkage; "teg" represents triethylene glycol; and "Chol" represents cholesterol. FIG. 24 discloses "Target" sequences as SEQ ID NOS 612-624, 3, 2, 1, and 625-703, "Sense Strand" sequences as SEQ ID NOS 704-798, and "Antisense Strand" sequences as SEQ ID NOS 799-893, all respectively, in order of columns.

FIGS. 26A-26C depict concentration-dependent silencing of huntingtin mRNA by HTT10150, in both passive (A) and lipid-mediated delivery (B). Chemical modifications enable passive uptake without negative impact on siRNA RISC (RNA Induced Silencing Complex) entry. HeLa cells were incubated with modified (containing both hydrophobic and base chemical modifications) or unmodified HTT10150 at concentrations shown in the absence (A) and presence (B) of RNAIMAX. Level of huntingtin mRNA was measured using QUANTIGENE (Affymetrix) at 72 hours normalized to housekeeping gene, PPIB (cyclophillin B), and presented as percent of untreated control (n=3, mean+/−SD). UNT—untreated cells. IC50 values calculated (C) as described herein.

FIGS. 31A-31G depict results from intrastriatal administration of hsiRNA$^{HTT}$ and FM-hsiRNA$^{HTT}$. (A) hsiRNA$^{HTT}$ expression levels in a brain cross-section. (B) FM-hsiRNA$^{HTT}$ expression levels in brain cross-section. (C) FM-hsiRNA$^{HTT}$ expression levels in the cortex. (D) FM-hsiRNA$^{HTT}$ expression levels in the striatum. (E) FM-hsiRNA$^{HTT}$ expression levels in the cerebellum. (F) hsiRNA$^{HTT}$ and FM-hsiRNA$^{HTT}$ silencing using 3 µg, 6 µg and 12 µg doses. (G) hsiRNA$^{HTT}$ and FM-hsiRNA$^{HTT}$ silencing one-, two- and four-weeks post-injection.

FIG. 36 depicts exemplary internucleotide linkages.

DETAILED DESCRIPTION

Figure 1A:
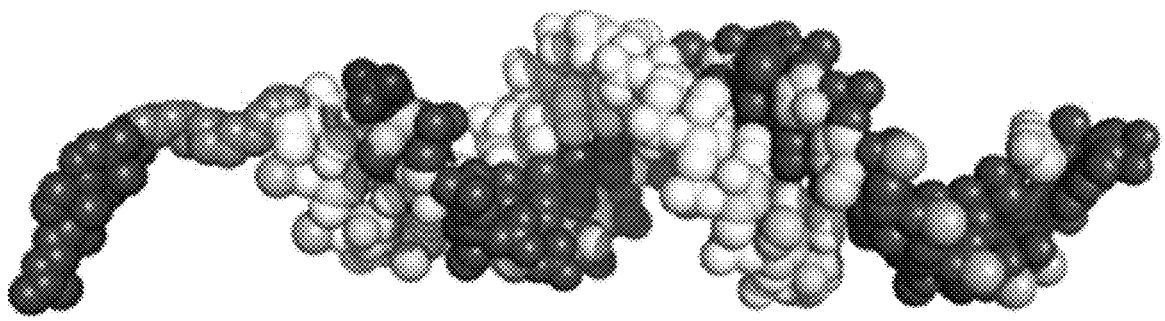
FIGS. 1A-1D depict a hydrophobic siRNA structural/chemical composition, uptake and efficacy in primary human cytotrophoblasts (CTBs). (A) Schematically depicts hydrophobically modified and stabilized siRNAs (hsiRNAs) according to certain embodiments. sFlt1-i13-2283 hsiRNA and matching NTC was added to CTBs at concentration shown. (B) Level of sFLT1 protein was measured by ELISA (#MVR100, R&D systems) in conditioned culture medium after 72 h treatment. (C) depicts sFlt1-i13 mRNA levels, and (D) depicts Flt1-FL mRNA levels that were measured using QUANTIGENE (Affymetrix) at 72 hours, (n=3, mean+/−SD). UNT—untreated cells, NTC—non-targeting control with matching chemistry.

In a first aspect, provided herein is compound (I): an oligonucleotide of at least 16 contiguous nucleotides, said oligonucleotide having a 5' end, a 3' end and complementarity to a target, wherein:
  (1) the oligonucleotide comprises alternating 2'-methoxy-ribonucleotides and 2'-fluoro-ribonucleotides;
  (2) the nucleotides at positions 2 and 14 from the 5' end are not 2'-methoxy-ribonucleotides;
  (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In one embodiment, the oligonucleotide has sufficient complementarity to the target to hybridize. In certain embodiments, the complementarity is >95%, >90%, >85%, >80%, >75%, >70%, >65%, >60%, >55% or >50%. In one embodiment, the oligonucleotide has perfect complementarity to the target.

In one embodiment of the oligonucleotide, the target is mammalian or viral mRNA. In another embodiment, the target is an intronic region of said mRNA. In another embodiment, the target is a 5' UTR region of said mRNA. In another embodiment, the mRNA corresponds to a portion of soluble Flt1 (sFlt1). In a particular embodiment, the mRNA corresponds to a portion (e.g., an intronic region) of sFlt i13 (e.g., sFlt-i13 long or sFlt-i13 short). In another particular embodiment, the mRNA corresponds to a portion (e.g., an intronic region) of sFlt i15a. In another embodiment, the mRNA corresponds to a portion of the Huntingtin gene (e.g., a mutant Huntingtin gene).

In a second aspect, provided herein is a double-stranded, chemically-modified nucleic acid, comprising a first oligonucleotide compound (I) and a second oligonucleotide compound (II), wherein:
(1) a portion of the first oligonucleotide is complementary to a portion of the second oligonucleotide;
(2) the second oligonucleotide comprises alternating 2'-methoxy-ribonucleotides and 2'-fluoro-ribonucleotides;
(3) the nucleotides at positions 2 and 14 from the 3' end of the second oligonucleotide are 2'-methoxy-ribonucleotides; and
(4) the nucleotides of the second oligonucleotide are connected via phosphodiester or phosphorothioate linkages.

In one embodiment, the first oligonucleotide is the antisense strand and the second oligonucleotide is the sense strand.

In one embodiment, the double-stranded nucleic acid comprises one or more mismatch within the complementary portions of the first and second oligonucleotide. In a particular embodiment, the double-stranded nucleic acid contains one mismatch within the complementary portions of the first and second oligonucleotide.

In one embodiment of the nucleic acid, the second oligonucleotide is linked to a hydrophobic molecule at the 3' end of the second oligonucleotide. In one embodiment, the linkage between the second oligonucleotide and the hydrophobic molecule comprises polyethylene glycol. In a particular embodiment, the linkage between the second oligonucleotide and the hydrophobic molecule comprises triethylene glycol.

In another embodiment of the nucleic acid, the nucleotides at positions 1 and 2 from the 3' end of second oligonucleotide are connected to adjacent nucleotides via phosphorothioate linkages. In yet another embodiment, the nucleotides at positions 1 and 2 from the 3' end of second oligonucleotide, and the nucleotides at positions 1 and 2 from the 5' end of second oligonucleotide, are connected to adjacent ribonucleotides via phosphorothioate linkages.

In a third aspect, provided herein is an oligonucleotide having the structure of compound (Ia):

$$X(\text{-K-B-K-A})_j(\text{-S-B-S-A})_r(\text{-S-B})_t\text{—OR} \quad \text{(Ia)}$$

wherein:
X is selected from the group consisting of:

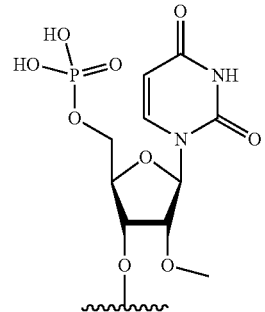

X1

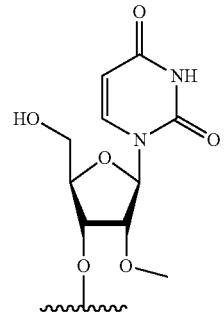

X2

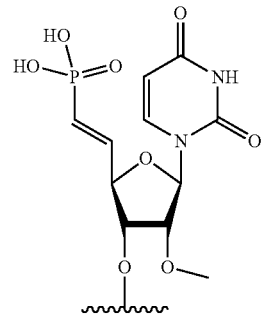

X3

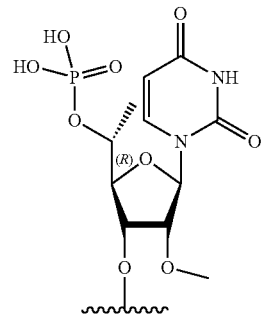

X4

-continued

X5
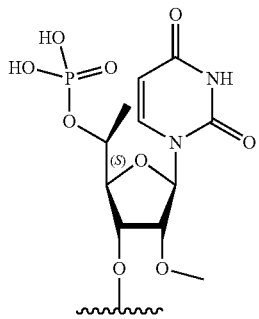

X6
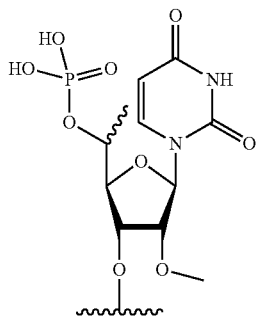

X7
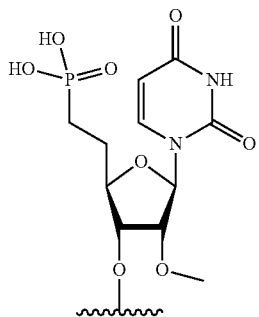

X8
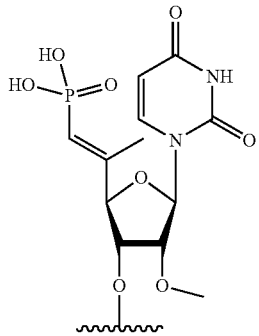

A, for each occurrence, independently is a 2'-methoxy-ribonucleotide;
B, for each occurrence, independently is a 2'-fluoro-ribonucleotide;
K, for each occurrence independently is a phosphodiester or phosphorothioate linker;
S is a phosphorothioate linker;
R, for each occurrence, independently is selected from hydrogen and a capping group (e.g., an acyl group such as acetyl);
j is 4, 5, 6 or 7;
r is 2 or 3; and
t is 0 or 1.

In a particular embodiment, R is hydrogen. In another particular embodiment, X is XY1. In still another particular embodiment, X is X3.

In one embodiment, the oligonucleotide of compound (Ia) has the structure of compound (Ib):

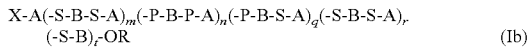

wherein:
X is as defined above;
A, for each occurrence, independently is a 2'-methoxy-ribonucleotide;
B, for each occurrence, independently is a 2'-fluoro-ribonucleotide;
S is a phosphorothioate linker;
P is a phosphodiester linker;
R is as defined above;
m is 0 or 1;
n is 4, 5 or 6;
q is 0 or 1;
r is 2 or 3; and
t is 0 or 1.

Figure 17:
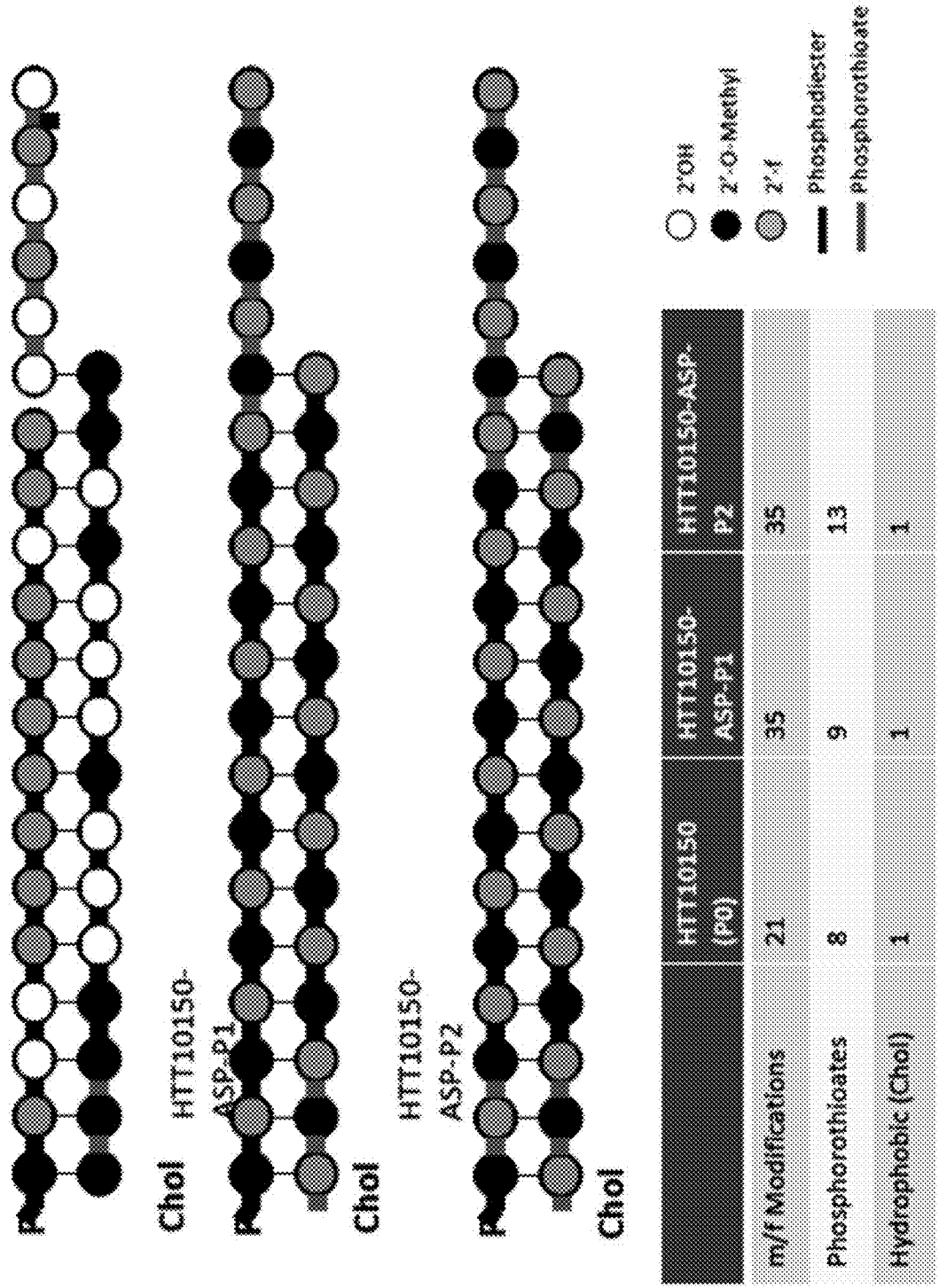
FIG. 17 depicts the number of phosphorothioates and number of modified nucleotide monomers compared to the P0, P1, and P2 modification patterns.
Figure 18:
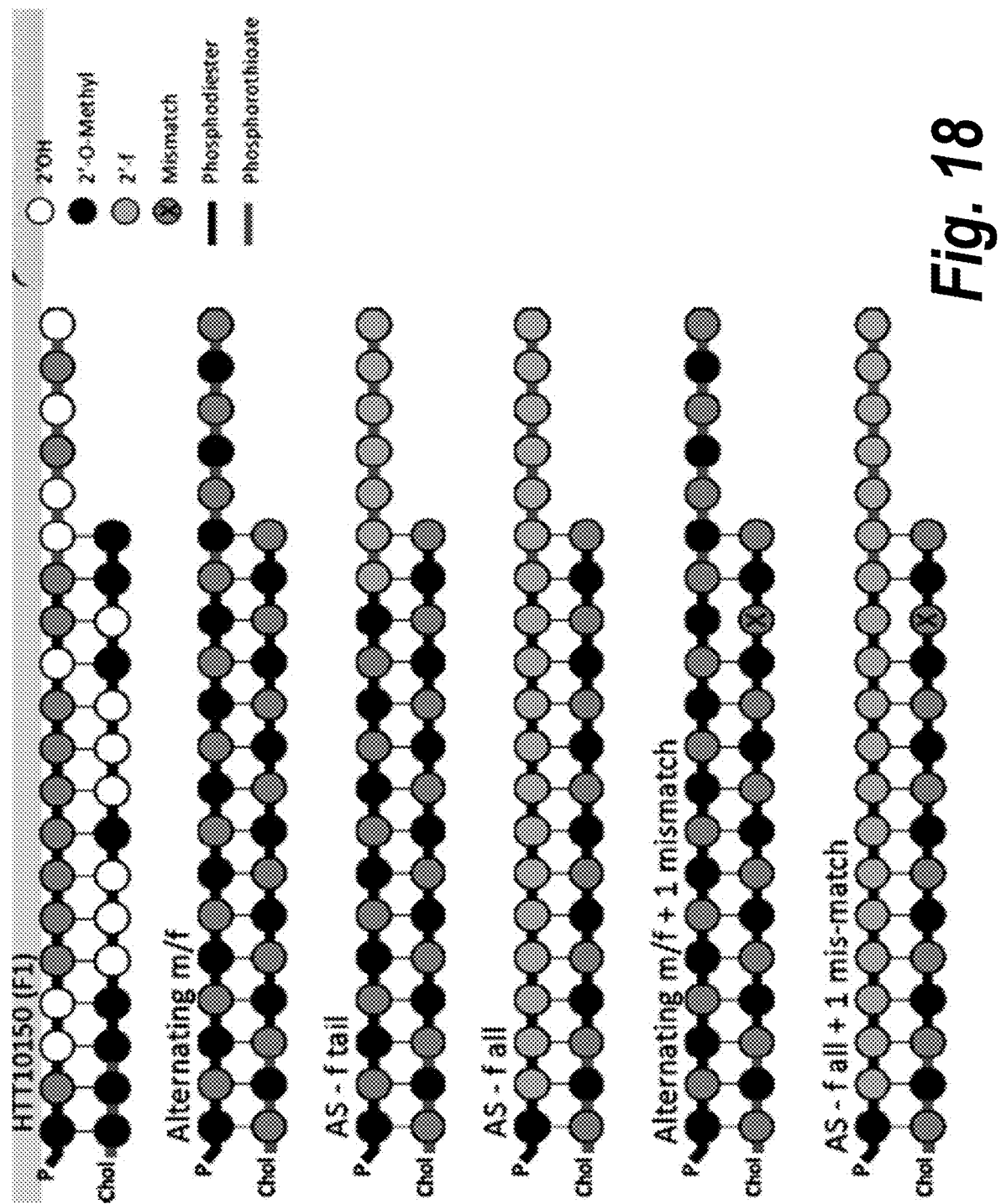
FIG. 18 depicts alternative modification patterns.
Figure 19:
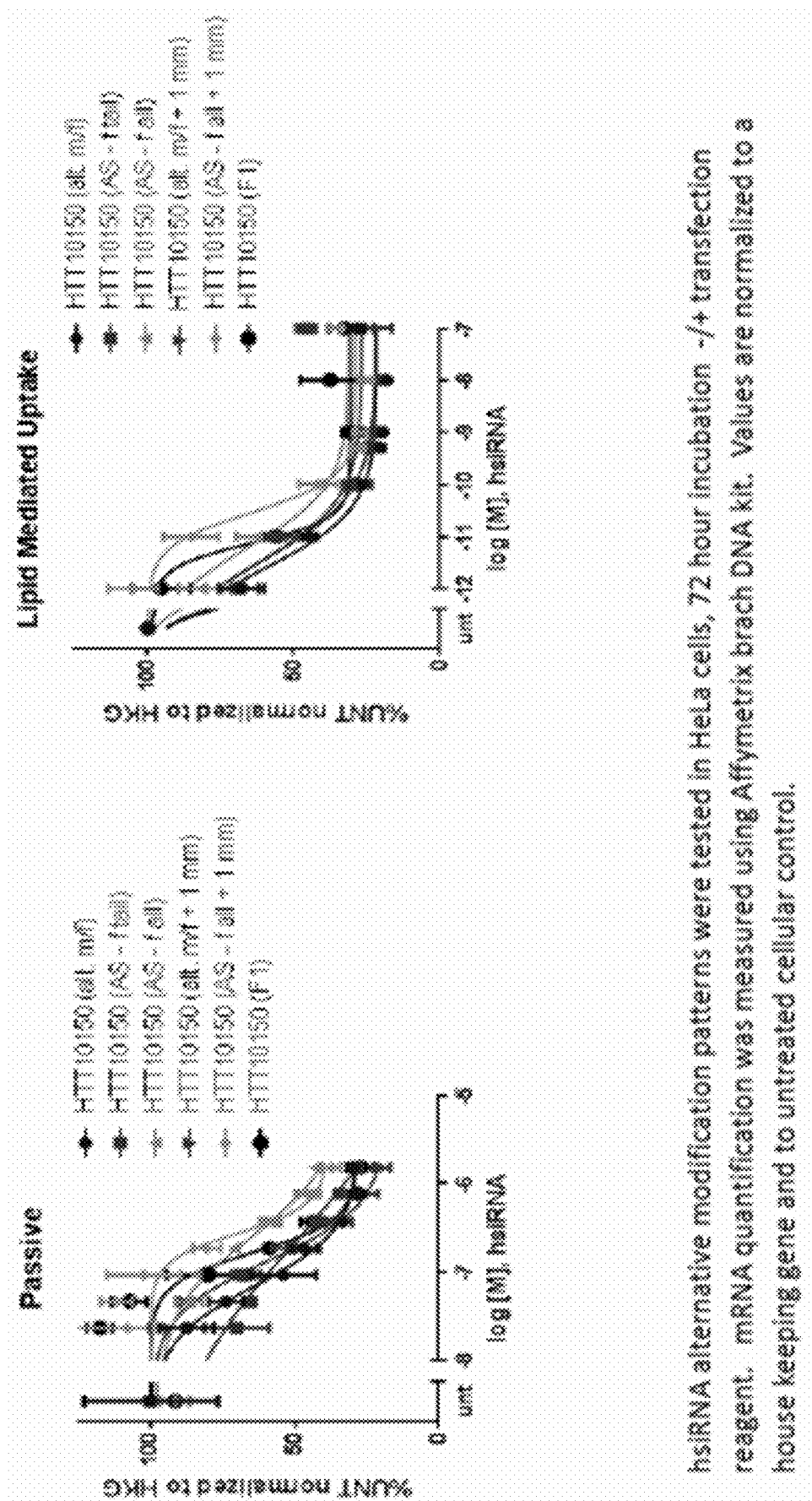
FIG. 19 depicts data related to uptake of siRNA having alternative modification patterns.
Figure 20:
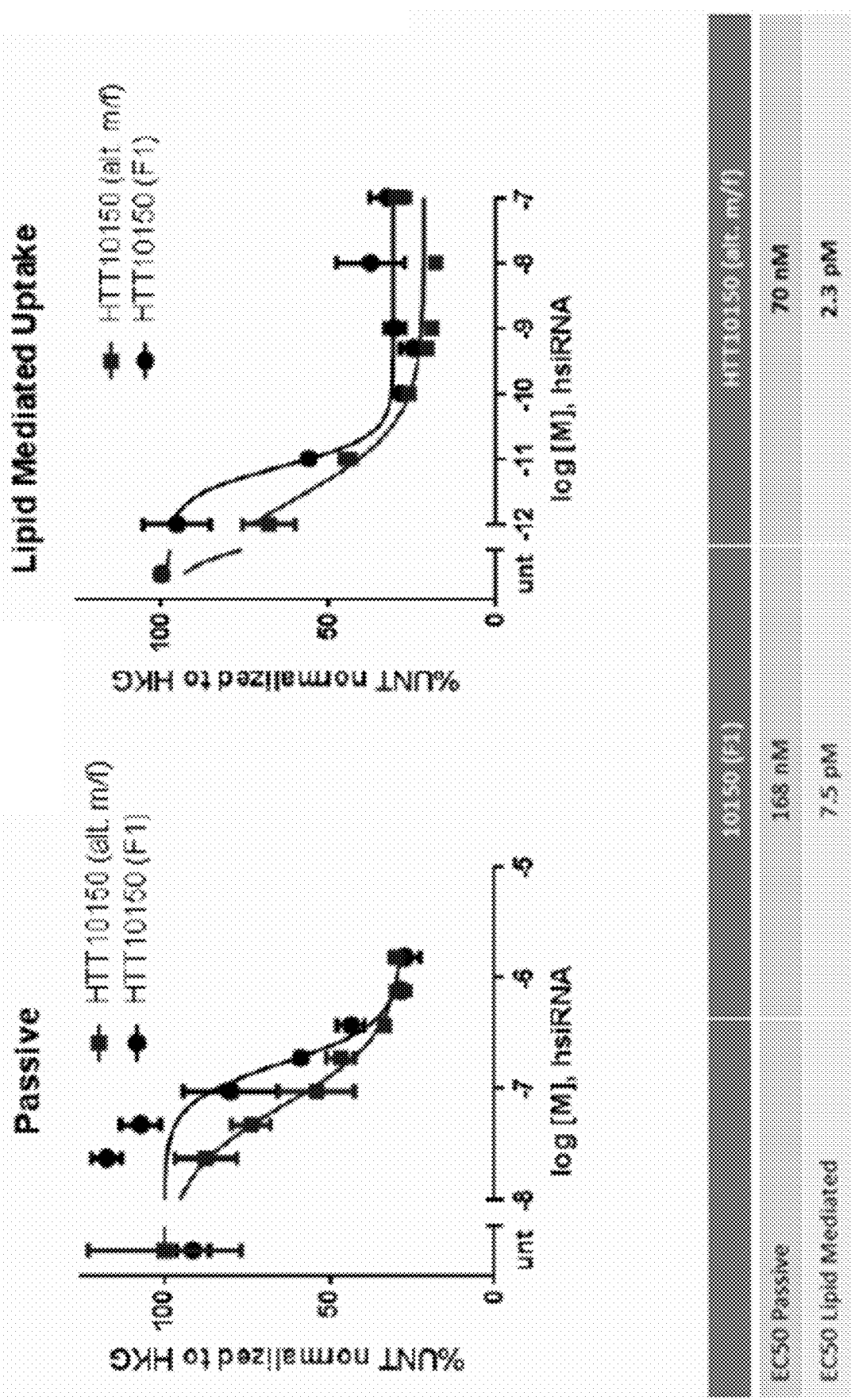
FIG. 20 depicts data showing that siRNA having an alternating 2'-O-Methyl (2'-methoxy)/2'-fluoro pattern show increased efficacy in vitro.
Figure 21:
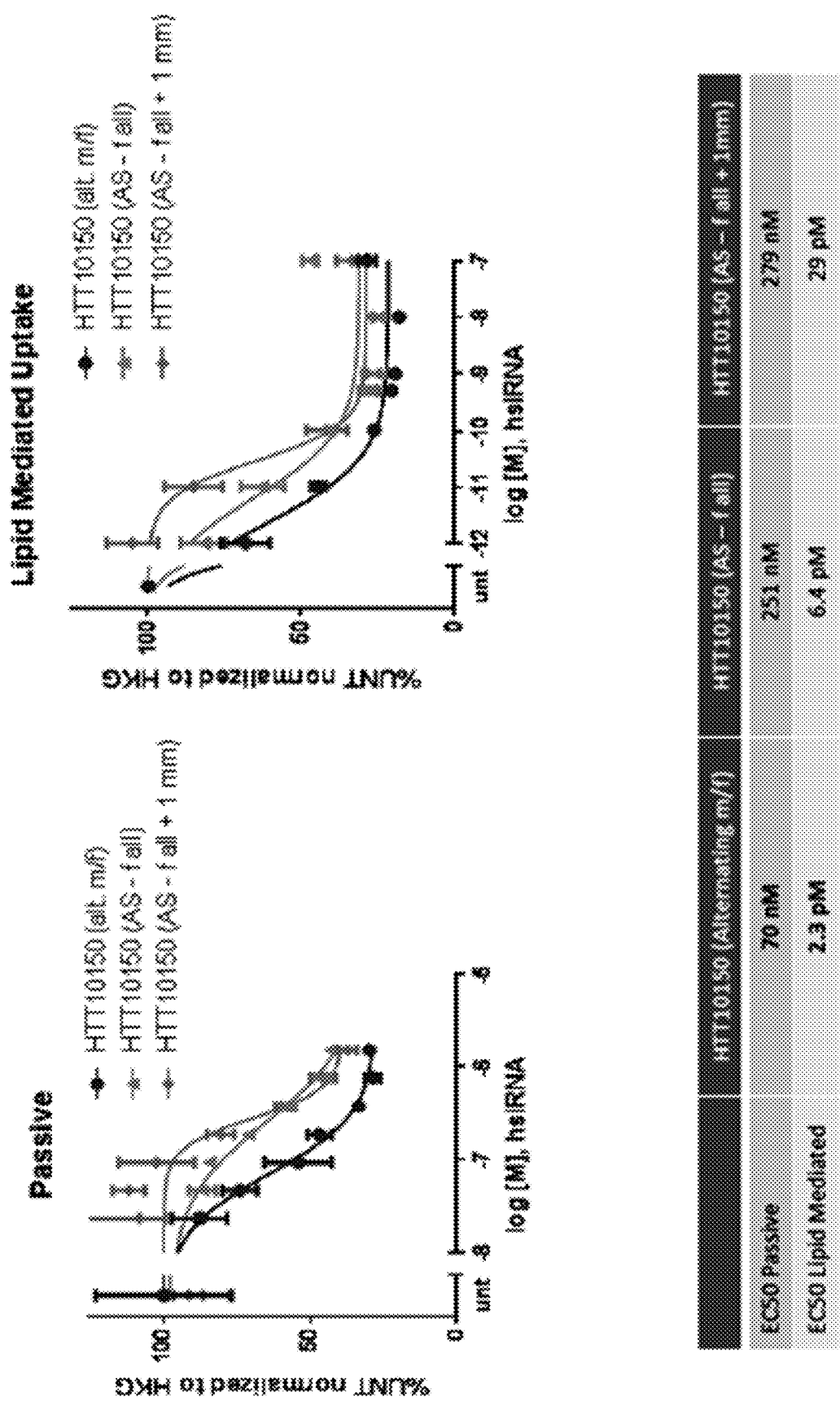
FIG. 21 depicts data showing that siRNA having a fully fluorinated antisense strand exhibit reduced efficacy as compared to the corresponding siRNA having an alternating 2'-methoxy/2'-fluoro pattern.
Figure 22:
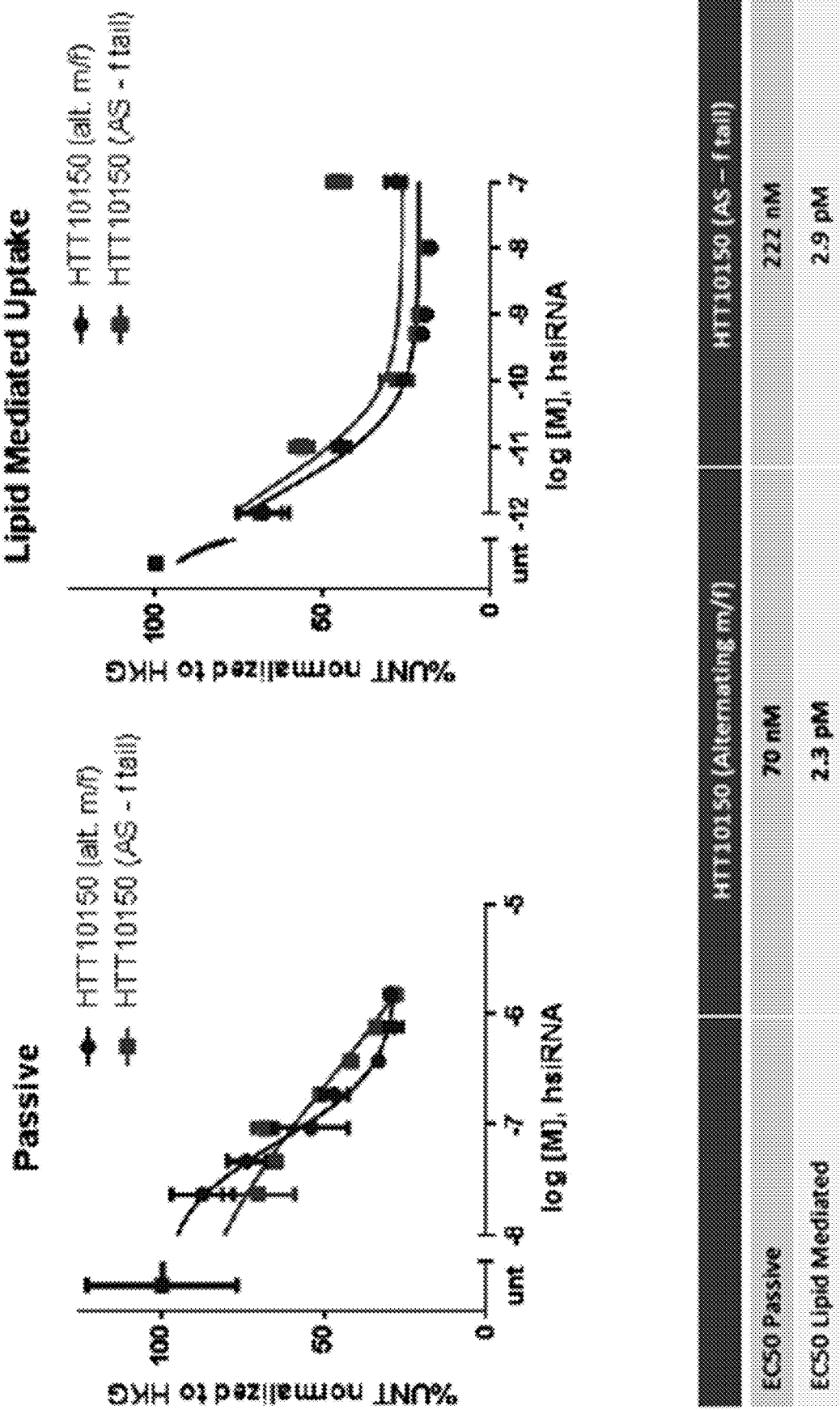
FIG. 22 depicts data showing that siRNA having a fluorinated antisense tail do not exhibit improved efficacy as compared to the corresponding siRNA having a fully alternating 2'-methoxy/2'-fluoro pattern.

In a first particular embodiment of compound (Ib), m is 0; n is 6; q is 1; r is 2; and t is 1. See, e.g., species P1 of FIG. 7 and species HTT10150-ASP-P1 of FIG. 17.

In a second particular embodiment of compound (Ib), m is 1; n is 5; q is 1; r is 2; and t is 1. See, e.g., species P2 of FIG. 7.

In a third particular embodiment of compound (Ib), m is 1; n is 5; q is 0; r is 3; and t is 1. See, e.g., species HTT10150-ASP-P2 of FIG. 17.

In a particular embodiment, R is hydrogen. In another particular embodiment, X is X1. In still another particular embodiment, X is X3.

In a fourth aspect, provided herein is a double-stranded, chemically-modified nucleic acid comprising a first oligonucleotide and a second oligonucleotide, wherein:
(1) the first oligonucleotide is an oligonucleotide as described herein (e.g., compound (I), (Ia) or (Ib));
(2) a portion of the first oligonucleotide is complementary to a portion of the second oligonucleotide; and
(3) the second oligonucleotide has the structure of compound (IIa):

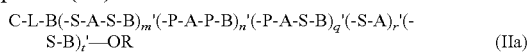

wherein:
C is a hydrophobic molecule;
A, for each occurrence, independently is a 2'-methoxy-ribonucleotide;
B, for each occurrence, independently is a 2'-fluoro-ribonucleotide;
L is a linker comprising an ethylene glycol chain, an alkyl chain, a peptide, RNA, DNA, a phosphodiester, a phosphorothioate, a phosphoramidate, an amide, a carbamate, or a combination thereof;
S is a phosphorothioate linker;
P is a phosphodiester linker;
R, for each occurrence, independently is selected from hydrogen and a capping group (e.g., an acyl group such as acetyl);
m' is 0 or 1;
n' is 4, 5 or 6;
q' is 0 or 1;
r' is 0 or 1; and
t' is 0 or 1.

In one embodiment, L is a linker comprising 0-20, 0-10 or 0-4 repeat units of ethyleneglycol. In a particular embodiment, L is a linker comprising 3 repeat units of ethyleneglycol (i.e., triethylene glycol). In another particular embodiment, L is selected from L1, L2 and L3:

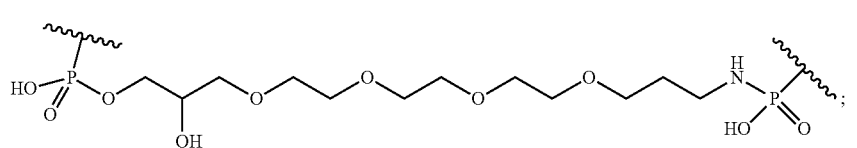

(L1)

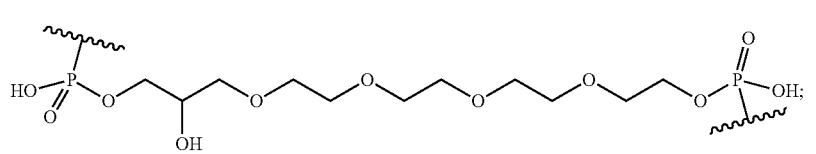

(L2)

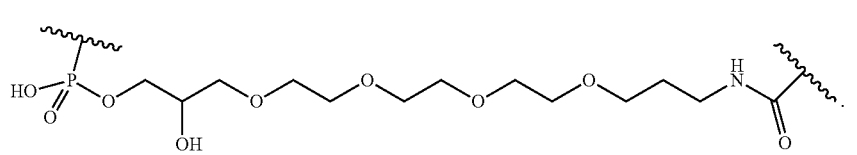

(L3)

In one embodiment of the double-stranded nucleic acid, the hydrophobic molecule is cholesterol. In another embodiment, the first oligonucleotide has 3-7 more ribonucleotides than the second oligonucleotide. In another particular embodiment, each R is hydrogen.

In one embodiment, the double-stranded nucleic acid comprises one or more mismatch within the complementary portions of the first and second oligonucleotide. In a particular embodiment, the double-stranded nucleic acid contains one mismatch within the complementary portions of the first and second oligonucleotide.

In one embodiment, the double-stranded nucleic acid comprises 11-16 base pair duplexes, wherein the nucleotides of each base pair duplex have different chemical modifications (e.g., one nucleotide has a 2'-fluoro modification and the other nucleotide has a 2'-methoxy). In a particular embodiment, the double-stranded nucleic acid has 15 base pair duplexes.

In one embodiment of the double-stranded nucleic acid, the first oligonucleotide has structure: X(-S-B-S-A)(-P-B-P-A)$_5$(-P-B-S-A)(-S-B-S-A)$_2$(-S-B)—OR; and the second oligonucleotide has the structure: C-L-B(-S-A-S-B) (-P-A-P-B)$_5$(-S-A)(-S-B)—OR. See, e.g., species P2 of FIG. 7. In a particular embodiment, the double-stranded nucleic acid has the structure of compound (IIIa):

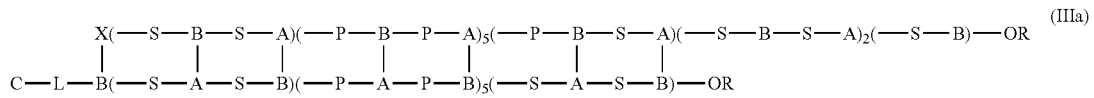

(IIIa)

wherein each | represents a hydrogen bonding interaction (i.e., a base-pairing interaction).

In a particular embodiment of compound (IIIa), the first oligonucleotide comprises the sequence 5' UAAAUUUG-GAGAUCCGAGAG 3' (SEQ ID NO: 4); the second oligonucleotide comprises the sequence 3' AUUUAAACCUC-UAGG 5' (SEQ ID NO: 5); X is X3; and C is cholesterol. In a further embodiment, R is hydrogen. In a further embodiment, L comprises triethylene glycol. In a particular embodiment, L is L3.

In another particular embodiment of compound (IIIa), the first oligonucleotide comprises the sequence 5' UAUAAAUGGUAGCUAUGAUG 3' (SEQ ID NO: 6); the second oligonucleotide comprises the sequence 3' AUAUUUACCAUCGAU 5' (SEQ ID NO: 7); X is X3; and C is cholesterol. In a further embodiment, R is hydrogen. In a further embodiment, L comprises triethylene glycol. In a particular embodiment, L is L3.

In another particular embodiment of compound (IIIa), the first oligonucleotide comprises the sequence 5' UUAAU-CUCUUUACUGAUAUA 3' (SEQ ID NO: 8); the second oligonucleotide comprises the sequence 3' AAUUA-GAGAAAUGAC 5' (SEQ ID NO: 9); X is X3; and C is cholesterol. In a further embodiment, R is hydrogen. In a further embodiment, L comprises triethylene glycol. In a particular embodiment, L is L3.

In another embodiment of the double-stranded nucleic acid, the first oligonucleotide has structure: X(-P-B-P-A)$_6$(-P-B-S-A)(-S-B-S-A)$_2$(-S-B)—OR; and the second oligonucleotide has the structure: C-L-B(-S-A-S-B)(-P-A-P-B)$_6$—OR. See, e.g., species P1 of FIG. 7. In a particular embodiment, the double-stranded nucleic acid has the structure of compound (IIIb)):

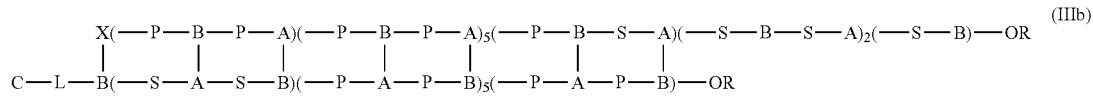

wherein each | represents a hydrogen bonding interaction (i.e., a base-pairing interaction).

In a particular embodiment of compound (IIIb), the first oligonucleotide comprises the sequence 5' UAAAUUUG-GAGAUCCGAGAG 3' (SEQ ID NO: 4); the second oligonucleotide comprises the sequence 3' AUUUAAACCUC-UAGG 5' (SEQ ID NO: 5); X is X3; and C is cholesterol. In a further embodiment, R is hydrogen. In a further embodiment, L comprises triethylene glycol. In a particular embodiment, L is L3.

In another particular embodiment of compound (IIIb), the first oligonucleotide comprises the sequence 5' UAUAAAUGGUAGCUAUGAUG 3' (SEQ ID NO: 6); the second oligonucleotide comprises the sequence 3' AUAUUUACCAUCGAU 5' (SEQ ID NO: 7); X is X3; and C is cholesterol. In a further embodiment, R is hydrogen. In a further embodiment, L comprises triethylene glycol. In a particular embodiment, L is L3.

In another particular embodiment of compound (IIIb), the first oligonucleotide comprises the sequence 5' UUAAU-CUCUUUACUGAUAUA 3' (SEQ ID NO: 8); the second oligonucleotide comprises the sequence 3' AAUUA-GAGAAAUGAC 5' (SEQ ID NO: 9); X is X3; and C is cholesterol. In a further embodiment, R is hydrogen. In a further embodiment, L comprises triethylene glycol. In a particular embodiment, L is L3.

In another embodiment of the double-stranded nucleic acid, the first oligonucleotide has structure: X(-S-B-S-A)(-P-B-P-A)$_5$(-S-B-S-A)$_3$(-S-B)—OR; the second oligonucleotide has structure: C-L-B(-S-A-S-B)(-P-A-P-B)$_5$(-S-A-S-B)—OR; and the nucleic acid has the structure of Formula (IIIc):

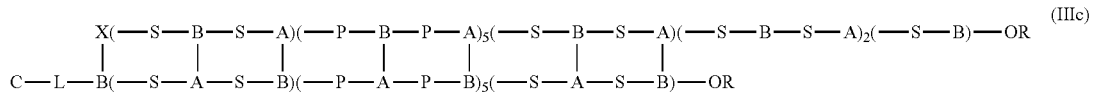

wherein each | represents a hydrogen bonding interaction (i.e., a base-pairing interaction).

In another particular embodiment of compound (IIIc), the first oligonucleotide comprises the sequence 5' UUAAU-CUCUUUACUGAUAUA 3' (SEQ ID NO: 8); the second oligonucleotide comprises the sequence 3' AAUUA-GAGAAAUGAC 5' (SEQ ID NO: 9); X is X3; and C is cholesterol. In a further embodiment, R is hydrogen. In a further embodiment, L comprises triethylene glycol. In a particular embodiment, L is L3.

Figure 23:
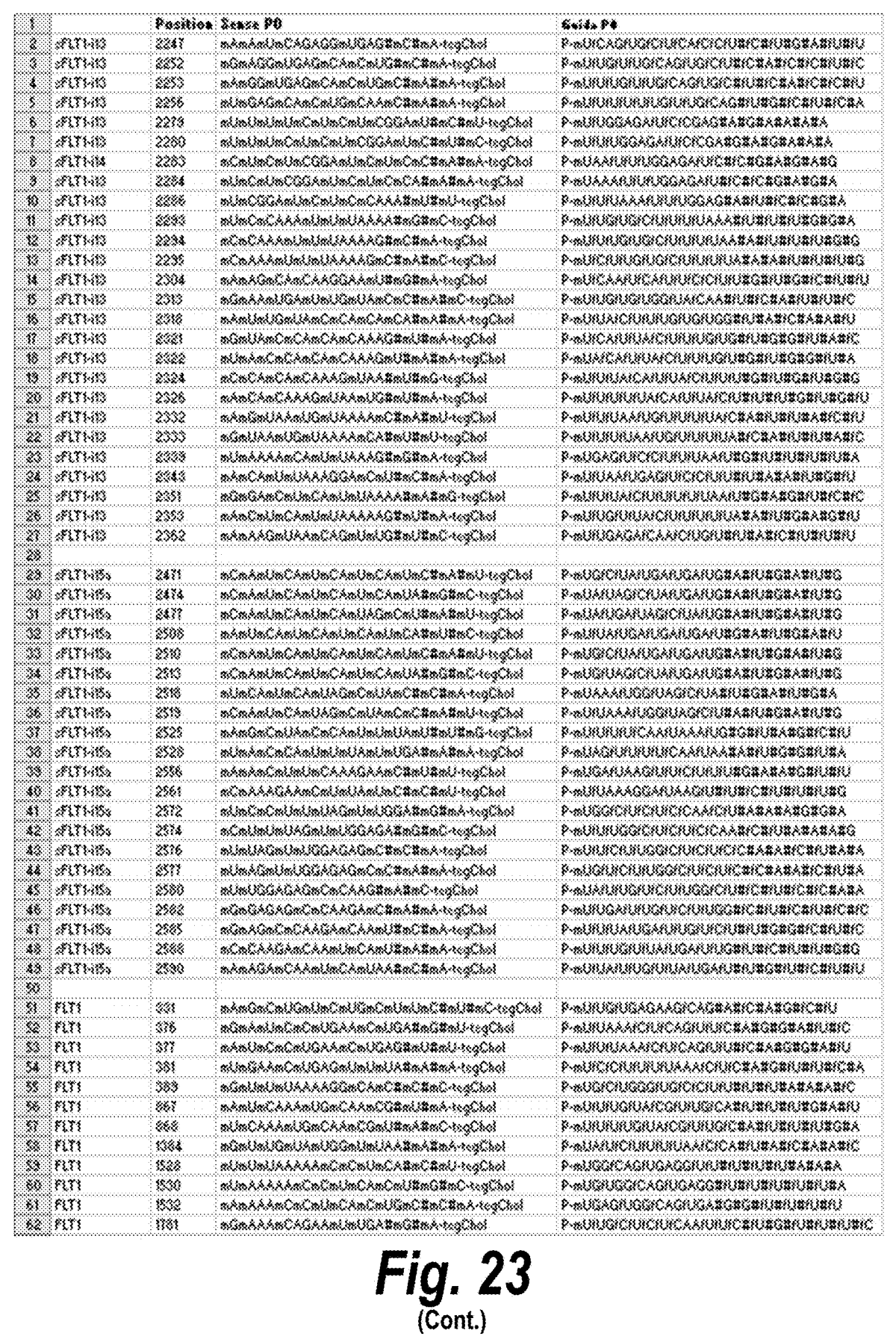
Figure 23:
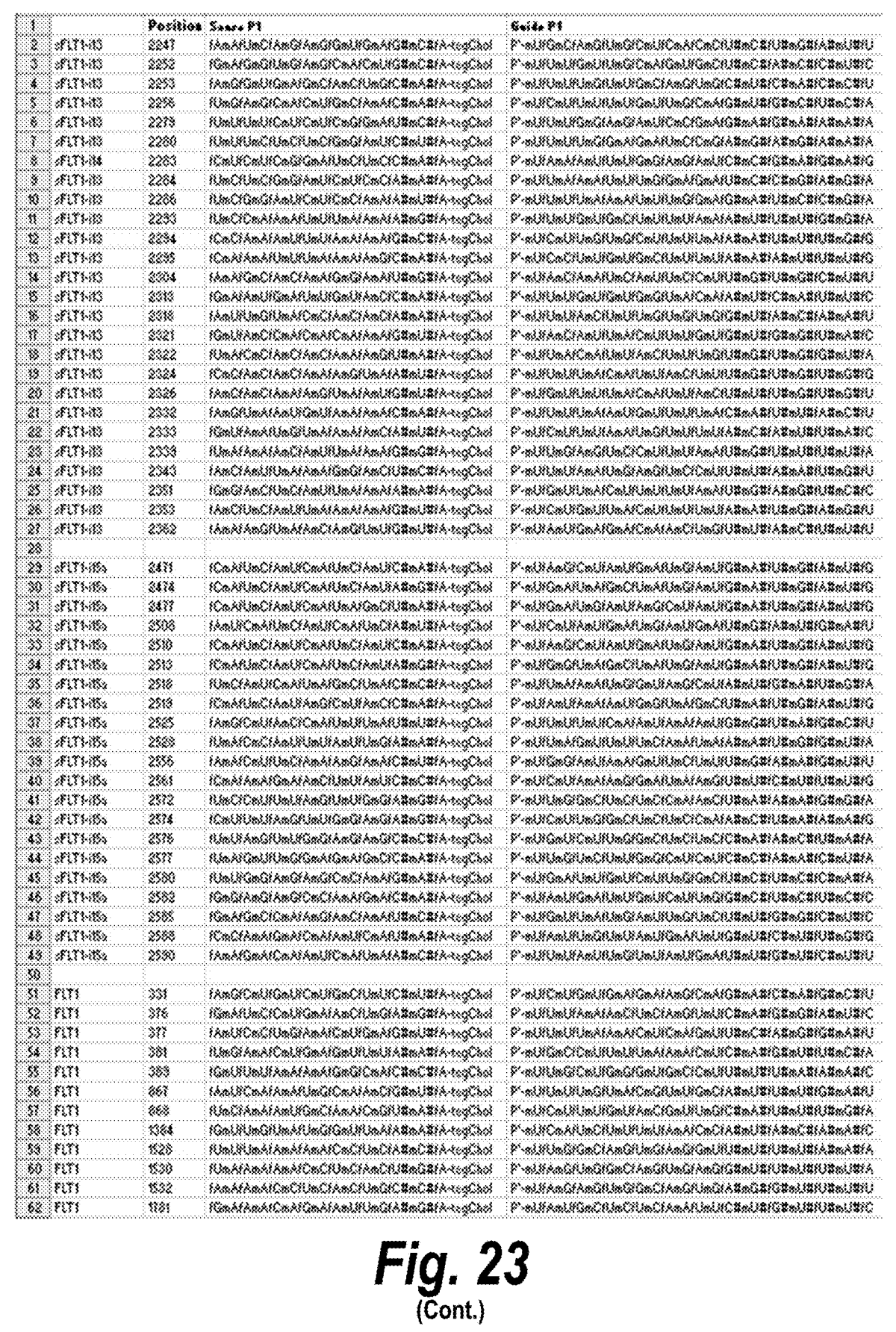
Figure 23:
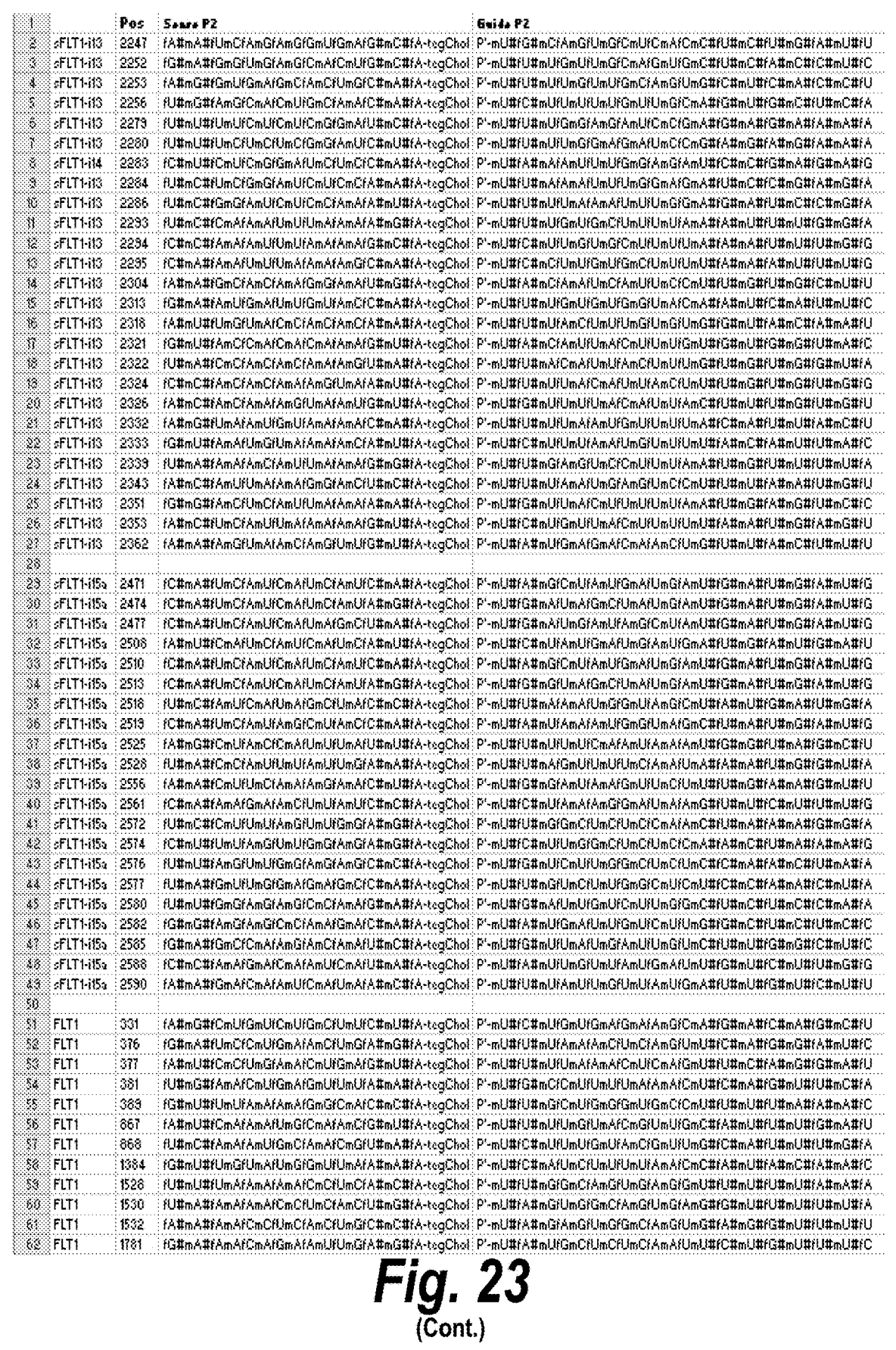
Figure 24:
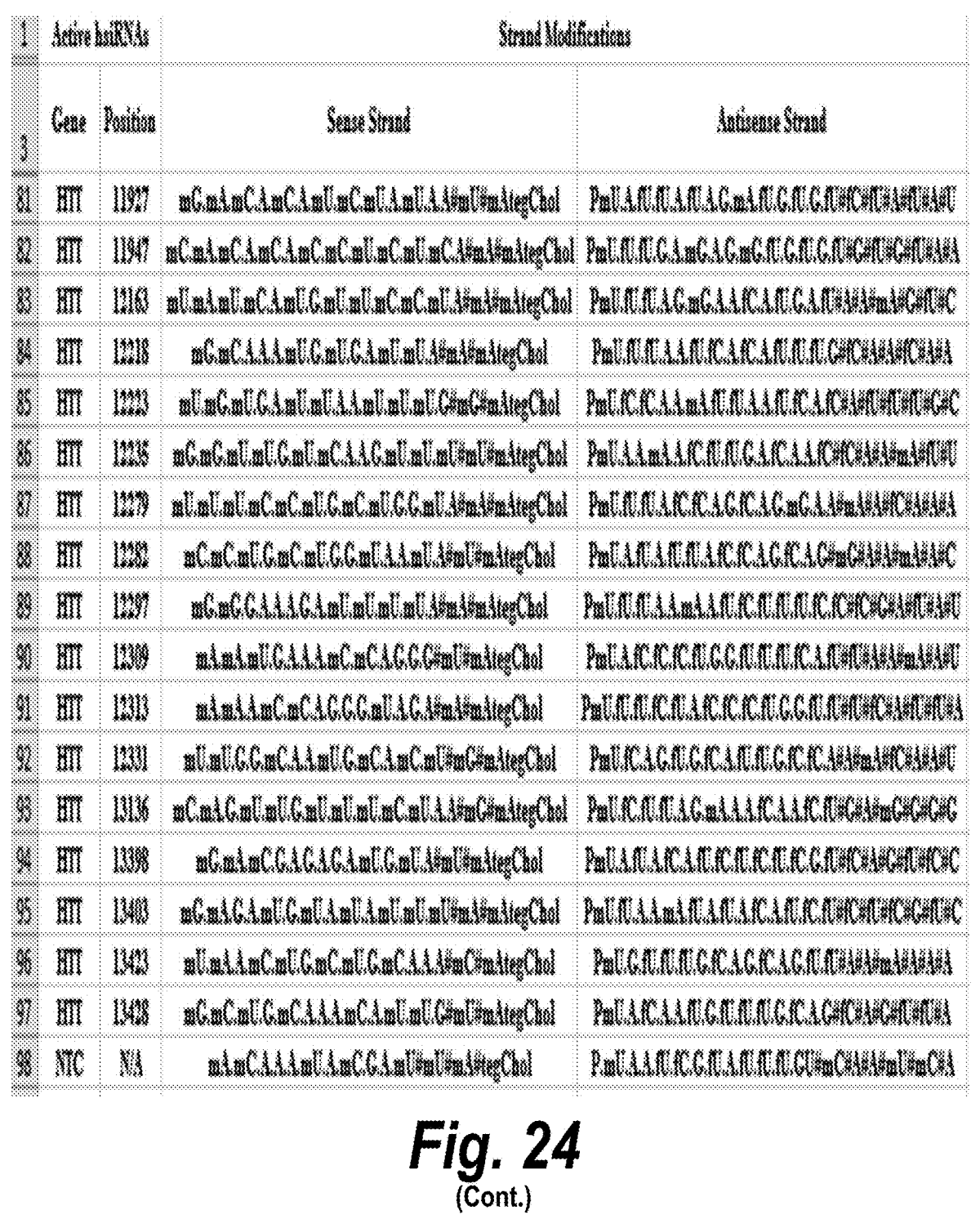

In certain embodiments, compounds (I), (Ia) and (Ib) comprise a sequence corresponding to a "Guide PO" species of FIG. 23 or a an "Antisense Strand" of FIG. 24. In certain embodiments, compounds (II) and (IIa) comprise a sequence corresponding to a "Sense PO" species of FIG. 23 or a "Sense Strand" species of FIG. 24.

In another aspect, provided herein is a composition comprising a first nucleic acid of compound (IIIa), wherein the first oligonucleotide comprises the sequence 5' UAAAUUUGGAGAUCCGAGAG 3' (SEQ ID NO: 4); the second oligonucleotide comprises the sequence 3' AUUUAAACCUCUAGG 5' (SEQ ID NO: 5); X is X3; L is L3; and C is cholesterol; and a second nucleic acid of compound (IIIa), wherein the first oligonucleotide comprises the sequence 5' UAUAAAUGGUAGCUAUGAUG 3' (SEQ ID NO: 6); the second oligonucleotide comprises the sequence 3' AUAUUUACCAUCGAU 5' (SEQ ID NO: 7); X is X3; L is L3; and C is cholesterol.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base cytosine (e.g., cytidine or a chemically-modified derivative thereof), By "soluble FLT1 (sFLT1)" (also known as sVEGF-R1) is meant a soluble form of the FLT1 receptor that has sFLT1 biological activity (e.g., sFlt1-i13 short, sFlt1-i13 long and/or sFlt1-i15a). The biological activity of an sFLT1 polypeptide may be assayed using any standard method, for example, by assaying for one or more clinical symptoms of PE, eclampsia and/or HELLP, by assaying sFLT1 mRNA and/or protein levels, by assaying sFLT1 binding to VEGF and the like. sFLT1 proteins lack the transmembrane domain and the cytoplasmic tyrosine kinase domain of the FLT1 receptor. sFLT1 proteins can bind to VEGF and P1GF bind with high affinity, but cannot induce proliferation or angiogenesis and are therefore functionally different from the Flt-1 and KDR receptors. sFLT1 was initially purified from human umbilical endothelial cells and later shown to be produced by trophoblast cells in vivo. As used herein, sFlt-1 includes any sFlt-1 family member or isoform, e.g., sFLT1-i13 (e.g., FLT1-i13 short and/or sFLT1-i13 long (sFLT1_v1), sFlt1-i15a (sFLT1_v2), sFLT1-e15a, sFLT1_v3, sFLT1_v4 and the like.

By "trophoblast" is meant the mesectodermal cell layer covering the blastocyst that erodes the uterine mucosa and through which the embryo receives nourishment from the mother. Trophoblast cells contribute to the formation of the placenta.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, NH2, NHR, NR$_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

In some embodiments, the compounds, oligonucleotides and nucleic acids described herein may be modified to comprise the internucleotide linkages provided in FIG. 36. In particular embodiments, the compounds, oligonucleotides and nucleic acids described herein comprise internuclotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

Figure 37:
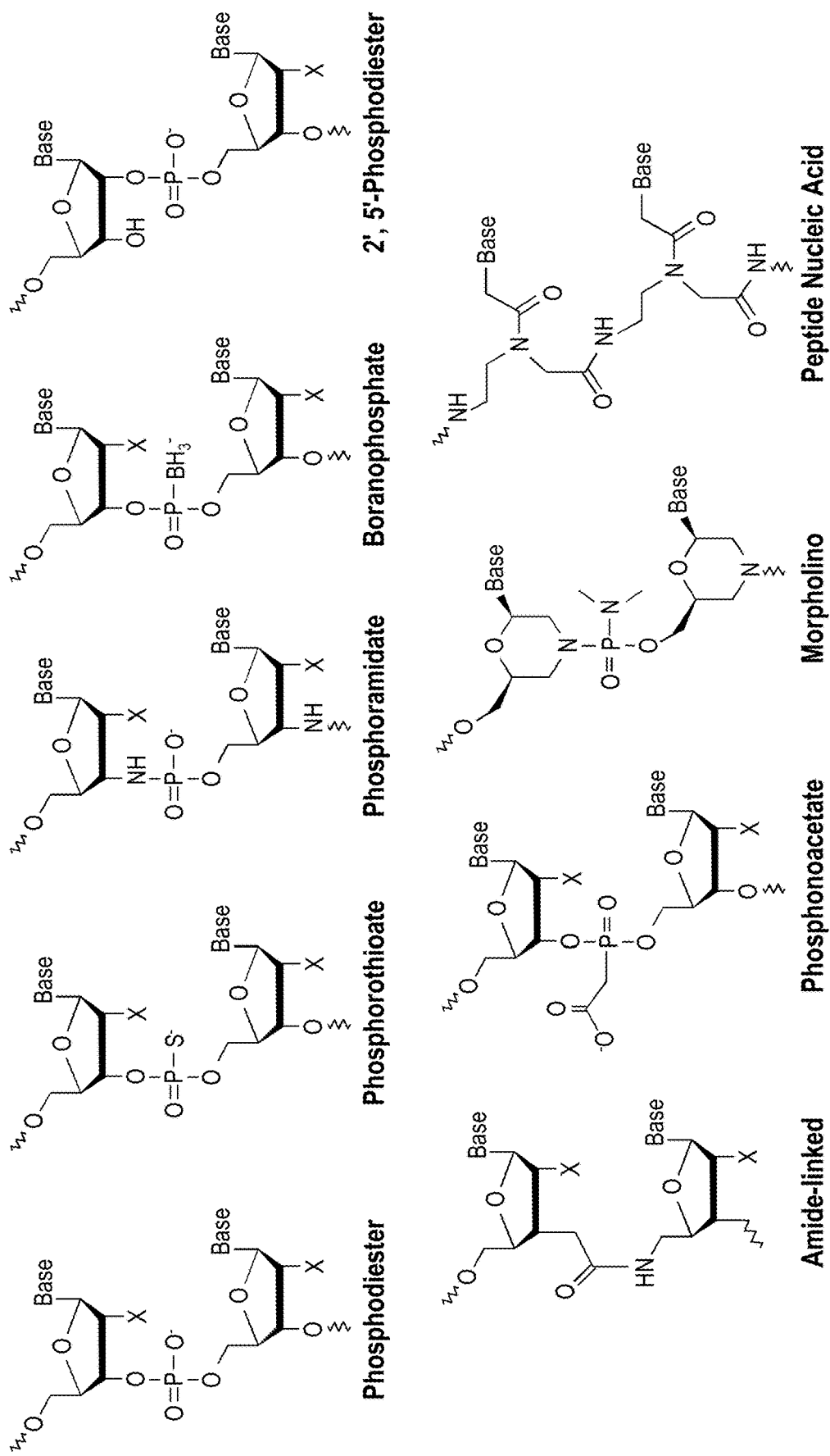
FIG. 37 depicts exemplary internucleotide backbone linkages.

In some embodiments, the compounds, oligonucleotides and nucleic acids described herein may be modified to comprise the internucleotide backbone linkages provided in FIG. 37.

In certain embodiments, provided herein are compounds comprising a phosphate moiety (e.g., X1, X4, X5 and X6), a phosphonate moiety (e.g., X3, X7 and X8). These moieties will be partially or completely ionized as a function of the moiety's pKa and the pH of the environment. It is understood that negatively charged ions will be balanced by a cationic moiety, e.g., an alkali metal such as sodium or potassium, an alkali earth metal such as calcium or magnesium, or an ammonium or guanidinium ion.

Pharmaceutical Compositions and Methods of Administration

In one aspect, provided herein is a pharmaceutical composition comprising a therapeutically effective amount of one or more compound, oligonucleotide, or nucleic acid as described herein, and a pharmaceutically acceptable carrier. In one embodiment, the pharmaceutical composition comprises one or more double-stranded, chemically-modified nucleic acid as described herein, and a pharmaceutically acceptable carrier. In a particular embodiment, the pharmaceutical composition comprises one double-stranded, chemically-modified nucleic acid as described herein, and a pharmaceutically acceptable carrier. In another particular embodiment, the pharmaceutical composition comprises two double-stranded, chemically-modified nucleic acids as described herein, and a pharmaceutically acceptable carrier.

In a particular embodiment, the pharmaceutical composition comprises a first nucleic acid of compound (IIIa), wherein the first oligonucleotide comprises the sequence 5' UAAAUUUGGAGAUCCGAGAG 3' (SEQ ID NO: 4); the second oligonucleotide comprises the sequence 3' AUUUAAACCUCUAGG 5' (SEQ ID NO: 5); X is X3; and C is cholesterol; and a second nucleic acid of compound (IIIa), wherein the first oligonucleotide comprises the sequence 5' UAUAAAUGGUAGCUAUGAUG 3' (SEQ ID NO: 6); the second oligonucleotide comprises the sequence 3' AUAUUUACCAUCGAU 5' (SEQ ID NO: 7); X is X3; and C is cholesterol.

The invention pertains to uses of the above-described agents for prophylactic and/or therapeutic treatments as described Infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

In one aspect, the present invention provides for both prophylactic and therapeutic methods of treating a subject at risk of (or susceptible to) a disease or disorder caused, in whole or in part, by secreted Flt1 protein. In one embodiment, the disease or disorder is a liver disease or disorder. In another embodiment, the disease or disorder is a kidney disease or disorder. In one embodiment, the disease or disorder is a placental disease or disorder. In one embodiment, the disease or disorder is a pregnancy-related disease or disorder. In a preferred embodiment, the disease or disorder is a disorder associated with the expression of soluble Flt1 protein and in which amplified expression of the soluble Flt1 protein leads to clinical manifestations of PE (preeclampsia), postpartum PE, eclampsia and/or HELLP (i.e., HELLP syndrome).

In another aspect, the present invention provides for both prophylactic and therapeutic methods of treating a subject at risk of (or susceptible to) a disease or disorder caused, in whole or in part, by a gain of function mutant protein. In one embodiment, the disease or disorder is a trinucleotide repeat disease or disorder. In another embodiment, the disease or disorder is a polyglutamine disorder. In a preferred embodiment, the disease or disorder is a disorder associated with the expression of huntingtin and in which alteration of huntingtin, especially the amplification of CAG repeat copy number, leads to a defect in huntingtin gene (structure or function) or huntingtin protein (structure or function or expression), such that clinical manifestations include those seen in Huntington's disease patients.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain, spinal column, placenta, liver and/or kidneys) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder (e.g., Huntington's disease) or a liver-, kidney- or pregnancy-related disease or disorder (e.g., PE, postpartum PE, eclampsia and/or HELLP). In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

In one aspect, provided herein is a method of treating or managing preeclampsia, postpartum preeclampsia, eclampsia or HELLP syndrome comprising administering to a subject in need of such treatment or management a therapeutically effective amount of a compound, oligonucleotide, or nucleic acid as described herein, or a pharmaceutical composition comprising said compound, oligonucleotide, or nucleic acid.

In another aspect, provided herein is a method of treating or managing Huntington's disease comprising administering to a patient in need of such treatment or management a therapeutically effective amount of a compound, oligonucleotide, or nucleic acid as described herein, or a pharmaceutical composition comprising said compound, oligonucleotide, or nucleic acid.

Design of siRNA Molecules

In some embodiments, an siRNA molecule of the invention is a duplex consisting of a sense strand and complementary antisense strand, the antisense strand having sufficient complementary to an htt mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA should be specific for a target sequence, e.g., a target sequence set forth in FIG. 23. In one embodiment, the target sequence is found in sFlt1. In one embodiment, a target sequence is found in a mutant huntingtin (htt) allele, but not a wild-type huntingtin allele. In another embodiment, a target sequence is found in both a mutant huntingtin (htt) allele, and a wild-type huntingtin allele. In another embodiment, a target sequence is found in a wild-type huntingtin allele. The first strand should be complementary to the target sequence, and the other strand is substantially complementary to the first strand. (See FIG. 23 for exemplary sense and antisense strands.) In one embodiment, the target sequence is outside the expanded CAG repeat of the mutant huntingin (htt) allele. In another embodiment, the target sequence is outside a coding region of the target gene. Exemplary target sequences are selected from the 5' untranslated region (5'-UTR) or an intronic region of a target gene. Cleavage of mRNA at these sites should eliminate translation of corresponding mutant protein. Target sequences from other regions of the htt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed.

In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)-(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant huntingtin mRNA), the siRNA may be incubated with target cDNA (e.g., huntingtin cDNA) in a *Drosophila*-based in vitro mRNA expression system. Radiolabeled with $^{32}$P, newly synthesized target mRNAs (e.g., huntingtin mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a sequence set forth in FIG. 23 or 24, and an antisense strand comprising a sequence set forth in FIG. 23 or 24.

Sites of siRNA-mRNA complementation are selected which result in optimal mRNA specificity and maximal mRNA cleavage.

siRNA-Like Molecules siRNA-like molecules of the invention have a sequence (i.e., have a strand having a sequence) that is "sufficiently complementary" to a target sequence of a htt mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:U, G:G, A:A, C:C, U:U). In a further preferred embodiment, the "bulge" is centered at nucleotide positions 12 and 13 from the 5' end of the miRNA molecule.

Gene Silencing Oligonucleotides

In certain exemplary embodiments, gene expression (i.e., htt gene expression) can be modulated using oligonucleotide-based compounds comprising two or more single stranded antisense oligonucleotides that are linked through their 5'-ends that allow the presence of two or more accessible 3'-ends to effectively inhibit or decrease htt gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidite or H-phosphonate chemistry which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

Modified RNA Silencing Agents

In certain aspects of the invention, an RNA silencing agent (or any portion thereof) of the invention as described supra may be modified such that the activity of the agent is further improved. For example, the RNA silencing agents described in Section II supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, fN-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

EXAMPLES

Example 1. Background and Significance of Preeclampsia (PE)

Overwhelming evidence from epidemiological and experimental studies now indicates that PE is caused by elevated levels of "soluble decoy" proteins (soluble FLT1s (sFLT1s)) from the Flt1 gene (VEGFR1) in the mother's blood stream (Young, B. C., Levine, R. J. & Karumanchi, S. A. Pathogenesis of preeclampsia. Annual review of pathology 5, 173-192 (2010); Maynard, S. E. et al. Excess placental soluble fms-like tyrosine kinase 1 (sFlt1) may contribute to endothelial dysfunction, hypertension, and proteinuria in preeclampsia. The Journal of clinical investigation 111, 649-658 (2003); Levine, R. J. et al. Circulating angiogenic factors and the risk of preeclampsia. The New England journal of medicine 350, 672-683 (2004); Heydarian, M. et al. Novel splice variants of sFlt1 are upregulated in preeclampsia. Placenta 30, 250-255 (2009)). FLT1 is a receptor tyrosine kinase (RTK) predominantly expressed in the placenta. A general mechanism for RTK modulation is production of truncated, secreted forms of the receptor that act as dominant negative regulators of the overall signaling pathway. Ligand sequestration by such soluble decoys inhibits intracellular signaling by the full-length receptor, thereby desensitizing the system to ligand concentration (Vorlova, S. et al. Induction of antagonistic soluble decoy receptor tyrosine kinases by intronic polyA activation. Molecular cell 43, 927-939 (2011).). In the case of FLT1, the soluble decoys are expressed from truncated mRNAs generated by polyadenylation within two introns (i13 and i15) upstream of the exons encoding the full length FLT1 (fl-FLT1) transmembrane (TM) and kinase domains.

In mammals, FLT1 is predominantly expressed in the placenta, with human placental Flt1 mRNA levels being 10-100 times higher than those observed in other adult tissues (Cerdeira, A. S. & Karumanchi, S. A. Angiogenic factors in preeclampsia and related disorders. Cold Spring Harbor perspectives in medicine 2 (2012)). Whereas the full-length isoform predominates in all tissues in non-pregnant adult humans (Id.), placental expression is dominated by three truncated isoforms, sFlt1-i13 short, sFlt1-i13 long and sFlt1-i15a, all of which encode sFLT1 proteins. This same pattern of high Flt1 in placenta and low expression in other non-pregnant adult tissues is observed in rodents. However, because rodents lack the intron 14 polyadenylation site, they only express a single soluble decoy form: sFlt1-i13. In PE, both full-length (fl-Flt1) and truncated Flt1 mRNAs accumulate to higher levels in the placenta than in normal pregnancies, with the truncated isoforms being even more pronounced. These changes at the mRNA level likely explain the significant rise in sFLT1 proteins in the maternal bloodstream during PE.

1.1 Applicability of siRNAs for Treatment of PE siRNA-based therapeutics were designed for the treatment of PE. Both preclinical and clinical data support decreasing sFLT1 as a valid therapeutic strategy for prolonging PE pregnancies (Thadhani, R. et al. Pilot study of extracorporeal removal of soluble fms-like tyrosine kinase 1 in preeclampsia. Circulation 124, 940-950 (2011)). Further, the unique region specific to each sFLT1 protein is very small, with only a handful of unique amino acids being appended to each C-terminus. This small target size hinders development of conventional drugs (e.g., small molecules and antibodies) targeting only sFLT1s and not fl-FLT1. On the other hand, the target window at the RNA level is much larger, with the i13 and i15 mRNA isoforms having 435 and 567 unique bases, respectively, neither of which are present in fl-Flt1 mRNA. Because RNAi requires a target size of only 19-22 nucleotides, this was determined to be more than sufficient nucleotide space in which to design multiple isoform-selective siRNAs. From a clinical perspective, the possibility that a single dose delivered subcutaneously will be sufficient to prevent runaway sFLT1 expression for several weeks could make treatment simple and affordable.

Novel chemically-modified oligonucleotides known as self-delivering hydrophobically modified siRNAs (hsiRNAs) (FIG. 1A) could provide the most significant advantage for a cost effective therapeutic. While their current cost of chemical synthesis ($200 per gram, with approximately $20 per dose at 1 mg/kg dose levels) is relatively high, the price is expected to decrease dramatically (10-50 fold) with a kg-level scale-up. Further, hsiRNAs can be fully synthesized using solid support chemistry in less than 10 hours. Like other oligonucleotides, dried hsiRNAs are highly stable, can be stored for extensive time (i.e., years) at ambient temperature, and can be brought into solution just prior to injection. Further, hsiRNA half-life in vivo is of sufficient duration that a single intravenous dose is well suited for a two to six week inhibition of sFLt1 production.

The ONTs that neutralize sFlt1 described herein are the first novel preeclampsia therapy based on a mechanistic understanding of the disease, and could be cost-effectively and easily administered throughout the world.

1.2 Pilot Product Target Profile for RNAi-Based Treatment of PE

Special considerations for developing an RNAi-based treatment for PE are discussed below.

1.3 Multiple sFLT1 mRNA Isoforms

By performing polyadenylation site sequencing (PAS-Seq (Heyer, E. E., Ozadam, H., Ricci, E. P., Cenik, C. & Moore, M. J. An optimized kit-free method for making strand-specific deep sequencing libraries from RNA fragments. Nucleic Acids Res 43, e2 (2015))) on total RNA from multiple normal and PE placentas, it was determined that PE placentas overexpress i13 and i15 sFLT1 variants with, i15 being responsible for 55% of reads and i13 responsible for approximately 45% of reads. Without intending to be bound by scientific theory, the intrinsic variability in isoform ratios in different samples indicates that targeting both isoforms might be the best option to cover the majority of PE patients. Thus, the candidate drug product was defined as an equimolar mixture of two hsiRNAs: one targeting both short and long sFLT1-i13 and another targeting sFlt1-i15a. The FDA has already allowed an siRNA mixture to be defined as a single drug entity when the component siRNAs are identically formulated or chemically modified and their PK/PD profiles are very similar (e.g., multi-siRNA formulations targeting VEGF-A/KSP (Tabernero, J. et al. First-in-humans trial of an RNA interference therapeutic targeting VEGF and KSP in cancer patients with liver involvement. Cancer Discovery 3, 406-417 (2013)); HBV (Wooddell, C. I. et al. Hepatocyte-targeted RNAi Therapeutics for the Treatment of Chronic Hepatitis B Virus Infection. Molecular Therapy: The Journal of the American Society of Gene Therapy 21, 973-985 (2013)), Arrowhead, etc.). Although using a mixture adds complexity to CMC (Chemistry, Manufacturing and Controls), this is outweighed by the advantage that the mixture will allow treatment of wider PE populations independent of isoform variant overexpression ratios. In certain embodiments, a mixture of two candidates is administrated subcutaneously (SC) in saline as an excipient.

In certain embodiments, the desired level of sFLT1 silencing is only 30-40%, as a higher degree of silencing might be disadvantageous. Preliminary data indicated that a 10-20 mg/kg dose produced >50% silencing in mice, so lesser silencing may simply be achieved with lower dosing. Because the desired product profile is a one-time injection, however, higher doses might be required to extend effect duration. Thus, in certain embodiments, i13 or i15 may be used alone as a clinical candidate.

1.4 Overall Safety and Toxicity Considerations

ONT-related toxicity can be due to target-specific effects (e.g., too much silencing of sFlt1 isoforms), target-independent effects (i.e., unintentional silencing of non-target mRNAs) or class-related chemistry-specific events. The ability to target the i13 and i15 variants separately dramatically reduces the chances of any major target-related toxicity. Further, the i13 and i15 variants are placenta- and pregnancy-specific, with low or undetectable expression in other adult tissues. Therefore, clinically limiting toxicity will most likely be target-independent. These types of effects include siRNA off-targeting, RNA-based induction of the innate immune response, and general toxicity related to the chosen mode of delivery (e.g., hydrophobic modifications in combination with phosphorothioates). The most advanced bioinformatics was employed up-front upfront to optimize oligonucleotide design to minimize potential off-target events (Uchida, S. et al. An integrated approach for the systematic identification and characterization of heart-enriched genes with unknown functions. BMC Genomics 10, 100 (2009)). Further, all riboses in the seed sequence (i.e., nucleotides 2-8 of the guide strand) were 2'-F and 2'-O-methyl modified, which modifications by themselves are well-established to minimize off-target events (Jackson, A. L. et al. Position-specific chemical modification of siRNAs reduces "off-target" transcript silencing. RNA 12, 1197-1205 (2006)). While evaluation of off-targeting signatures could be established in vitro and in mouse samples using microarray profiling (Jackson, A. L. et al. Position-specific chemical modification of siRNAs reduces "off-target" transcript silencing. RNA 12, 1197-1205 (2006); Anderson, E., Boese, Q., Khvorova, A. & Karpilow, J. Identifying siRNA-induced off-targets by microarray analysis. Methods in molecular biology 442, 45-63 (2008); Anderson, E. M. et al. Experimental validation of the importance of seed complement frequency to siRNA specificity. RNA 14, 853-861 (2008); Birmingham, A. et al. 3' UTR seed matches, but not overall identity, are associated with RNAi off-targets. Nat Methods 3, 199-204 (2006); Fedorov, Y. et al. Off-target effects by siRNA can induce toxic phenotype. RNA 12, 1188-1196 (2006)). Because the overlap between siRNA off-targeting signatures in tissue culture/animal models and humans is generally minimal (Burchard, J. et al. MicroRNA-like off-target transcript regulation by siRNAs is species specific. RNA 15, 308-315 (2009)), the value of such studies is questionable. For each sFLT1 isoform, two different sequences were selected for in vivo evaluation (one lead and one back-up) (FIG. 3). If the lead fails due to off-targeting-induced toxicity, the second sequence is used as a backup (Jackson, A. L. & Linsley, P. S. Recognizing and avoiding siRNA off-target effects for target identification and therapeutic application. Nature Reviews. Drug Discovery 9, 57-67 (2010)). As there is currently no formal guidance specific to siRNA therapeutics, the standard recommendation for NCE (New Chemical Entity) development, including demonstrating safety in two animal models (Hughes M, I. J., Kurtz A, et al. (ed. C. N. Sittampalam G S, Nelson H, et al., editors) (Eli Lilly & Company and the National Center for Advancing Translational Sciences, Bethesda (Md.); 2012)), is followed.

The lead compounds were fully chemically-modified (meaning no unmodified riboses remained) using an alternating 2'-O-methyl/2'-F pattern. The combination of 2' OMe/2'-F is known to block innate immune response activation (Nair, J. K. et al. Multivalent N-Acetylgalactosamine-Conjugated siRNA Localizes in Hepatocytes and Elicits Robust RNAi-Mediated Gene Silencing. Journal of the American Chemical Society (2014)). Lack of interferon pathway activation was confirmed with an in vitro human whole blood cytokine activation assay looking at IL-1β, IL-1RA, IL-6, IL-8, IL-10, IL-12(p70), IP-10, G-CSF, IFN-γ, MCP-1, MIP-1α, MIP-1β, and TNF-α (Bio-Plex Pro Magnetic Cytokine Assay; BioRad Laboratories) and in vivo (after injection in mice) looking at G-CSF, TNF, IL-6, IP-10, KC, and MCP-1 (Cytokine/Chemokine Magnetic Bead Panel; Millipore) (Kumar, V. et al. Shielding of Lipid Nanoparticles for siRNA Delivery: Impact on Physicochemical Properties, Cytokine Induction, and Efficacy. Molecular Therapy. Nucleic acids 3, e210 (2014)).

Figure 4A:
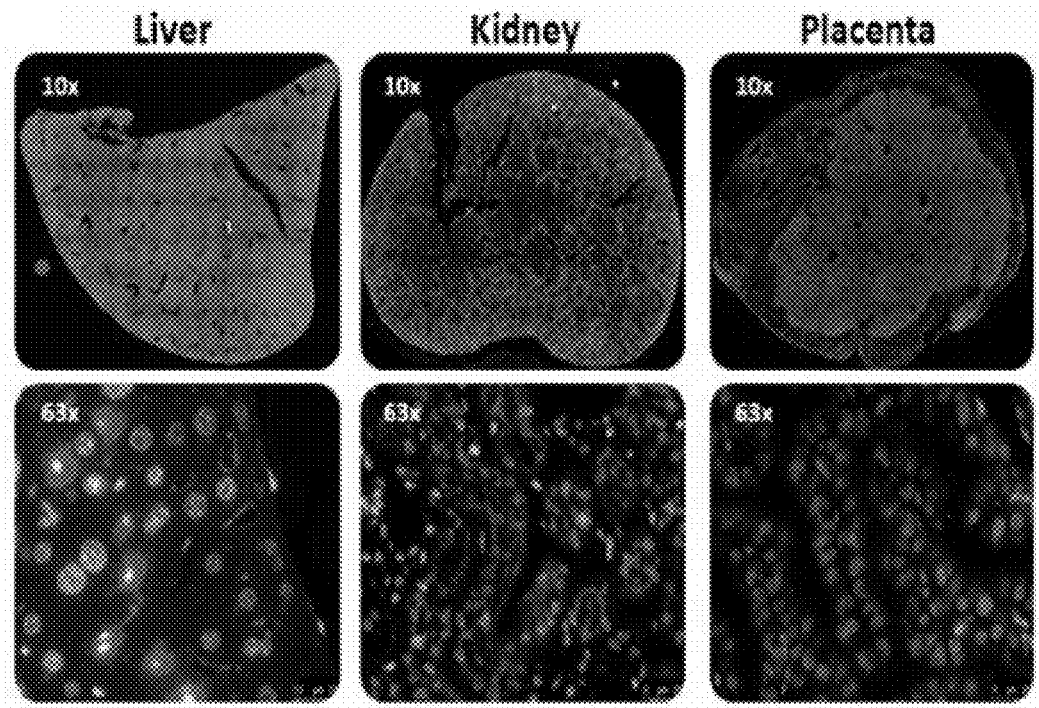
FIGS. 4A-4B depict hsiRNA efficiency of delivery to liver, kidney and placenta. (A) A wild-type pregnant mouse (E15) was injected with Cy3-sFLT1-2283-P2 (red) (10 mg/kg; IV via tail vein). Tissues were fixed after 24 hours, processed and imaged at 10× and 63× on a Leica tiling fluorescent microscope; nuclei stained with DAPI (blue). (B) Shows tissue distribution of sFLT1-2283 (40 mg/kg) 5 days post injection analyzed by PNA assay (n=7, mean+SEM).
Figure 4B:
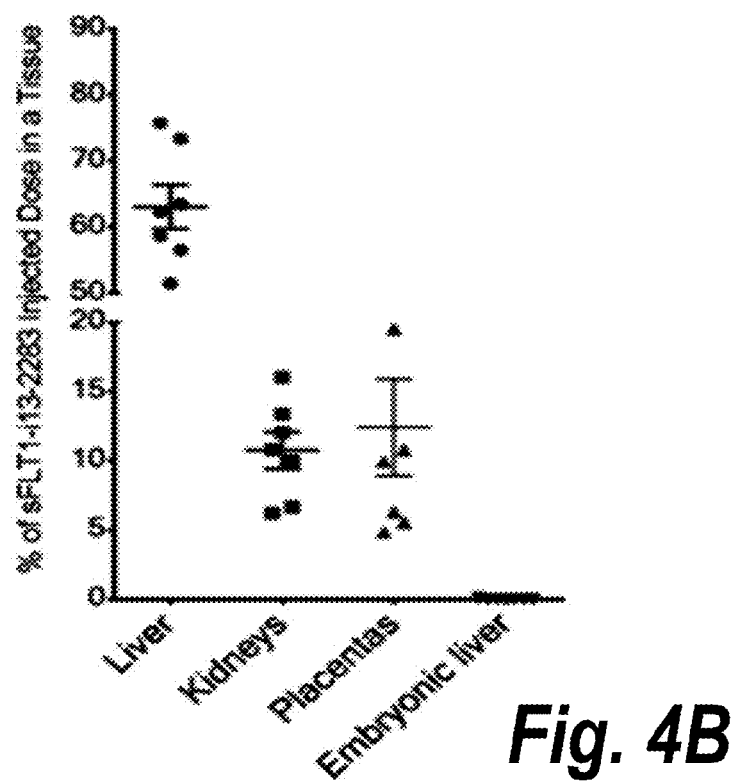

Without intending to be bound by scientific theory, based on data from other oligonucleotide chemistries (Wooddell, C. I. et al. Hepatocyte-targeted RNAi Therapeutics for the Treatment of Chronic Hepatitis B Virus Infection. Molecular Therapy: The Journal of the American Society of Gene Therapy 21, 973-985 (2013); Coelho, T. et al. Safety and efficacy of RNAi therapy for transthyretin amyloidosis. The New England Journal of Medicine 369, 819-829 (2013)), dose limiting toxicity is most likely related to liver function. Preliminary studies determined that up to 50% of the injected dose of the hsiRNAs accumulated in liver, with delivery being specific to endothelial, kupffer and stellate cells, not hepatocytes (FIG. 4). With other phosphorothioate-containing oligonucleotides, slight reversible elevation of liver enzymes and mild reversible injection side reactions have been noted as side effects (Frazier, K. S. Antisense Oligonucleotide Therapies: The Promise and the Challenges from a Toxicologic Pathologist's Perspective. Toxicologic pathology 43, 78-89 (2015)), but usually this liver enzyme elevation is only observed after long-term continuous dosing with high dose levels. Because this treatment is necessarily short-term (just one or two injections over a period of one to two months) and does not target hepatocytes, liver toxicity may not be an issue. Nonetheless, these concerns will be studied in detail.

Development of any therapeutic targeting pregnant women has additional safety considerations. A major concern is potential transfer of hsiRNAs to the fetus and any possible toxicity this might cause. In preliminary studies, no detectable oligonucleotide transfer to the fetus was observed using fluorescent microscopy, or using a highly sensitive PNA (Peptide Nucleic Acid)-based quantitative assay (FIG. 4). Nor were any effects on fetal growth, number of miscarriages, placental histology or other teratogenic effects observed.

1.5 Assay and Model Systems to Evaluate Lead Compounds
Fluorescence Microscopy Evaluation of in Situ Tissue Distribution hsiRNA variants with a Cy3 or Cy5.5 (lower auto-fluorescence) dye attached through a non-degradable linker to the 5' end of sense (passenger) strand were synthesized. This compound was biologically stable with no detectable Cy3 cleavage within 24 hours. The fluorescent sense strand hybridized to its complementary guide strand (thus forming a double-stranded hsiRNA) was administrated to animals and oligonucleotide distribution patterns were examined in 4 μm tissue sections also stained with DAPI or/and cell type selective antibodies. Parallel sections could be stained with standard histology markers enabling detailed histology mapping. Because hsiRNAs are already heavily hydrophobically modified, dye addition has little effect on overall hydrophobicity and therefore minimal impact on oligonucleotide distribution. This assay allowed rapid evaluation of tissue and cell-type distribution and was complemented by a PNA-based quantitative assay for direct guide strand detection.

PNA Hybridization for Quantitative Guide Strand Detection in Tissue Lysates

Figure 5:
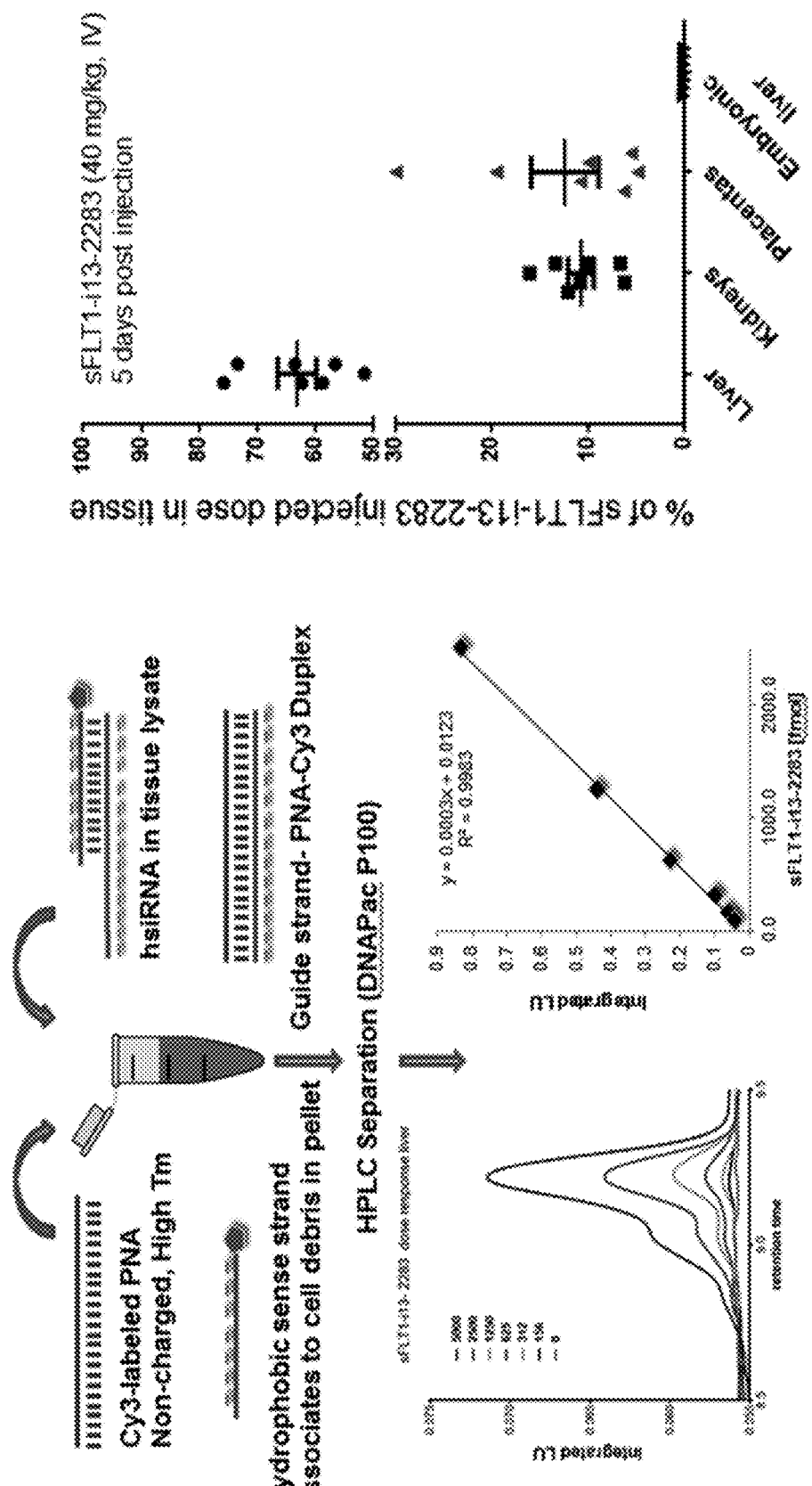
FIG. 5 depicts in vivo quantification of a compound of the invention by PNA assay.
Figure 6:
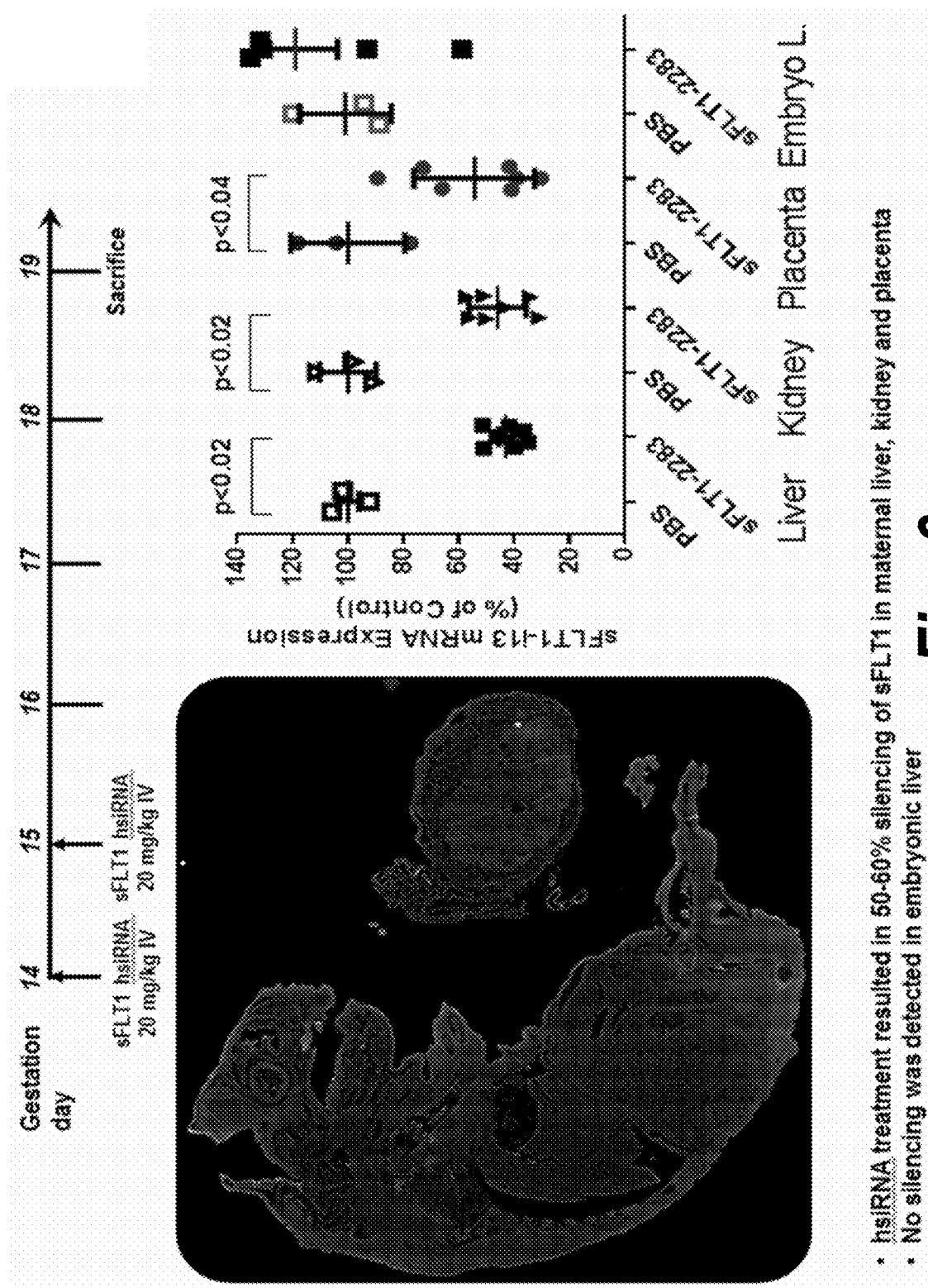
FIG. 6 depicts data showing silencing of Flt1 by a compound of the invention in WT pregnant mice.

To enable direct quantification of intact guide stand in tissues, a novel assay was developed and implemented wherein the guide strand was hybridized to a fully complementary Cy3-labeled PNA (peptide nucleic acid) oligonucleotide, and the corresponding duplex was separated from excess single stranded PNA by HPLC (FIG. 5). Since PNA is non-charged and has extremely tight binding to the guide strand, it out-competes both the hsiRNA sense strand and any endogenous target sequences. Fluorescence detection of the Cy3-PNA:guide hybrid provided a direct measure of guide strand abundance in tissue lysates. In conjunction with an HPLC auto injector, this assay enabled guide strand quantification in hundreds of samples overnight. The assay was also highly sensitive, with a limit of detection less than 10 fmole/gram, and hybrids containing full-length, partially degraded, 5'-phosphorylated and 5'-dephosphorylated guide strand can all be quantified as separate peaks or shoulders in the HPLC trace. Because this assay could detect both labeled and unlabeled compounds, it can be directly transitioned to future CRO's for clinical sample analysis.

QUANTIGENE (Affymetrix) Assay for Direct Detection of Flt1 mRNA Variants in Cells and Tissues QUANTIGENE is a highly sensitive 96-well based assay in which mRNA is directly detected through signal amplification directly from tissue and/or cell lysates. By linking this direct detection assay to a 192 well automatic TissueLyser, a high-throughput version was developed which enabled processing of dozens of samples per animal. Thus, quantitative data on expression of targeted and housekeeping genes was generated in many animals at once. In pilot studies, n=8 was sufficient to detect 40% modulation of sFlt1 mRNA isoform expression with 80% confidence.

ELISA (#MVR100, R&D Systems) for Detection of sFLT1 Proteins in Conditioned Media and Blood This 96-well based assay required only 10 μL of biological fluid per sample. This assay has been optimized over many years for both in vitro and in vivo studies. It is clinically compatible and allows for evaluation of circulating sFLT1 protein levels without animal sacrifice, and will be particularly useful for non-human primate studies.

Normal Mouse Pregnancy Model

The sFlt1l-i13 variants are expressed during mouse pregnancy with i13 levels exponentially increasing from days 14-19. Perfect homology between the sFLT1-i13-2283 compound and the i13 mouse variant allows the study both of efficacy and of safety in this simple rodent model.

Preeclampsia Models

Reduced Uterine Perfusion Pressure (RUPP) model of placental ischemia and hypoxia model of preeclampsia is used as described further below.

Baboon Wild-Type Pregnancy Model

The sFlt1-i15a variant is not expressed in rodents during pregnancy, thus overall combination efficacy and safety will be evaluated in wild-type pregnant baboons using ELISA, a non-invasive assay as readout of efficacy.

Preliminary Data

A simple and cost-effective PE therapeutic using RNAi to limit excess placental expression of sFLT1 proteins was developed. For this to work, the following objectives were achieved: (1) appropriate siRNA targeting sites in sFlt1 mRNAs were identified; (2) whether RNA silencing was possible in the placenta using generalized (i.e., intravenous or subcutaneous) delivery was determined; and (3) novel siRNA chemistries were developed that would enable preferential delivery to placental trophoblasts, the cell type responsible for excess sFLT1 production.

Using tissue-specific RNA-Seq data available from the Human Protein Atlas (See proteinatlas.org) and PAS-Seq data from multiple normal and PE human placentas, it was determined that, while the full length (fl) isoform predominates in all tissues in non-pregnant adult humans, placental expression is dominated by three truncated isoforms, sFlt1-i13-short, sFlt1-i13-long and sFlt1-i15a, generated by polyadenylation within introns 13 and 15, respectively. Targeting the intronic regions with hsiRNAs enabled selective silencing of truncated isoforms without interfering with fl-Flt1 mRNA abundance.

A novel type of siRNA chemistry was developed that enabled efficient delivery to endothelial cells and demonstrated selective trafficking to the labyrinth region of the placenta (i.e., to trophoblasts, the cell type responsible for sFLT1 expression). Without any additional formulation, up to 12% of the injected dose accumulated in the placenta with no detectable fetal transfer. This technology is the first demonstration of selective labyrinth targeting by any ONT, enabling silencing of sFLT1 protein at it major site of expression.

Over 50 siRNA variants were designed and screened (See FIG. 23). Hyper-functional, fully chemically-modified hsiR-NAs were identified that selectively targeted the i13 and i15 isoforms without interfering with fl-FLT1 expression (FIG. 3). Using these hsiRNAs, efficient silencing of i13 and i15 was demonstrated in primary human trophoblasts with no formulation (FIG. 2B). A combination of sFLT1-i13-2283 and sFLT-i15a-2519 hsiRNAs was selected as the lead candidate for treatment of PE (FIG. 3).

It was determined that in-tissue compound concentrations in pregnant mice could reach 100 μg/gram with a single subcutaneous (SC) or intravenous (IV) injection, producing more than 50-80% reduction in sFlt1-i13 mRNA (FIGS. 3 and 4, respectively). Without intending to be bound by scientific theory, with this level of delivery, silencing is expected to persist for weeks in humans, and thus a limited number of injections to be necessary. Indeed, just one SC injection could be sufficient to silence sFLT1 for several weeks, resulting in significant PE pregnancy extension, possibly even to full-term.

Example 2. Hydrophobically Modified siRNAs (hsiRNA): Fully Chemically-Modified siRNA/Antisense Hybrids A panel of chemistries and formulations were considered as potential approaches for placental delivery. These included LNA antisense, LNPs, chol-conjugates/DPC Gal-Nacs and hsiRNA. hsiRNAs by far exceeded other chemistries in placental delivery (discussed further infra) and were selected for further investigation. The efficiency of hsiRNA uptake in primary trophoblasts was evaluated. Efficient uptake by all cells upon addition of Cy3-labeled compound to the media was observed. The hsiRNAs are asymmetric compounds, with a short duplex region (e.g., 15 base-pairs) and a single-stranded fully phosphorothioated tail, where all bases are fully modified using alternating 2'-F/2'-O-methyl pattern (providing stabilization and avoidance of PKR response), and the 3' end of the passenger strand (i.e., sense strand) is conjugated to a hydrophobic moiety via a linker (e.g., TEG-Cholesterol). The hydrophobic moiety promotes quick membrane association, while the single-stranded phosphorothioated tail is essential for cellular internalization by a mechanism similar to that used by conventional antisense oligonucleotides (D. M. Navaroli, J. C., L. Pandarinathan, K. Fogarty, C., Standley, L. L., K. Bellve, M. Prot, A. Khvorova and & Corvera, S. Self-delivering therapeutic siRNA internalization through a distinct class of early endosomes. PNAS, under review, (2015)). Addition of Cy3-labeled hsiRNA to any cultured cell type shows quick and efficient internalization through an EE1 related part of the endocytosis pathway. A previous version of this technology (Byrne, M. et al. Novel Hydrophobically Modified Asymmetric RNAi Compounds (sd-rxRNA) Demonstrate Robust Efficacy in the Eye. Journal of Ocular Pharmacology and Therapeutics: The Official Journal of the Association for Ocular Pharmacology and Therapeutics (2013)), where only 50% of bases are 2'F/2'-O-methyl modified, is in Phase II clinical trials for dermal fibrosis.

A chemical modification pattern that does not interfere with primary RISC entry was developed. A wide range of chemical variations were generated and an alternating 2'F/2'-O-methyl pattern was identified that optimally configures the guide strand to adopt a geometry that closely mimics that of an individual strand in an A-form RNA duplex. The A-form RNA duplex is recognized by the RISC complex and supports proper positioning of the target mRNA within the cleavage site (Ameres, S. L., Martinez, J. & Schroeder, R. Molecular basis for target RNA recognition and cleavage by human RISC. Cell 130, 101-112 (2007); Schirle, N. T., Sheu-Gruttadauria, J. & MacRae, I. J. Gene Regulation. Structural basis for microRNA targeting. Science 346, 608-613 (2014)). By starting the alternating pattern with a 5'-phosphorylated 2'-O-methyl ribose (a 5' phosphate is necessary for PIWI domain interaction, Ago2 recognition), the 2'F modifications are placed in even numbered positions 2-14. Positions 2 and 14 were previously shown to be intolerant of bulkier 2'-ribose modifications (Jackson, A. L. et al. Position-specific chemical modification of siRNAs reduces "off-target" transcript silencing. RNA 12, 1197-1205 (2006); Kenski, D. M. et al. siRNA-optimized Modifications for Enhanced In Vivo Activity. Molecular therapy. Nucleic Acids 1, e5 (2012)).

Figure 7A:
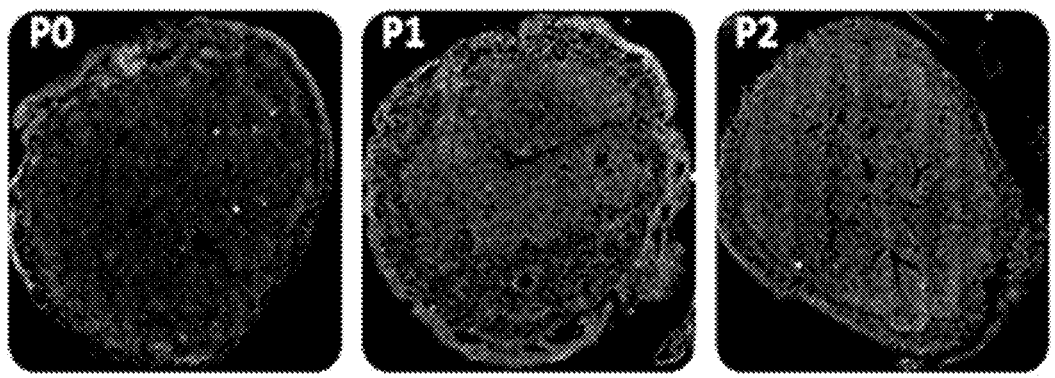
FIGS. 7A-7C depict the impact of hsiRNA chemistry and route of administration on placental accumulation and distribution. (A) A wild-type pregnant mouse (E15) was injected with Cy3-sFLT1-2283 (red) (10 mg/kg; IV via tail vein). Placentas were fixed after 24 hours, processed, and imaged on a Leica tiling fluorescent microscope; nuclei stained with DAPI (blue). (B) Depicts accumulation of sFLT1-i13-2283 (10 mg/kg) after 24 hours, and analyzed by PNA assay (n=3, mean+SEM). (C) Schematically represents different modification patterns of sFLT1-i13-2283 hsiRNA. P—5'-phosphate; Chol-teg—Cholesterol-teg linker; white spheres—RNA; black spheres—2'-O-methyl; grey spheres—2'-Fluoro; red spheres—phosphorothioate.
Figure 7B:
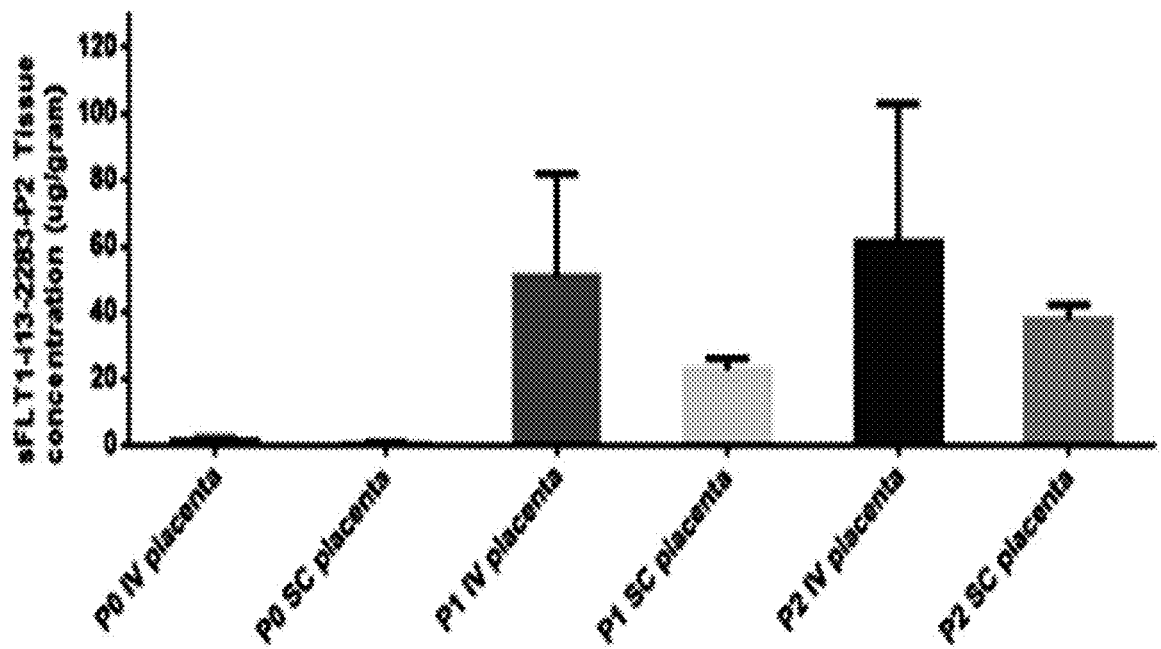
Figure 7C:
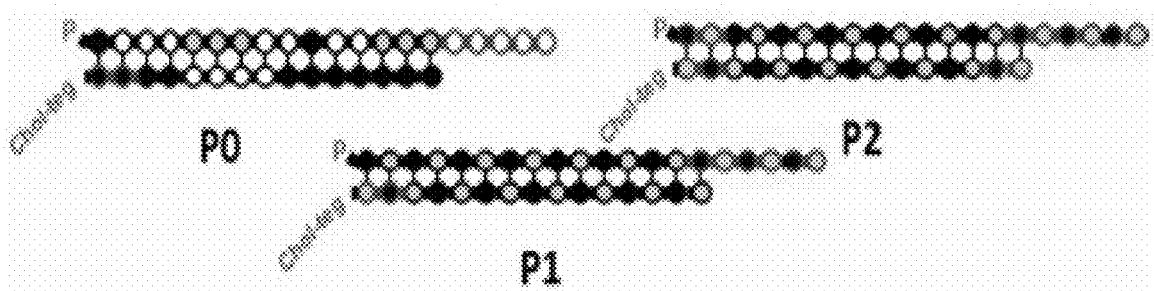

These fully chemically stabilized compounds were at least as or more effective as naked siRNA in RISC entry and represent the first complete chemical modification pattern with no negative impact on RISC function. This discovery was transformative for the PE project, as complete chemical stabilization is absolutely essential for tissue accumulation upon systemic administration. FIG. 7 shows that no full-length compound could be detected in mouse placentas 24 hours post administration of a version wherein 40% of the riboses were still 2'-OH (PO chemistry). In comparison, both fully 2'-F/2'-0-methyl modified versions (P1 and P2 chemistries) accumulated to above therapeutically efficacious levels (FIG. 7). Another benefit of non-RNA containing siRNAs is ease of manufacturing—their DNA-like chemistry with no necessity for orthogonal ribose protection shortens de-protection procedures and increases coupling efficiencies. Finally, complete elimination of all 2'-OH groups helps with avoidance of the innate immune response, which relies mainly on 2'-OH interactions (Alexopoulou, L., Holt, A. C., Medzhitov, R. & Flavell, R. A. Recognition of double-stranded RNA and activation of NF-kappaB by Toll-like receptor 3. Nature 413, 732-738 (2001); Choe, J., Kelker, M. S. & Wilson, I. A. Crystal structure of human toll-like receptor 3 (TLR3) ectodomain. Science 309, 581-585 (2005)).

Figure 39A:
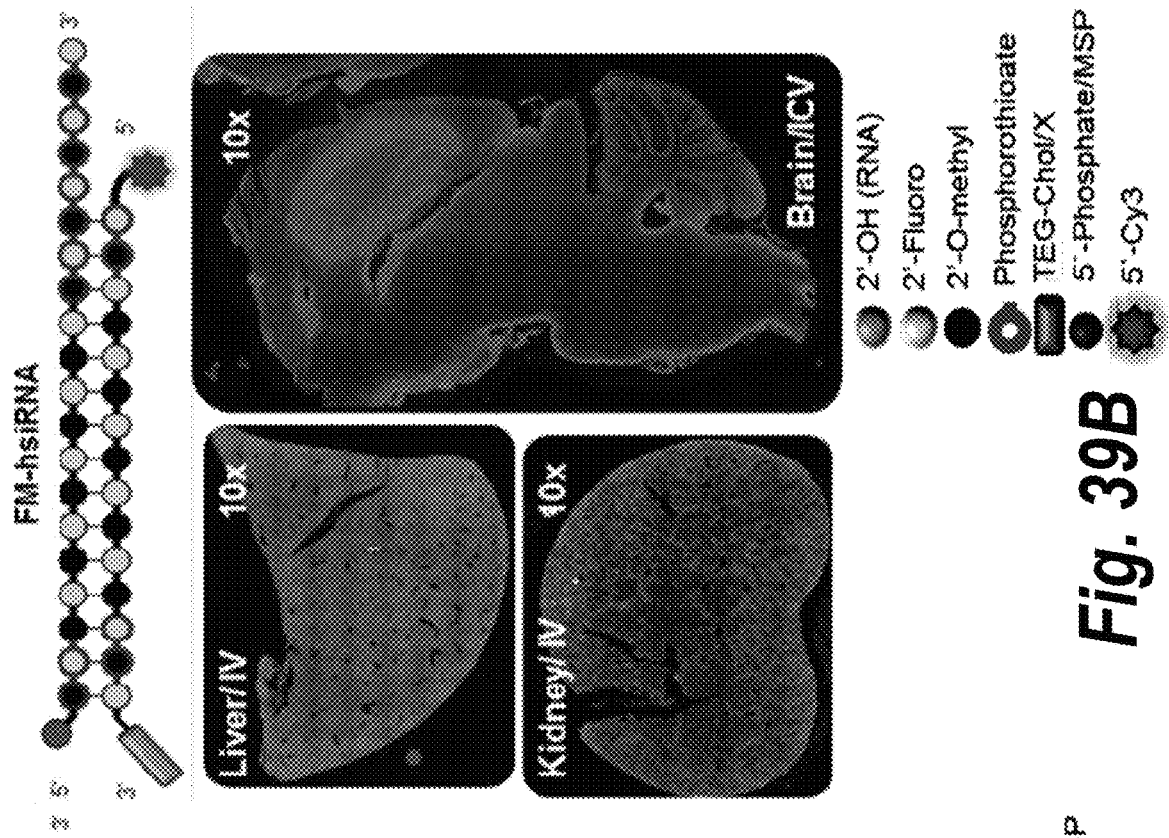
FIGS. 39A-39D depict conjugate mediated siRNA delivery and duration of effect in vivo. hsiRNA (A) and fully modified FM-hsiRNA (B) were injected IV (10 mg/kg) or ICV (60 ug) and distribution evaluated by microscopy (10×, Leica, Dapi, blue, Nuclei, Cy3, red, hsiRNA). Full stabilization dramatically enhances tissues retention. (C). Intact guide strand quantification analyzed by PNA assay (n=3, mean+SEM) in livers and kidneys 5 days after IV injection. (D) FM-hsiRNAs silences Htt mRNA in mouse striatum 1 month after injection (IS, 12 ug), QUANTIGENE. Partially modified hsiRNAs loses silencing after 1 week.
Figure 39B:
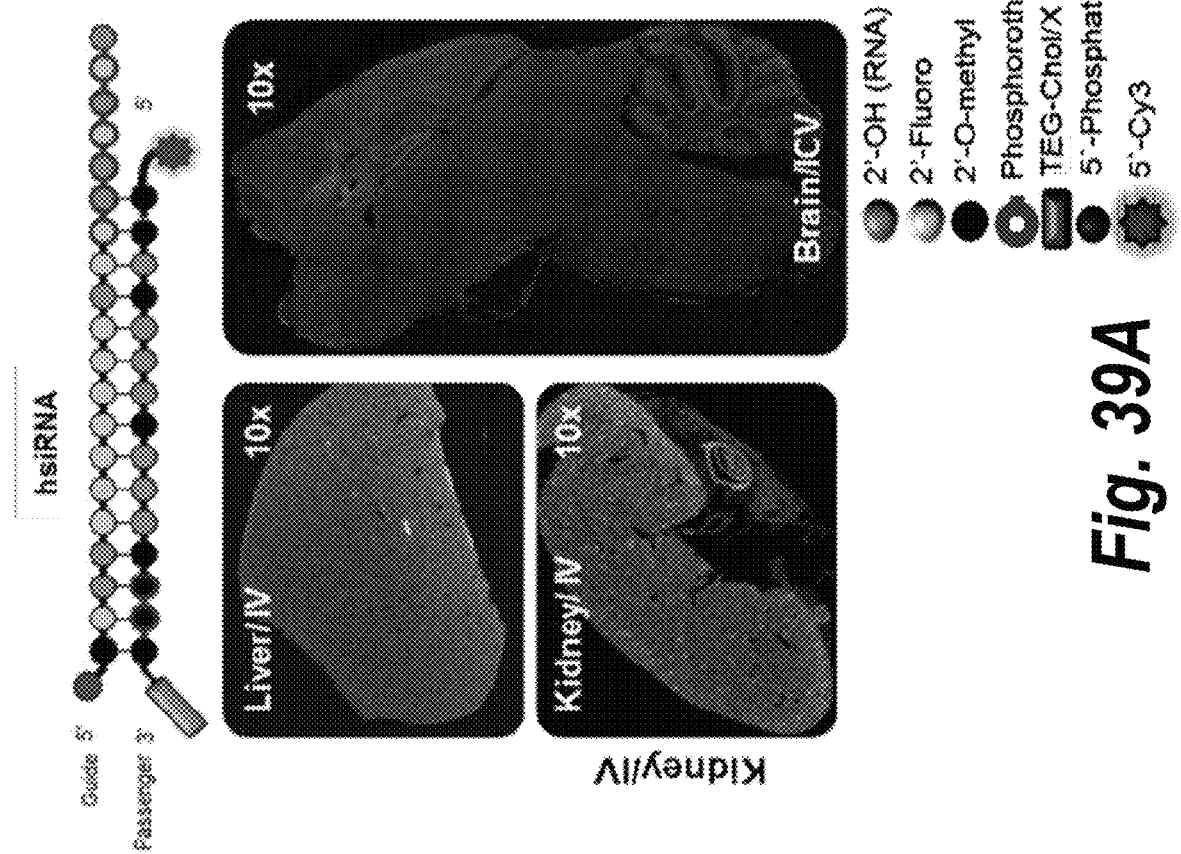
Figure 39C:
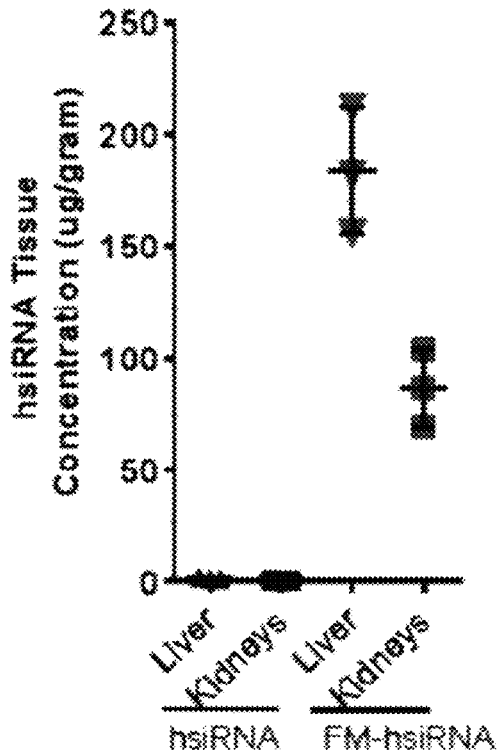
Figure 39D:
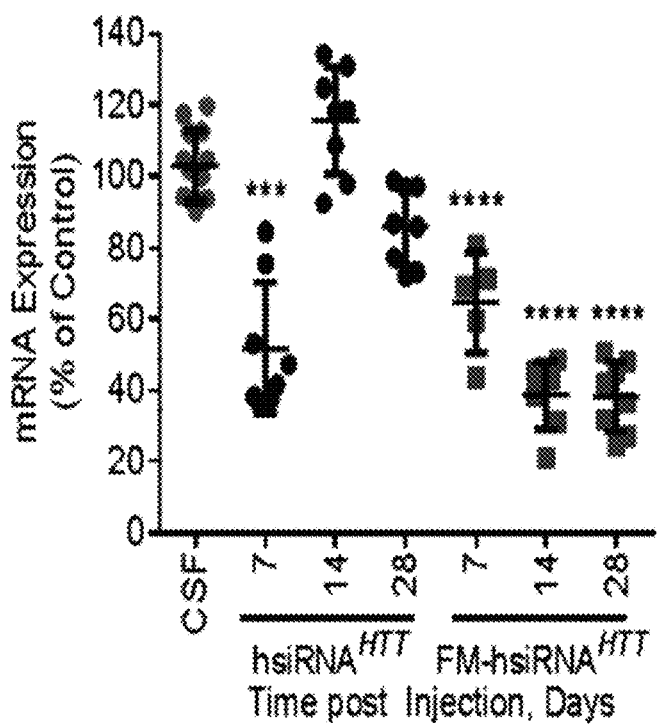

The discovery of this modification pattern has redefined an established paradigm for therapeutic siRNA design. Partial modification of siRNAs with 2'-O-methyl and 2'-fluoro dramatically increases their stability in vitro, leading to the errant assumption that partial modification would sufficiently stabilize oligonucleotides in vivo. However, this assumption is false (FIG. 39A,B; see Hassler et al., 2016 Nature Biotech). Visual (fluorescence; FIG. 39B) and quantitative (PNA-based; FIG. 39C) assays show that chemical modification of every 2'-OH (FM-hsiRNA) significantly enhances stability, accumulation, and retention of compounds in most tissues upon systemic (intravenous) or CSF (intracerebroventricular, ICV) administration. Partially stabilized hsiRNAs (40% of ribose's retain 2'-OH) performed poorly in comparison to FM-hsiRNAs. Moreover, CNS injection of FM-hsiRNA supports maximal silencing at least one month after injection (FIG. 39D, longer term studies ongoing)—a significant enhancement over the weeklong duration of silencing by partially modified compounds (FIG. 39D).

Replacing every 2'-OH group with 2'-O-methyl or 2'-fluoro has two additional benefits. The absence of a 2'-OH simplifies synthesis—the DNA-like chemistry eliminates the need for orthogonal ribose protection, thereby shortening the deprotection procedure and increasing the coupling efficiency. Moreover, the absence of 2'-OH groups minimizes innate immune activation 27 28, which is essential for enhancing therapeutic index.

Figure 38A:
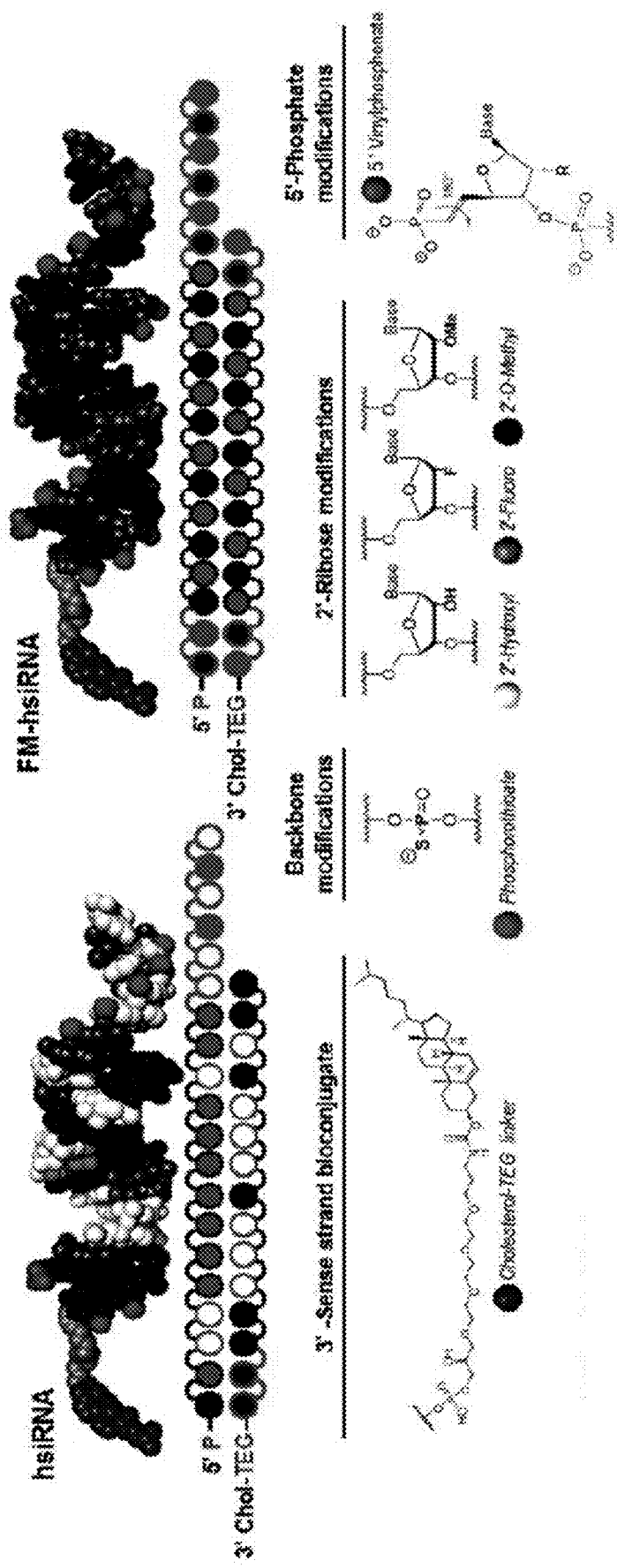
FIGS. 38A-38E depict fully metabolically stabilized hsiRNAs (FM-hsiRNAs). (A) Schematics of partially and fully modified hsiRNAs. (B) hsiRNA and FM-hsiRNA have equal ability to enter RISC (HeLa, 72 hours, QUANTI-GENE). (C) FM-hsiRNA, but not naked siRNA, supports passive delivery. (D) Metabolically stable 5'-E-VP is as active as 5'-P. (E) 5'-E-VP enables sustained delivery to distant tissues (7 days post injection, PNA assay).
Figure 38B:
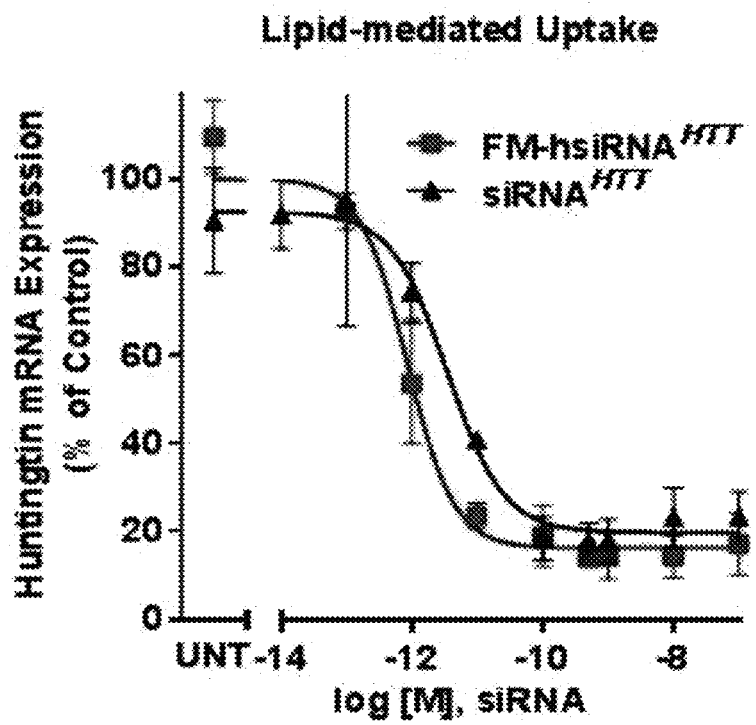
Figure 38C:
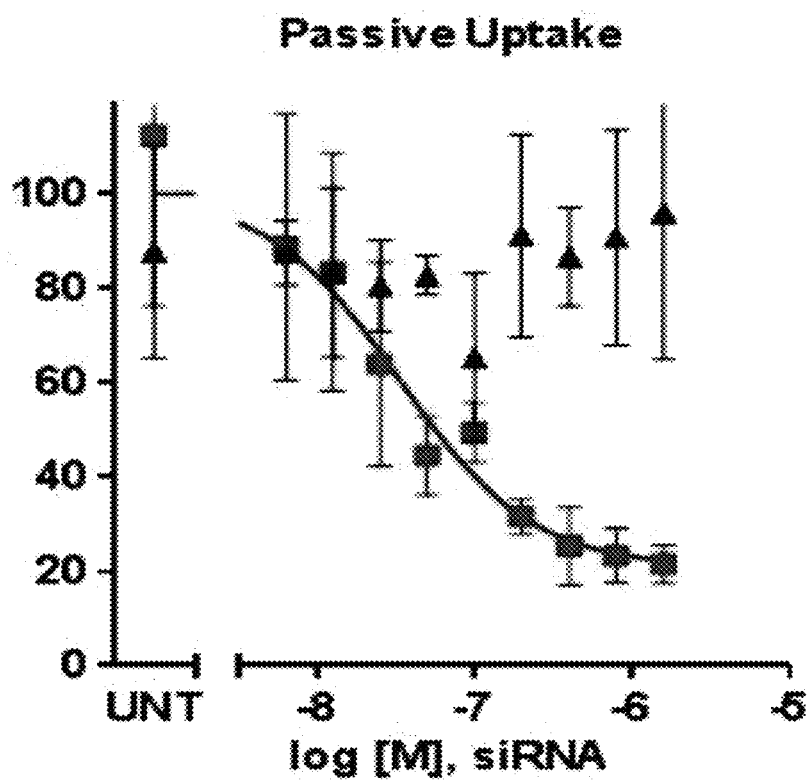
Figure 38D:
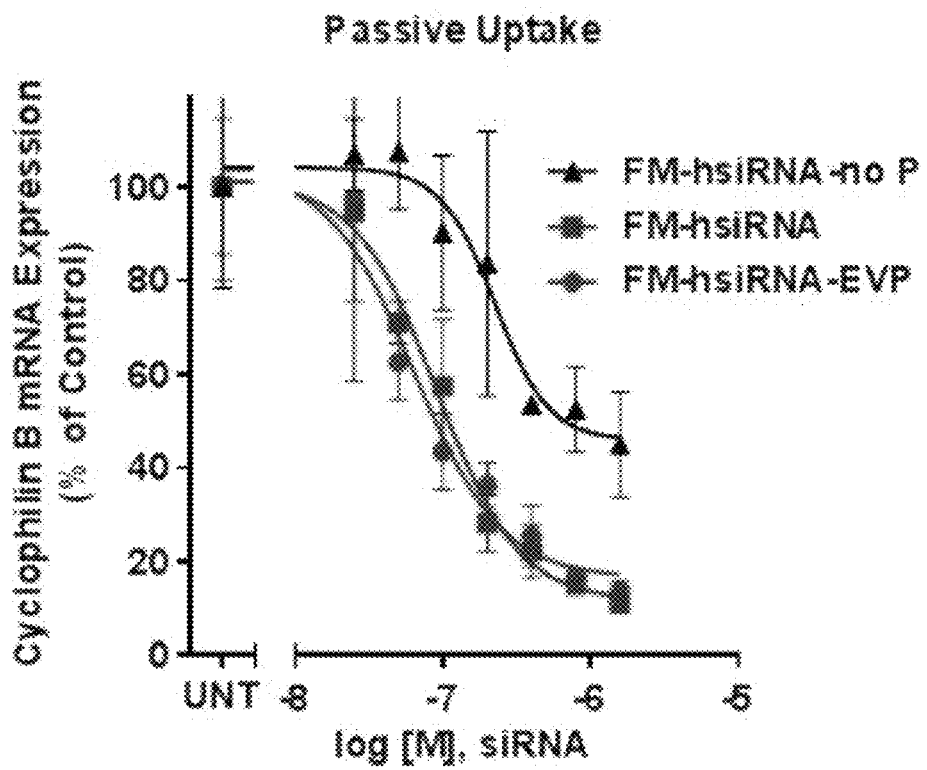
Figure 38E:
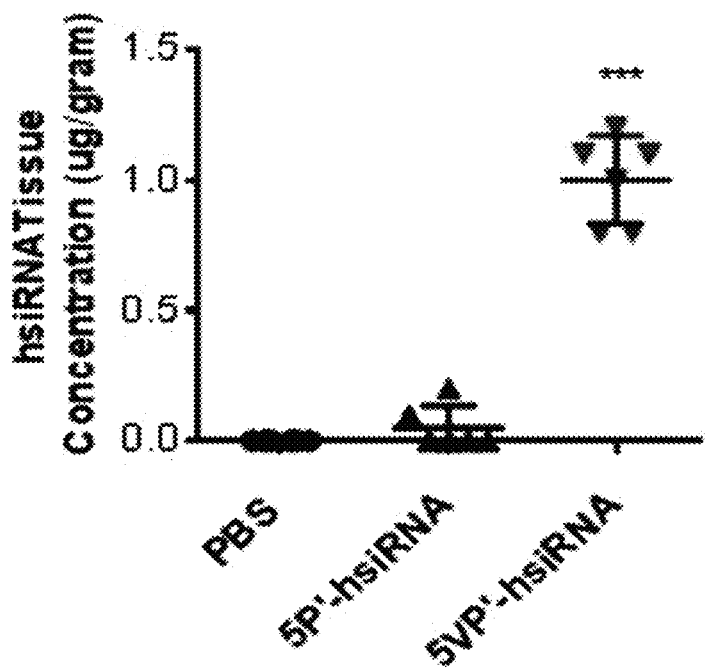

Metabolic stability studies were performed on FM-hsiRNA and it was found that the primary degradation product (90% within 2 hours of systemic administration) of FM-hsiRNA results from removal of the 5' phosphate from the guide strand. Without a 5' phosphate, the compound cannot bind RISC and is, therefore, inactive (FIG. 38C). Consequently, the 5' phosphate was replaced with its stable stereo-compatible analog 5'-(E)-vinylphosphonate (5'-E-VP) (also referred to herein as X3). The 5'-E-VP-modified hsiRNA is equally active as 5'-P-hsiRNA (FIG. 38C), but it significantly enhances retention of guide strand in tissues distal to the injection site after one week (FIG. 38D). The 5'-E-VP modification is expected to further increase duration of effect in vivo.

Example 3. hsiRNAs Enabled Selective Delivery to Placental Labyrinth Trophoblasts with no Detectable Fetal Transfer To evaluate hsiRNA distribution in vivo, normal pregnant mice (day 15) were injected with Cy3-labeled sFlt-i13-2283 hsiRNA and distribution examined at by two independent assays. Gross tissue fluorescence microscopy revealed that most of the oligonucleotides accumulated to three tissues: liver endothelium, kidney endothelium and placental labyrinth (FIG. 4). Without intending to be bound by scientific theory, this distribution profile was most likely defined by a combination of blood flow/filtration rate and the cholesterol receptor concentration on cell surfaces. Using the novel FDA-compliant PNA-hybridization assay described above, it was demonstrated that overall drug concentration in placenta exceeded efficacious levels (approximately 100 ng/gram) by orders of magnitude upon a single 10 mg/kg injection (FIG. 4). This level of tissue delivery was roughly the same for IV and SC administration, with approximately 50%, 10% and 12% of the compound distributing to liver, kidney and placenta, respectively, 24 hours post-injection (FIG. 4). Interestingly, only half of this was cleared from the liver (slightly more in kidney) after five days, indicating that a single administration might be sufficient to induce long-term silencing.

In addition to comparing the impact of full 2'-F/2'-O-methyl modification on PK (pharmacokinetics), the phosphorothioate (PS) content was slightly altered. While the P1 chemistry had PS linkages at the 3'-ends of both strands (for a total of 8), the P2 chemistry incorporated another two PS's at the 5' end of each strand (for a total of 12). Terminal PS linkages provided a defense against exonucleases, and so are essential for long-term stability in extremely aggressive nuclease environments. Overall, these two chemistries were comparable in levels of oligonucleotides delivery at 24 hours (FIG. 7), but might have different degradation profiles after long term tissue exposure, affecting duration of the silencing effect. They also have slightly different liver: placenta distribution ratios, which might also be somewhat affected by the route of administration (FIG. 7).

3.1. Selection and Identification of Lead Candidate: i13/i15 Mix and Efficacy in Primary Trophoblasts The i13 and i15 Flt1 mRNA isoforms contained 435 and 567 unique nucleotides, respectively, not present in fl-Flt1 mRNA. Unfortunately, the majority of this sequence space was dominated by homo-polymeric repeats and regions of high GC content, neither of which are targetable by RNAi. Undeterred, a panel of more than 50 hsiRNAs was designed against any feasible targetable sequence using standard siRNA design parameters (Birmingham, A. et al. A protocol for designing siRNAs with high functionality and specificity. Nature protocols 2, 2068-2078 (2007)) including assessment of GC content, specificity and low seed compliment frequency (Anderson, E. M. et al. Experimental validation of the importance of seed complement frequency to siRNA specificity. RNA 14, 853-861 (2008)), elimination of sequences containing miRNA seeds, and examination of thermodynamic bias (Khvorova, A., Reynolds, A. & Jayasena, S. D. Functional siRNAs and miRNAs exhibit strand bias. *Cell* 115, 209-216 (2003); Schwarz, D. S. et al. Asymmetry in the assembly of the RNAi enzyme complex. *Cell* 115, 199-208 (2003)). FIG. 3B shows the targeting positions of hsiRNAs identified to be highly functional.

In the design criteria, targeting sites with perfect homology in other primates were favored to simplify both formal toxicology and efficacy studies in non-human primates and the baboon PE model described below. The mouse expresses only an i13 variant. Luckily, the most efficacious hsiRNA, sFLT1-i13-2283, happened to have perfect complementarity to the mouse i13 isoform, enabling direct in vivo efficacy and toxicity evaluation of this compound in both normal and PE mouse pregnancy models. FIG. 3C shows a table with targeting sites and IC50 values of the best compounds identified to efficiently silence the i13 and i15 isoforms. IC50 values for efficacious compounds ranged between 40-100 nM in both HeLa cells and primary human trophoblasts.

Figure 1B:
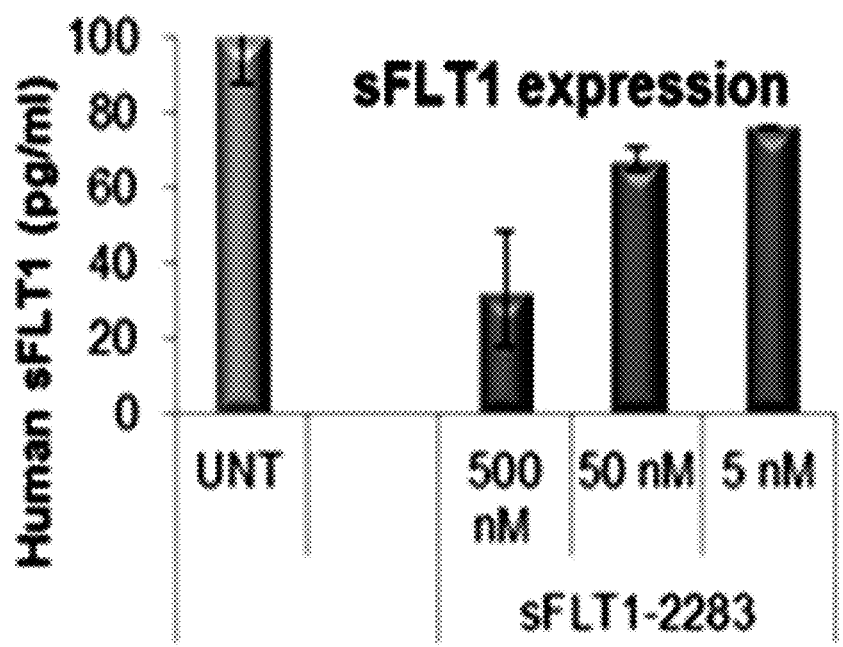
Figure 1C:
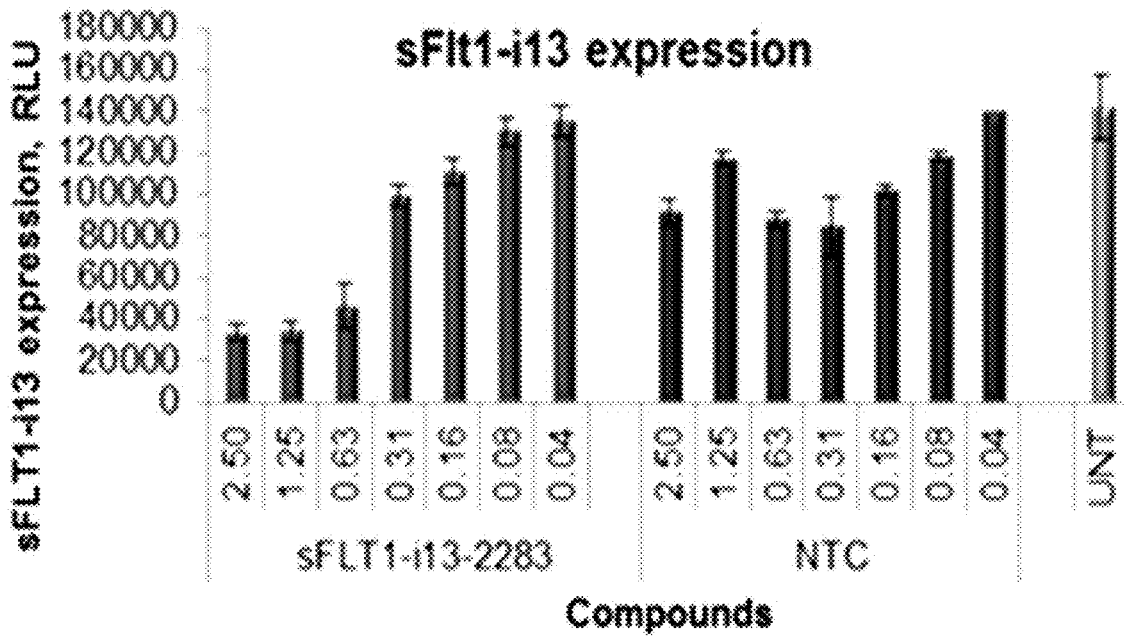
Figure 1D:
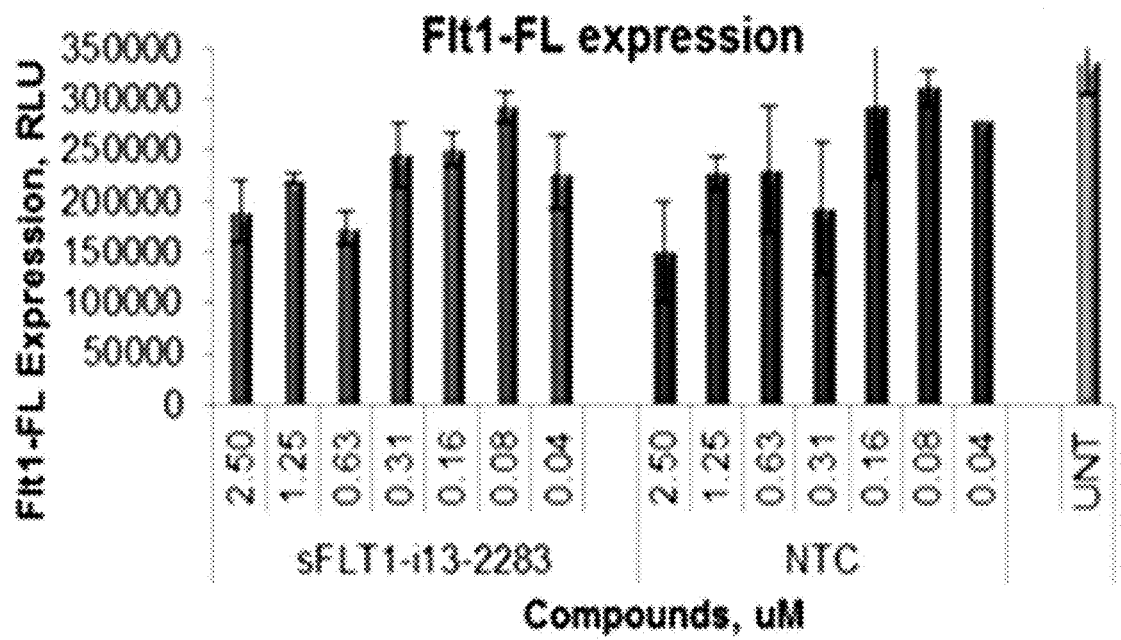

FIG. 1C shows an example of the dose response of sFLT1-i13-2283 in primary human trophoblasts used for IC50 value calculation. It is important to emphasize that silencing with hsiRNAs was achieved upon addition of non-formulated compound to the trophoblast media. The level of mRNA knockdown was determined at 72 hours using the above-described QUANTIGENE assay. To control for any potential non-specific effects, i13 or i15 levels were always normalized to a housekeeping gene. A Non-Targeting-Control (NTC) of identical chemistry was used in all experiments to control for chemical class effects. The levels of full length Flt1 mRNA were not affected (FIG. 1D). To evaluate silencing at the protein level, sFLT1 concentration in conditioned medium was measured using ELISA (QUANTIKINE FLT1, MVR100, R&D Systems) (FIG. 1B).

To move forward, two hsiRNA pairs were selected: sFLT1-i13-2283 (5' CTCTCGGATCTCCAAATTTA 3' (SEQ ID NO: 10))/sFLT1-i15a-2519 (5' CATCATAGCTAC-CATTTATT 3' (SEQ ID NO: 11)) and sFLT1-i13-2318 (5' ATTGTACCACACAAAGTAAT 3' (SEQ ID NO: 12))/ sFLT-i15a-2585 (5' GAGCCAAGACAATCATAACA 3' (SEQ ID NO: 13)) (FIG. 1C). The first pair was the lead drug candidate and was used in all studies. The second pair was a backup. While sequence-specific toxicity is unlikely to be an issue, a backup compound combination that was readily available in case of any sequence-dependent toxicity appeared was desired. In summary, functional hydrophobically-modified siRNAs that selectively target sFlt1-i13 and sFlt1-i15a isoforms were identified. Efficient internalization and silencing of the corresponding targets in primary human trophoblasts was determined at both the mRNA and protein levels.

These data indicate that novel siRNA chemistry has been developed that enables efficient delivery to placental trophoblasts, the primary site of sFLT1 overexpression during PE, and allowed potent silencing of circulating sFLT1 upon systemic administration.

Example 4. Reduction of Huntingtin in Both Primary Neurons and Mouse Brain with Unformulated, Stabilized, Hydrophobic siRNAs The use of hydrophobically modified ASO-siRNA hybrids, which have the potential to offer both better efficacy and distribution in vivo and knockdown in primary neurons in vitro, was explored. The huntingtin gene was used as a target for mRNA knockdown. Huntington's disease is monogenic (Mangiarini, L. et al. Exon 1 of the HTT gene with an expanded CAG repeat is sufficient to cause a progressive neurological phenotype in transgenic mice. *Cell* 87, 493-506 (1996)) with a number of cellular mechanisms leading to disease pathology (Zuccato, C., Valenza, M. & Cattaneo, E. Molecular Mechanisms and Potential Therapeutical Targets in Huntington's Disease. *Physiological Reviews* 90, 905-981 (2010)) making it an excellent candidate for possible future oligonucleotide therapeutics.

A panel of hydrophobically modified siRNAs targeting the Huntingtin gene was developed. See FIG. 24. Efficacy and potency was observed both in primary neurons in vitro, and in vivo in mouse brain upon a single low dose injection without any formulation for delivery. These compounds combine a number of different chemical and structural modifications found both in earlier model siRNAs and hsiRNAs, as well as in ASOs. These properties, which include stabilizing base modifications, cholesterol conjugation, and a fully phosphorothioated single stranded tail, make these hsiRNAs excellent tools for studying gene function in hard-to-target primary cells and organs that can be adapted for use in a number of different biologically relevant systems.

Figure 8:
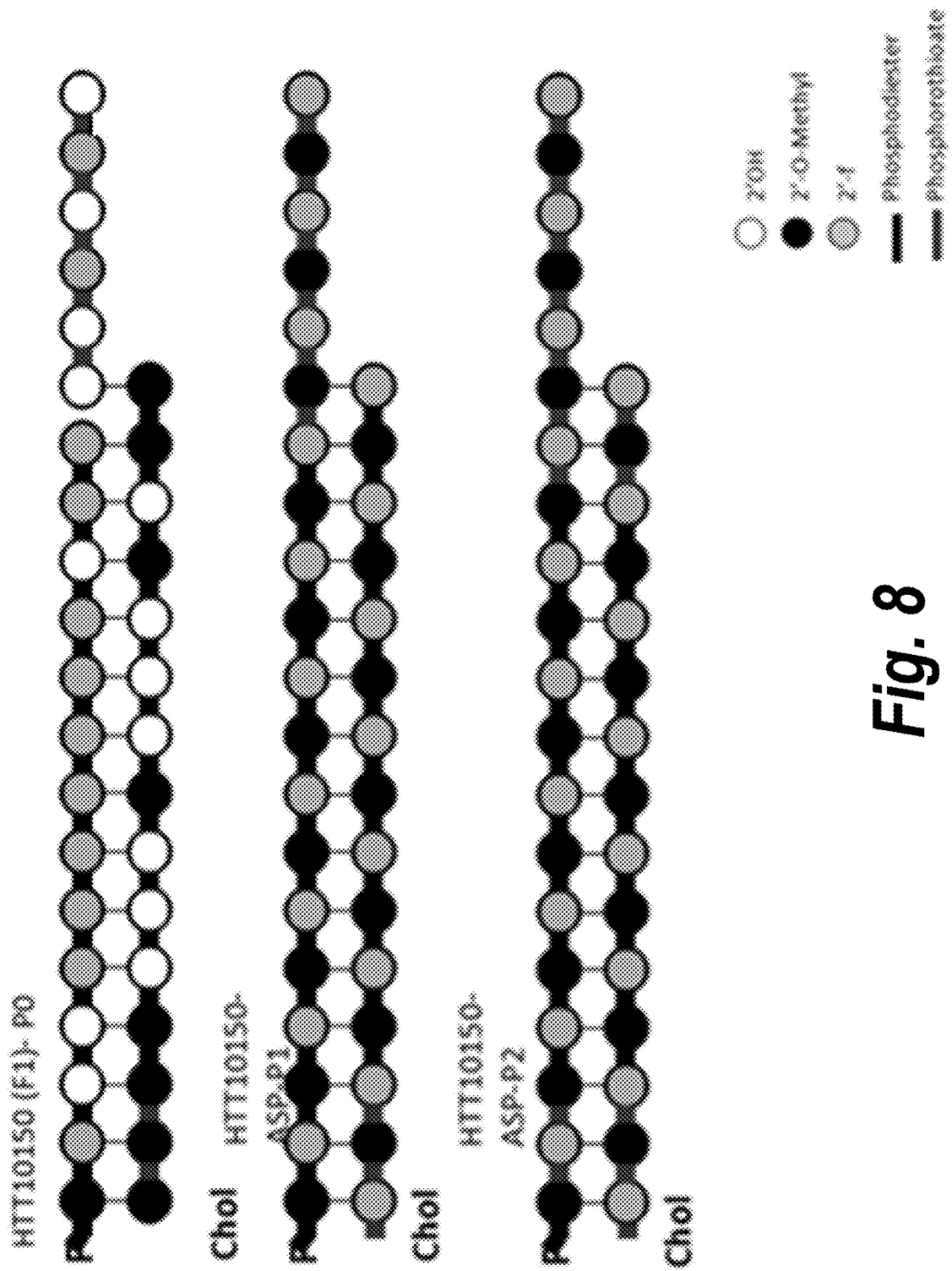
FIG. 8 depicts the structure and stabilization pattern of siRNA compounds of the invention.
Figure 9:
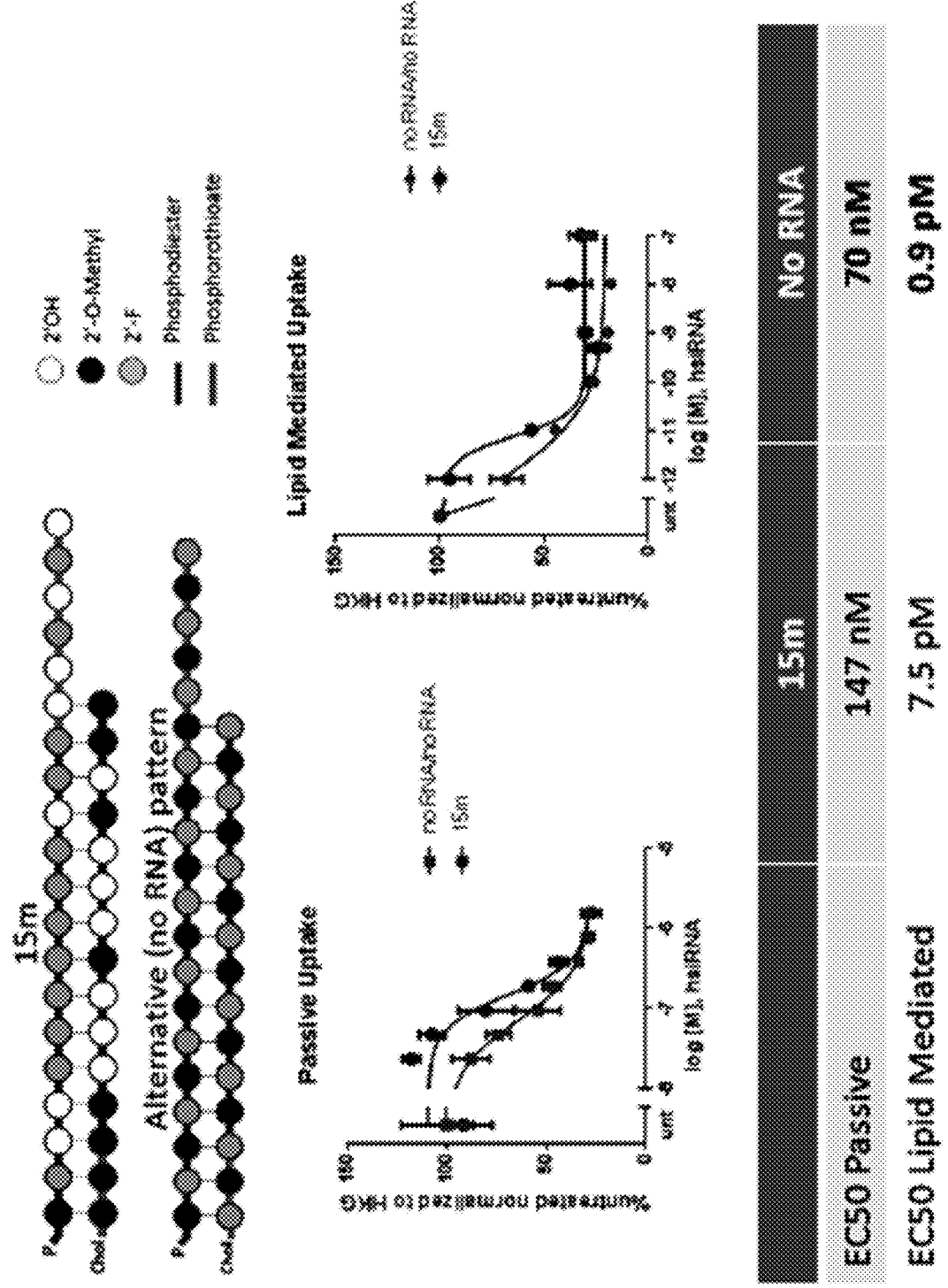
FIG. 9 depicts the modification pattern of compounds of the invention and the resulting increase of in vitro efficacy.
Figure 10:
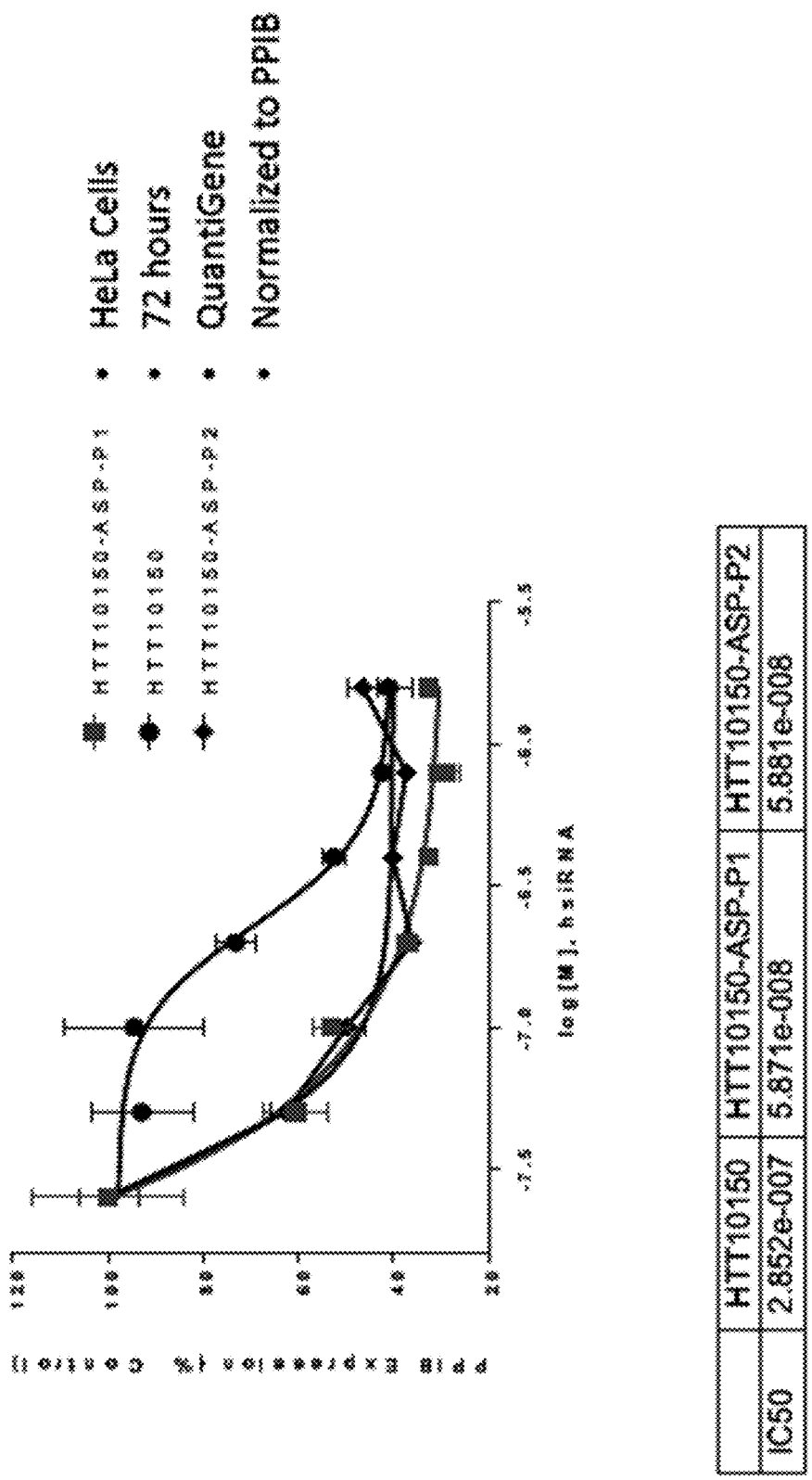
FIG. 10 depicts data showing the increased potency of compounds of the invention versus a comparator compounds that do not feature ASP (advanced stabilization pattern) chemical modifications.
Figure 11:
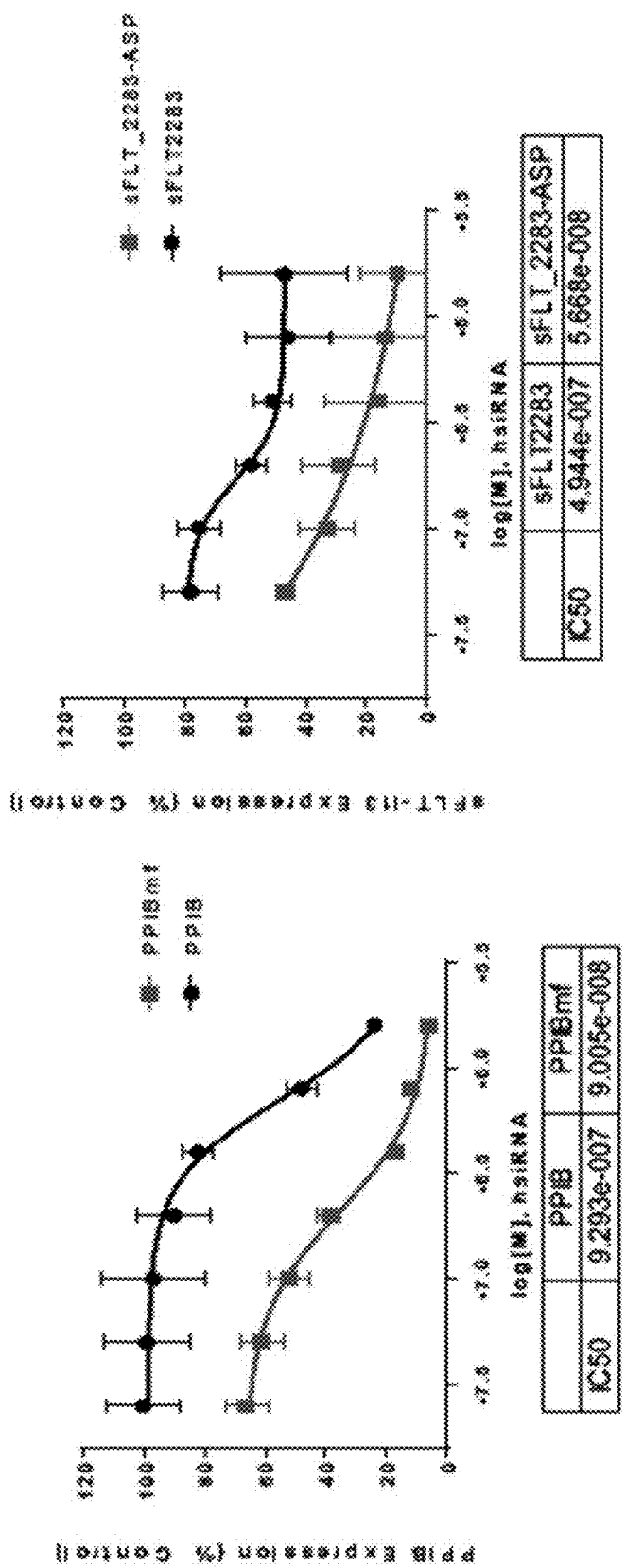
FIG. 11 depicts data showing the increased potency of compounds of the invention versus a comparator compounds that do not feature ASP (advanced stabilization pattern) chemical modifications.
Figure 12:
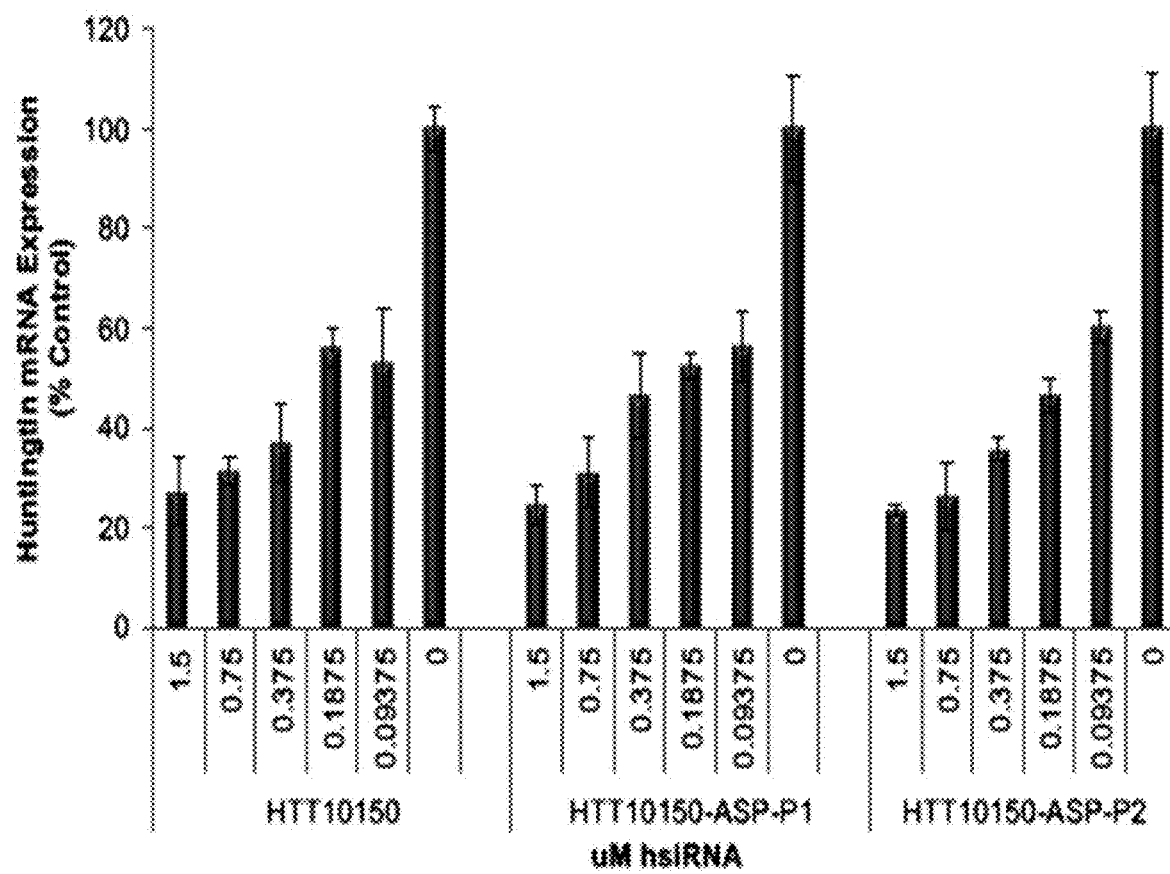
FIG. 12 depicts the efficacy of HTT10150-ASP-P1 and HTT10150-ASP-P2 versus HTT10150 in neurons.
Figure 13:
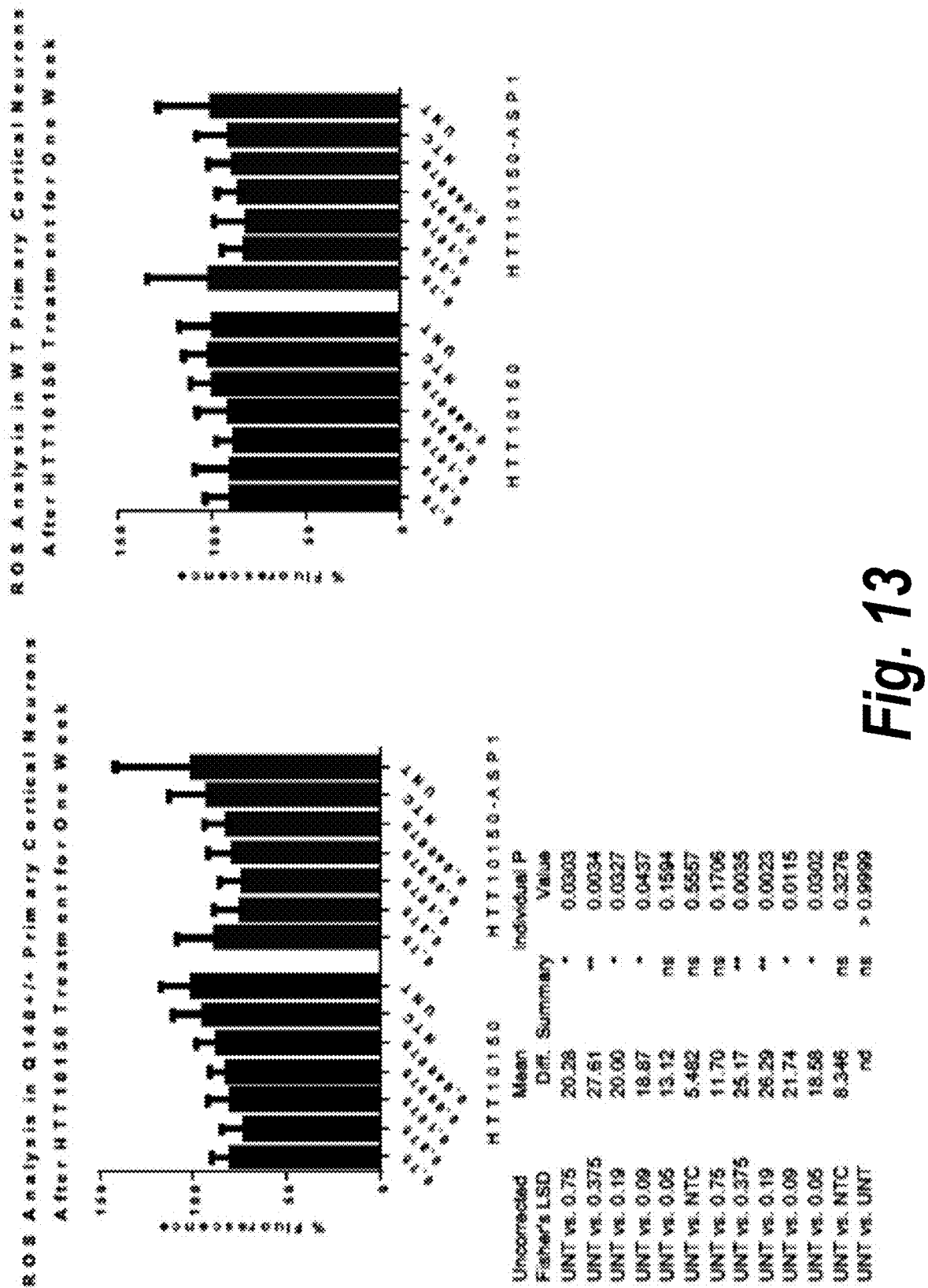
FIG. 13 depicts data showing that HTT10150-ASP is more potent in ROS modulation in Q140.
Figure 14:
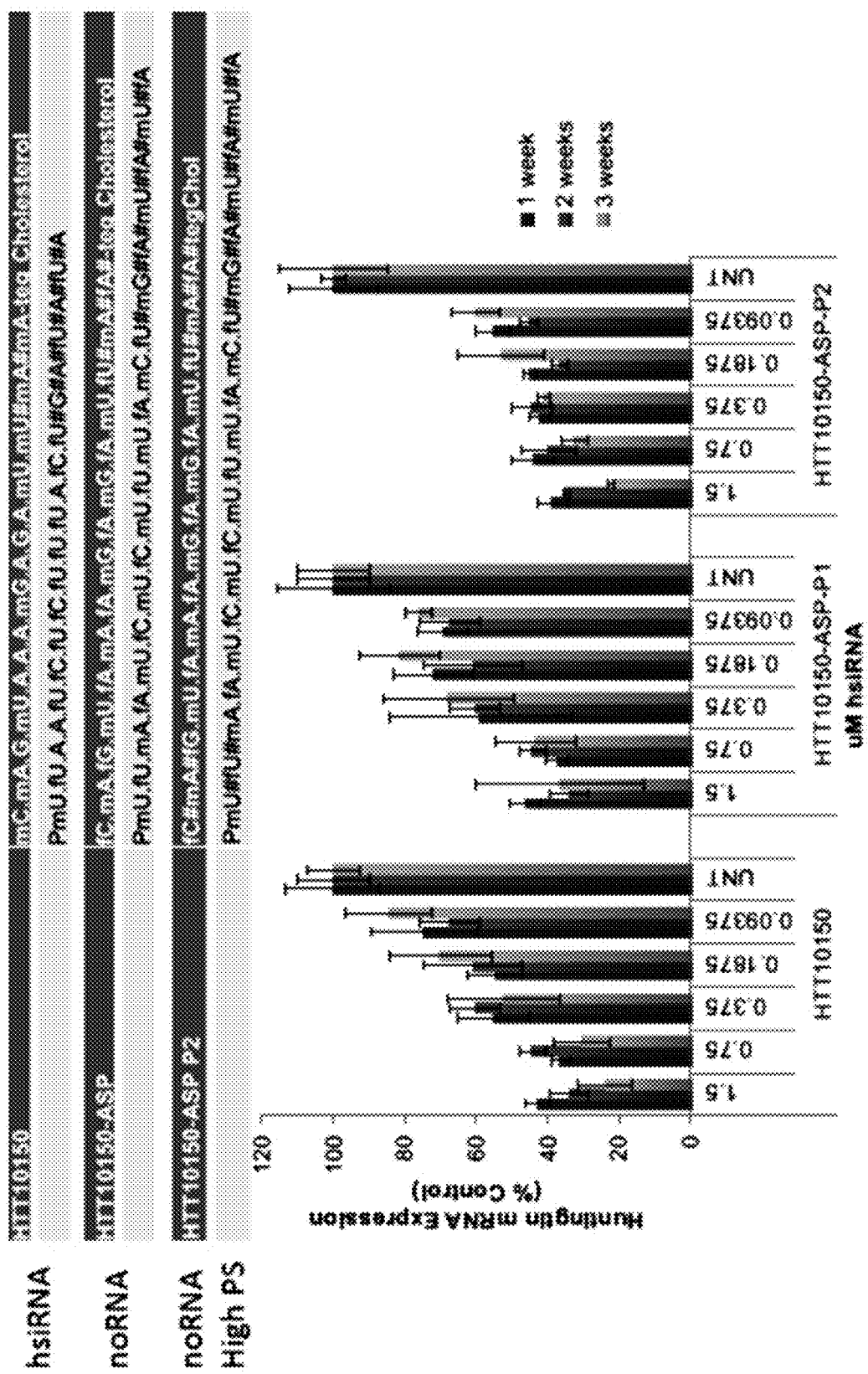
FIG. 14 depicts data showing that HTT10150-ASP-P2 shows better long term silencing and potency in neurons.
Figure 15:
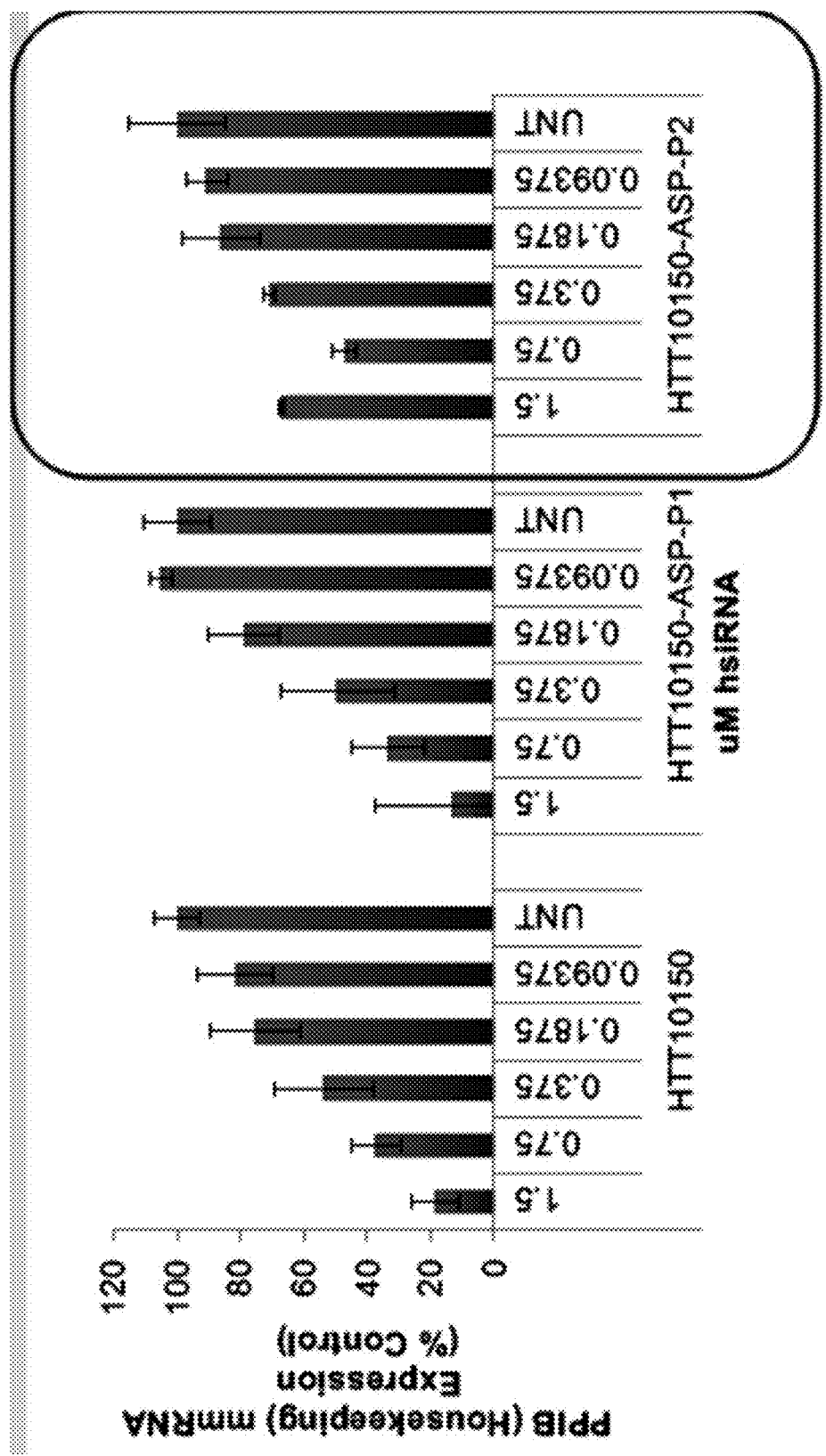
FIG. 15 depicts data showing that HTT10150-ASP-P2 shows reduced toxicity in primary neurons.
Figure 16:
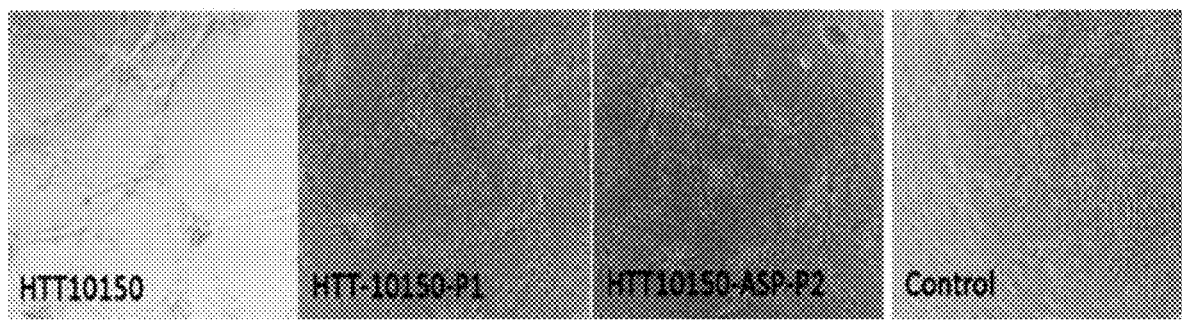
FIG. 16 depicts data showing visibly reduced toxicity of compounds having ASP patterns versus HTT10150.

4.1 hsiRNA—Hydrophobically Modified siRNA/Antisense Hybrids were Efficiently Internalized by Primary Neurons The hsiRNAs were asymmetric compounds, with a short duplex region (e.g., 15 base-pairs) and single-stranded fully phosphorothioated tail. All pyrimidines in these compounds were 2'-Fluoro or 2'-O-Methyl modified (providing stabilization), and the 3' end of the passenger strand was conjugated to TEG-Cholesterol (FIG. 1A, FIG. 8). The cholesterol conjugate enabled quick membrane association, while the single stranded phosphorothioated tail was necessary for cellular internalization by a mechanism similar to the one used by conventional antisense oligonucleotides. Addition of Cy3-labeled hsiRNA to primary cortical neurons resulted in immediate (within minutes) cellular association (FIG. 1B). Interestingly, the uptake was first observed preferentially in dendrites, followed by re-localization to the cellular body (FIG. 9). The uptake was uniform across all cells in the dish, affirming efficient internalization. Notably, approximately 60% of htt-mRNA was found to be localized in the nuclei (data not shown).

4.2 Identification of hsiRNAs Targeting Huntingtin

Figure 25A:
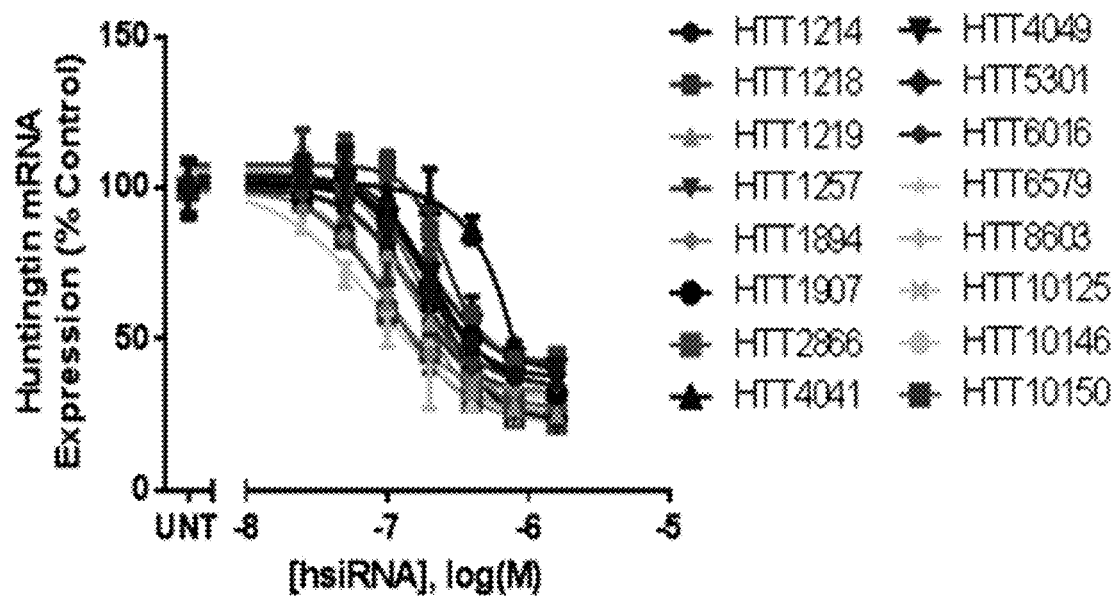
FIGS. 25A-25B depict graphically depict concentration-dependent silencing of huntingtin mRNA by HTT10150 in HeLa cells. Level of huntingtin mRNA was measured using QUANTIGENE (Affymetrix) at 72 hours normalized to housekeeping gene, PPIB (cyclophillin B), and presented as percent of untreated control (n=3, mean+/−SD). UNT—untreated cells, NTC—non-targeting control. A) Dose response of 16 active sequences in passive uptake (no formulation). B) Dose response of eight selected sequences in lipid-mediated uptake (using Invitrogen LIPO-FECTAMINE RNAIMAX Transfection Reagent). Dose response data was fitted using GraphPad Prism 6.03.
Figure 25B:
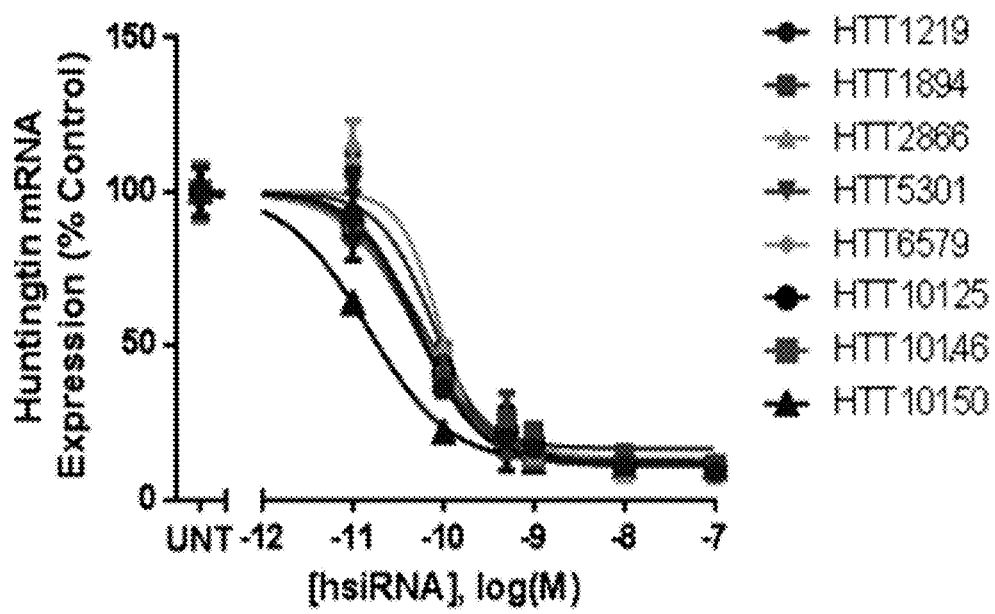

A panel of 94 hsiRNA compounds (FIG. 24) targeting huntingtin mRNA was designed and synthesized. These sequences spanned the gene and were selected to comply with standard siRNA design parameters (Birmingham, A. et al. A protocol for designing siRNAs with high functionality and specificity. *Nat Protoc* 2, 2068-2078 (2007)) including assessment of GC content, specificity and low seed compliment frequency (Anderson, E. M. et al. Experimental validation of the importance of seed complement frequency to siRNA specificity. *RNA* 14, 853-861 (2008)), elimination of sequences containing miRNA seeds, and examination of thermodynamic bias (Khvorova, A., Reynolds, A. & Jayasena, S. D. Functional siRNAs and miRNAs Exhibit Strand Bias. *Cell* 115, 209-216 (2003); Schwarz, D. S. et al. Asymmetry in the Assembly of the RNAi Enzyme Complex. *Cell* 115, 199-208 (2003)). More than 50% of bases were chemically modified, to provide in vivo stability and minimization of immune response (Judge, A., Bola, G., Lee, A. & MacLachlan, I. Design of Noninflammatory Synthetic siRNA Mediating Potent Gene Silencing in Vivo. *Molecular Therapy* 13, 494-505 (2006)). The modifications imposed additional restrictions on sequence space, reducing the hit rate. Impact on Huntingtin mRNA expression was measured after 72 hours exposure to 1.5 µM hsiRNA (passive uptake, no formulation) in HeLa cells by QUANTIGENE assay with 7% of sequences showing more than 70% silencing. At 1.5 µM hsiRNA, 24 hsiRNAs reduced Htt mRNA levels to less than 50% of control levels, including 7 hsiRNAs that reduced Htt mRNA levels below 30% of control. Functional target sites were spread across the gene with the exception of the distal part of the 3'UTR, later explained by preferential expression of the shorter htt isoform in HeLa cells (Li, S. H. et al. Huntington's disease gene (IT15) is widely expressed in human and rat tissues. *NEURON* 11, 985-993 (1993)). IC50 values were identified for sixteen active sequences, selected based on primary screen activity and cross-species conservation (FIG. 25). IC50 values ranged from 90 to 766 nM in passive uptake (no formulation) and from 4 to 91 pM in lipid-mediated uptake (FIG. 24). Fully chemically-optimized active compounds were readily identified, indicating that a much smaller library should be sufficient in future screens for other genes, although hit rate is likely to be variable from target to target. The hsiRNA targeting position 10150 (HTT10150 (i.e., 5' CAGUAAAGAGAUUAA 3' (SEQ ID NO: 9))) was used for further studies. To ensure that the hsiRNA chemical scaffold did not negatively impact efficacy and potency of HTT10150, the modified and unmodified versions of the compound were tested in both passive and lipid-mediated silencing assays (FIG. 26). As expected, only the modified sequence was successful at cellular delivery and Htt silencing by passive uptake (IC50=33.5 nM), while both the modified and unmodified compounds showed similar IC50 values in lipid mediated delivery (0.9 pM and 3.5 pM respectively) suggesting that the hsiRNA scaffold modifications did not interfere with RNA-Induced Silencing Complex (RISC) loading.

Figure 27A:
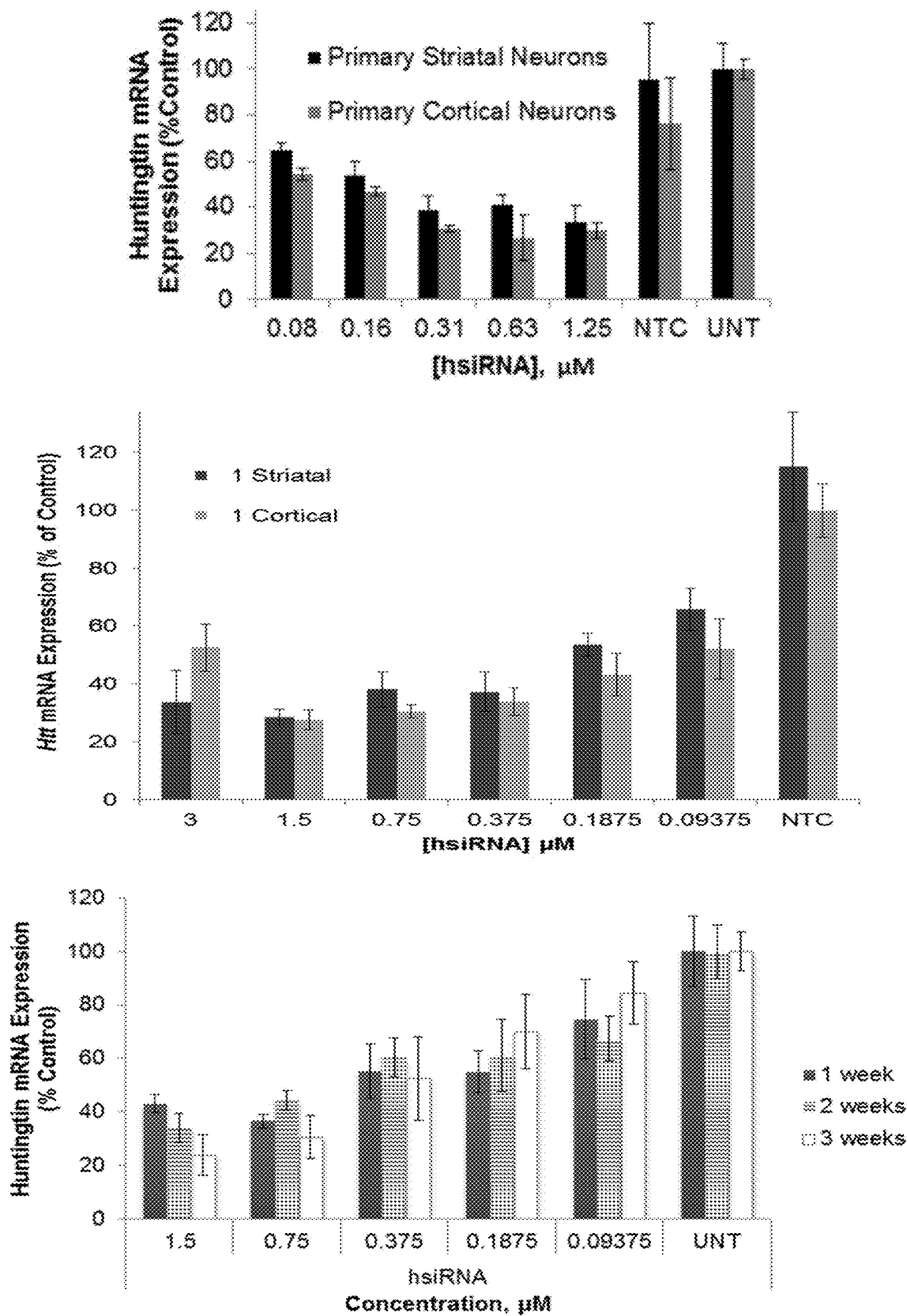
FIGS. 27A-27B graphically depict concentration-dependent silencing of huntingtin mRNA and protein by HTT10150 in primary neurons (passive uptake). Primary neurons were incubated with HTT10150 at concentrations shown. Level of huntingtin mRNA was measured using QUANTIGENE (Affymetrix) normalized to housekeeping gene, PPIB (cyclophillin B), and presented as percent of untreated control (n=3, mean+/−SD). UNT—untreated cells. (A) In primary cortical and striatal neurons, 1 week. (B) Huntingtin protein levels after one week incubation with HTT10150 were detected by western blot and normalized to β-Tubulin.
Figure 27B:
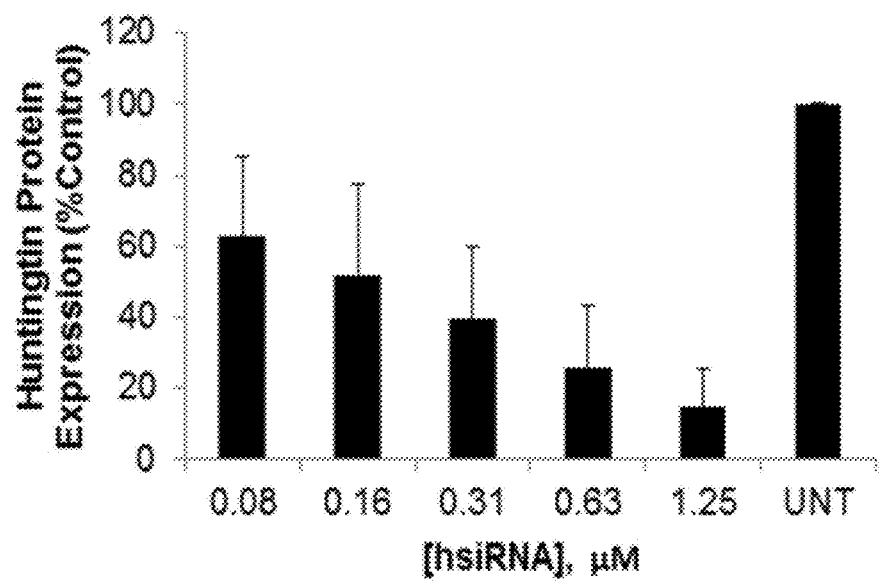
Figure 33:
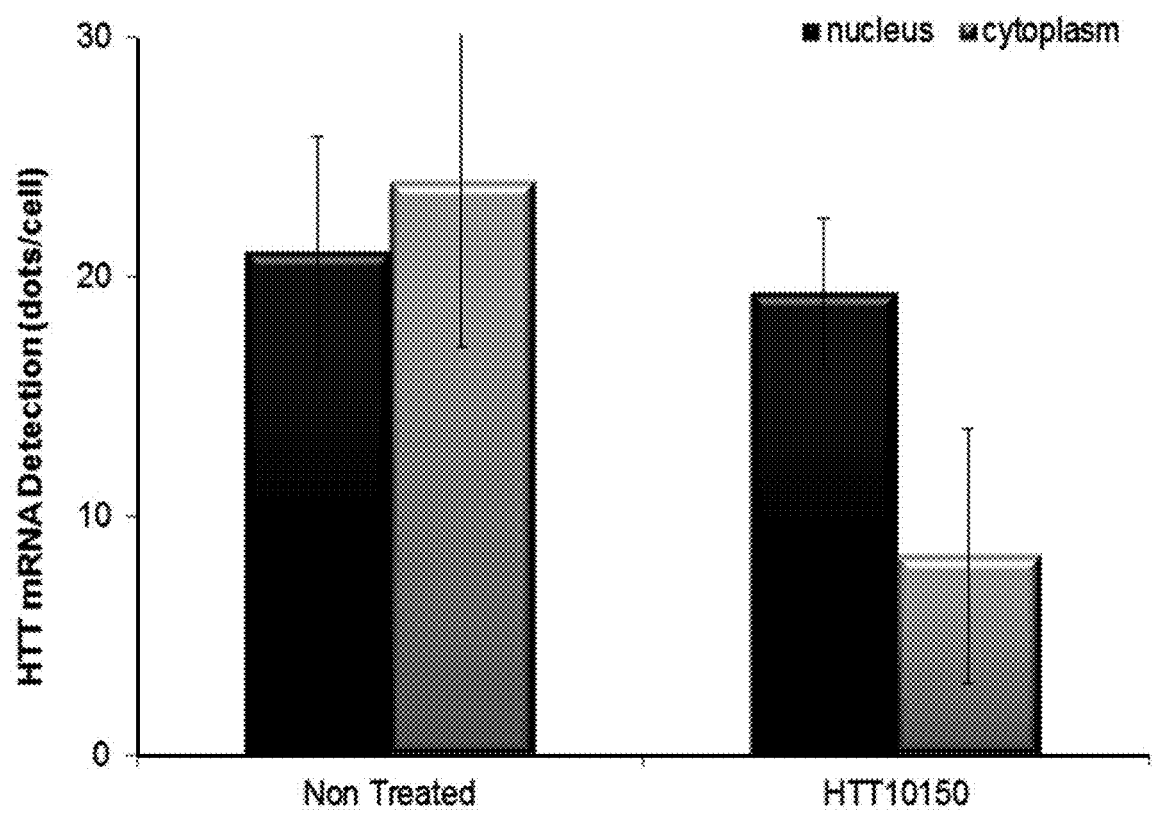
FIG. 33 depicts the preferential elimination of cytoplasmic Htt mRNA over nuclear Htt mRNA by HTT10150.

4.3 Potent and Specific Gene Silencing with Unformulated hsiRNAs in Primary Neurons HTT10150 was further tested for mRNA silencing in primary neurons isolated from FVBN mice. Efficacy was seen at both 72 hours and one week following simple unformulated compound addition to cortical neurons (FIG. 27A) with maximum silencing (70%) observed at the 1.25 µM concentration. hsiRNA$^{HTT}$ treatment of cortical neurons preferentially eliminated cytoplasmic, over nuclear, Htt mRNA (FIG. 33). HTT10150 also showed similar silencing in primary striatal neurons (FIG. 27B). Protein levels were measured after one week by Western blot, confirming mRNA data with 85% reduction of protein upon treatment with 1.25 µM of compound. HTT10150 hsiRNA did not affect the expression levels of housekeeping controls (Ppib and Tubb1) or the overall viability of primary neuronal cells, as measured by the ALAMARBLUE assay, up to a 2 µM concentration. Similar results were obtained with another hsiRNA targeting Htt mRNA, supporting that the observed phenomena is not unique to HTT10150. In other experiments, a slight impact on cell viability was observed at 3 µM.

To evaluate duration of effect upon a single HTT10150 treatment, the silencing was measured at one week, two week, and three week intervals. The half-life of the loaded RISC complex was weeks (Song, E. et al. Sustained Small Interfering RNA-Mediated Human Immunodeficiency Virus Type 1 Inhibition in Primary Macrophages. *Journal of Virology* 77, 7174-7181 (2003)), and silencing was expected to be long lasting in non-dividing cells. Indeed, single treatment with hsiRNAs was sufficient to induce htt silencing at all times tested. Three weeks was the longest the primary neurons could be maintained in culture. Other systems will be used for longer-term experiments.

Figure 28:
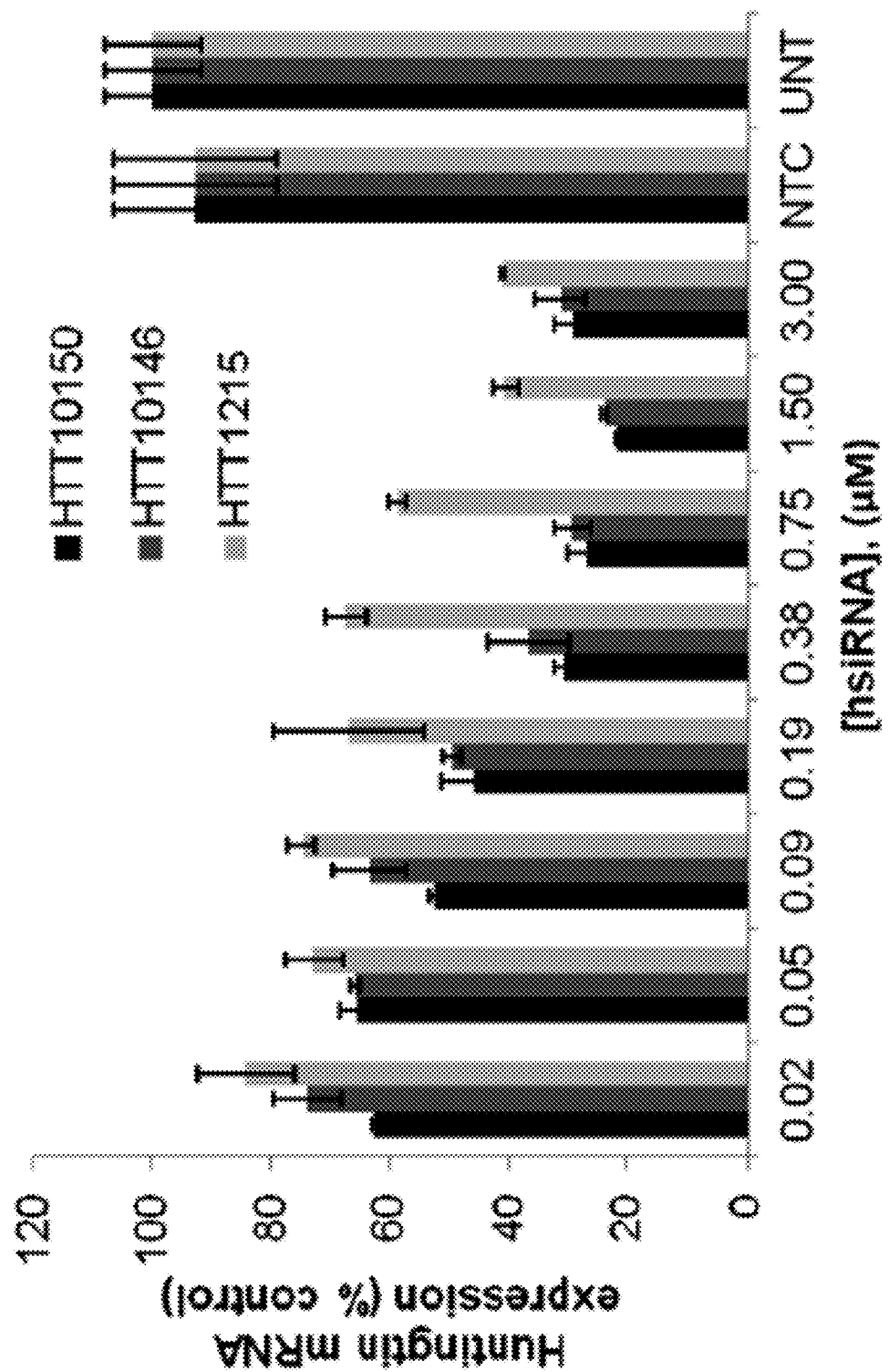
FIG. 28 depicts huntingtin mRNA levels. Primary cortical neurons were incubated with three HTT hsiRNA sequences HTT10150, HTT10146, and HTT1215 at concentrations shown. Level of huntingtin mRNA was measured using QUANTIGENE (Affymetrix) normalized to housekeeping gene, PPIB (cyclophillin B), and presented as percent of untreated control (n=3, mean+/−SD). UNT—untreated cells.

To demonstrate the general applicability of hsiRNAs as a tool for neuronal gene silencing, and to confirm this chemistry scaffold as valid for neuronal delivery, similar experiments were performed with several other hsiRNAs targeting HTT and with one targeting the house-keeping gene PPIB (Cyclophilin B) (FIG. 28). Silencing as high as 70 and 90% was achieved with HTT and PPIB, respectively.

In summary, these data demonstrate that hydrophobically modified siRNA is a simple and straightforward approach for gene silencing in primary neurons, and can be adapted for multiple gene targets.

4.4 hsiRNA Distribution in Vivo in Mouse Brain Upon Single Injection hsiRNAs are efficiently internalized by different types of neurons in vitro. The selected hsiRNA, HTT10150, was further evaluated for its potential to silence gene expression in the brain in vivo. To determine the distribution profile of HTT10150 upon in vivo administration, 12.5 µg of Cy3 labelled hsiRNA (See FIG. 7 for sequence) was injected intrastriatally and, after 24 hours, the brain was perfused, sectioned, and oligonucleotide distribution was visualized by fluorescence microscopy (Leica DM5500-DFC365FX). The artificial CSF injected samples processed concurrently were used to set up microscopic imaging settings to control for background tissue epifluorescence.

The majority of compound showed a steep gradient of diffusion away from the injection site, with most of the ipsilateral striatum being covered. Interestingly, hsiRNAs were detected on the non-injected side (contralateral) side of the brain (both cortex and striatum), although relative concentrations appeared much lower. Higher magnification images showed significant association of hsiRNA with fiber tracks, most likely due to the presence of a hydrophobic modification. This aspect of hsiRNA may make it useful as a labelling reagent to visualize brain signalling architecture. In addition to fiber tracks and neurite labelling, hsiRNA could be detected as punctate staining in the perinuclear space of different cell types, including neurons, as evident from co-localization with NeuN (neuronal marker) stained cells only 24 hours after injection.

4.5 hsiRNA Efficacy in Vivo in Mouse Brain Upon Single Injection

To determine HTT10150 efficacy in vivo, wild type FVBN mice were dosed intrastriatally with a single injection of between 3 and 25 µg (0.1-0.9 mg/kg) of compound and mRNA silencing was examined both ipsilateral and contralateral to the injection site. Eight animals were dosed per treatment group and three individual punches were taken from each side of the striatum for mRNA and protein quantification. Level of huntingtin expression were measured by QUANTIGENE Assay and normalized to a housekeeping gene.

Statistical analysis was performed by one-way ANOVA comparison against CSF or PBS control with Bonferroni corrections for repeat measures using GraphPad Prism (Online methods for details). All groups induced silencing that was significant against CSF, PBS, and non-targeting control treated animals. At the site of administration (ipsilateral side), dose-dependent silencing reaching statistical significance was observed at all concentrations. The 25 µg treatment induced 77% silencing (p<0.0001), and the 12.5 µg treatment was repeated with two groups of animals on different days and showed statistically significant silencing of 66% and 42%.

While initial distribution studies showed a steep gradient of diffusion away from the injection site with a minimal amount of compound migrating to the contralateral side, treatment with the higher doses of 25 µg and 12.5 µg resulted in statistically significant silencing (p<0.0001) on the non-injected side. However, the level of silencing was significantly less (only 36% for the 25 µg group) than on the treated side of the brain.

To further measure HTT10150 efficacy in vivo, dose-response studies were performed in wild type FVB/NJ mice injected intrastriatally with 3.1, 6.3, 12.5, or 25 µg of HTT10150. As controls, mice were injected with a non-targeting control hsiRNA (NTC), artificial CSF, or PBS. In punch biopsies taken from the ipsilateral and contralateral striatum, HTT10150 reduced Htt mRNA levels in a dose-dependent manner (FIG. 34).

The Htt mRNA is significantly reduced in the ipsilateral side of striatum. Robust dose-dependent silencing was observed with up to 77% (one way Anova p<0.0001) reduction in Htt mRNA expression level at high dose expression levels. Interestingly, statistically significant, but less pronounced, silencing was observed in the contralateral striatum and cortex. The silencing reaches statistical significance with both one-way and two-way Anova (values for two-way Anova are presented in FIG. 34). While some level of fluorescence was detectable in these brain regions with high laser intensity, it is technically challenging to detect as it is very close to the tissue autofluoresence and thus has not been described herein. It is clear that levels of silencing effect are at least correlative to the sharp gradient of distribution from the side of injection.

Figure 34A:
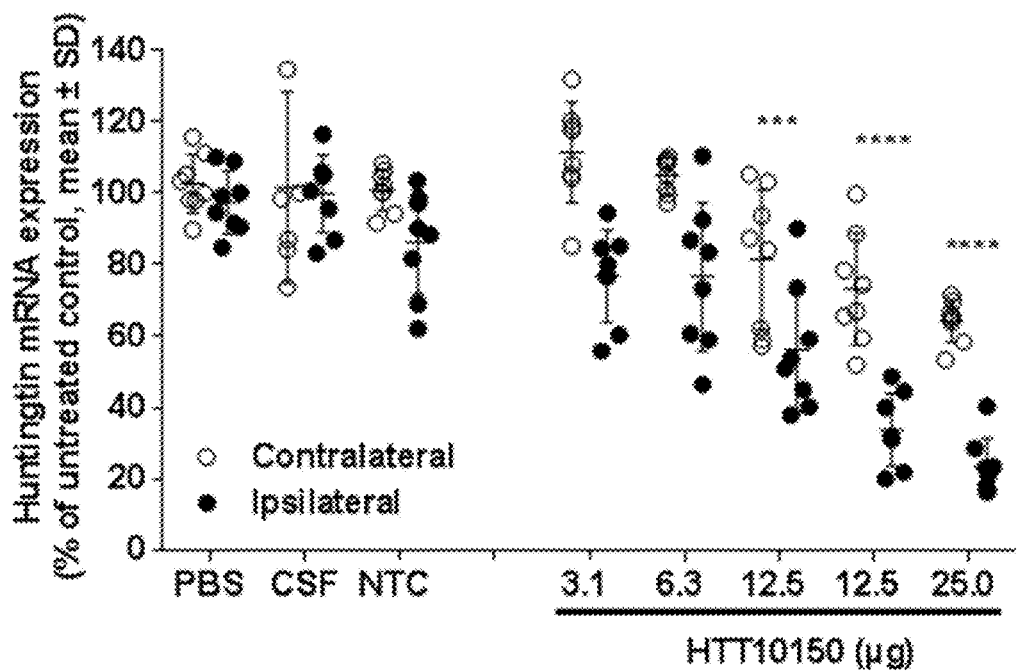
FIGS. 34A-34C depict results of single hsiRNA intrastriatal injections inducing dose-dependent silencing in vivo. (A) Huntingtin mRNA expression. (B) Huntingtin mRNA expression. (C) Htt mRNA expression.
Figure 34B:
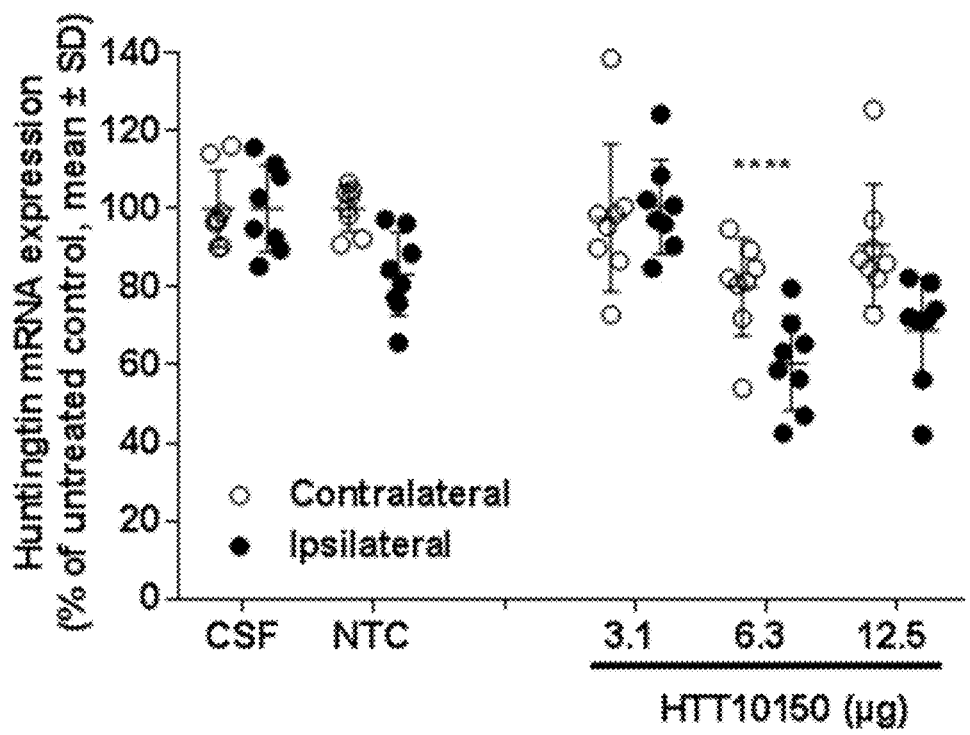
Figure 34C:
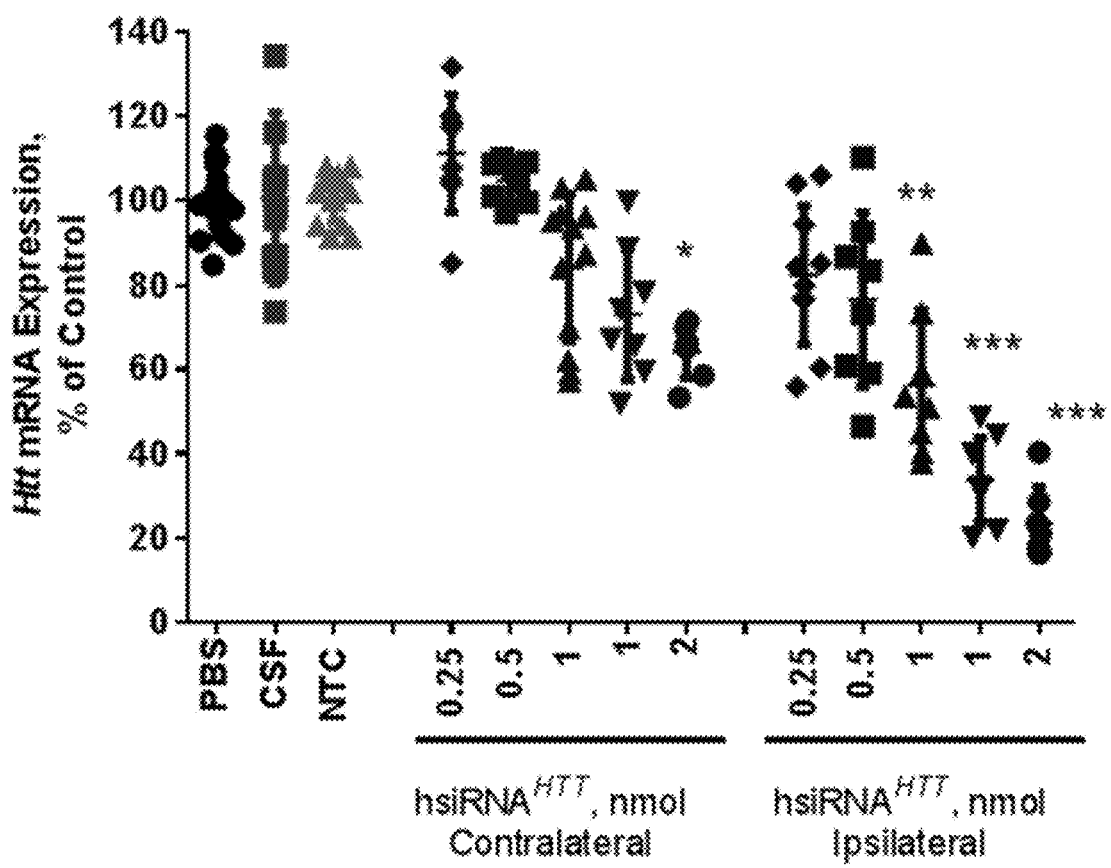

The Htt mRNA silencing is observed with HTT10150 but not with non-targeting control or a CSF (FIG. 34). In addition, the HTT10150 does not affect expression of several housekeeping genes (PPIB, HPRT). In combination, this is indicative of silencing being caused by HTT10150 mRNA silencing and not by off-target effects.

In summary, these data show that a single intrastriatal injection of hsiRNA is sufficient to induce potent gene silencing around the site of administration. This effect was reproducible across different treatment groups and independent experiments.

4.6 Neuronal Viability Following Single hsiRNA Injection in Mouse Brain

Cholesterol modification of non-modified, naked siRNA has previously been used for improvement of siRNA brain distribution, with toxicity at high doses being identified as a potential limitation. To evaluate the degree of non-specific chemistry related effects on the brain, DARPP32 expression, an established marker for dopamine receptor expression on medium spiny neurons in the striatum and representative of neuronal viability, was investigated. Additionally, potential induction of an immune response was performed by assessing the extent of microglia activation upon hsiRNA injection.

Figure 35:
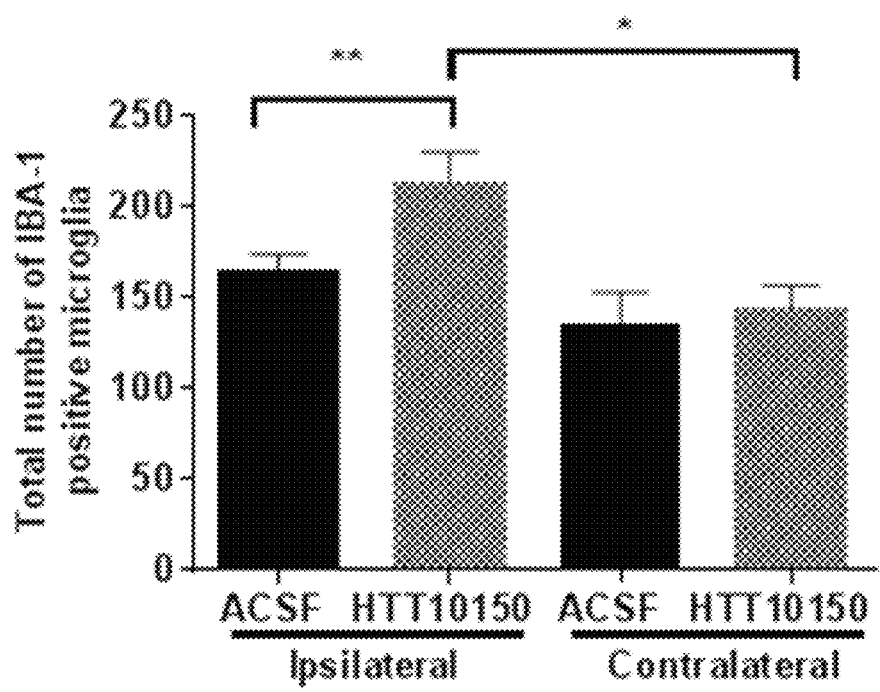
FIG. 35 depicts quantification of an inflammatory response at the site of injection of HTT10150.

To assess innate immune response activation by hsiRNAs in vivo, MA1-positive microglial cells were quantified in brain sections from mice injected with 12.5 µg HT10150 or artificial CSF. IBA-1 is specific to microglial cells and is up-regulated following injury to the brain, allowing resting and activated microglia to be distinguished. Total microglia counts showed only 25% increase in the ipsilateral striatum at five days post injection indicating a lack of any major inflammatory response (FIG. 35).

No significant impact on DARPP32 expression was observed for doses up to 12.5 µg suggesting persistent neuronal viability. Similarly, minimal microglial activation was visualized at the 12.5 µg dose indicative of a limited immune response in the presence of the modified hsiRNA. The 25 µg dose did induce some reduction in DARPP32 just around the site of injection indicative of toxicity and establishing the maximum dose levels for this chemical scaffold upon the indicated route of administration. A 10-12.5 µg single administration of hsiRNA efficiently silenced HTT mRNA in three, well powered, independent studies with robust silencing of 62, 42 and 52% without toxicity. These data indicate that this technology can be widely used for functional studies of other neurologically significant targets.

Figure 32:
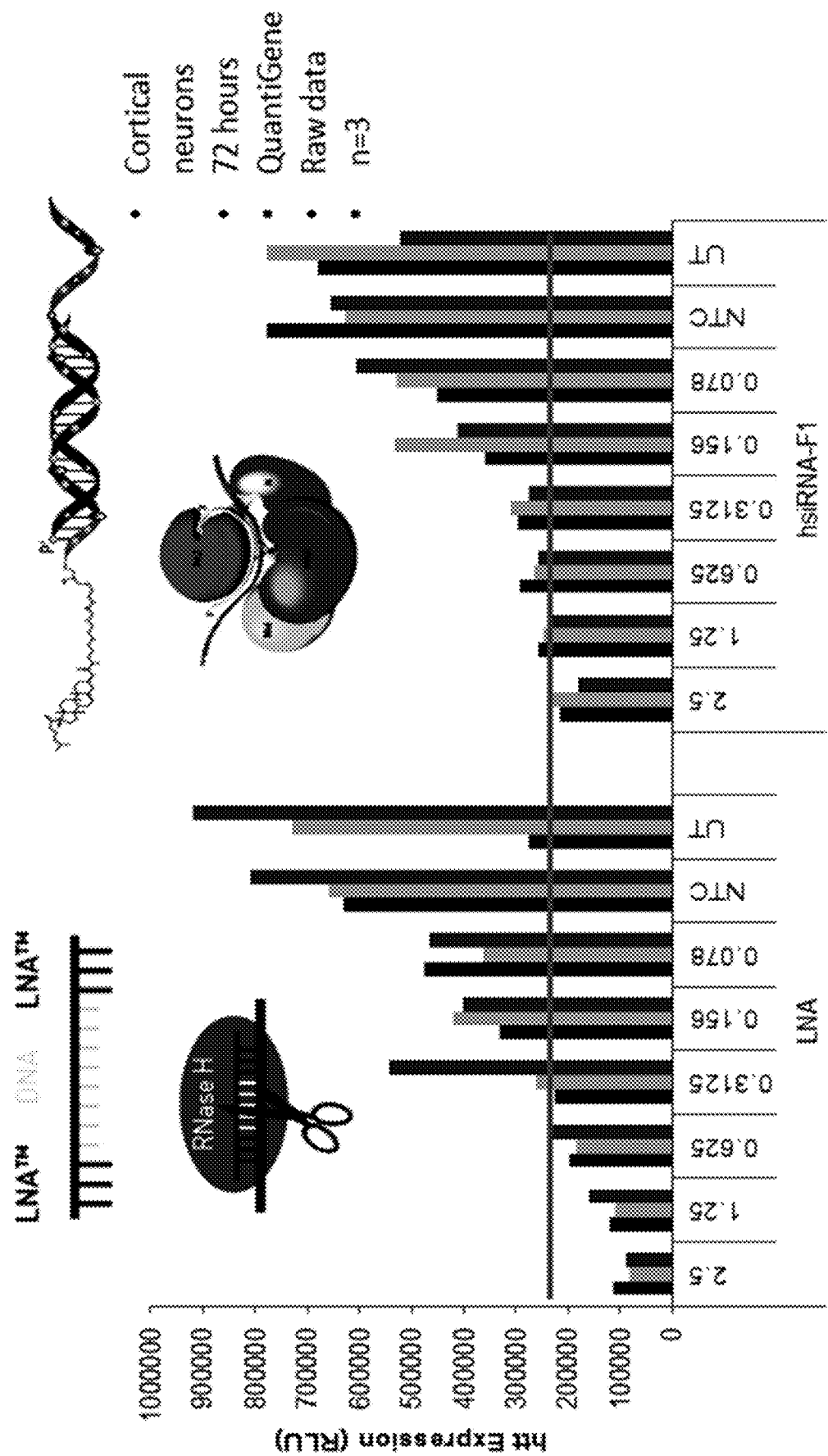
FIG. 32 depicts a comparison of hsiRNA$^{HTT}$ (hsiRNA-F1) vs LNA-GAPMER silencing of Htt across a range of concentrations.

4.7 hsiRNA$^{HTT}$, but not an LNA-GAPMER Oligonucleotide, Exhibits a Silencing Plateau A silencing plateau is observed only with RNAi (cytoplasmic; hsiRNA-F1) but not RNAseH (predominantly nuclear; LNA-GAPMER) compounds. The observed silencing plateau (FIG. 32) is specific to the HTT gene.

4.8 Discussion

This study demonstrates that the use of hydrophobically modified siRNA for delivery to primary cells is a valuable tool to enable functional and genomic studies of neuronal pathways and neurological disorders.

The ability to cause gene silencing in primary neurons without the use of toxic formulation has a significant impact on neuroscience research, facilitating a more in depth study of neurological disorders in the context of primary cell lines, and ultimately providing a more relevant understanding of in vivo function and pathology. Most neuronal studies are done in stable cell lines due to ease of delivery and cell maintenance, but using artificial cell systems can lead to artifacts in the data that can be attributed to manipulation of these cell lines, a problem that can be avoided by using primary cells (Cheung, Y.-T. et al. Effects of all-trans-retinoic acid on human SH-SYSY neuroblastoma as in vitro model in neurotoxicity research. *NeuroToxicology* 30, 127-135 (2009); Gilany, K. et al. The proteome of the human neuroblastoma cell line SH-SYSY: An enlarged proteome. *Biochimica et Biophysica Acta (BBA)—Proteins and Proteomics* 1784, 983-985 (2008); Lopes, F. M. et al. Comparison between proliferative and neuron-like SH-SYSY cells as an in vitro model for Parkinson disease studies. *Brain Research* 1337, 85-94 (2010); Zhang, W. et al. Cyclohexane 1,3-diones and their inhibition of mutant SOD1-dependent protein aggregation and toxicity in PC12 cells. *BIOORGANIC & MEDICINAL CHEMISTRY* 1-17 (2011). doi:10.1016/j.bmc.2011.11.039). Current methods for delivering siRNA to primary neurons include the use of lentiviral vectors, Adeno-Associated Viruses (AAV), or Lipofectamine™-mediated transfection (Karra, D. & Dahm, R. Transfection Techniques for Neuronal Cells. *Journal of Neuroscience* 30, 6171-6177 (2010)). By conjugating a hydrophobic moiety such as cholesterol directly to the siRNA itself and by utilizing an additional single stranded phosphorothioated tail for enhanced uptake, it has been demonstrated herein that, not only can siRNA be delivered efficiently into primary neurons in vitro with minimal toxicity, but also remains a potent silencer of mRNA.

Without intending to be bound by scientific theory, one of the major advantages of RNAi over antisense technology is that the loaded RISC is expected to remain active for a long period of time in non-dividing cells (Bartlett, D. W. Insights into the kinetics of siRNA-mediated gene silencing from live-cell and live-animal bioluminescent imaging. *Nucleic Acids Research* 34, 322-333 (2006)). Additionally, a limited number of loaded RISCs are sufficient for the induction of RNAi-mediated silencing (Stalder, L. et al. The rough endoplasmatic reticulum is a central nucleation site of siRNA-mediated RNA silencing. The *EMBO Journal* 32, 1115-1127 (2013)). The data presented herein demonstrates silencing for up to three weeks in vitro in primary cortical neurons upon a single treatment with hsiRNA, supporting the notion that RNAi-mediated silencing can be both efficient and long lasting. The data presented herein also shows that these compounds can be used to target multiple regions in two different genes, which demonstrates the adaptability of hsiRNA for the study of alternative neurological pathways and diseases.

While a single intra-striatal injection of hsiRNA resulted in potent gene silencing near the injection site in vivo, the effect was not evenly spread throughout the brain. Although limited, spread to other areas of the brain (demonstrated by in vivo efficacy studies) could be happening through a number of mechanisms. These include movement in the CSF, spread via fiber tracts which were shown to have a large visual density of Cy3-labeled hsiRNA in distribution studies, or possibly through retrograde transport (Stewart, G. R. & Sah, D. Retrograde Transport of siRNA and Therapeutic Uses to Treat Neurological Disorders. *United States Patent Application Publication US* 2008/0039415 A1, 1-18 (2008)), although further studies will be conducted to determine the actual mechanism.

The technology presented herein is useful for understanding functional genomics of particular brain regions, as well as for studying relationships between brain regions. Additionally, the study of some neurological disorders (for example memory disorders (Samuelson, K. W. Post-traumatic stress disorder and declarative memory functioning: a review. *Dialogues in Clinical Neuroscience* 13, 346-351 (2011))) can benefit from limited and regionally targeted distribution and silencing. However, due to its distribution profile, hsiRNA as it currently exists is not a viable therapeutic for general neurological disorders like Huntington's disease. Multiple injections may work to increase overall silencing in small rodents, but in order to adapt this technology for use in larger animal brains and humans, and to achieve even and widespread distribution, other chemical modifications and therapeutic methods of delivery will be utilized. There are a number of ways in which this might be approached. First, chemical adjustments to the hsiRNA composition itself can be made. These include conjugating it to a different lipid, supplementing the backbone with additional phosphorothioate groups, or by addition of hydrophobic moieties to the nucleotides themselves (Vaught, J. D., Dewey, T. & Eaton, B. E. T7 RNA Polymerase Transcription with 5-Position Modified UTP Derivatives. *J. Am. Chem. Soc.* 126, 11231-11237 (2004)). All of these modifications could support a range of hydrophobicities that would allow for more improved distribution across a larger distance. Increased bioavailability could also be achieved with different modes of injection such as into the CSF instead of intrastriatally, increasing the likelihood of exposure to the whole brain. However, delivery via the CSF could favor localization of hsiRNA to brain regions other than the striatum, making it a less than ideal delivery method for the treatment of Huntington's disease. Another possibility is formulated delivery by packaging these hydrophobically modified siRNAs into exosomes and liposomes (less toxic than current Lipofectamine™ formulations) and using these natural and synthetic nanocarriers to deliver cargo in a more evenly distributed fashion (Alvarez-Erviti, L. et al. Delivery of siRNA to the mouse brain by systemic injection of targeted exosomes. *Nat Biotechnol* 1-7 (2011). doi:10.1038/nbt.1807; Marcus, M. & Leonard, J. FedExosomes: Engineering Therapeutic Biological Nanoparticles that Truly Deliver. *Pharmaceuticals* 6, 659-680 (2013)). However, potency and efficacy of the delivered hsiRNA still needs to be validated for these methods.

In conclusion, HTT10150 was efficient for targeting huntingtin mRNA in primary neurons in vitro and locally in the mouse brain in vivo. This compound did not require any formulation for delivery to primary cells and enabled gene functional studies for huntingtin as well as other targets, making it a very useful tool for the study of neurological disorders. Potential advances to this technology should allow for hsiRNA to function as a therapeutic treatment for Huntington's disease as well as other neurological diseases in the future.

4.9 Methods

Cell Culture

HeLa cells were maintained in DMEM (Corning Cellgro) supplemented with 10% fetal bovine serum (Gibco) and 100 U/mL penicillin/streptomycin (Invitrogen) and grown at 37° C. and 5% $CO_2$. Cells were split every 2-5 days up to passage 15 and then discarded.

Cell Culture for Passive Uptake

Cells were plated in DMEM with 6% FBS at 10,000 cells/well in 96-well tissue culture treated plates. hsiRNA was diluted in OptiMEM (Gibco) to 2× final concentration and 50 µL diluted hsiRNA was added to 50 µL of cells for 3% FBS final. Cells were incubated for 72 hours at 37° C. and 5% $CO_2$.

Cell Culture for Lipid-Mediated Uptake

Cells were plated in DMEM with 6% FBS at 10,000 cells/well in 96-well tissue culture treated plates. hsiRNA was diluted in OptiMEM to 4× final concentration. LIPO-FECTAMINE RNAIMAX Transfection Reagent (Invitrogen #13778150) was diluted to 4× final concentration (final=0.3 µL/25 µL/well). RNAIMAX and hsiRNA were mixed 1:1 and 50 µL was added to 50 µl, of cells for 3% FBS final. Cells were incubated for 72 hours at 37° C. and 5% $CO_2$.

Preparation of Primary Neurons

Primary cortical neurons were obtained from E15.5 mouse embryos of WT (FVBN) mice. Pregnant females were anesthetized by IP injection of Avertin (250 mg/kg weight) followed by cervical dislocation. Embryos were removed and transferred into a Petri dish with ice-cold DMEM/F12 medium (Invitrogen). Brains were removed and meninges were carefully detached. Cortices were isolated and transferred into a 1.5-ml tube with pre-warmed papain solution for 25 minutes at 37° C. and 5% $CO_2$ to dissolve tissue. Papain solution was prepared as follows: papain (Worthington #54N15251) was dissolved in 2 mL HibernateE (Brainbits) and 1 mL EBSS (Worthington). Separately, DNase (Worthington #54M15168) was re-suspended in 0.5 mL HibernateE. Then, 0.25 mL of re-suspended DNase was transferred to re-suspended papain for the final solution. After the 25 minute incubation, papain solution was removed and 1 mL NbActiv4 (Brainbits) supplemented with 2.5% FBS was added to the tissue. The cortices were then dissociated by pipetting up and down with a fire polished, glass Pasteur pipet. Cortical neurons were counted and plated at $1 \times 10^6$ cells/ml. For live-cell imaging studies, culture plates were pre-coated with poly-L-lysine (Sigma #P4707) and $2 \times 10^5$ cells were added to the glass center of each dish. For silencing assays, neurons were plated on poly-L-lysine pre-coated 96-well plates (BD BIOCOAT #356515) at $1 \times 10^5$ cells per well. After overnight incubation at 37° C. and 5% $CO_2$ an equal volume of NbActiv4 (Brainbits) supplemented with anti-mitotics, 0.484 µL/mL of 5'UtP (Sigma #U6625) and 0.2402 µL/mL of 5'FdU (Sigma #F3503), to prevent the growth of non-neuronal cells, was added to neuronal cultures. Half of the volume of media was replaced every 48 hours (with new NbActiv4 with anti-mitotics) until the neurons were treated with siRNA. Once the cells were treated, media was not removed, only added. All subsequent media additions contained anti-mitotics.

mRNA Quantification mRNA was quantified using the QUANTIGENE 2.0 Assay (Affymetrix #QS0011). Cells were lysed in 250 μL diluted lysis mixture (Affymetrix #13228), 1 part lysis mixture, 2 parts $H_2O$, with 0.167 μg/μL proteinase K (Affymetrix #QS0103) for 30 minutes at 55° C. Cell lysates were mixed thoroughly and 40 μL (approximately 8000 cells) of lysate were added to the capture plate along with 40 μL additional diluted lysis mixture without proteinase K. Probe sets were diluted as specified in the Affymetrix protocol. For HeLa cells, 20 μL of human HTT or PPIB probe set (Affymetrix #SA-50339, #SA-10003) was added to appropriate wells for a final volume of 100 μL. For primary neurons, 20 μL of mouse HTT or PPIB probe set (Affymetrix #SB-14150, #SB-10002) was used.

Tissues were treated similarly, using 300 μL of Homogenizing Buffer (Affymetrix #10642) with 2 μg/μL proteinase K for a 5 mg tissue punch. Tissues were then homogenized in 96-well plate format on the QIAGEN TissueLyser II and 40 μL were added to the capture plate. Probe sets were diluted as specified in the Affymetrix protocol and 60 μL of either HTT or PPIB probe sets (Affymetrix #SB-14150, #SB-10002) were added to each well of the capture plate for a final volume of 100 μL. For DARPP32 quantification, only 10 μL of tissue sample and 30 μL of homogenizing buffer were added to each well with 60 μL of mouse Ppp1r1b probe set (Affymetrix #SB-21622). Signal was amplified according to the Affymetrix protocol. Luminescence was detected on either the Veritas Luminometer or the Tecan M 1000.

Live Cell Staining

To monitor live cell hsiRNA uptake, cells were plated at a density of $2\times10^5$ cells per 35 mm glass-bottom dish as described in the preparation of primary neurons above. Prior to imaging, cell nuclei were stained in phenol red free NbActiv4 using NUCBLUE (Molecular Probes by Life Technologies #R37605) as indicated by the manufacturer. Imaging was performed in phenol red free NbActiv4. Cells were treated with 0.5 μM of Cy3-labeled hsiRNA, and live cell imaging was performed over time. All live cell confocal images were acquired with a Zeiss confocal microscope and images were processed using ImageJ (1.47v) software.

Immunohistochemistry/Immunofluorescence

For distribution studies, brains were injected with 1 nmol (12.5 μg) of Cy3-labeled hsiRNA. After 24 hours, mice were sacrificed and brains were removed and sent to the DERC Morphology Core at UMASS Medical School to be embedded in paraffin and sliced into 4 μm sections and mounted on glass slides. Sections were de-parafinized for 8 minutes in xylene two times. Sections were then rehydrated with serial ethanol dilutions (100%, 95%, 80%) for 4 minutes each, then washed twice for two minutes with PBS. For NueN staining, slides were boiled for 5 minutes in antigen retrieval buffer and then left to sit at room temperature for 20 minutes, followed by a 5-minute wash with PBS. Slides were then blocked with 5% normal goat serum in PBS+0.05% Tween20 for 1 hour and washed once with PBS+0.05% Tween20 for 5 minutes. Primary antibody (1:1000 dilution in PBS+0.05% Tween20) was added to slides for a 1 hour incubation followed by three 5-minute washes with PBS+ 0.05% Tween20. Secondary antibody (1:1000 dilution in PBS+0.05% Tween20) was added to slides for a 30-minute incubation in the dark followed by three 5-minute washes with PBS+0.05% Tween20. Slides were then stained with DAPI (Molecular Probes by Life Technologies #D3571), diluted to 250 ng/mL in PBS, for one minute followed by three 1-minute washes with PBS. Mounting media and coverslips were applied to slides and left to dry over night before imaging on Leica DM5500-DFC365FX microscope at indicated magnification.

For toxicity and microglia activation studies extracted, perfused brains were sliced into 40 μm sections on the Leica 2000T Vibratome in ice cold PBS. Immunohistochemistry was performed on every 6th section against DARPP32 (Millipore, 1:10,000 dilution) and IBA-1 (Millipore, 1:500 dilution). Sections were mounted and visualized by light microscopy. Four images were taken at 20× in the striatum of both injected and non-injected sides of each section. The number of DARPP32 positive neurons was quantified using ImageJ. Activated microglia was quantified by morphology of stained cells for IBA-1.

Animals, Stereotaxic Injections

Wild-type (FVBN) mice received microinjections by stereotactic placement into the right striata (coordinates (relative to bregma) were 1.0 mm anterior, 2.0 mm lateral, and 3.0 mm ventral). Animals were deeply anesthetized prior to injection with 1.2% Avertin. For both toxicity (DARPP32) and efficacy studies, mice received injections of either PBS or artificial cerebrospinal fluid (2 μL per striata, N=8 mice), 12.5 μg of NTC hsiRNA (2 μL of 500 μM stock solution per striata, N=8 mice), 25 μg of HTT10150 hsiRNA (2 μL of 1 mM stock solution per striata, N=8 mice), 12.5 μg of HTT10150 hsiRNA (2 μL of 500 μM stock solution per striata, N=16 mice total, two sets of 8 mice on two different days), 6.3 μg of HTT10150 hsiRNA (2 μL of 250 μM stock solution per striata, N=8 mice), or 3.1 μg of HTT10150 hsiRNA (2 μL of 125 μM stock solution per striata, N=8 mice) and euthanized 5 days later. Brains were harvested and three 300 μm coronal sections were made. One 2 mm punch was taken per side (injected and non-injected) for each section and placed in RNAlater (Ambion #AM7020) for 24 hours at 4° C. Each punch was processed as an individual sample for the QUANTIGENE assay analysis. All animal procedures were approved by the University of Massachusetts Medical School Institutional Animal Care and Use Committee (IACUC, protocol number A-2411).

Statistical Analysis

Data analyses were done using GraphPad Prism 6 version 6.04 software (GraphPad Software, Inc., San Diego, CA). For concentration dependent curve IC50s, a curve was fitted using log(inhibitor) vs. response—variable slope (four parameters). The bottom of the curve was set to be no less than zero and the top of the curve was set to be no greater than 100. For each independent mouse experiment, the level of knockdown at each dose was normalized to the mean of the control group, which was the non-injected side of the PBS or artificial CSF groups, so that all data were expressed as a proportion of the control. In vivo data were analyzed using the Kruskal-Wallis test (one-way ANOVA) with Bonferroni corrections for multiple comparisons. Differences in all comparisons were considered significant at P-values less than 0.05.

Cell Culture for Passive Uptake (Primary screen and dose response)

Cells were plated in DMEM (Gibco) with 6% FBS (Gibco) at 10,000 cells/well in 96-well tissue culture treated plates. HsiRNA was diluted in OptiMEM (Gibco) to 2× final concentration and 50 uL diluted hsiRNA was added to 50 μL of cells for 3% FBS final. Cells were incubated for 72 hours at 37 C and 5% $CO_2$.

Cell Culture for Lipid-Mediated Uptake

Cells were plated in DMEM (Gibco) with 6% FBS (Gibco) at 10,000 cells/well in 96-well tissue culture treated plates. HsiRNA was diluted in OptiMEM (Gibco) to 4× final concentration. LIPOFECTAMINE RNAIMAX Transfection Reagent (Invitrogen CAT #13778150) was diluted to 4× final concentration (final=0.3 µL/25 µL/well). RNAIMAX and hsiRNA were mixed 1:1 and 50 µL was added to 50 uL of cells for 3% FBS final. Cells were incubated for 72 hours at 37 C and 5% $CO_2$.

mRNA Quantification mRNA was quantified using the QUANTIGENE 2.0 Assay (Affymetrix QS0011). Cells were lysed in 250 µL diluted lysis mixture, 1 part lysis mixture, 2 parts H2O, with 0.167 µg/µL proteinase K (Affymetrix QS0103) for 30 minutes at 55 C. Cell lysates were mixed thoroughly and 40 µL (~8000 cells) of lysate were added to capture plate along with 40 µL additional diluted lysis mixture without proteinase K. Tissues were treated similarly, using 300 µL of Homoginizing Buffer (Affymetrix) with 2 µg/µL proteinase K for a 5 mg tissue punch. Tissues were then homogenized in 96-well plate format on Qaigen TissueLyzer and 40 µL were added to capture plate. Probe sets were diluted as specified in Affymetrix protocol and 20 µL of either HTT or PPIB probes (Affymetrix: SA-50339, SA-10003) were added to each well of capture plate for final volume of 100 µL. Signal was amplified according to manufacture protocol. Luminescence was detected on either the Veritas Luminometer or the Tecan M 1000.

Live Cell Staining and Brain Sections Immunostaining

For live cell uptake monitoring, cells were plated at a density of $2×10^5$ cells per 35 mm glass-bottom dish and grown overnight. Prior to imaging, cell organelles were stained in HBSS (Gibco) using staining reagents purchased from Life Technologies unless specified: cell nuclei, endoplasmic reticulum and lysosomes were respectively stained using the NUCBLUE Live READYPROBE, ER-TRACKER Green (Bodipy FL Glibenclamide) and LYSOTRACKER Deep Red reagents as indicated by the manufacturer. Imaging was performed in non-supplemented DMEM without phenol red (Invitrogen). Cells were treated with 0.5 µM of Cy3-labeled hsiRNA, and live cell imaging was performed over time.

Confocal Imaging

All confocal images were acquired with a CSU10B Spinning Disk Confocal System scan head (Solamere Technology Group) mounted on a TE-200E2 inverted microscope (Nikon) with a 60× Plan/APO oil lens and a Coolsnap HQ2 camera (Roper). Images were processed using ImageJ (1.47v) software. Number of neurons without or with hsiRNA was counted using ImageJ software. Brain sections images were acquired with a z-axis spacing of 1 µm.

Probe Validation

HTT detection probe sets were validated in neurons. Two types of probe sets (exon-exon—identical hybridization sequence (exon 27-35); and exon-exon—different hybridization sequence (exon 27-35 and exon 60-67)) were used to validate specificity. It was observed that the majority of detected signal from the probes is specific to htt-mRNA (data not shown). Two additional types of probe-sets (exon-intron—different hybridization sequence (exon 27-35 and intron 60-61); and exon-exon—difference hybridization sequence (exon 27-35 and exon 60-67)) were used to validate that the nuclear signal is not intron specific. It was observed that the intron-specific probe shows little overlap in the nuclei specific to transcription sites, and that the exon-specific probes show a higher degree of overlap.

Example 5. Full Metabolic Stabilization is Essential for Conjugate-Mediated siRNA Delivery in Vivo Small interfering RNA (siRNA)-based drugs require chemical modifications/formulation to promote stability, minimize innate immunity, and enable delivery to target tissues. Partially modified siRNAs (up to 70% of bases modified) are typically used to explore the effectiveness of bioconjugates for RNAi delivery. The data disclosed herein shows that full modification (100% of bases modified) is absolutely essential for conjugate-mediated siRNA delivery systemically. Full modification dramatically improved distribution, potency and duration of affect upon local administration. Tissues, including liver and kidney, retained two orders of magnitude higher levels of fully modified hydrophobic siRNAs (FM-hsiRNA), which supports robust silencing of targets.

Screening a panel of small, asymmetric, fully modified variants based on an alternating 2'-methoxy, 2'-fluoro pattern, a scaffold was identified which was successfully applied to 100% of tested compounds without compromising silencing efficacy. Thus, fully modified, asymmetric siRNAs provided a scaffold upon which to discover new chemistries that promote siRNA delivery and expand the clinical utility of RNAi.

This example compares side-by-side the impact of fully modified versus conventionally modified siRNA scaffolds on conjugate-mediated in vivo distribution and efficacy. Hydrophobically (e.g., cholesterol) modified asymmetric siRNAs were used as an example (FIG. 29). Cholesterol conjugation to partially modified siRNAs results in robust cellular uptake in vitro (Khvorova A., S. W., Kamens J., Samarsky D., Woolf T., Cardia J. Reduced size self-delivering RNAi compounds. USA patent (2014); Lorenz, C., Hadwiger, P., John, M., Vornlocher, H. P. & Unverzagt, C. Steroid and lipid conjugates of siRNAs to enhance cellular uptake and gene silencing in liver cells. *Bioorg Med Chem Lett* 14, 4975-4977, doi:10.1016/j.bmcl.2004.07.01850960-894X(04)00908-4 [pii] (2004)) and potent silencing locally in vivo (Byrne, M. et al. Novel hydrophobically modified asymmetric RNAi compounds (sd-rxRNA) demonstrate robust efficacy in the eye. *Journal of ocular pharmacology and therapeutics: the official journal of the Association for Ocular Pharmacology and Therapeutics* 29, 855-864, doi: 10.1089/jop.2013.0148 (2013)), but only marginal systemic efficacy (Soutschek, J. et al. Therapeutic silencing of an endogenous gene by systemic administration of modified siRNAs. *Nature* 432, 173-178, doi:10.1038/nature03121 (2004)), thus representing a good model for evaluation of the potential impact role of complete siRNA modification on delivery.

Non-modified RNA degrades quickly by combination of endonucleases and exonucleases; thus both internal and terminal modifications are necessary for stability. Complete chemical modification of siRNAs can interfere with RNA Induced Silencing Complex (RISC) interactions, but several configurations have been reported to have activity compatible with naked compounds, although in a context of only limited number of sequences (Deleavey, G. F. et al. The 5' binding MID domain of human Argonaute2 tolerates chemically modified nucleotide analogues. *Nucleic acid therapeutics* 23, 81-87, doi:10.1089/nat.2012.0393 (2013); Stokman, G., Qin, Y., Racz, Z., Hamar, P. & Price, L. S. Application of siRNA in targeting protein expression in kidney disease. *Advanced drug delivery reviews* 62, 1378-1389, doi: 10.1016/j.addr.2010.07.005 (2010)).

Inability to cleave the sense strand is one of the limiting factors for fully chemically modified siRNA RISC entry. Use of an asymmetric scaffold (15 bases in the sense strand, 20 bases in the guide strand) lowered the duplex Tm, and thus eased the sense dissociation required for efficient RISC loading. In addition, the presence of a single-stranded, fully phosphorothioated tail enhanced conjugated mediated cellular internalization of these type of compounds by a mechanism similar to conventional antisense compounds.

The efficacy of a panel of fully modified hsiRNA variants was compared based on patterns reported by the Dagma and Bhat laboratories. The initial screen was performed in the context of a huntingtin-targeting hsiRNA identified recently (Alterman et al., 2015, Molecular Therapy, under review). It was demonstrated that an alternating 2'-fluoro, 2'-methoxy pattern, starting with chemically phosphorylated 2'-methoxy-modified U in the 5' position of the guide strand performed the best, although several other configurations were nearly as functional (FIG. 29). It was determined to be important to start the modification pattern with the chemically phosphorylated 2'-methoxy in position one of the antisense strand. Starting the same pattern with 2'-fluoro was shown to have a detrimental impact on efficacy, at least in some of the sequences. Without intending to be bound by scientific theory, this was likely related to placement of 2'-methoxy in positions 2 and 14 of the guide strand, which are not well tolerated in the context of heavily modified duplexes. Chemical phosphorylation of the guide strand was also determined to be essential as terminal 2'-methoxy U was not a good substrate for intracellular kinases. In addition, terminal phosphorothioates were added on both the 3' and 5' ends of the oligonucleotide to provide additional exonuclease resistance. FIG. 29 shows the structure and PyMOL model of the most optimal configuration compared to a conventionally modified hsiRNA.

Figure 29A:
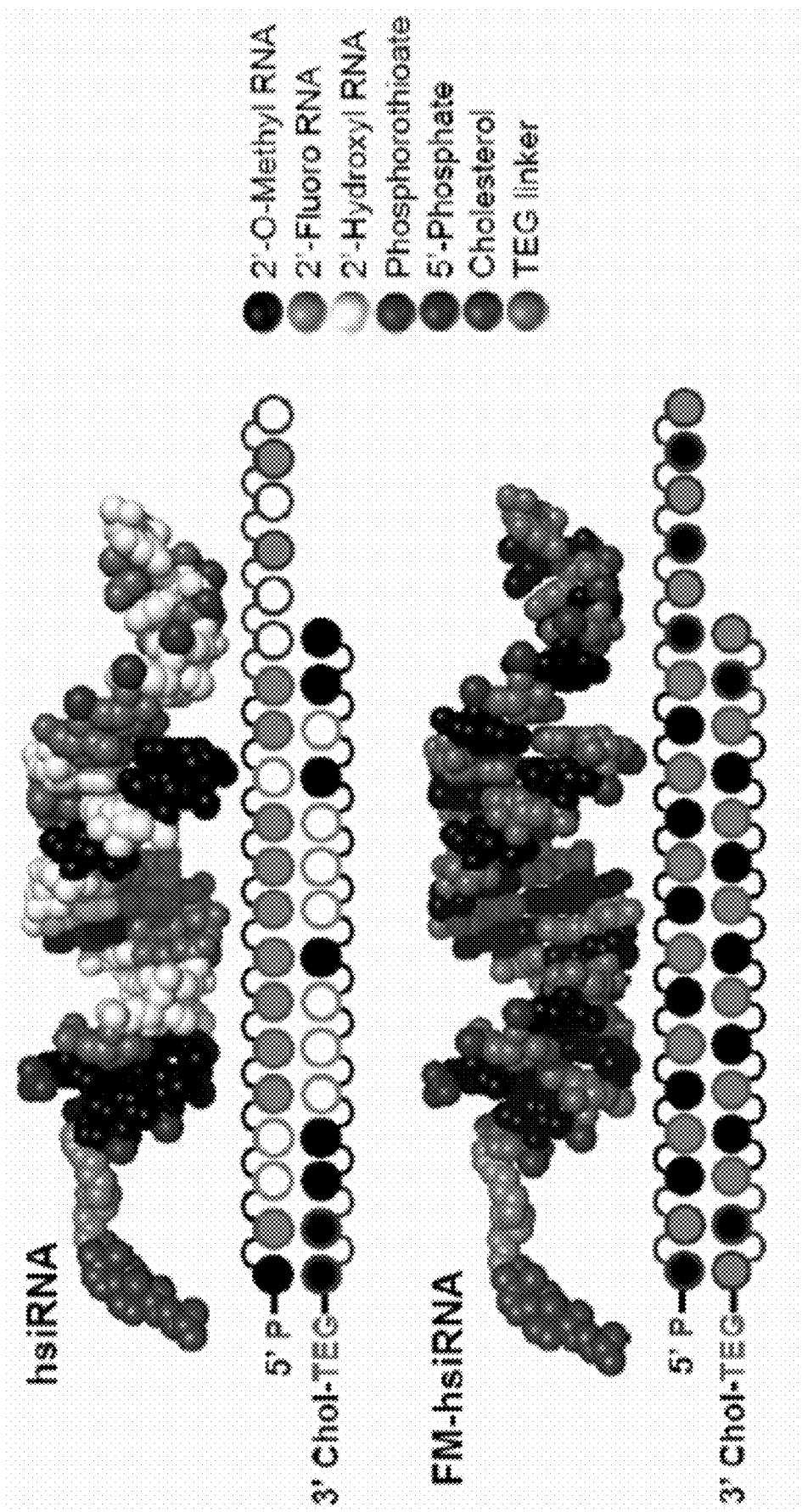
FIGS. 29A-29F depict hsiRNAs and their properties. (A) schematic structures of conventionally modified hsiRNA and fully modified hsiRNA (FM-hsiRNA). (B) modifications used in hsiRNAs. (C) hsiRNA$^{HTT}$ efficacy in HeLa cells. (D) hsiRNA$^{HTT}$ efficacy in primary neurons. (E) hsiRNA$^{PPIB}$ efficacy in primary trophoblasts. (F) hsiRNA$^{SFLI}$ efficacy in primary trophoblasts.
Figure 29B:
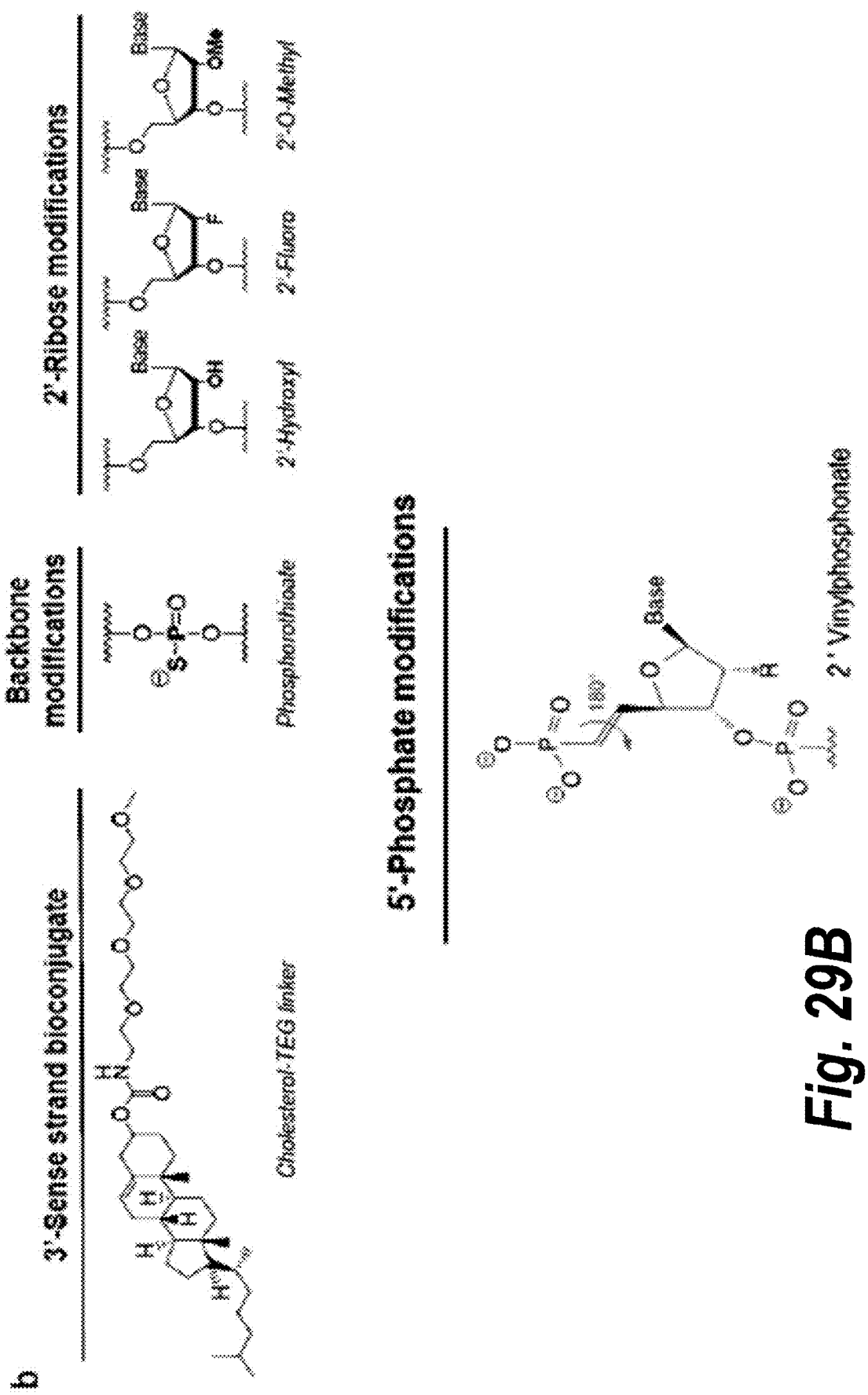
Figure 29C:
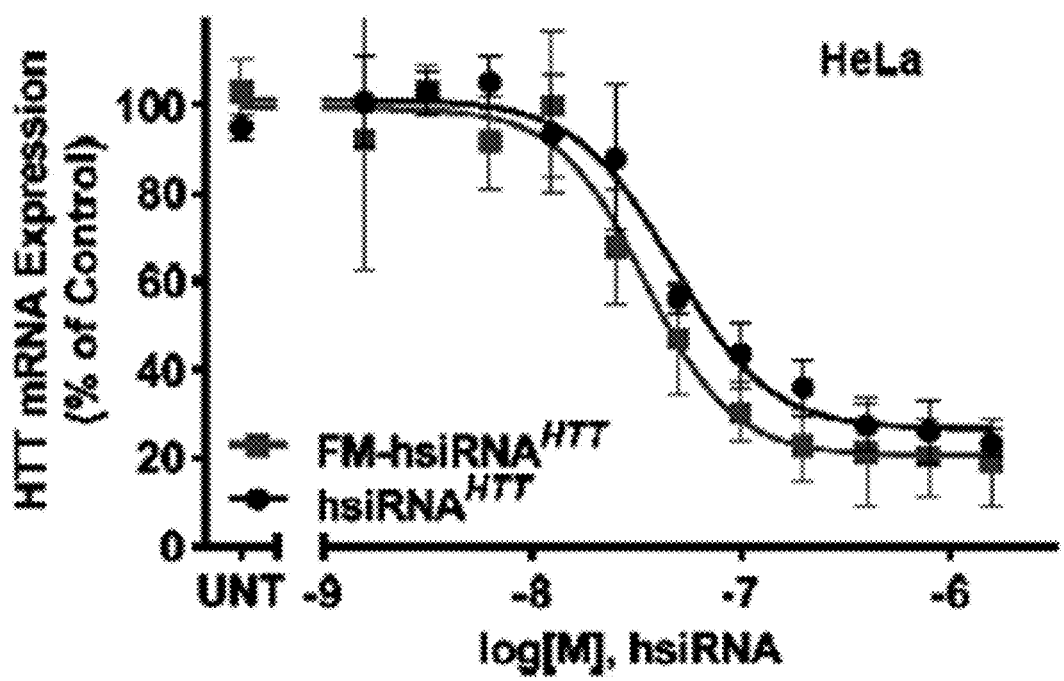
Figure 29D:
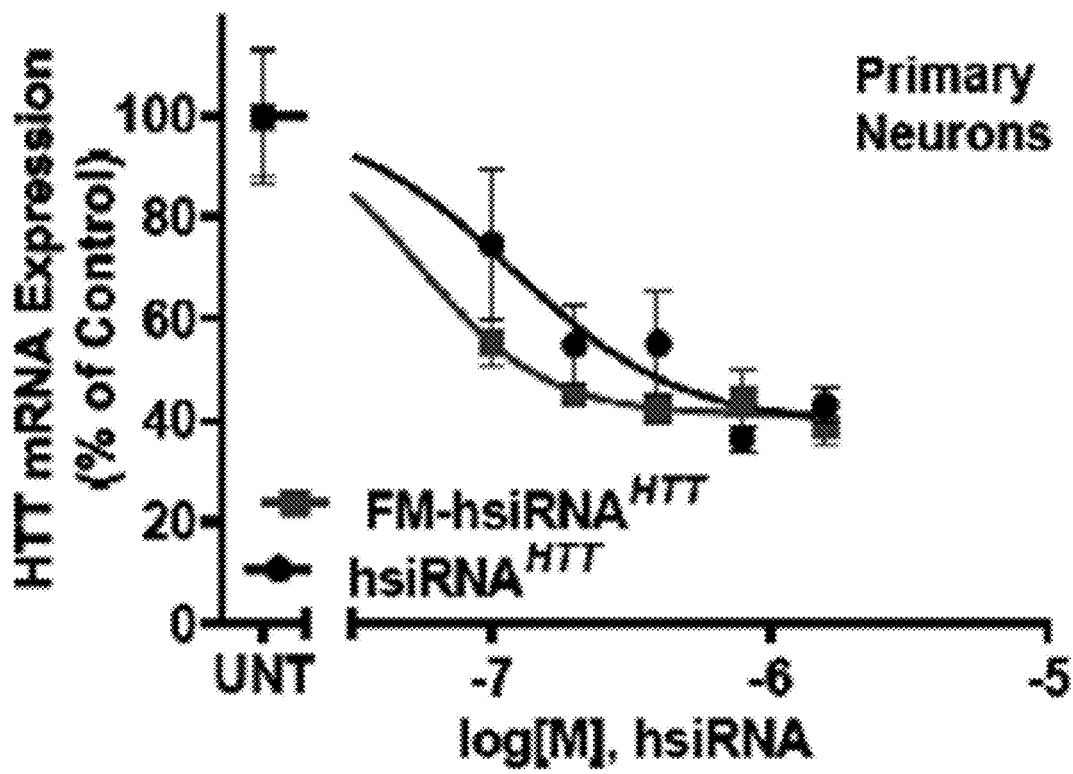
Figure 29E:
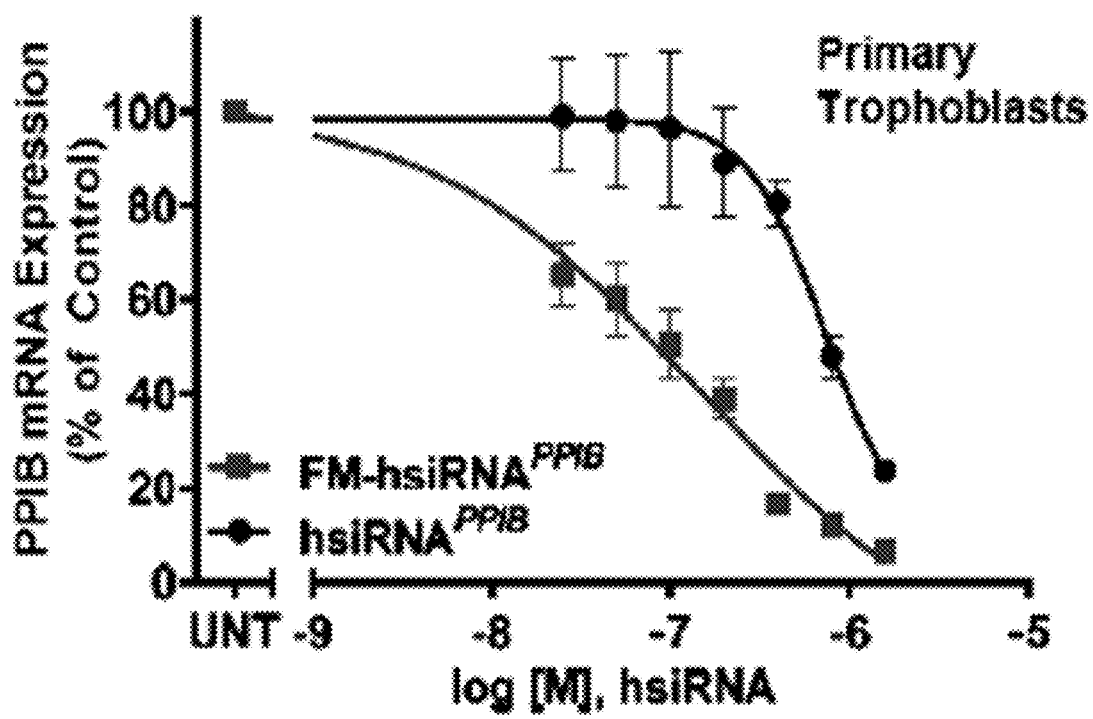
Figure 29F:
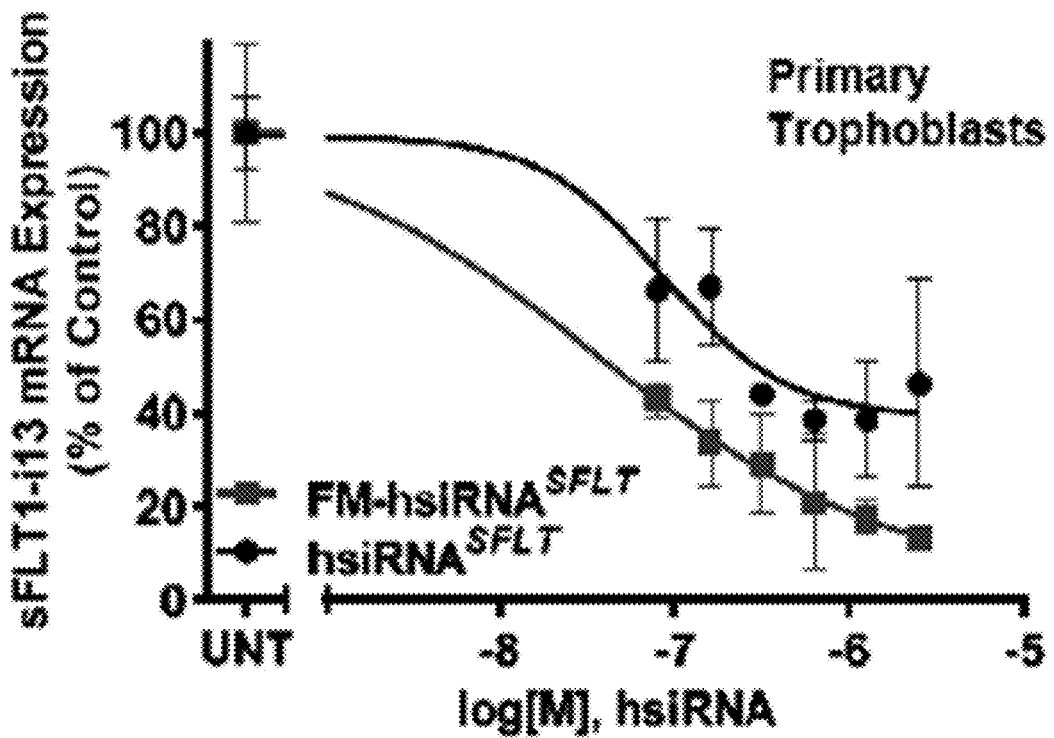

This chemical modification pattern was applied to several previously identified functional hsiRNA sequences, and demonstrated similar or improved efficacy (FIGS. 29C-29D). Interestingly, the most profound improvement effect was observed in primary trophoblasts in suspension, where cholesterol-mediated uptake took longer and, thus, relative impact of additional stabilization was more significant. In addition, this chemical modification pattern was applied to several published sequences targeting Tie-2 and Sod1, with similar success.

To generalize that these phenomena were relevant to other conjugates, the efficacy of partially and fully modified GalNac conjugated siRNAs was investigated in primary hepatocytes. It was demonstrated that similarly, fully metabolically stabilized compounds were significantly more active in hepatocytes than partially modified compounds.

Generally, the introduction of chemical modifications often has negative impacts on siRNA efficacy, with naked, hyper-functional siRNA losing efficacy in the context of extensive chemical modification patterns. The A-form RNA helix necessary for efficient recognition by the RISC complex is favored by C3'-endo ribose confirmation, preferentially adopted by 2'-fluoro and 2'-methoxy modifications. Alternating modifications modulates thermodynamic stability essential for efficient RISC entry, which has been studied in detail for 2'-FANA and 2'-fluro hybrids previously.

Partial siRNA modification (all pyrimidines) resulted in a dramatic enhancement of stability in vitro (increased from minutes to days in up to 50% FBS or human serum, which is similar to the enhancement in stability reported for fully modified siRNAs. In vivo, oligonucleotides distribute through the tissues and are constantly exposed to an aggressive nuclease environment, which conditions are impossible to mimic in vitro. Thus, stability of these modification patterns might quite different.

To evaluate the impact of complete modification on hydrophobic siRNAs efficacy and distribution in vivo, 10 mg/kg of partially modified and fully modified Cy 3-labelled hsiRNAs were administered to mice intravenously (IV) and subcutaneously (SC) (FIG. 30). Twenty four hours later, tissue distribution was evaluated by fluorescent microscopy, and levels of guide strand tissue accumulation were measured quantitatively using HPLC-based separation of the PNA-based assay. The PNA assay was a simple high throughput assay enabling quantitative evaluation of oligonucleotide retention in the tissues, and was adopted from the one described and used in Axon labs for clinical samples evaluation.

Figure 30A:
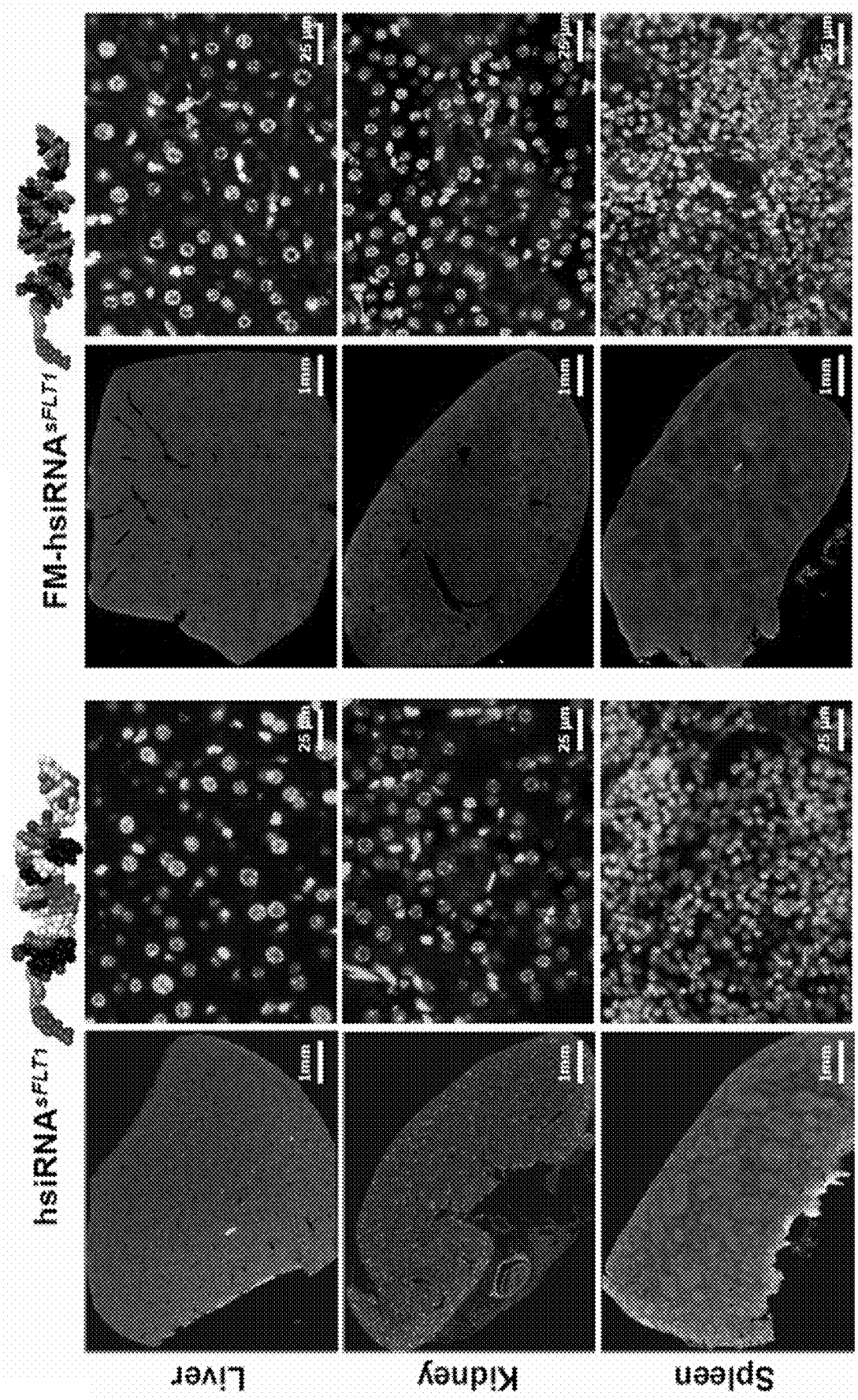
FIGS. 30A-30G depict full metabolic stabilization in conjugate-mediated siRNA delivery in vivo. (A) schematics of partially (hsiRNA) and fully metabolically stabilized hsiRNA-FMS compounds. (B) levels of hsiRNA$^{sFLT}$ accumulation post-IV administration. (C) levels of hsiRNA$^{sFLT}$ accumulation post-SC administration. (D) levels of FM-hsiRNA$^{sFLT}$ accumulation post-IV administration. (E) levels of FM-hsiRNA$^{sFLT}$ accumulation post-SC administration. (F) sFLT1 mRNA expression in liver and kidney 120 hours post-IV administration of hsiRNAs$^{FLT}$. (G) sFLT1 mRNA expression in liver and kidney 120 hours post-IV administration of FM-hsiRNA$^{sFLT}$.
Figure 30B:
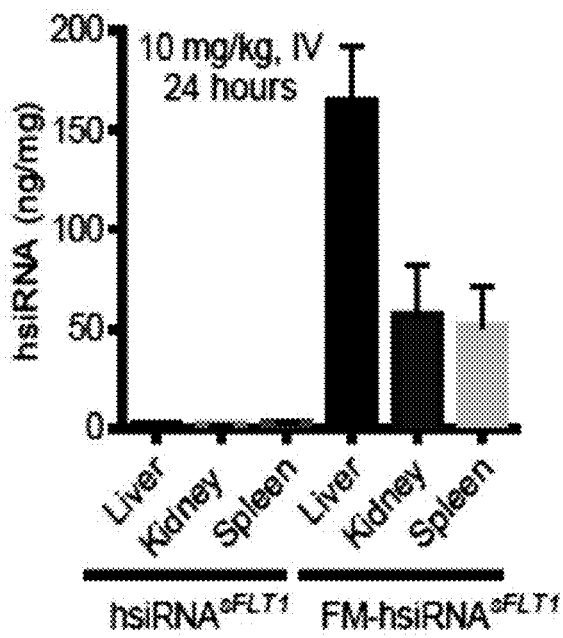
Figure 30C:
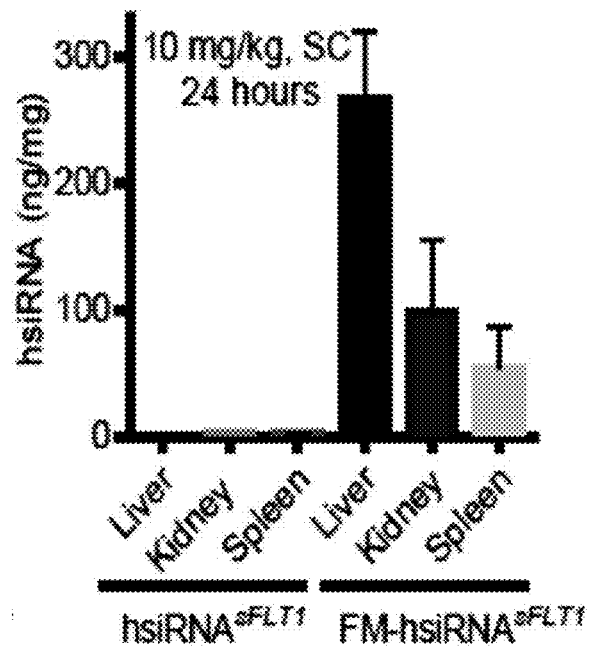
Figure 30D:
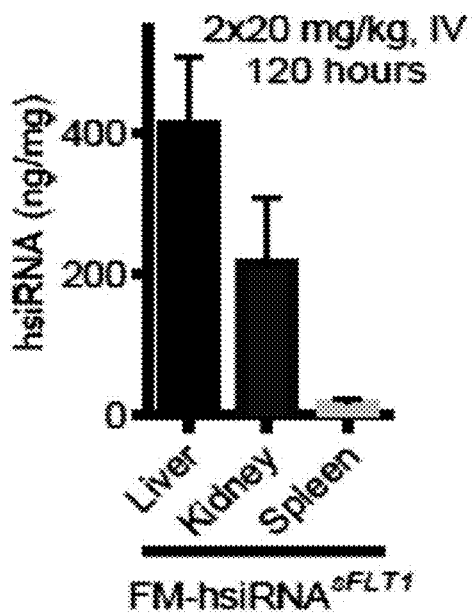
Figure 30E:
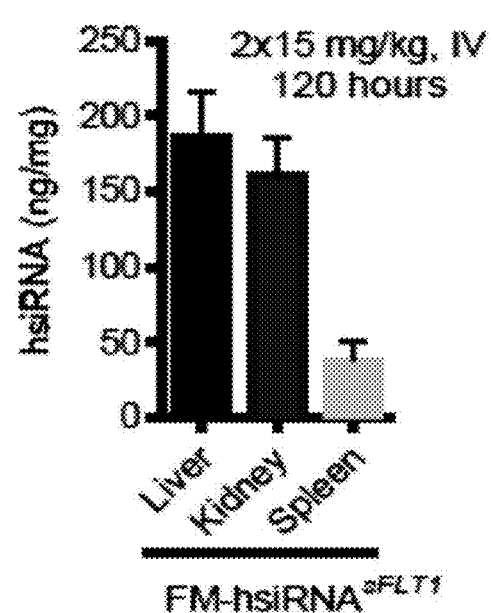
Figure 30F:
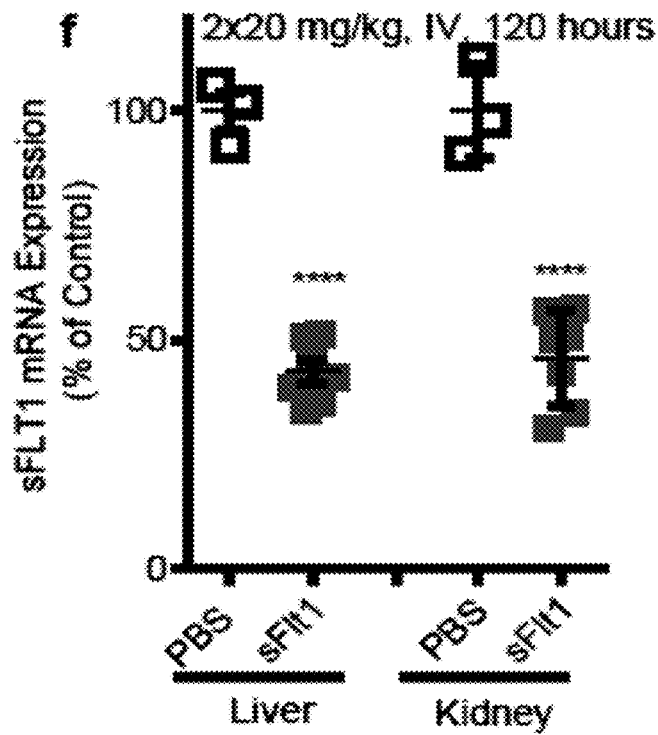
Figure 30G:
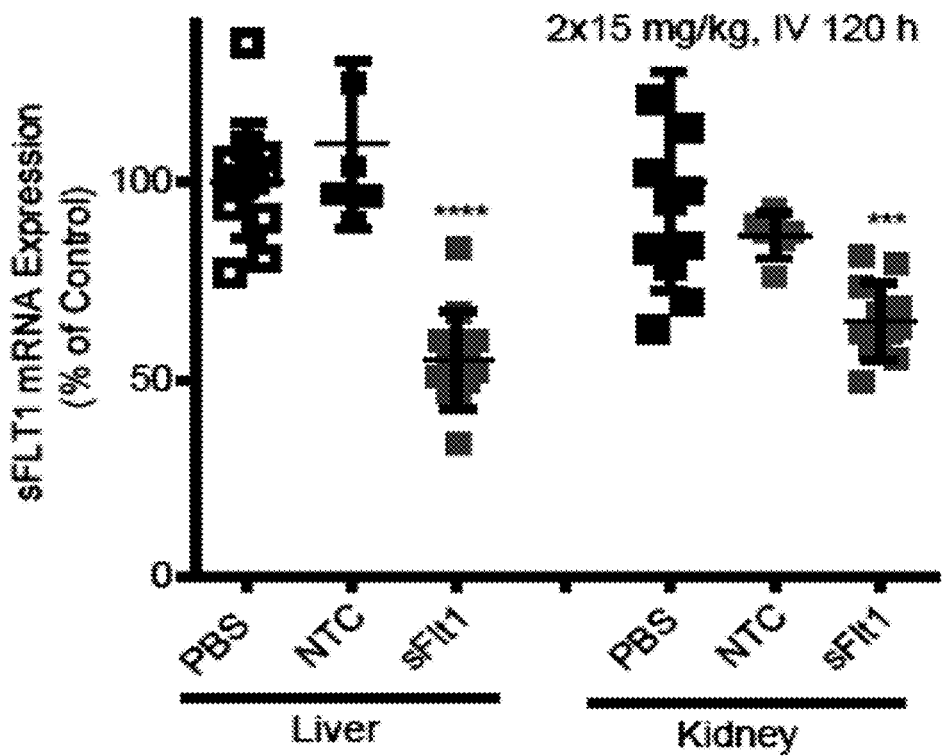

First, a dramatic enhancement of fluorescence retention and distribution to main organs was observed with fully metabolically stabilized compounds (FIG. 30A). While levels of fluorescence after a single injection of partially modified hsiRNAs was marginal and mainly limited to liver and kidney, full metabolic stabilization resulted in dramatic oligonucleotide accumulation in liver, kidney and spleen, as well as efficient distribution to other tissues, including fat and skin. The levels of accumulation by IV and SC administration were compared, and they were found to be similar (FIGS. 30B and 30C). Interestingly, the FM-hsiRNAs preferentially accumulated in endothelial cells and macrophages, and only secondarily accumulated in hepatocytes. Thus, hydrophobically modified compound differed in distribution from GalNac, which preferentially delivered to liver hepatocytes.

When measured quantitatively, the results were even more striking. While with partially modified compound had minimal levels of intact guide strand detected in tissues at 24 hours, fully modified compounds accumulated to levels of approximately 200 ng/mg in liver, kidney and spleen (FIG. 30B, 30C) and at ng/mg levels in several other tissues. Strikingly, with FM-hsiRNA, a similar level of intact guide strand was detected five days after administration, accounting for close to 80% of the injected dose (FIG. 30). This indicated that fully modified compounds were not only delivered to tissues, but retained in the tissues for extended periods of time.

These data are consistent with previously published attempts to use hydrophobic modifications (cholesterol, fatty acids, etc.) for systemic delivery of partially modified siRNAs, where repetitive dosing of high concentrations of compounds, i.e., 50-80 mg/kg, was necessary to detect any silencing activity.

As the levels of liver and kidney accumulation exceeded levels that are generally necessary to induce silencing (usually above 10-20 ng/mg), it was confirmed whether observed robust delivery resulted in functional silencing. Hydrophobically modified compounds preferentially delivered to endothelia, thus soluble isoforms of FLT1 (VEGFR1), which is preferentially expressed in endothelia, was targeted using recently identified hsiRNA compounds targeting sFLT1 (Turanov et al, 2015, prepared for publication).

Compounds were administered to two different mouse strains. In both cases, systemic administration of FM-hsiRNA induced robust silencing of sFTL1 in liver and kidney measured five days after administration. In a first study, the silencing was compared to PBS injected animals. In a second study to control for potential chemistry-related effects, both PBS and non-targeting control (NTC) of the same chemical composition was used. Only sFLT1 targeting FM-hsRNA, not the NTC, lowered the sFLT1 expression.

All oligonucleotides distributed preferentially to the liver, thus demonstrating liver efficacy as was expected. In addition, similar levels of compounds accumulated in the kidney, resulting in productive silencing. There is minimal data in the art on kidney siRNA delivery (Stokman, G., Qin, Y., Racz, Z., Hamar, P. & Price, L. S. Application of siRNA in targeting protein expression in kidney disease. *Advanced drug delivery reviews* 62, 1378-1389, doi:10.1016/j.addr.2010.07.005 (2010)). Partially modified (alternating 2'-methoxys) were studied for kidney proximal tubule delivery. A majority was cleared after four hours, and not detectable after 24 hours (Molitoris, B. A. et al. siRNA Targeted to p53 Attenuates Ischemic and Cisplatin-Induced Acute Kidney Injury. *Journal of the American Society of Nephrology: JASN* 20, 1754-1764, doi:10.1681/ASN.2008111204 (2009)).

Thus, full modification of siRNA was determined to be absolutely essential for systemic delivery and efficacy in vivo. In spite of the decade of effort in medicinal chemistry, the liver is currently the only target of non-formulated miRNAs having in vivo efficacy. Without intending to be bound by scientific theory, data presented herein might provide a partial explanation for this fact. As a vast majority of attempts to explore different conjugates (e.g., peptides, antibodies, small molecules, hydrophobic modifications, etc.) were performed in the context of partially modified siRNAs, the lack of in vivo stabilization might have been one of the major factors contributing to lack of robust efficacy; limiting the time available for the conjugates to promote uptake. It is also possible that the siRNAs described in the art that exhibited no or limited efficacy could have dramatically enhanced efficacy using the scaffolds as described herein.

Figure 31F:
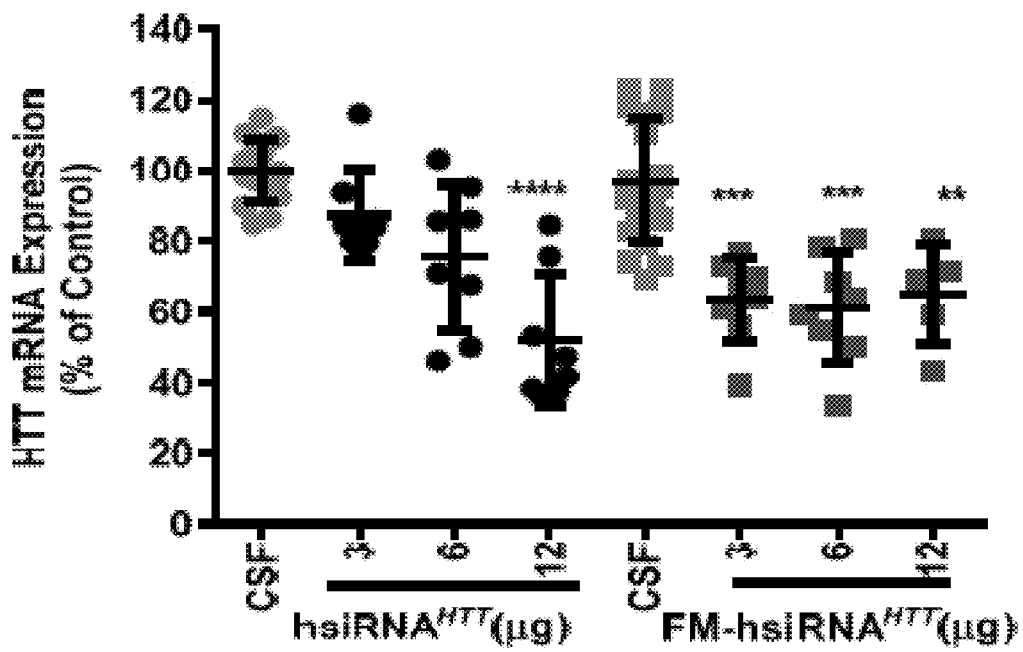
Figure 31G:
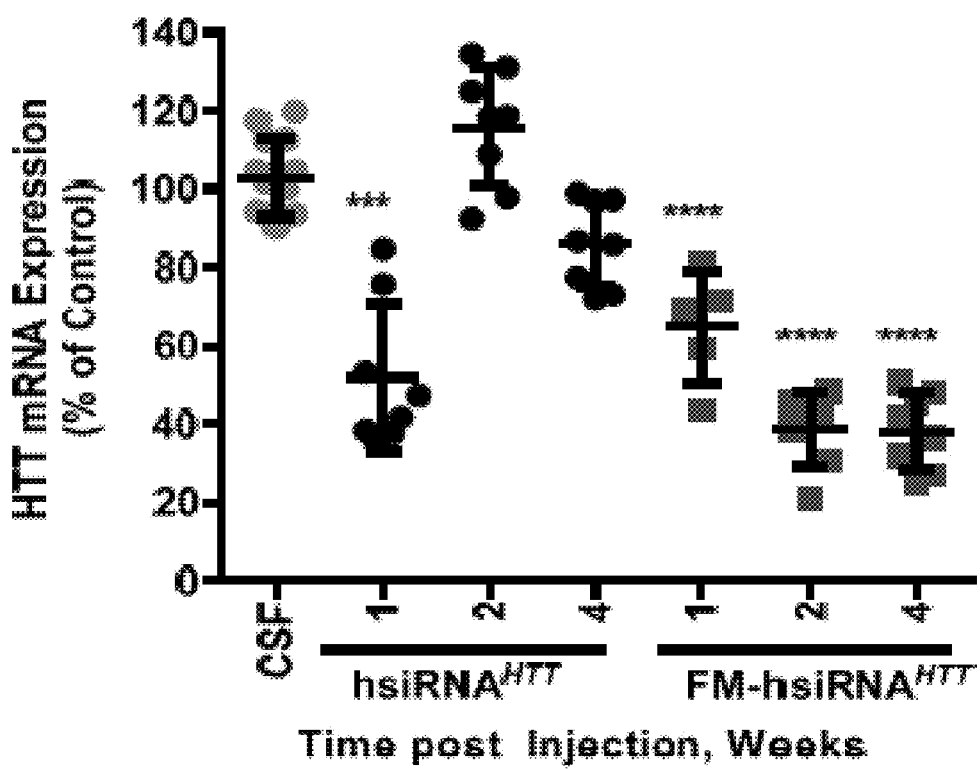

While it is clear that partially modified hydrophobic siRNAs are not active systemically, they can induce robust gene silencing in vivo upon local administration to tissues such as eye (Byrne (Supra)), skin (Khvorova (Supra)) and brain (Alterman et al, Molecular Therapy, under review). To evaluate the impact of full modification on siRNA efficacy upon local administration, conventional and fully modified siRNAs were injected intraventricularly into cerebrospinal fluid (CSF). Similarly to systemic administration, the use of fully modified hsiRNAs upon CSF infusion dramatically enhanced both the levels of oligonucleotide retention in a tissue, as well as the degree of distribution throughout the brain (FIG. 31A). With CY3 labelled FM-hsiRNA, compounds distributed to the cortex, striatum, cerebellum and other brain tissues (FIGS. 31 B-D), and a dramatic amount was retained around the injected ventricle. With conventional, partially modified hsiRNA, small amounts were detected around the ventricle and immediately adjusted tissues, but overall distribution was limited.

To test the potential impact of full stabilization on in vivo efficacy upon local administration, dose response and duration of effect of two types of compounds administrated directly (intrastriatally) in the brain were investigated.

When injected into the striatum, partially modified hsiRNA induced potent silencing (FIG. 31) at dose levels of 10 μg and above. Silencing disappeared at 6 μg and 3 μg. With fully modified hsiRNAs, similar levels of silencing were observed at all doses tested (FIG. 31F), indicating that fully modified compounds were more potent in vivo upon local administration.

When compared the duration of effect, the difference was even more striking. While partially modified induced silencing disappeared at two weeks, fully modified compounds continued to silence HTT gene for one, two and four weeks (FIG. 31G), with levels of modulation that appeared unaffected. Thus, locally, full chemical modification resulted in a dramatic induction of both potency and, more importantly, of duration of effect.

In summary, described herein is an siRNA scaffold having an alternating 2'-fluro, 2'-methoxy modification pattern applied to an asymmetric structural frame. As described herein, this scaffold can be successfully applied to a wide range of previously identified functional siRNAs compounds. The chemical modification pattern did not interfere with RISC entry, and it resulted in fully chemically modified compounds which were recognized by RISC complex as effectively as native RNAs. The exact impact of this chemistry on RISC cleavage kinetics will be investigated using single molecule approaches. Without intending to be bound by scientific theory, it is likely that use of a shorter (e.g., 15 bases) sense strand may ease dissociation of the uncleavable sense strand required for RISC loading, thus alleviating one of the limiting steps in RISC loading of fully stabilized compounds.

When administrated systemically, fully modified hsiRNAs accumulated in a vast range of tissues, including the liver, kidneys, spleen, fat, skin, etc., with confirmed silencing in the liver and kidneys. Robust efficacy in kidneys as demonstrated herein is a first example of conjugate-mediated delivery to this highly clinically relevant organ, opening options for development of novel therapies for kidney related diseases and disorders. In addition, full modification dramatically enhanced potency and, most importantly, enhanced the duration of effect of hydrophobically modified siRNAs in vivo upon local administration in the brain. Single injections resulted in silencing lasting for at least a month and likely longer, indicating that this chemistry provides a promise of long-term silencing upon single administration. It was surprising that with partially modified compounds, silencing lasted only for one week. In general, a loaded RISC complex is long lived, especially in non-dividing cells like neurons. Indeed, in primary neuronal cultures, a single treatment induced silencing for at least three weeks. The data described herein indicates that half-life of loaded RISC complex (at least for the sequences tested) in vivo in the brain is shorter than originally expected.

These data demonstrate that full chemical modification (i.e., additional stabilization) is a major contributor to in vivo efficacy of conjugate-delivered siRNAs. The data provided herein shows that simple, fully modified asymmetric siRNA scaffolds can be used for screening vast number of conjugation modalities, hopefully resulting in major advances to expand clinical utilization of RNAi beyond the liver.

Incorporation by Reference

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), CURRENT PROTOCOLS IN MOLECULAR BIOLOGY, John Wiley &Sons, NY (1993);

Ausubel, F. M. et al. eds., SHORT PROTOCOLS IN MOLECULAR BIOLOGY (4th Ed. 1999) John Wiley & Sons, NY. (ISBN 0-471-32938-X);

CONTROLLED DRUG BIOAVAILABILITY, DRUG PRODUCT DESIGN AND PERFORMANCE, Smolen and Ball (eds.), Wiley, New York (1984);

Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, New York, (1999);

Goodson, in MEDICAL APPLICATIONS OF CONTROLLED RELEASE, vol. 2, pp. 115-138 (1984); Hammerling, et al., in: MONOCLONAL ANTIBODIES AND T-CELL HYBRIDOMAS 563-681 (Elsevier, N.Y., 1981;

Harlow et al., ANTIBODIES: A LABORATORY MANUAL, (Cold Spring Harbor Laboratory Press, 2nd ed. 1988);

Kabat et al., SEQUENCES OF PROTEINS OF IMMUNOLOGICAL INTEREST (National Institutes of Health, Bethesda, Md. (1987) and (1991);

Kabat, E. A., et al. (1991) SEQUENCES OF PROTEINS OF IMMUNOLOGICAL INTEREST, Fifth Edition, U.S. Department of Health and Human Services, NIH Publication No. 91-3242;

Kontermann and Dubel eds., ANTIBODY ENGINEERING (2001) Springer-Verlag. New York. 790 pp. (ISBN 3-540-41354-5).

Kriegler, Gene Transfer and Expression, A Laboratory Manual, Stockton Press, NY (1990); Lu and Weiner eds., CLONING AND EXPRESSION VECTORS FOR GENE FUNCTION ANALYSIS (2001) BioTechniques Press. Westborough, MA. 298 pp. (ISBN 1-881299-21-X). MEDICAL APPLICATIONS OF CONTROLLED RELEASE, Langer and Wise (eds.), CRC Pres., Boca Raton, Fla. (1974);

Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).

Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6). SUSTAINED AND CONTROLLED RELEASE DRUG DELIVERY SYSTEMS, J. R. Robinson, ed., Marcel Dekker, Inc., New York, 1978

Winnacker, E. L. FROM GENES TO CLONES: INTRODUCTION TO $G_{ENE}$ TECHNOLOGY (1987) VCH Publishers, NY (translated by Horst Ibelgaufts). 634 pp. (ISBN 0-89573-614-4).

---

The invention claimed is:

1. A double-stranded small interfering RNA (siRNA) molecule comprising an antisense strand and a sense strand, the sense strand having complementarity to the antisense strand and the antisense strand comprising an oligonucleotide comprising a 5' end, a 3' end, and complementarity to a target mRNA molecule, wherein:

(1) the oligonucleotide comprises alternating 2'-methoxy-ribonucleotides and 2'-fluoro-ribonucleotides;

(2) the nucleotides at positions 2 and 14 from the 5' end of the oligonucleotide are 2'-fluoro-ribonucleotides;

(3) the nucleotides are connected to one another by way of phosphodiester or phosphorothioate linkages;

(4) the nucleotides at positions 1-6 from the 3' end of the oligonucleotide, or positions 1-7 from the 3' end of the oligonucleotide, are connected to one another by way of phosphorothioate linkages; and (5) the oligonucleotide comprises from 6-17 phosphorothioated bonds, wherein the oligonucleotide has a chemical structure represented by formula (Ia), in the 5'-to-3' direction:

$$X(\text{-K-B-K-A})_j(\text{-S-B-S-A})_r\text{-OR} \qquad (Ia)$$

wherein X is

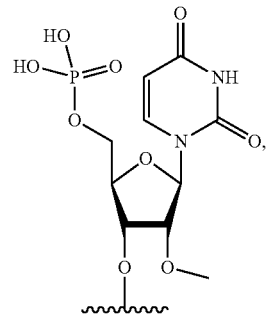
(X1)

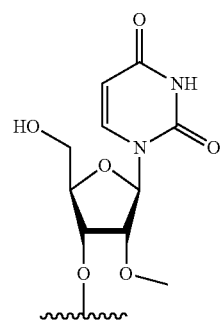
(X2)

-continued (X3)
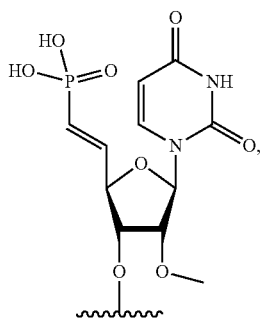

(X4)
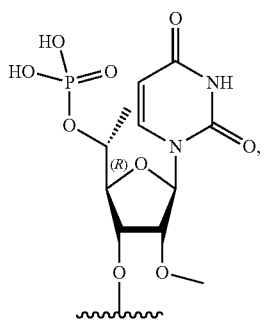

(X5)
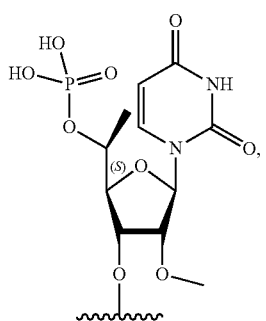

(X6)
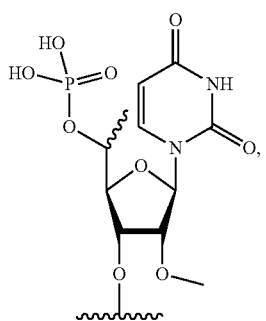

(X7)
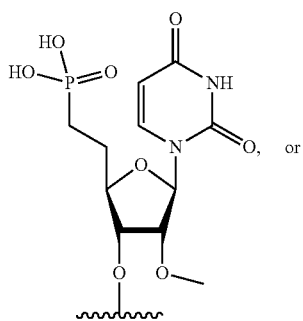, or

-continued (X8)
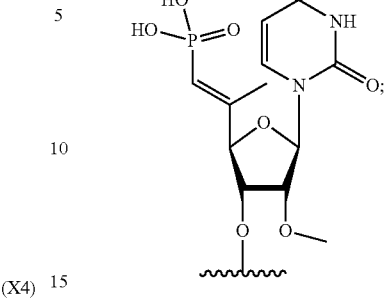

each A is, independently, a 2'-methoxy-ribonucleotide;
each B is, independently, a 2'-fluoro-ribonucleotide;
each K is, independently, a phosphodiester or phosphorothioate linkage;
each S is a phosphorothioate linkage;
R is a capping group;
j is an integer selected from 4, 5, 6, or 7; and
r is an integer selected from 2 and 3; and
wherein the siRNA molecule comprises a single-stranded tail of 5-8 bases.

2. The double-stranded siRNA molecule of claim 1, wherein X is (X3)
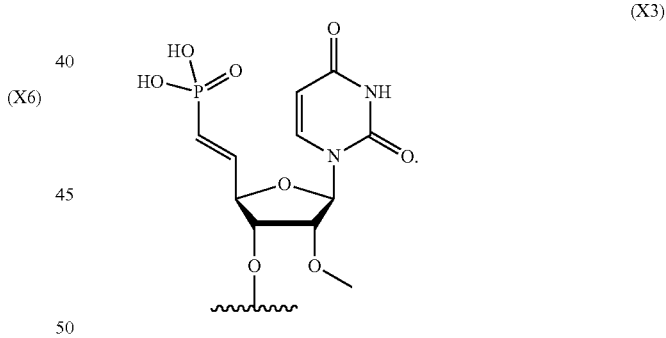

3. The double-stranded siRNA molecule of claim 1, wherein j is 7.

4. The double-stranded siRNA molecule of claim 2, wherein j is 7.

5. The double-stranded siRNA molecule of claim 1, wherein r is 3.

6. The double-stranded siRNA molecule of claim 2, wherein r is 3.

7. The double-stranded siRNA molecule of claim 3, wherein r is 3.

8. The double-stranded siRNA molecule of claim 1, wherein the oligonucleotide has a chemical structure represented by formula $X(\text{-K-B-K-A})_7(\text{-S-B-S-A})_3\text{-OR}$, in the 5'-to-3' direction, and wherein X is (X3)

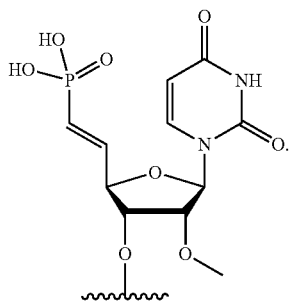

9. The double-stranded siRNA molecule of claim 1, wherein the target mRNA corresponds to a portion of a mutant Huntingtin allele.

10. The double-stranded siRNA molecule of claim 8, wherein the target mRNA corresponds to a portion of a mutant Huntingtin allele.

11. The double-stranded siRNA molecule of claim 1, wherein the antisense strand has a length of from 16 to 30 nucleotides.

12. The double-stranded siRNA molecule of claim 11, wherein the antisense strand has a length of 19, 20, 21, 22, or 23 nucleotides.

13. The double-stranded siRNA molecule of claim 12, wherein the antisense strand has a length of 20, 21, or 22 nucleotides.

14. The double-stranded siRNA molecule of claim 13, wherein the antisense strand has a length of 21 nucleotides.

15. The double-stranded siRNA molecule of claim 11, wherein the sense strand has a length of 16, 17, 18, 19, 20, or 21 nucleotides.

16. The double-stranded siRNA molecule of claim 15, wherein the sense strand has a length of 16, 17, or 18 nucleotides.

17. The double-stranded siRNA molecule of claim 16, wherein the sense strand has a length of 16 nucleotides.

18. The double-stranded siRNA molecule of claim 1, wherein the double-stranded siRNA molecule comprises a duplex region having a length of from 11 to 16 base pairs.

19. The double-stranded siRNA molecule of claim 18, wherein the double-stranded siRNA molecule comprises a duplex region having a length of 16 base pairs.

20. The double-stranded siRNA of claim 1, wherein the 3' end of the antisense strand comprises the tail.

21. The double-stranded siRNA of claim 20, wherein the tail is fully phosphorothioated.

22. A double-stranded siRNA molecule comprising an antisense strand and a sense strand, wherein the antisense strand comprises an oligonucleotide comprising a 5' end, a 3' end, and complementarity to a target mRNA molecule, wherein:
(1) the sense strand has complementarity to the antisense strand;
(2) the oligonucleotide comprises alternating 2'-methoxy-ribonucleotides and 2'-fluoro-ribonucleotides;
(3) the nucleotides at positions 2 and 14 from the 5' end of the oligonucleotide are 2'-fluoro-ribonucleotides;
(4) the nucleotides are connected to one another by way of phosphodiester or phosphorothioate linkages;
(5) the nucleotides at positions 1-6 from the 5' end of the oligonucleotide, or positions 1-7 from the 3' end of the oligonucleotide, are connected to one another by way of phosphorothioate linkages;
(6) the oligonucleotide comprises from 6-17 phosphorothioated bonds;
(7) each of the antisense strand and the sense strand is, independently, from 16 to 30 nucleotides in length, with the proviso that the antisense strand is 5-8 nucleotides longer than the sense strand; and
(8) the oligonucleotide has a chemical structure represented by formula (Ia), in the 5'-to-3' direction:

$$X(\text{-}K\text{-}B\text{-}K\text{-}A)_j(\text{-}S\text{-}B\text{-}S\text{-}A)_r\text{-}OR \qquad (Ia)$$

wherein X is (X1)

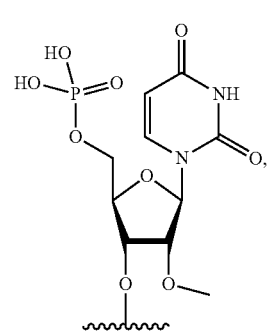

(X2)

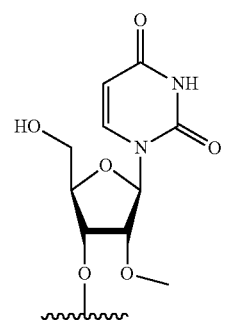

(X3)

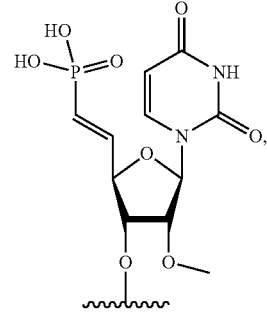

(X4)

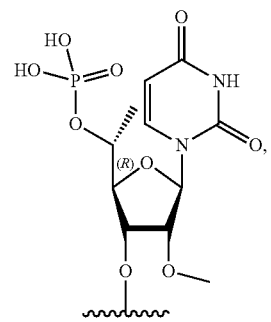

-continued

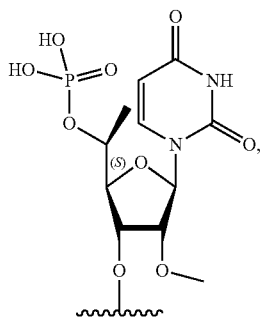
(X5)

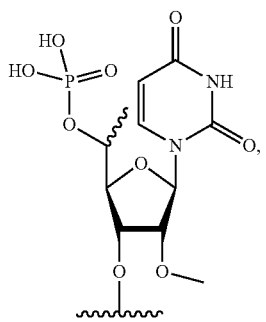
(X6)

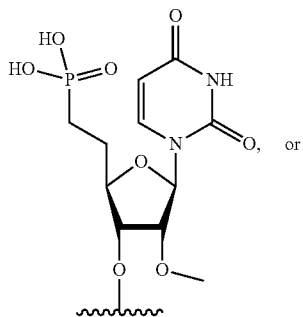
(X7)

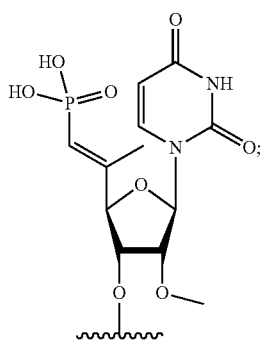
(X8)

each A is, independently, a 2'-methoxy-ribonucleotide;
each B is, independently, a 2'-fluoro-ribonucleotide;
each K is, independently, a phosphodiester or phosphorothioate linkage;
each S is a phosphorothioate linkage;
R is a capping group;
j is an integer selected from 4, 5, 6, or 7; and
r is an integer selected from 2 and 3.

23. The double-stranded siRNA molecule of claim 22, wherein X is

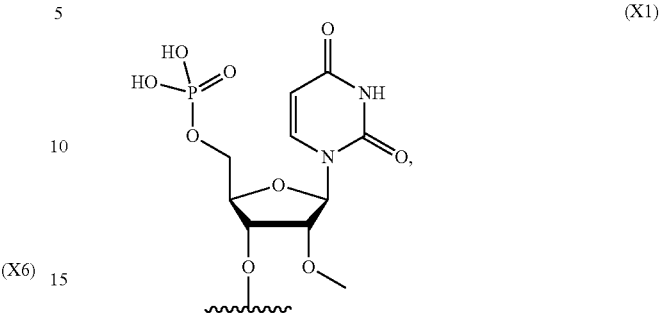
(X1)

j is 7, and r is 3.

24. The double-stranded siRNA molecule of claim 23, wherein the antisense strand has a length of 19, 20, 21, 22, or 23 nucleotides.

25. The double-stranded siRNA molecule of claim 24, wherein the antisense strand has a length of 20, 21, or 22 nucleotides.

26. The double-stranded siRNA molecule of claim 24, wherein the antisense strand has a length of 21 nucleotides.

27. The double-stranded siRNA molecule of claim 23, wherein the sense strand has a length of 16, 17, 18, 19, 20, or 21 nucleotides.

28. The double-stranded siRNA molecule of claim 27, wherein the sense strand has a length of 16, 17, or 18 nucleotides.

29. The double-stranded siRNA molecule of claim 28, wherein the sense strand has a length of 16 nucleotides.

30. The double-stranded siRNA molecule of claim 23, wherein the double-stranded siRNA molecule comprises a duplex region having a length of from 11 to 16 base pairs.

31. The double-stranded siRNA molecule of claim 30, wherein the double-stranded siRNA molecule comprises a duplex region having a length of 16 base pairs.

32. The double-stranded siRNA molecule of claim 22, wherein the antisense and sense strands are blunt-ended at the 3' end of the sense strand.

33. A double-stranded, and chemically-modified nucleic acid, comprising an antisense strand comprising at least 16 contiguous nucleotides and complementarity to a target, and a sense strand comprising complementarity to the antisense strand, wherein the antisense strand and the sense strand comprise a 5' end, a 3' end, and comprising a single-stranded tail of 5-8 nucleotides from the 3' end of the antisense strand, wherein each nucleotide of the single-stranded tail is connected to adjacent nucleotides via a phosphorothioate linkage;
wherein the antisense strand comprises:
(1) alternating 2'-methoxy-ribonucleotides and 2'-fluoro-ribonucleotides;
(2) nucleotides at positions 2 and 14 from the 5' end that are not 2'-methoxy-ribonucleotides; and
(3) nucleotides that are connected via phosphodiester or phosphorothioate linkages,
wherein the sense strand comprises:
(1) alternating 2'-methoxy-ribonucleotides and 2'-fluoro-ribonucleotides;
(2) nucleotides at positions 2 and 14 from the 3' end that are 2'-methoxy-ribonucleotides; and
(3) nucleotides that are connected via phosphodiester or phosphorothioate linkages.

34. The nucleic acid of claim 33, wherein the nucleotides at positions 1 and 2 from the 3' end of the sense strand are connected to adjacent nucleotides via phosphorothioate linkages.

35. The nucleic acid of claim 33, wherein the nucleotides at positions 1 and 2 from the 3' end of the sense strand, and the nucleotides at positions 1 and 2 from the 5' end of the sense strand, are connected to adjacent ribonucleotides via phosphorothioate linkages.

36. The nucleic acid of claim 33, wherein the sense strand is linked to a hydrophobic molecule at the 3' end.

37. The nucleic acid of claim 36, wherein the linkage between the sense strand and the hydrophobic molecule comprises polyethylene glycol.

38. The nucleic acid of claim 36, wherein the linkage between the sense strand and the hydrophobic molecule comprises triethylene glycol.

39. The nucleic acid of claim 36, wherein the hydrophobic molecule is cholesterol.

* * * * *